US009950010B1

(12) United States Patent
Jantz et al.

(10) Patent No.: US 9,950,010 B1
(45) **Date of Patent: *Apr. 24, 2018**

(54) GENETICALLY-MODIFIED CELLS COMPRISING A MODIFIED HUMAN T CELL RECEPTOR ALPHA CONSTANT REGION GENE

(71) Applicant: Precision BioSciences, Inc., Durham, NC (US)

(72) Inventors: Derek Jantz, Durham, NC (US); James Jefferson Smith, Morrisville, NC (US); Michael G. Nicholson, Chapel Hill, NC (US); Daniel T. MacLeod, Durham, NC (US); Jeyaraj Antony, Chapel Hill, NC (US); Victor Bartsevich, Durham, NC (US)

(73) Assignee: Precision BioSciences, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/864,984

(22) Filed: Jan. 8, 2018

Related U.S. Application Data

(63) Continuation of application No. 15/607,059, filed on May 26, 2017, now Pat. No. 9,889,161, which is a continuation of application No. PCT/US2016/055492, filed on Oct. 5, 2016.

(60) Provisional application No. 62/297,426, filed on Feb. 19, 2016, provisional application No. 62/237,394, filed on Oct. 5, 2015.

(51) Int. Cl.

| | |
|---|---|
| ***A61K 35/17*** | (2015.01) |
| ***C07K 16/30*** | (2006.01) |
| ***C12N 15/09*** | (2006.01) |
| ***A61K 39/00*** | (2006.01) |
| ***A61K 48/00*** | (2006.01) |
| ***C07K 14/725*** | (2006.01) |
| ***C07K 14/705*** | (2006.01) |
| ***C12N 5/0783*** | (2010.01) |
| ***C12N 15/113*** | (2010.01) |
| ***C12N 15/86*** | (2006.01) |

(52) U.S. Cl.
CPC .......... *A61K 35/17* (2013.01); *A61K 39/0011* (2013.01); *A61K 48/0008* (2013.01); *C07K 14/7051* (2013.01); *C07K 14/70503* (2013.01); *C07K 16/30* (2013.01); *C07K 16/3061* (2013.01); *C12N 5/0636* (2013.01); *C12N 15/09* (2013.01); *C12N 15/113* (2013.01); *C12N 15/86* (2013.01); *A61K 2039/505* (2013.01); *A61K 2039/5156* (2013.01); *A61K 2039/5158* (2013.01); *C07K 2317/53* (2013.01); *C07K 2319/02* (2013.01); *C07K 2319/03* (2013.01); *C07K 2319/33* (2013.01); *C07K 2319/40* (2013.01); *C07K 2319/74* (2013.01); *C12N 2510/00* (2013.01)

(58) Field of Classification Search
CPC ................ A61K 35/17; C07K 14/7051; C07K 14/70503; C07K 16/30; C07K 2317/60; C07K 2319/33; C07K 2319/73; C12N 15/09; C12N 5/0636; C12N 2510/00
See application file for complete search history.

(56) References Cited

U.S. PATENT DOCUMENTS

| | | | | |
|---|---|---|---|---|
| 4,873,192 | A | 10/1989 | Kunkel | |
| 6,015,832 | A | 1/2000 | Baker, Jr. et al. | |
| 6,506,803 | B1 | 1/2003 | Baker, Jr. et al. | |
| 6,559,189 | B2 | 5/2003 | Baker, Jr. et al. | |
| 6,635,676 | B2 | 10/2003 | Baker, Jr. et al. | |
| 8,021,867 | B2 | 9/2011 | Smith et al. | |
| 8,445,251 | B2 | 5/2013 | Smith et al. | |
| 8,956,828 | B2 | 2/2015 | Bonini et al. | |
| 2002/0045667 | A1 | 4/2002 | Baker et al. | |
| 2004/0043041 | A1 | 3/2004 | Baker et al. | |
| 2012/0321667 | A1 | 12/2012 | Sentman | |
| 2013/0315884 | A1* | 11/2013 | Galetto | C12N 5/0636 424/93.71 |
| 2014/0034902 | A1 | 2/2014 | Hwang et al. | |
| 2014/0301990 | A1* | 10/2014 | Gregory | A61K 35/26 424/93.21 |
| 2015/0376650 | A1* | 12/2015 | Auerbach | C12N 15/64 435/34 |
| 2016/0081314 | A1* | 3/2016 | Thurston | C07K 14/7051 800/6 |

(Continued)

FOREIGN PATENT DOCUMENTS

| | | | |
|---|---|---|---|
| WO | WO 2002/012514 | A2 | 2/2002 |
| WO | WO 2007/047859 | A2 | 4/2007 |

(Continued)

OTHER PUBLICATIONS

International Search Report and Written Opinion for Application No. PCT/US2016/055492 dated Feb. 3, 2017.
Airenne et al., "Baculovirus: an insect-derived vector for diverse gene transfer applications," Mol. Ther. 21(4), 739-749 (2013).
Altschul et al., "Basic local alignment search tool," J. Mol. Biol. 215, pp. 403-410 (1990).
Altschul et al., "Gapped BLAST and PSI-BLAST: a new generation of protein database search programs," Nucleic Acids Res. 25, pp. 3389-3402 (1997).
Arnould et al., "Engineering of large numbers of highly specific homing endonucleases that induce recombination on novel DNA targets," J. Mol. Biol. 355, pp. 443-458 (2006).
Baeckseung et al., 323. Efficient Generation of CART Cells by Homology Directed Transgene Integration into the TCR-Alpha Locus. Mol Ther. May 1, 2016;24(S1):S130.
Baxter et al., "Engineering domain fusion chimeras from I-OnuI family LAGLIDADG homing endonucleases," Nucleic Acids Research, 40(16), pp. 7985-8000 (2012).

(Continued)

*Primary Examiner* — Kevin K Hill
(74) *Attorney, Agent, or Firm* — Wolf, Greenfield & Sacks, P.C.

(57) ABSTRACT

Disclosed herein is a genetically-modified cell comprising in its genome a modified human T cell receptor alpha constant region gene, wherein the cell has reduced cell-surface expression of the endogenous T cell receptor. The present disclosure further relates to methods for producing such a genetically-modified cell, and to methods of using such a cell for treating a disease in a subject.

8 Claims, 62 Drawing Sheets

(56) References Cited

U.S. PATENT DOCUMENTS

2016/0120906 A1* 5/2016 Galetto ................ C12N 5/0636 424/93.21
2017/0016027 A1 1/2017 Lee et al.
2017/0333481 A1 11/2017 Jantz et al.
2017/0335010 A1 11/2017 Jantz et al.

FOREIGN PATENT DOCUMENTS

WO WO 2009/059195 A2 5/2009
WO WO 2012/167192 A2 12/2012
WO WO 2013/074916 A1 5/2013
WO WO 2013/153391 A1 10/2013
WO WO 14/191527 * 12/2014
WO WO 2014/191525 A1 12/2014
WO WO 2014/191527 A1 12/2014
WO WO 2015/057980 A1 4/2015
WO WO 2015/121454 A1 8/2015
WO WO 2015/167766 A1 11/2015
WO WO 2017/011519 A1 1/2017

OTHER PUBLICATIONS

Benoist et al., "In vivo sequence requirements of the SV40 early promotor region," Nature 290(5804), pp. 304-310 (1981).
Beurdeley et al., "Compact designer TALENs for efficient genome engineering," Nat. Commun. 4, p. 1762 (2013).
Boissel et al., "megaTALs: a rare-cleaving nuclease architecture for therapeutic genome engineering," Nucleic Acid Research 42(4), pp. 2591-2601 (2014).
Cahill et al., "Mechanisms of eukaryotic DNA double strand break repair," Front. Biosci. 11, pp. 1958-1976 (2006).
Chames et al., "In vivo selection of engineered homing endonucleases using double-strand break induced homologous recombination," Nucleic Acids Res. 33, p. e178 (2005).
Chang et al., "Inducible retroviral vectors regulated by lac repressor in mammalian cells," Gene 183, pp. 137-142 (1996).
Chen et al., "A novel adenoviral vector carrying an all-in-one Tet-On system with an autoregulatory loop for tight, inducible transgene expression," BMC Biotechnol. 15, 8 pages (2015).
Chen, "Exploiting the Intron-splicing Mechanism of Insect Cells to Produce Viral Vectors Harboring Toxic Genes for Suicide Gene Therapy," Mol. Ther. Nucleic Acids 1, e57; pp. 1-10 (2012).
Cheng et al., "Dendrimers as drug carriers: applications in different routes of drug administration," J. Pharm. Sci. 97(1): 123-143 (2008).
Chevalier and Stoddard, "Homing endonucleases: structural and functional insight into the catalysts of intron/intein mobility," Nucleic Acids Res. 29(18), pp. 3757-3774 (2001).
Cots et al., "Helper dependent adenovirus vectors: progress and future prospects," Curr. Gene Ther. 13(5) pp. 370-381 (2013).
Deshayes et al., "Cell-penetrating peptides: tools for intracellular delivery of therapeutics," Cell Mol. Life Sci. 62, pp. 1839-1849 (2005).
Deshayes et al., "Primary amphipathic cell-penetrating peptides: structural requirements and interactions with model membranes," Biochemistry 43, pp. 7698-7706 (2004).
Dinda et al., "Nanobiotechnology-based drug delivery in brain targeting," Cuff. Pharm. Biotechnol. 14, pp. 1264-1274 (2013).
Dingermann et al., "Establishment of a system for conditional gene expression using an inducible tRNA suppressor gene," Mal. Cell Biol. 12(9), pp. 4038-4045 (1992).
Durai et al., "Zinc finger nucleases: custom-designed molecular scissors for genome engineering of plant and mammalian cells," Nucleic Acids Res. 33, pp. 5978-5990 (2005).
Ellebrecht et al., "Reengineering chimeric antigen receptor T cells for targeted therapy of autoimmune disease," Science. Jul. 8, 2016;353(6295):179-84. doi: 10.1126/science.aaf6756. Epub Jun. 30, 2016. Author manuscript.
Fu et al., "High-frequency off-target mutagenesis induced by CRISPR-Cas nucleases in human cells," Nat. Biotechnol. 31, pp. 822-826 (2013).
Gao et al., "Efficient gene delivery into mammalian cells mediated by a recombinant baculovirus containing a whispovirus iel promoter, a novel shuttle promoter between insect cells and mammalian cells," J. Biotechnol. 131(2), pp. 138-143 (2007).
Gish et al., "Identification of protein coding regions by database similarity search," Nature Genet. 3, pp. 266-272 (1993).
Grizot et al., "Efficient targeting of a SCID gene by an engineered single-chain homing endonuclease," Nucleic Acids Res. 37, pp. 5405-5419 (2009).
Haase, et al., "Generation of a tumor- and tissue-specific episomal non-viral vector system," BMC Biotechnol. 13, pp. 49-54 (2013).
Hale et al., "Homology-Directed Recombination for Enhanced Engineering of Chimeric Antigen Receptor T Cells," Molecular Therapy 4, pp. 192-203 (2017).
Hegde et al., "Current status of chimeric antigen receptor engineered T cell-based and immune checkpoint blockade-based cancer immunotherapies," Cancer Immunol Immunother 66, pp. 1113-1121 (2017).
Hudecz et al., "Medium-sized peptides as built in carriers for biologically active compounds," Med. Res. Rev. 25, pp. 679-736 (2005).
Ibarra et al., "Efficient Targeted Gene Modification in Primary Human Hematopoietic Cells Using Co-Delivery of Nuclease mRNA and AAV Donors," Mol. Ther., 23(suppl. 1), p. S273 (2015).
Jacox et al., "Tissue-specific and ubiquitous expression patterns from alternative promoters of human genes," PLoS One 5(8), p. e12274 (2010).
Jearawiriyapaisam et al., "Sustained dystrophin expression induced by peptide-conjugated morpholino oligomers in the muscles of mdx mice," Mol. Ther. 16, pp. 1624-1629 (2008).
Jiang et al., "Cationic core-shell liponanoparticles for ocular gene delivery," Biomaterials. 33(30), pp. 7621-7630 (2012).
Kang et al., "Harnessing the capacity of cell-penetrating peptides for drug delivery to the central nervous system," Curr. Pharm. Biotechnol. 15(3), pp. 220-230 (2014).
Karlin et al., "Applications and statistics for multiple high-scoring segments in molecular sequences," Proc Natl Acad Sci U S A. Jun. 15, 1993;90(12):5873-7.
Kramer et al., "In vitro and in vivo comparative study of chimeric liver-specific promoters," Mol. Ther. 7, pp. 375-385 (2003).
Kunkel, "Rapid and efficient site-specific mutagenesis without phenotypic selection," Proc Natl Acad Sci U S A. Jan. 1985;82(2):488-92.
Lee et al., "Efficient Generation of CART Cells by Homology Directed Transgene Integration into the TCR-Alpha Locus," Molecular Therapy, vol. 24, Supplement 1, S130 (May 2016).
Lentz, et al., "Viral vectors for gene delivery to the central nervous system," Neurobiol. Dis. 48, pp. 179-188 (2012).
Li et al., "Generation of single-chain LAGLIDADG homing endonucleases from native homodimeric precursor proteins," Nucleic Acids. Res. 37, pp. 1650-1662 (2009).
Liu et al., "Therapeutic levels of factor IX expression using a muscle-specific promoter and adeno-associated virus serotype 1 vector," Hum. Gene Ther. 15, pp. 783-792 (2004).
MacLeod et al., Generation of a Novel Allogeneic CAR T Cell Platform Utilizing an Engineered Meganuclease and AAV Donor Template to Achieve Efficient Disruption of T Cell Receptor Expression and Simultaneous Homology-Directed Insertion of a CD19 CAR. Mol Ther. May 1, 2016;24(S1):S 156. Abstract.
Madden et al., "Applications of network BLAST server," Meth. Enzymol. 266, pp. 131-141 (1996).
Mak et al., "TAL effectors: function, structure, engineering and applications," Curr. Opin. Struct. Biol. 23, pp. 93-99 (2013).
Mali et al., "Cas9 as a versatile tool for engineering biology," Nat. Methods 10, pp. 957-963 (2013).
Mao et al., "Comparison of nonhomologous end joining and homologous recombination in human cells," DNA Repair 7(10), pp. 1765-1771 (2008). Author's manuscript.
Martin et al., "Gene delivery to the eye using adeno-associated viral vectors," Methods 28, pp. 267-275 (2002).
Mastorakos et al., "Hydroxyl PAMAM dendrimer-based gene vectors for transgene delivery to human retinal pigment epithelial cells," Nanoscale 7(9), pp. 3845-3856 (2015).

(56) References Cited

OTHER PUBLICATIONS

McCall et al., "Pathogen-inspired drug delivery to the central nervous system," Tissue Barriers. 2(4), e944449; 12 pages. (2014).
McCarty et al., "Self-complementary recombinant adeno-associated virus (scAAV) vectors promote efficient transduction independently of DNA synthesis," Gene Ther. 8, pp. 1248-1254 (2001).
Mishra et al., "Recent applications of liposomes in ophthalmic drug delivery," J. Drug Deliv. 2011, pp. 1-14 (2011).
Morgan et al., "Genetic Modification of T Cells," Biomedicines 4, pp. 1-14 (2016).
Papapetrou et al., "Gene Insertion Into Genomic Safe Harbors for Human Gene Therapy," Molecular Therapy 24(4), pp. 678-684 (2016).
Pham et al., "Generation of CAR-T Cells Lacking T Cell Receptor and Human Leukocyte Antigen Using Engineered Meganucleases" Molecular Therapy, 24(suppl. 1), p. S78 (2016).
Poirot et al., "Multiplex Genome-Edited T-cell Manufacturing Platform for "Off-the-Shelf" Adoptive T-cell Immunotherapies," Cancer Research, 75(18), pp. 3853-3864 (2015).
Qasim et al., "First Clinical Applicatoin of Talen Engineered Universal CAR19 T Cells in B-ALL," Blood 126(2046), pp. 1-3 (2015). Abstract only.
Qian et al., "Improved brain uptake of peptide-based CNS drugs via alternative routes of administrations of its nanocarrier delivery systems: a promising strategy for CNS targeting delivery of peptides," Expert Opin. Drug Metab. Toxicol. 10(11), (2014) 1491-1508.
Ran et al., "Genome engineering using the CRISPR-Cas9 system," Nat. Protoc. 8, pp. 2281-2308 (2013).
Reyon et al., "FLASH assembly of TALENs for high-throughput genome editing," Nat Biotechnol. May 2012;30(5):460-5. doi: 10.1038/nbt.2170. Author manuscript.
Sather et al., "Efficient modification of CCR5 in primary human hematopoietic cells using a megaTAL nuclease and AAV donor template," Science Translation Medicine. 7(307), pp. 1-14 (2015).
Seligman et al., "Mutations altering the cleavage specificity of a homing endonuclease," Nucleic Acids Res. 30, pp. 3870-3879 (2002).
Sha et al., "Chimaeric antigen receptor T-cell therapy for tumour immunotherapy," Bioscience Reports 37, pp. 1-12 (2017).
Sharma et al., "Formulation and optimization of polymeric nanoparticles for intranasal delivery of lorazepam using Box-Behnken design: in vitro and in vivo evaluation," Biomed Res Int. 2014;2014:156010. doi: 10.1155/2014/156010. Epub Jul. 14, 2014.
Sharma et al., "Next generation delivery system for proteins and genes of therapeutic purpose: why and how?" Biomed Res Int. 2014;2014:327950. doi: 10.1155/2014/327950. Epub Jul. 15, 2014.
Simeoni et al., "Insight into the mechanism of the peptide-based gene delivery system MPG: implications for delivery of siRNA into mammalian cells," Nucleic Acids Res. 31, pp. 2717-2724 (2003).
Sowa et al., "In vitro and in vivo testing of a novel regulatory system for gene therapy for intervertebral disc degeneration," Spine, 36(10), pp. E623-E628 (2011).
Spear et al., "Strategies to genetically engineer T cells for cancer immunotherapy," Cancer Immunol Immunother. Jun. 2016;65(6):631-49. doi: 10.1007/s00262-016-1842-5. Epub May 2, 2016. Author manuscript.
Stoddard, "Homing endonuclease structure and function," Q. Rev. Biophys. 47 pages. (2005).
Sussman et al., "Isolation and characterization of new homing endonuclease specificities at individual target site positions," J. Mol. Biol. 342, pp. 31-41 (2004).
Thomsen et al., "Promoter-regulatory region of the major immediate early gene of human cytomegalovirus," Proc. Natl. Acad. Sci. USA 81(3), pp. 659-663 (1984).
Tong et al., "Eye drop delivery of nano-polymeric micelle formulated genes with cornea-specific promoters," J. Gene Med. 9(11), pp. 956-966 (2007).
Torikai et al., "A foundation for universal T-cell based immunotherapy: T cells engineered to express a CD19-specific chimeric-antigen-receptor and eliminate expression of endogenous TCR," Blood 119(24), pp. 5697-5705 (2012).
Vannucci et al., "Viral vectors: a look back and ahead on gene transfer technology," New Microbiol. 36, pp. 1-22 (2013).
Yoshikai et al., "Organization and sequences of the variable joining and constant region genes of the human t cell receptor alpha-chain," Nature, 316(6031), pp. 837-840 (1985).
Yuasa et al., "Adeno-associated virus vector-mediated gene transfer into dystrophin-deficient skeletal muscles evokes enhanced immune response against the transgene product," Gene Ther. 9, pp. 1576-1588 (2002).
Zhang et al., "A greedy algorithm for aligning DNA sequences," J. Comput. Biol. 7(1-2), pp. 203-214(2000).
Zhang et al., "Engineering CAR-T cells," Biomarker Research 5(22), pp. 1-6 (2017).
Zuris et al., "Efficient Delivery of Genome-Editing Proteins In Vitro and In Vivo," Nat. Biotechnol. 33, pp. 73-80 (2015). Author's manuscript. Published online Oct. 30, 2014. doi: 10.1038/nbt.3081.

* cited by examiner

A.
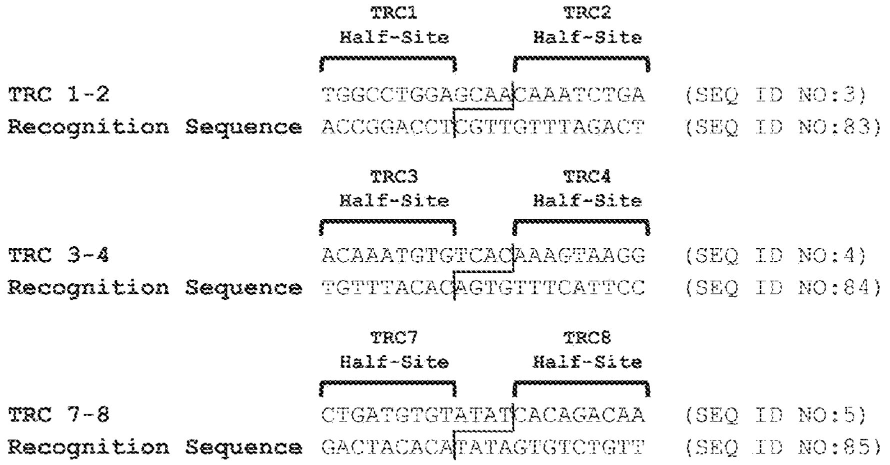
B.
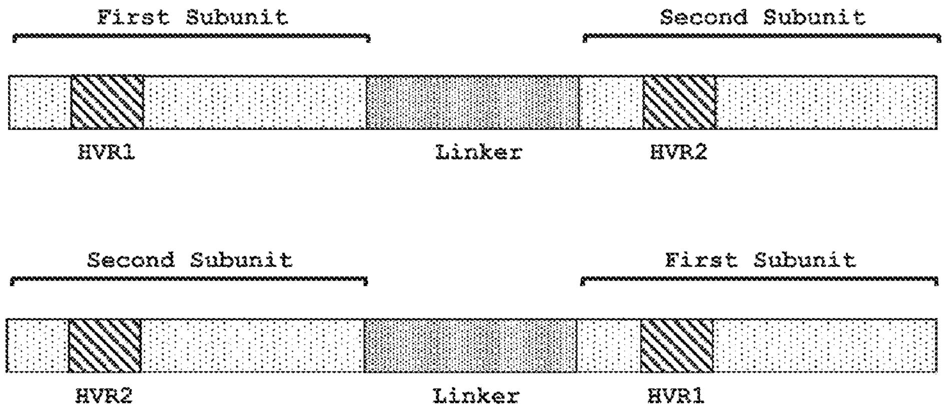
FIGURE 1

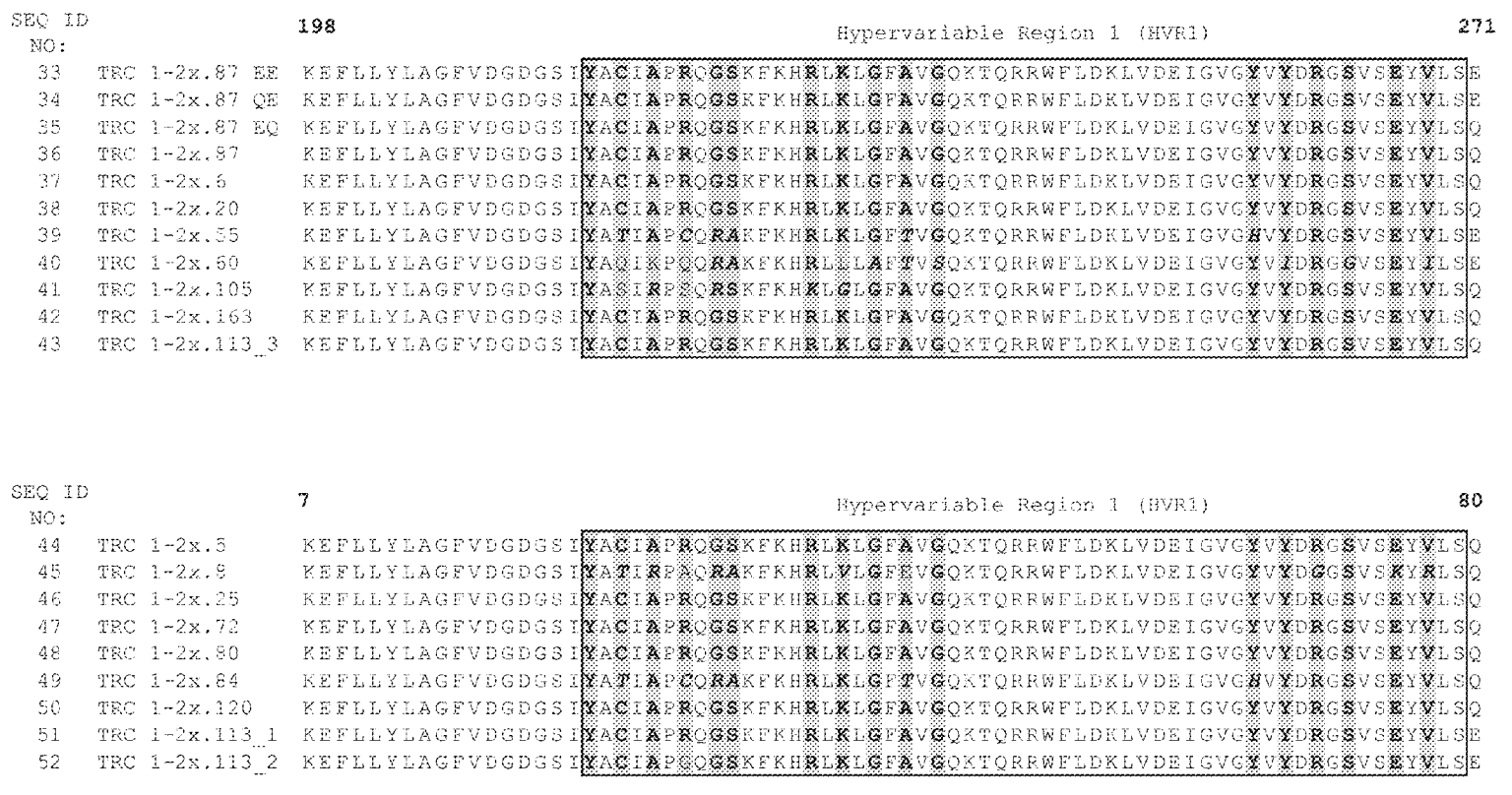

| SEQ ID NO: | | 198 — Hypervariable Region 1 (HVR1) — 271 |
|---|---|---|
| 33 | TRC 1-2x.87 EE | KEFLLYLAGFVDGDGSIYACIAPRQGSKFKHRLKLGFAVGQKTQRRWFLDKLVDEIGVGYVYDRGSVSEYVLSE |
| 34 | TRC 1-2x.87 QE | KEFLLYLAGFVDGDGSIYACIAPRQGSKFKHRLKLGFAVGQKTQRRWFLDKLVDEIGVGYVYDRGSVSEYVLSE |
| 35 | TRC 1-2x.87 EQ | KEFLLYLAGFVDGDGSIYACIAPRQGSKFKHRLKLGFAVGQKTQRRWFLDKLVDEIGVGYVYDRGSVSEYVLSQ |
| 36 | TRC 1-2x.87 | KEFLLYLAGFVDGDGSIYACIAPRQGSKFKHRLKLGFAVGQKTQRRWFLDKLVDEIGVGYVYDRGSVSEYVLSQ |
| 37 | TRC 1-2x.6 | KEFLLYLAGFVDGDGSIYACIAPRQGSKFKHRLKLGFAVGQKTQRRWFLDKLVDEIGVGYVYDRGSVSEYVLSQ |
| 38 | TRC 1-2x.20 | KEFLLYLAGFVDGDGSIYACIAPRQGSKFKHRLKLGFAVGQKTQRRWFLDKLVDEIGVGYVYDRGSVSEYVLSQ |
| 39 | TRC 1-2x.55 | KEFLLYLAGFVDGDGSIYATIAPCQRAKFKHRLKLGFTVGQKTQRRWFLDKLVDEIGVGHVYDRGSVSEYVLSE |
| 40 | TRC 1-2x.60 | KEFLLYLAGFVDGDGSIYAQIKPQQRAKFKHRLLLAFTVSQKTQRRWFLDKLVDEIGVGYVIDRGGVSEYILSE |
| 41 | TRC 1-2x.105 | KEFLLYLAGFVDGDGSIYASIRPSQRSKFKHKLGLGFAVGQKTQRRWFLDKLVDEIGVGYVYDRGSVSEYVLSQ |
| 42 | TRC 1-2x.163 | KEFLLYLAGFVDGDGSIYACIAPRQGSKFKHRLKLGFAVGQKTQRRWFLDKLVDEIGVGYVYDRGSVSEYVLSQ |
| 43 | TRC 1-2x.113_3 | KEFLLYLAGFVDGDGSIYACIAPRQGSKFKHRLKLGFAVGQKTQRRWFLDKLVDEIGVGYVYDRGSVSEYVLSQ |

| SEQ ID NO: | | 7 — Hypervariable Region 1 (HVR1) — 80 |
|---|---|---|
| 44 | TRC 1-2x.5 | KEFLLYLAGFVDGDGSIYACIAPRQGSKFKHRLKLGFAVGQKTQRRWFLDKLVDEIGVGYVYDRGSVSEYVLSQ |
| 45 | TRC 1-2x.9 | KEFLLYLAGFVDGDGSIYATIRPAQRAKFKHRLVLGFEVGQKTQRRWFLDKLVDEIGVGYVYDGGSVSKYRLSQ |
| 46 | TRC 1-2x.25 | KEFLLYLAGFVDGDGSIYACIAPRQGSKFKHRLKLGFAVGQKTQRRWFLDKLVDEIGVGYVYDRGSVSEYVLSQ |
| 47 | TRC 1-2x.72 | KEFLLYLAGFVDGDGSIYACIAPRQGSKFKHRLKLGFAVGQKTQRRWFLDKLVDEIGVGYVYDRGSVSEYVLSQ |
| 48 | TRC 1-2x.80 | KEFLLYLAGFVDGDGSIYACIAPRQGSKFKHRLKLGFAVGQKTQRRWFLDKLVDEIGVGYVYDRGSVSEYVLSQ |
| 49 | TRC 1-2x.84 | KEFLLYLAGFVDGDGSIYATIAPCQRAKFKHRLKLGFTVGQKTQRRWFLDKLVDEIGVGHVYDRGSVSEYVLSQ |
| 50 | TRC 1-2x.120 | KEFLLYLAGFVDGDGSIYACIAPRQGSKFKHRLKLGFAVGQKTQRRWFLDKLVDEIGVGYVYDRGSVSEYVLSQ |
| 51 | TRC 1-2x.113_1 | KEFLLYLAGFVDGDGSIYACIAPRQGSKFKHRLKLGFAVGQKTQRRWFLDKLVDEIGVGYVYDRGSVSEYVLSE |
| 52 | TRC 1-2x.113_2 | KEFLLYLAGFVDGDGSIYACIAPGQGSKFKHRLKLGFAVGQKTQRRWFLDKLVDEIGVGYVYDRGSVSEYVLSE |

FIGURE 2A

| | 272 … 344 |
|---|---|
| TRC 1-2x.87 EE | IKPLHNFLTQLQPFLKLKQKQANLVLKIIEQLPSAKESPDKFLEVCTWVDQIAALNDSKTRKTTSETVRAVLD |
| TRC 1-2x.87 QE | IKPLHNFLTQLQPFLKLKQKQANLVLKIIEQLPSAKESPDKFLEVCTWVDQIAALNDSKTRKTTSETVRAVLD |
| TRC 1-2x.87 EQ | IKPLHNFLTQLQPFLKLKQKQANLVLKIIEQLPSAKESPDKFLEVCTWVDQIAALNDSKTRKTTSETVRAVLD |
| TRC 1-2x.87 | IKPLHNFLTQLQPFLKLKQKQANLVLKIIEQLPSAKESPDKFLEVCTWVDQIAALNDSKTRKTTSETVRAVLD |
| TRC 1-2x.6 | IKPLHNFLTQLQPFLKLKQKQANLVLKIIEQLPSAKESPDKFLEVCTWVDQIAALNDSKTRKTTSETVRAVLD |
| TRC 1-2x.20 | IKPLHNFLTQLQPFLKLKQKQANLVLKIIEQLPSAKESPDKFLEVCTWVDQIAALNDSKTRKTTSETVRAVLD |
| TRC 1-2x.55 | IKPLHNFLTQLQPFLKLKQKQANLVLKIIEQLPSAKESPDKFLEVCTWVDQIAALNDSKTRKTTSETVRAVLD |
| TRC 1-2x.60 | IKPLHNFLTQLQPFLKLKQKQANLVLKIIEQLPSAKESPDKFLEVCTWVDQIAALNDSKTRKTTSETVRAVLD |
| TRC 1-2x.105 | IKPLHNFLTQLQPFLKLKQKQANLVLKIIEQLPSAKESPDKFLEVCTWVDQIAALNDSKTRKTTSETVRAVLD |
| TRC 1-2x.163 | IKPLHNFLTQLQPFLKLKQKQANLVLKIIEQLPSAKESPDKFLEVCTWVDQIAALNDSKTRKTTSETVRAVLD |
| TRC 1-2x.113_3 | IKPLHNFLTQLQPFLKLKQKQANLVLKIIEQLPSAKESPDKFLEVCTWVDQIAALNDSKTRKTTSETVRAVLD |

| | 81 … 153 |
|---|---|
| TRC 1-2x.5 | IKPLHNFLTQLQPFLKLKQKQANLVLKIIEQLPSAKESPDKFLEVCTWVDQIAALNDSKTRKTTSETVRAVLD |
| TRC 1-2x.8 | IKPLHNFLTQLQPFLKLKQKQANLVLKIIEQLPSAKESPDKFLEVCTWVDQIAALNDSKTRKTTSETVRAVLD |
| TRC 1-2x.25 | IKPLHNFLTQLQPFLKLKQKQANLVLKIIEQLPSAKESPDKFLEVCTWVDQIAALNDSKTRKTTSETVRAVLD |
| TRC 1-2x.72 | IKPLHNFLTQLQPFLKLKQKQANLVLKIIEQLPSAKESPDKFLEVCTWVDQIAALNDSKTRKTTSETVRAVLD |
| TRC 1-2x.80 | IKPLHNFLTQLQPFLKLKQKQANLVLKIIEQLPSAKESPDKFLEVCTWVDQIAALNDSKTRKTTSETVRAVLD |
| TRC 1-2x.84 | IKPLHNFLTQLQPFLKLKQKQANLVLKIIEQLPSAKESPDKFLEVCTWVDQIAALNDSKTRKTTSETVRAVLD |
| TRC 1-2x.120 | IKPLHNFLTQLQPFLKLKQKQANLVLKIIEQLPSAKESPDKFLEVCTWVDQIAALNDSKTRKTTSETVRAVLD |
| TRC 1-2x.113_1 | IKPLHNFLTQLQPFLKLKQKQANLVLKIIEQLPSAKESPDKFLEVCTWVDQIAALNDSKTRKTTSETVRAVLD |
| TRC 1-2x.113_2 | IKPLHNFLTQLQPFLKLKQKQANLVLKIIEQLPSAKESPDKFLEVCTWVDQIAALNDSKTRKTTSETVRAVLD |

FIGURE 2B

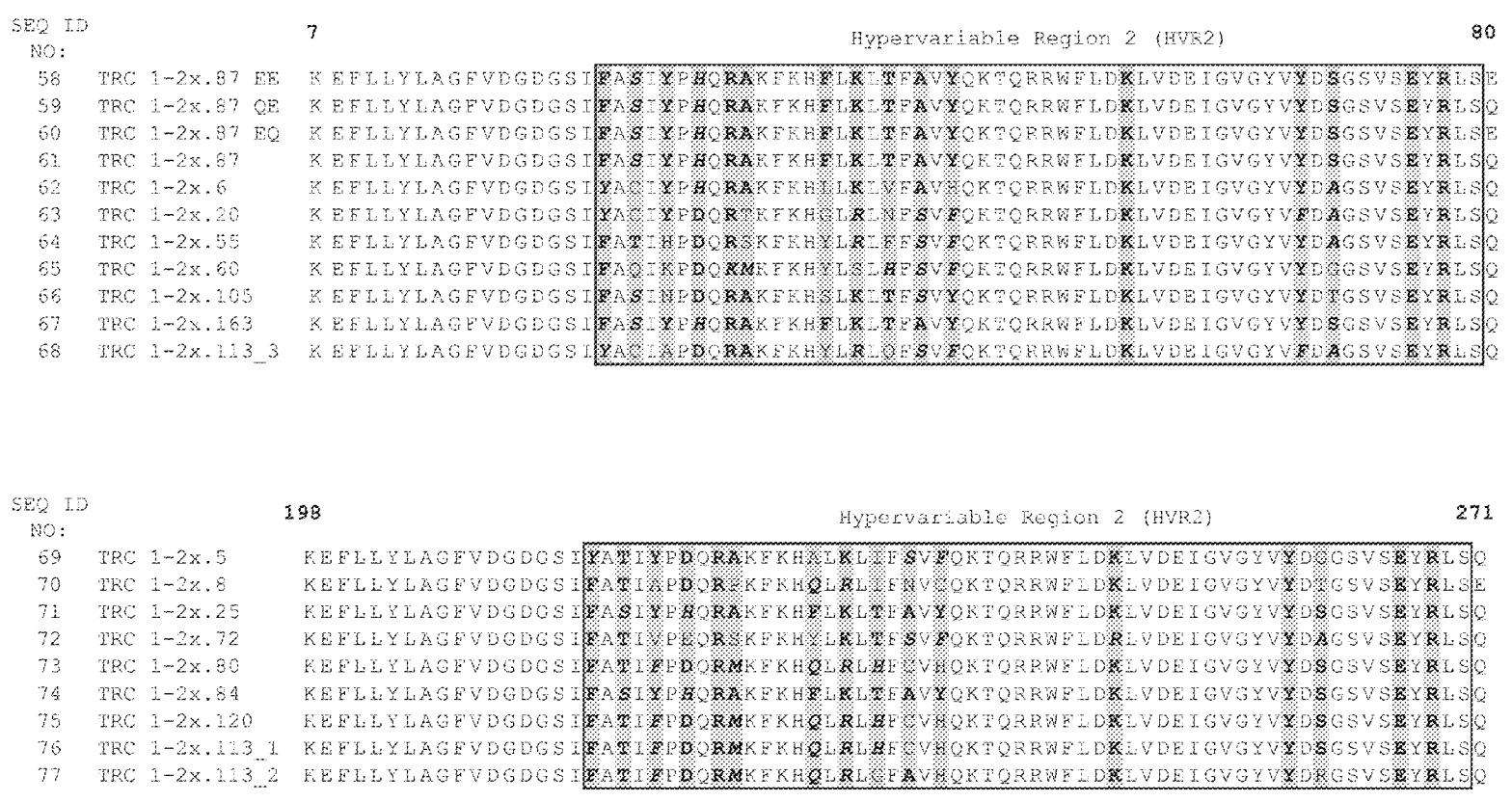

| SEQ ID NO: | | 7 | Hypervariable Region 2 (HVR2) 80 |
|---|---|---|---|
| 58 | TRC 1-2x.87 EE | KEFLLYLAGFVDGDGSI | FASIYPHQRAKFKHFLKLTFAVYQKTQRRWFLDKLVDEIGVGYVYDSGSVSEYRLSE |
| 59 | TRC 1-2x.87 QE | KEFLLYLAGFVDGDGSI | FASIYPHQRAKFKHFLKLTFAVYQKTQRRWFLDKLVDEIGVGYVYDSGSVSEYRLSQ |
| 60 | TRC 1-2x.87 EQ | KEFLLYLAGFVDGDGSI | FASIYPHQRAKFKHFLKLTFAVYQKTQRRWFLDKLVDEIGVGYVYDSGSVSEYRLSE |
| 61 | TRC 1-2x.87 | KEFLLYLAGFVDGDGSI | FASIYPHQRAKFKHFLKLTFAVYQKTQRRWFLDKLVDEIGVGYVYDSGSVSEYRLSQ |
| 62 | TRC 1-2x.6 | KEFLLYLAGFVDGDGSI | YACIYPHQRAKFKHLLKLVFAVHQKTQRRWFLDKLVDEIGVGYVYDAGSVSEYRLSQ |
| 63 | TRC 1-2x.20 | KEFLLYLAGFVDGDGSI | YACIYPDQRTKFKHGLRLNFSVFQKTQRRWFLDKLVDEIGVGYVFDAGSVSEYRLSQ |
| 64 | TRC 1-2x.55 | KEFLLYLAGFVDGDGSI | FATIHPDQRSKFKHYLRLFFSVFQKTQRRWFLDKLVDEIGVGYVYDAGSVSEYRLSQ |
| 65 | TRC 1-2x.60 | KEFLLYLAGFVDGDGSI | FAQIKPDQKMKFKHYLSLHFSVFQKTQRRWFLDKLVDEIGVGYVYDGGSVSEYRLSQ |
| 66 | TRC 1-2x.105 | KEFLLYLAGFVDGDGSI | FASINPDQRAKFKHSLKLTFSVYQKTQRRWFLDKLVDEIGVGYVYDTGSVSEYRLSQ |
| 67 | TRC 1-2x.163 | KEFLLYLAGFVDGDGSI | FASIYPHQRAKFKHFLKLTFAVYQKTQRRWFLDKLVDEIGVGYVYDSGSVSEYRLSQ |
| 68 | TRC 1-2x.113_3 | KEFLLYLAGFVDGDGSI | YACIAPDQRAKFKHYLRLQFSVFQKTQRRWFLDKLVDEIGVGYVFDAGSVSEYRLSQ |

| SEQ ID NO: | | 198 | Hypervariable Region 2 (HVR2) 271 |
|---|---|---|---|
| 69 | TRC 1-2x.5 | KEFLLYLAGFVDGDGSI | YATIYPDQRAKFKHALKLIFSVFQKTQRRWFLDKLVDEIGVGYVYDGGSVSEYRLSQ |
| 70 | TRC 1-2x.8 | KEFLLYLAGFVDGDGSI | FATIAPDQRFKFKHQLRLIFNVCQKTQRRWFLDKLVDEIGVGYVYDTGSVSEYRLSE |
| 71 | TRC 1-2x.25 | KEFLLYLAGFVDGDGSI | FASIYPHQRAKFKHFLKLTFAVYQKTQRRWFLDKLVDEIGVGYVYDSGSVSEYRLSQ |
| 72 | TRC 1-2x.72 | KEFLLYLAGFVDGDGSI | FATIVPEQRSKFKHYLKLTFSVFQKTQRRWFLDRLVDEIGVGYVYDAGSVSEYRLSQ |
| 73 | TRC 1-2x.80 | KEFLLYLAGFVDGDGSI | FATIFPDQRMKFKHQLRLHFCVHQKTQRRWFLDKLVDEIGVGYVYDSGSVSEYRLSQ |
| 74 | TRC 1-2x.84 | KEFLLYLAGFVDGDGSI | FASIYPHQRAKFKHFLKLTFAVYQKTQRRWFLDKLVDEIGVGYVYDSGSVSEYRLSQ |
| 75 | TRC 1-2x.120 | KEFLLYLAGFVDGDGSI | FATIFPDQRMKFKHQLRLHFCVHQKTQRRWFLDKLVDEIGVGYVYDSGSVSEYRLSQ |
| 76 | TRC 1-2x.113_1 | KEFLLYLAGFVDGDGSI | FATIFPDQRMKFKHQLRLHFCVHQKTQRRWFLDKLVDEIGVGYVYDSGSVSEYRLSQ |
| 77 | TRC 1-2x.113_2 | KEFLLYLAGFVDGDGSI | FATIFPDQRMKFKHQLRLGFAVHQKTQRRWFLDKLVDEIGVGYVYDRGSVSEYRLSQ |

FIGURE 3A

```
                  81                                                                        153
TRC 1-2x.87 EE    IKPLHNFLTQLQPFFLKLKQKQANLVLKIIEQLPSAKESPDKFLEVCTWVDQIAALNDSKTRKTTSETVRAVLD
TRC 1-2x.87 QE    IKPLHNFLTQLQPFFLKLKQKQANLVLKIIEQLPSAKESPDKFLEVCTWVDQIAALNDSKTRKTTSETVRAVLD
TRC 1-2x.87 EQ    IKPLHNFLTQLQPFFLKLKQKQANLVLKIIEQLPSAKESPDKFLEVCTWVDQIAALNDSKTRKTTSETVRAVLD
TRC 1-2x.87       IKPLHNFLTQLQPFFLKLKQKQANLVLKIIEQLPSAKESPDKFLEVCTWVDQIAALNDSKTRKTTSETVRAVLD
TRC 1-2x.6        IKPLHNFLTQLQPFFLKLKQKQANLVLKIIEQLPSAKESPDKFLEVCTWVDQIAALNDSKTRKTTSETVRAVLD
TRC 1-2x.20       IKPLHNFLTQLQPFFLKLKQKQANLVLKIIEQLPSAKESPDKFLEVCTWVDQIAALNDSKTRKTTSETVRAVLD
TRC 1-2x.55       IKPLHNFLTQLQPFFLKLKQKQANLVLKIIEQLPSAKESPDKFLEVCTWVDQIAALNDSKTRKTTSETVRAVLD
TRC 1-2x.60       IKPLHNFLTQLQPFFLKLKQKQANLVLKIIEQLPSAKESPDKFLEVCTWVDQIAALNDSKTRKTTSETVRAVLD
TRC 1-2x.105      IKPLHNFLTQLQPFFLKLKQKQANLVLKIIEQLPSAKESPDKFLEVCTWVDQIAALNDSKTRKTTSETVRAVLD
TRC 1-2x.163      IKPLHNFLTQLQPFFLKLKQKQANLVLKIIEQLPSAKESPDKFLEVCTWVDQIAALNDSKTRKTTSETVRAVLD
TRC 1-2x.113_3    IKPLHNFLTQLQPFFLKLKQKQANLVLKIIEQLPSAKESPDKFLEVCTWVDQIAALNDSKTRKTTSETVRAVLD

                  272                                                                       344
TRC 1-2x.5        IKPLHNFLTQLQPFFLKLKQKQANLVLKIIEQLPSAKESPDKFLEVCTWVDQIAALNDSKTRKTTSETVRAVLD
TRC 1-2x.8        IKPLHNFLTQLQPFFLKLKQKQANLVLKIIEQLPSAKESPDKFLEVCTWVDQIAALNDSKTRKTTSETVRAVLD
TRC 1-2x.25       IKPLHNFLTQLQPFFLKLKQKQANLVLKIIEQLPSAKESPDKFLEVCTWVDQIAALNDSKTRKTTSETVRAVLD
TRC 1-2x.72       IKPLHNFLTQLQPFFLKLKQKQANLVLKIIEQLPSAKESPDKFLEVCTWVDQIAALNDSKTRKTTSETVRAVLD
TRC 1-2x.80       IKPLHNFLTQLQPFFLKLKQKQANLVLKIIEQLPSAKESPDKFLEVCTWVDQIAALNDSKTRKTTSETVRAVLD
TRC 1-2x.84       IKPLHNFLTQLQPFFLKLKQKQANLVLKIIEQLPSAKESPDKFLEVCTWVDQIAALNDSKTRKTTSETVRAVLD
TRC 1-2x.120      IKPLHNFLTQLQPFFLKLKQKQANLVLKIIEQLPSAKESPDKFLEVCTWVDQIAALNDSKTRKTTSETVRAVLD
TRC 1-2x.113_1    IKPLHNFLTQLQPFFLKLKQKQANLVLKIIEQLPSAKESPDKFLEVCTWVDQIAALNDSKTRKTTSETVRAVLD
TRC 1-2x.113_2    IKPLHNFLTQLQPFFLKLKQKQANLVLKIIEQLPSAKESPDKFLEVCTWVDQIAALNDSKTRKTTSETVRAVLD
```

FIGURE 3B

| SEQ ID NO: | | 7 … Hypervariable Region 1 (HVR1) … 80 |
|---|---|---|
| 53 | TRC 3-4x.3 | KEFLLYLAGFVDGDGSIYATICPCQTLKFKHYLTLSFSVYQKTQRRWFLDKLVDEIGVGYVYDQGSVSCYRLSQ |
| 54 | TRC 3-4x.19 | KEFLLYLAGFVDGDGSIYATICPDQALKFKHYLSLTFAVYQKTQRRWFLDKLVDEIGVGYVYDQGSVSCYRLSQ |

| | 81 … 153 |
|---|---|
| TRC 3-4x.3 | IKPLHNFLTQLQPFLKLKQKQANLVLKIIEQLPSAKESPDKFLEVCTWVDQIAALNDSKTRKTTSETVRAVLD |
| TRC 3-4x.19 | IKPLHNFLTQLQPFLKLKQKQANLVLKIIEQLPSAKESPDKFLEVCTWVDQIAALNDSKTRKTTSETVRAVLD |

FIGURE 4

| SEQ ID NO: | | 198 Hypervariable Region 2 (HVR2) 271 |
|---|---|---|
| 78 | TRC 3-4x.3 | KEFLLYLAGFVDGDGSIHACIQPQQDVKFKHQLHLRFTVHQKTQRRWFLDKLVDEIGVGYVYDAGSVSTYCLSQ |
| 79 | TRC 3-4x.19 | KEFLLYLAGFVDGDGSIHACIQPNQSMKFKHYLHLRFTVHQKTQRRWFLDKLVDETGVGYVYDAGSVSTYCLSQ |

| | 272 344 |
|---|---|
| TRC 3-4x.3 | IKPLHNFLTQLQPFLKLKQKQANLVLKIIEQLPSAKESPDKFLEVCTWVDQIAALNDSKTRKTTSETVRAVLD |
| TRC 3-4x.19 | IKPLHNFLTQLQPFLKLKQKQANLVLKIIEQLPSAKESPDKFLEVCTWVDQIAALNDSKTRKTTSETVRAVLD |

FIGURE 5

| SEQ ID NO: | | 7 | Hypervariable Region 1 (HVR1) | 80 |
|---|---|---|---|---|
| 55 | TRC 7-8x.7 | KEFLLYLAGFVDGDGSIYACITPQQDMKFKHRLQLRFCVTQKTQRRWFLDKLVDEIGVGYVQDCGSVSEYRLSE | | |

| SEQ ID NO: | | 198 | Hypervariable Region 1 (HVR1) | 271 |
|---|---|---|---|---|
| 56 | TRC 7-8x.9 | KEFLLYLAGFVDGDGSIYACITPQQDMKFKHRLQLRFCVTQKTQRRWFLDKLVDEIGVGYVQDHGCASEYRLSE | | |
| 57 | TRC 7-8x.14 | KEFLLYLAGFVDGDGSIYACITPQQDMKFKHRLQLRFCVTQKTQRRWFLDKLVDEIGVGYVQDKGSASEYRLSE | | |

FIGURE 6A

| | 81 | 153 |
|---|---|---|
| TRC 7-8x.7 | IKPLHNFLTQLQPFLKLKQKQANLVLKIIEQLPSAKESPDKFLEVCTWVDQIAALNDSKTRKTTSETVRAVLD | |

| | 272 | 344 |
|---|---|---|
| TRC 7-8x.9 | IKPLHNFLTQLQPFLKLKQKQANLVLKIIEQLPSAKESPDKFLEVCTWVDQIAALNDSKTRKTTSETVRAVLD | |
| TRC 7-8x.14 | IKPLHNFLTQLQPFLKLKQKQANLVLKIIEQLPSAKESPDKFLEVCTWVDQIAALNDSKTRKTTSETVRAVLD | |

FIGURE 6B

| SEQ ID NO: | | 198 — Hypervariable Region 2 (HVR2) — 271 |
|---|---|---|
| 80 | TRC 7-8x.7 | KEFLLYLAGFVDGDGSIVASIKPEQVAKFKHRLKLEFYVYQKTQRRWFLDKLVDEIGVGYVYDLGSASRYVLSQ |

| SEQ ID NO: | | 7 — Hypervariable Region 2 (HVR2) — 80 |
|---|---|---|
| 81 | TRC 7-8x.9 | KEFLLYLAGFVDGDGSITACIKPDQAAKFKHRLILEFTVCQKTQRRWFLDKLVDEIGVGYVVDQGSVSEYRLSQ |
| 82 | TRC 7-8x.14 | KEFLLYLAGFVDGDGSIWASIRPTQLAKFKHALNLGFAVYQKTQRRWFLDKLVDEIGVGYVYDSGSVSKYTLSE |

FIGURE 7A

```
              272                                                                       344
TRC 7-8x.7    IKPLHNFLTQLQPFLKLKQKQANLVLKIIEQLPSAKESPDKFLEVCTWVDQIAALNDSKTRKTTSETVRAVLD

              81                                                                        153
TRC 7-8x.9    IKPLHNFLTQLQPFLKLKQKQANLVLKIIEQLPSAKESPDKFLEVCTWVDQIAALNDSKTRKTTSETVRAVLD
TRC 7-8x.14   IKPLHNFLTQLQPFLKLKQKQANLVLKIIEQLPSAKESPDKFLEVCTWVDQIAALNDSKTRKTTSETVRAVLD
```

FIGURE 7B

A.
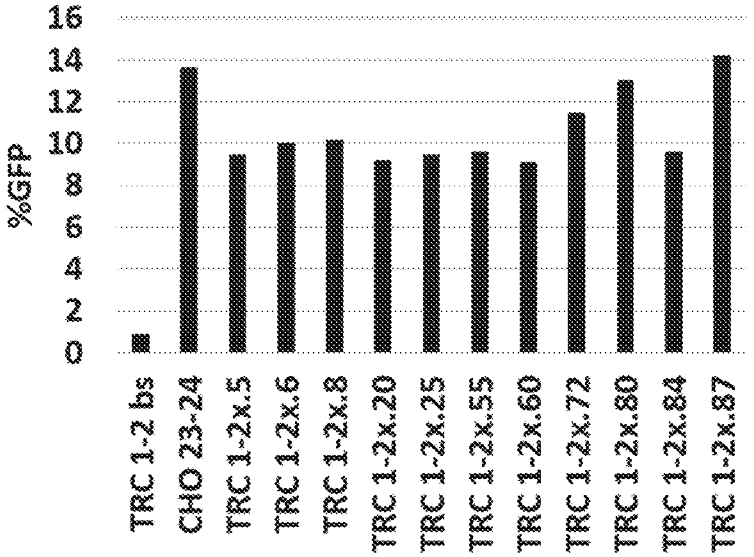
B.
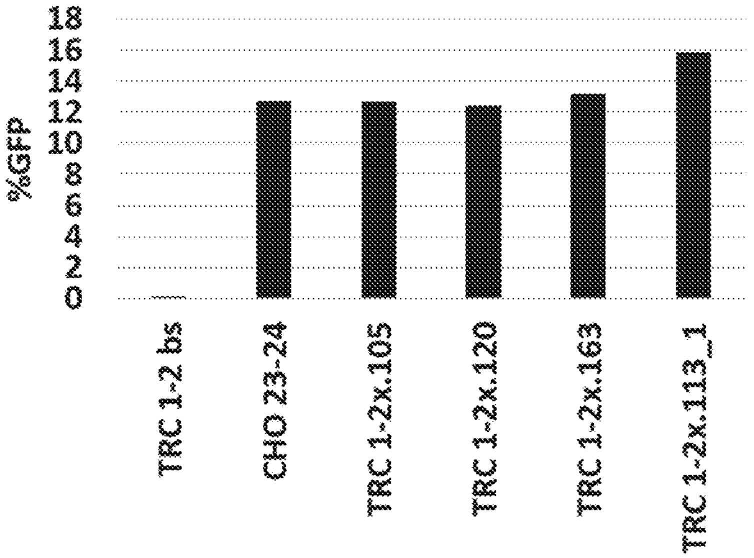
FIGURE 9

C.
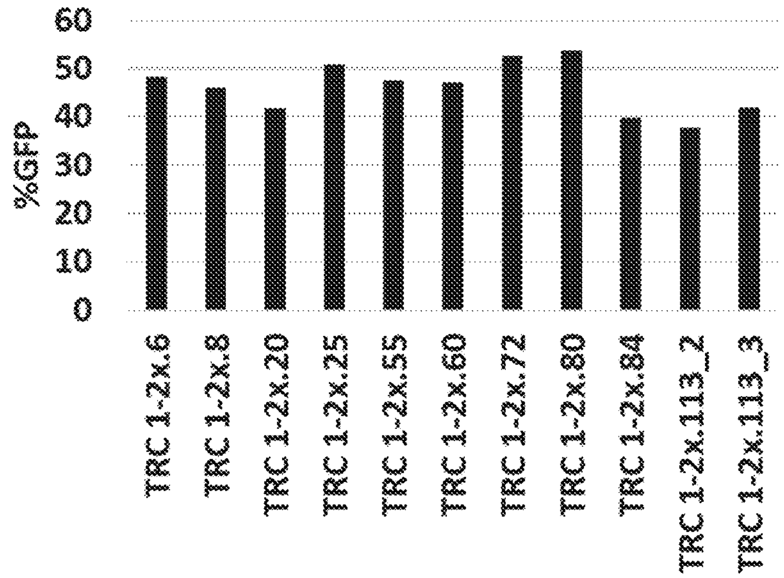
D.
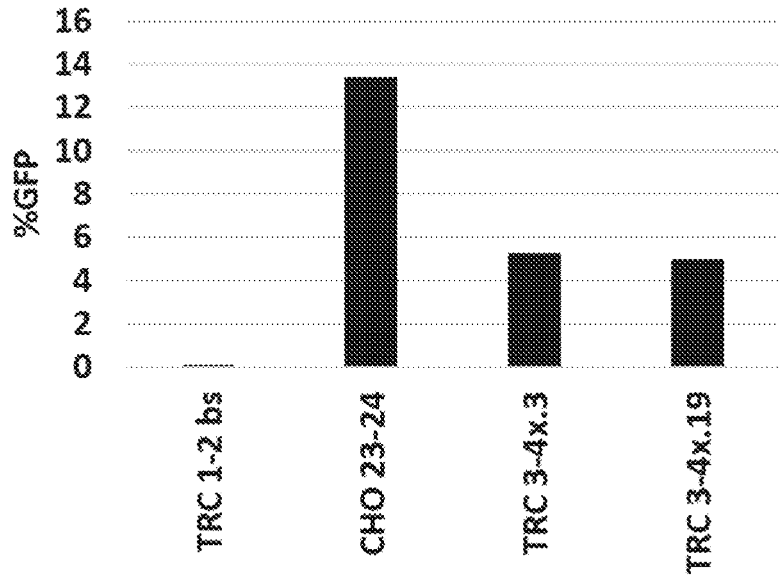
FIGURE 9 (cont.)

E.
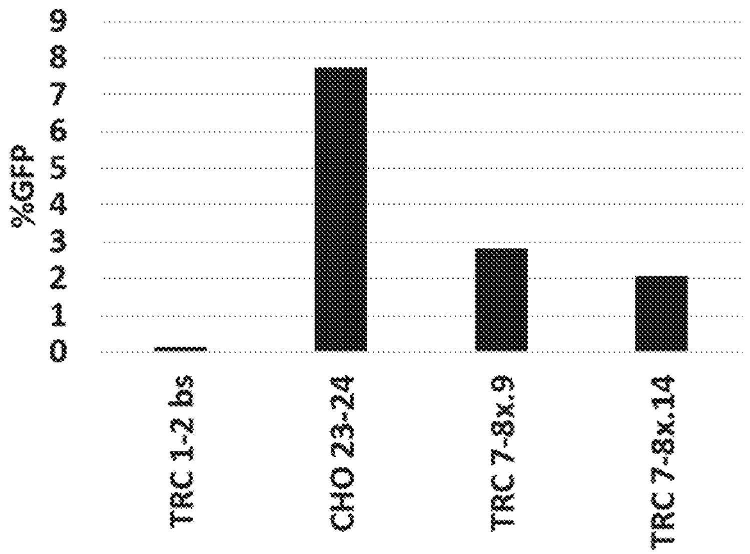
F.
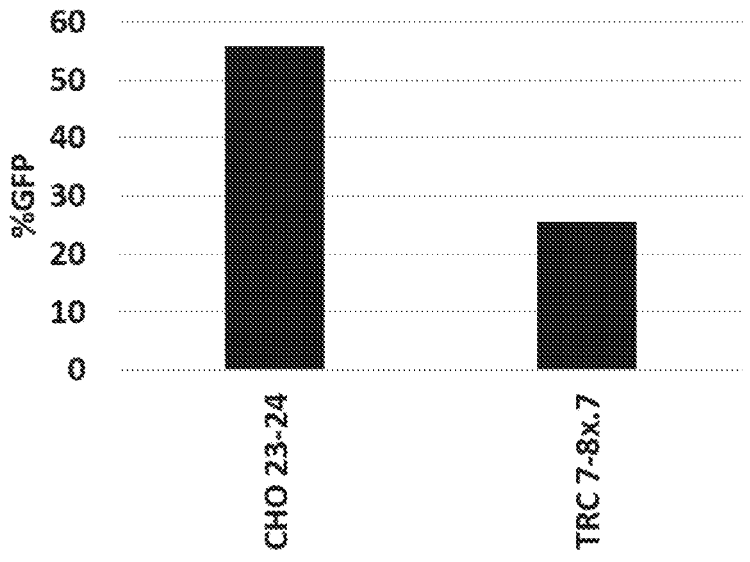
FIGURE 9 (cont.)

G.

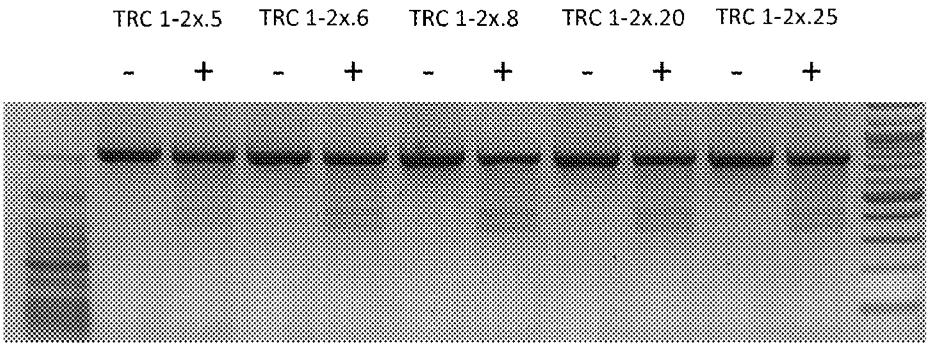
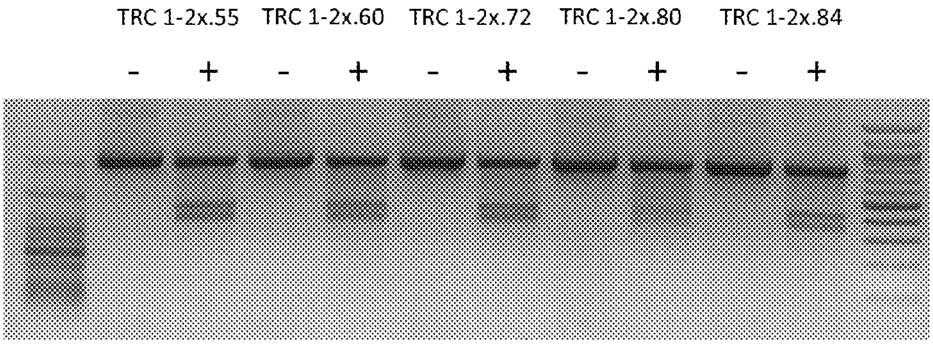
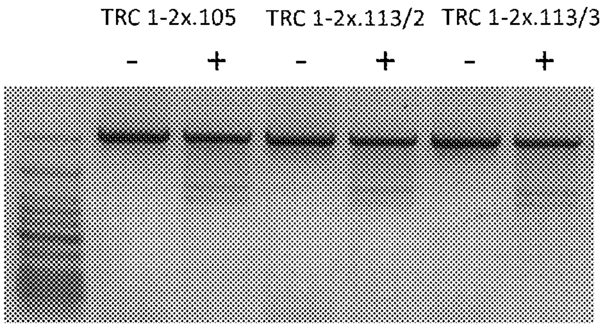
FIGURE 11

| SEQ ID NO: | | 162 … 233 |
|---|---|---|
| 86 | Wild-Type | ATGGACTTCAAGAGCAACAGTGCTG**TGGCCTGGAGCAACAAATCTGA**CTTTGCATGTGCAAACGCCTTCAAC |
| 87 | Indel | ATGGACTTCAAGAGCAACAGTGCTGTGGCCTGGAG---CAAATCTGACTTTGCATGTGCAAACGCCTTCAAC |
| 88 | Indel | ATGGACTTCAAGAGCAACA-----------------AACAAATCTGACTTTGCATGTGCAAACGCCTTCAAC |
| 89 | Indel | ATGGACTTCAAGAGCAACAGTGCTGTGGCCTGGAG-----AATCTGACTTTGCATGTGCAAACGCCTTCAAC |
| 90 | Indel | ATGGACTTCAAGAGCAACAGTGCTGTGGCCTGGAG-------TCTGACTTTGCATGTGCAAACGCCTTCAAC |
| 91 | Indel | ATGGACTTCAAGAGCAA--------------------ACAAATCTGACTTTGCATGTGCAAACGCCTTCAAC |
| 92 | Indel | ATGGACTTCAAGAGCAACAGTGCTGTGGCCTGGAG--ACAAATCTGACTTTGCATGTGCAAACGCCTTCAAC |
| 93 | Indel | ATGGACTTCAAGAGCAACAGTGCTGTGGCCTGGAGCAA----TCTGACTTTGCATGTGCAAACGCCTTCAAC |
| 94 | Indel | ATGGACTTCAAGAGCAACAGTGCTGTGGCCTGGAGCAACGCAACAAATCTGACTTTGCATGTGCAAACGCCTTCAAC |
| 95 | Indel | ATGGACTTCAAGAGCAACAGTGCTGTGGCCTGGAGCAAAGAACAAATCTGACTTTGCATGTGCAAACGCCTTCAAC |

FIGURE 14

| Sample | Nucleofection | Virus |
|---|---|---|
| 1 | Mock (Water) | 405 AAV |
| 2 | Mock (Water) | 406 AAV |
| 3 | Mock (Water) | Mock (Water) |
| 4 | TRC1-2x87EE | 405 AAV |
| 5 | TRC1-2x87EE | 406 AAV |
| 6 | TRC1-2x87EE | Mock (Water) |

A.
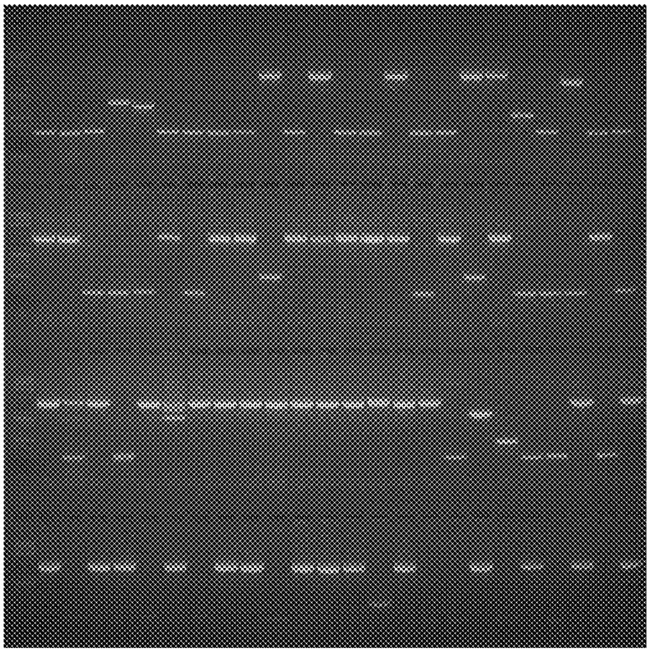
B.
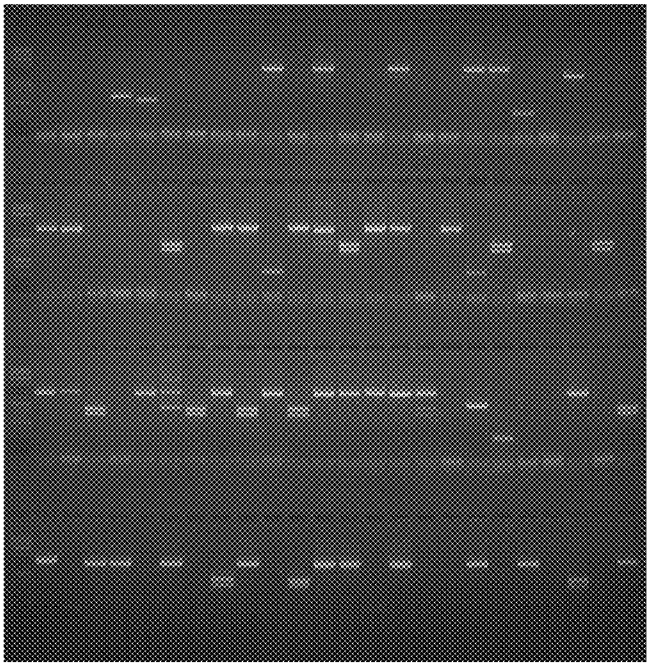
FIGURE 20

A.
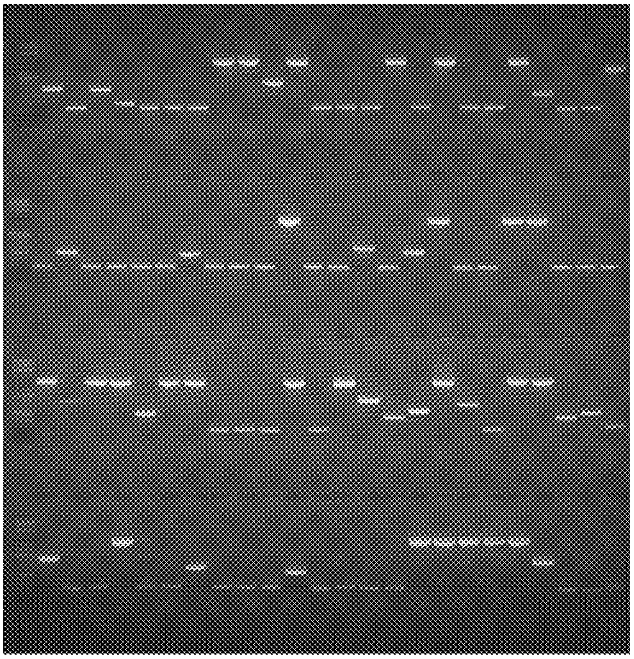
B.
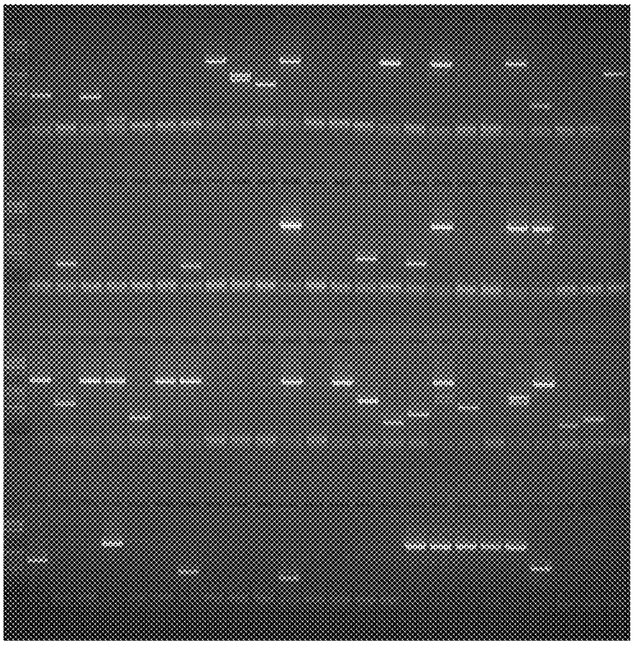
FIGURE 21

A.

```
SEQ ID
 NO:                    162                                                                        233
 92   Wild-Type         ATGGACTTCAAGAGCAACAGTGCTGTGGCCTGGAGCAACAAATCTGACTTTGCATGTGCAAACGCCTTCAAC
102   Indel             ATGGACTTCAAGAGCAACAGTGCTGTGGCCTGG--CAACAAATCTGACTTTGCATGTGCAAACGCCTTCAAC
103   Indel             ATGGACTTCAAGAGCAACAGTGCTGTGGC----------AAATCTGACTTTGCATGTGCAAACGCCTTCAAC
104   Indel             ATGGACTTCAAGAGCAACAGTGCTGTGGCCTGGA----CAAATCTGACTTTGCATGTGCAAACGCCTTCAAC
105   Indel             ATGGACTTCAAGAGCAACAGTGCTGTGGCCTGGAGCAA---ATCTGACTTTGCATGTGCAAACGCCTTCAAC
106   Indel             ATGGACTTCAAGAGCAACAGTGCTGTGGCCTGGAGCAA----------------TGTGCAAACGCCTTCAAC
107   Indel             ATGGACTTCAAGAGCAACAGTGCTGTGGCCTGGA---ACAAATCTGACTTTGCATGTGCAAACGCCTTCAAC
108   Indel             ATGGACTTCAAGAGCAACAGTGCTGTGGCCTGGAGCA-CAAATCTGACTTTGCATGTGCAAACGCCTTCAAC
109   Indel             ATGGACTTCAAGAGCAACAGTGCTGTGGCCTGGAGCAA----------------TGTGCAAACGCCTTCAAC
110   Indel             AT------------------------------------CAAATCTGACTTTGCATGTGCAAACGCCTTCAAC
```

B.

```
SEQ ID
 NO:                    181                                                            214
111   Wild-Type         GTGCTGTGGCCTGGAGCAA----------------------------CAAATCTGACTTTGC
112   Insertion         GTGCTGTGGCCTGGAGCAAGAATTCATGCGGCCGCAATCTAGAGCAACAAATCTGACTTTGC
```

*EagI Site*

FIGURE 22

A.
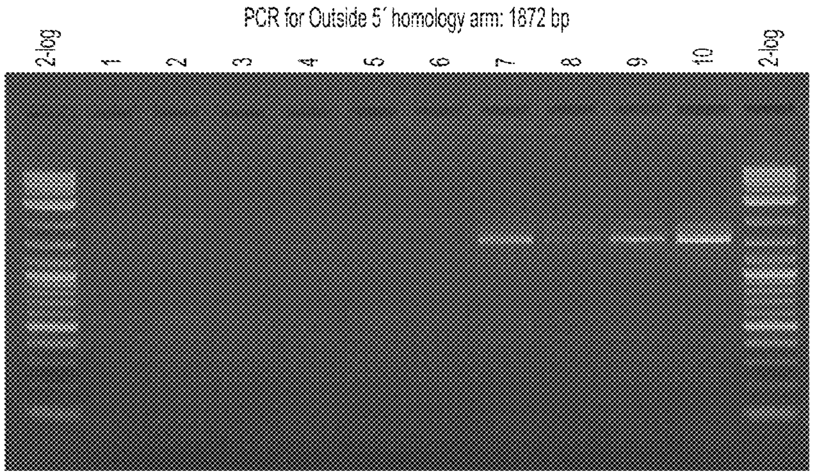
B.
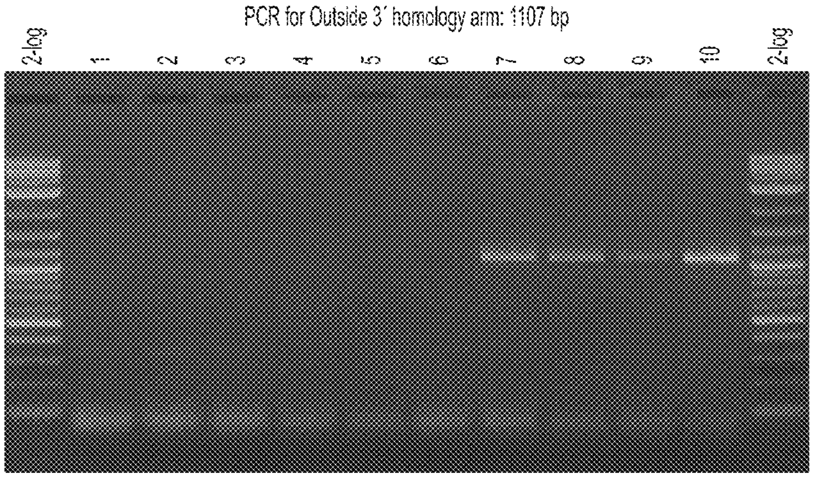
FIGURE 27

A.

B.

A.

B.

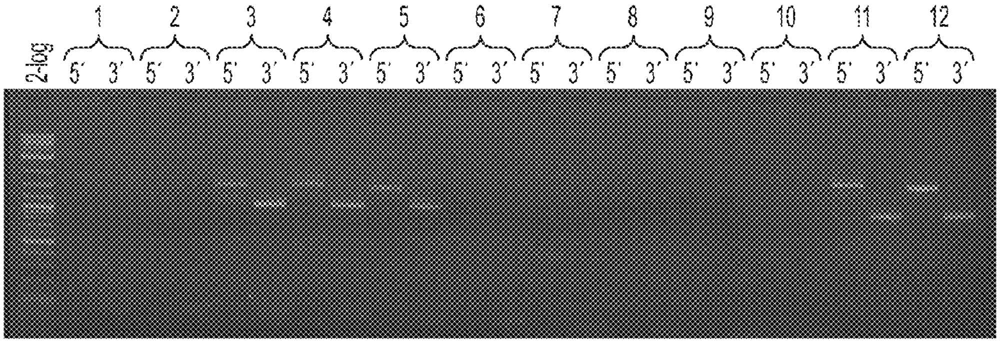
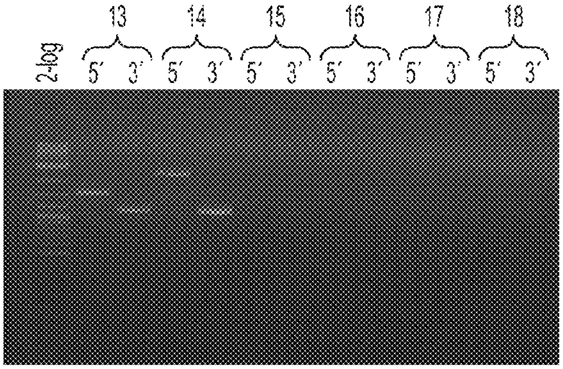
FIGURE 40

SEQUENCE LISTING

```
<160> NUMBER OF SEQ ID NOS: 125

<210> SEQ ID NO 1
<211> LENGTH: 4627
<212> TYPE: DNA
<213> ORGANISM: Homo sapiens

<400> SEQUENCE: 1

atatccagaa ccctgaccct gccgtgtacc agctgagaga ctctaaatcc agtgacaagt      60

ctgtctgcct attcaccgat tttgattctc aaacaaatgt gtcacaaagt aaggattctg     120

atgtgtatat cacagacaaa actgtgctag acatgaggtc tatggacttc aagagcaaca     180

gtgctgtggc ctggagcaac aaatctgact ttgcatgtgc aaacgccttc aacaacagca     240

ttattccaga agacaccttc ttccccagcc caggtaaggg cagctttggt gccttcgcag     300

gctgtttcct tgcttcagga atggccaggt tctgcccaga gctctggtca atgatgtcta     360

aaactcctct gattggtggt ctcggcctta tccattgcca ccaaaaccct ctttttacta     420

agaaacagtg agccttgttc tggcagtcca gagaatgaca cgggaaaaaa gcagatgaag     480
```

-continued

```
agaaggtggc aggagagggc acgtggccca gcctcagtct ctccaactga gttcctgcct    540
gcctgccttt gctcagactg tttgcccctt actgctcttc taggcctcat tctaagcccc    600
ttctccaagt tgcctctcct tatttctccc tgtctgccaa aaaatctttc ccagctcact    660
aagtcagtct cacgcagtca ctcattaacc caccaatcac tgattgtgcc ggcacatgaa    720
tgcaccaggt gttgaagtgg aggaattaaa aagtcagatg aggggtgtgc ccagaggaag    780
caccattcta gttgggggag cccatctgtc agctgggaaa agtccaaata acttcagatt    840
ggaatgtgtt ttaactcagg gttgagaaaa cagctacctt caggacaaaa gtcagggaag    900
ggctctctga agaaatgcta cttgaagata ccagccctac caagggcagg gagaggaccc    960
tatagaggcc tgggacagga gctcaatgag aaaggagaag agcagcaggc atgagttgaa   1020
tgaaggaggc agggccgggt cacagggcct tctaggccat gagagggtag acagtattct   1080
aaggacgcca gaaagctgtt gatcggcttc aagcagggga gggacaccta atttgctttt   1140
cttttttttt tttttttttt tttttttttt tgagatggag ttttgctctt gttgcccagg   1200
ctggagtgca atggtgcatc ttggctcact gcaacctccg cctcccaggt tcaagtgatt   1260
ctcctgcctc agcctcccga gtagctgaga ttacaggcac ccgccaccat gcctggctaa   1320
ttttttgtat ttttagtaga gacagggttt cactatgttg gccaggctgg tctcgaactc   1380
ctgacctcag gtgatccacc cgcttcagcc tcccaaagtg ctgggattac aggcgtgagc   1440
caccacaccc ggcctgcttt tcttaaagat caatctgagt gctgtacgga gagtgggttg   1500
taagccaaga gtagaagcag aaagggagca gttgcagcag agagatgatg gaggcctggg   1560
cagggtggtg gcagggaggt aaccaacacc attcaggttt caaaggtaga accatgcagg   1620
gatgagaaag caaagagggg atcaaggaag gcagctggat tttggcctga gcagctgagt   1680
caatgatagt gccgtttact aagaagaaac caaggaaaaa atttggggtg cagggatcaa   1740
aactttttgg aacatatgaa agtacgtgtt tatactcttt atggcccttg tcactatgta   1800
tgcctcgctg cctccattgg actctagaat gaagccaggc aagagcaggg tctatgtgtg   1860
atggcacatg tggccagggt catgcaacat gtactttgta caaacagtgt atattgagta   1920
aatagaaatg gtgtccagga gccgaggtat cggtcctgcc agggccaggg gctctcccta   1980
gcaggtgctc atatgctgta agttccctcc agatctctcc acaaggaggc atggaaaggc   2040
tgtagttgtt cacctgccca agaactagga ggtctggggt gggagagtca gcctgctctg   2100
gatgctgaaa gaatgtctgt tttttccttttt agaaagttcc tgtgatgtca agctggtcga   2160
gaaaagcttt gaaacaggta agacaggggt ctagcctggg tttgcacagg attgcggaag   2220
tgatgaaccc gcaataaccc tgcctggatg agggagtggg aagaaattag tagatgtggg   2280
aatgaatgat gaggaatgga aacagcggtt caagacctgc ccagagctgg gtggggtctc   2340
tcctgaatcc ctctcaccat ctctgacttt ccattctaag cactttgagg atgagtttct   2400
agcttcaata gaccaaggac tctctcctag gcctctgtat tcctttcaac agctccactg   2460
tcaagagagc cagagagagc ttctgggtgg cccagctgtg aaatttctga gtcccttagg   2520
gatagcccta aacgaaccag atcatcctga ggacagccaa gaggttttgc cttctttcaa   2580
gacaagcaac agtactcaca taggctgtgg gcaatggtcc tgtctctcaa gaatcccctg   2640
ccactcctca cacccaccct gggcccatat tcatttccat ttgagttgtt cttattgagt   2700
catccttcct gtggtagcgg aactcactaa ggggcccatc tggacccgag gtattgtgat   2760
gataaattct gagcacctac cccatcccca gaagggctca gaaataaaat aagagccaag   2820
tctagtcggt gtttcctgtc ttgaaacaca atactgttgg ccctggaaga atgcacagaa   2880
```

-continued

```
tctgtttgta aggggatatg cacagaagct gcaagggaca ggaggtgcag gagctgcagg   2940

cctcccccac ccagcctgct ctgccttggg gaaaaccgtg ggtgtgtcct gcaggccatg   3000

caggcctggg acatgcaagc ccataaccgc tgtggcctct tggttttaca gatacgaacc   3060

taaactttca aaacctgtca gtgattgggt tccgaatcct cctcctgaaa gtggccgggt   3120

ttaatctgct catgacgctg cggctgtggt ccagctgagg tgaggggcct tgaagctggg   3180

agtggggttt agggacgcgg gtctctgggt gcatcctaag ctctgagagc aaacctccct   3240

gcagggtctt gcttttaagt ccaaagcctg agcccaccaa actctcctac ttcttcctgt   3300

tacaaattcc tcttgtgcaa taataatggc ctgaaacgct gtaaaatatc ctcatttcag   3360

ccgcctcagt tgcacttctc ccctatgagg taggaagaac agttgtttag aaacgaagaa   3420

actgaggccc cacagctaat gagtggagga agagagacac ttgtgtacac cacatgcctt   3480

gtgttgtact tctctcaccg tgtaacctcc tcatgtcctc tctccccagt acggctctct   3540

tagctcagta gaaagaagac attacactca tattacaccc caatcctggc tagagtctcc   3600

gcaccctcct cccccagggt ccccagtcgt cttgctgaca actgcatcct gttccatcac   3660

catcaaaaaa aaactccagg ctgggtgcgg gggctcacac ctgtaatccc agcactttgg   3720

gaggcagagg caggaggagc acaggagctg gagaccagcc tgggcaacac agggagaccc   3780

cgcctctaca aaaagtgaaa aaattaacca ggtgtggtgc tgcacacctg tagtcccagc   3840

tacttaagag gctgagatgg gaggatcgct tgagccctgg aatgttgagg ctacaatgag   3900

ctgtgattgc gtcactgcac tccagcctgg aagacaaagc aagatcctgt ctcaaataat   3960

aaaaaaaata agaactccag ggtacatttg ctcctagaac tctaccacat agccccaaac   4020

agagccatca ccatcacatc cctaacagtc ctgggtcttc ctcagtgtcc agcctgactt   4080

ctgttcttcc tcattccaga tctgcaagat tgtaagacag cctgtgctcc ctcgctcctt   4140

cctctgcatt gcccctcttc tccctctcca aacagaggga actctcctac ccccaaggag   4200

gtgaaagctg ctaccacctc tgtgcccccc cggcaatgcc accaactgga tcctacccga   4260

atttatgatt aagattgctg aagagctgcc aaacactgct gccaccccct ctgttccctt   4320

attgctgctt gtcactgcct gacattcacg gcagaggcaa ggctgctgca gcctcccctg   4380

gctgtgcaca ttccctcctg ctccccagag actgcctccg ccatcccaca gatgatggat   4440

cttcagtggg ttctcttggg ctctaggtcc tgcagaatgt tgtgaggggt ttattttttt   4500

ttaatagtgt tcataaagaa atacatagta ttcttcttct caagacgtgg ggggaaatta   4560

tctcattatc gaggccctgc tatgctgtgt atctgggcgt gttgtatgtc ctgctgccga   4620

tgccttc                                                             4627
```

```
<210> SEQ ID NO 2
<211> LENGTH: 142
<212> TYPE: PRT
<213> ORGANISM: Homo sapiens

<400> SEQUENCE: 2

Pro Asn Ile Gln Asn Pro Asp Pro Ala Val Tyr Gln Leu Arg Asp Ser
1               5                   10                  15

Lys Ser Ser Asp Lys Ser Val Cys Leu Phe Thr Asp Phe Asp Ser Gln
            20                  25                  30

Thr Asn Val Ser Gln Ser Lys Asp Ser Asp Val Tyr Ile Thr Asp Lys
        35                  40                  45

Thr Val Leu Asp Met Arg Ser Met Asp Phe Lys Ser Asn Ser Ala Val
```

```
    50                  55                  60

Ala Trp Ser Asn Lys Ser Asp Phe Ala Cys Ala Asn Ala Phe Asn Asn
65                  70                  75                  80

Ser Ile Ile Pro Glu Asp Thr Phe Phe Pro Ser Pro Glu Ser Ser Cys
                85                  90                  95

Asp Val Lys Leu Val Glu Lys Ser Phe Glu Thr Asp Thr Asn Leu Asn
            100                 105                 110

Phe Gln Asn Leu Ser Val Ile Gly Phe Arg Ile Leu Leu Leu Lys Val
        115                 120                 125

Ala Gly Phe Asn Leu Leu Met Thr Leu Arg Leu Trp Ser Ser
    130                 135                 140


<210> SEQ ID NO 3
<211> LENGTH: 22
<212> TYPE: DNA
<213> ORGANISM: Homo sapiens

<400> SEQUENCE: 3

tggcctggag caacaaatct ga                                              22


<210> SEQ ID NO 4
<211> LENGTH: 22
<212> TYPE: DNA
<213> ORGANISM: Homo sapiens

<400> SEQUENCE: 4

acaaatgtgt cacaaagtaa gg                                              22


<210> SEQ ID NO 5
<211> LENGTH: 22
<212> TYPE: DNA
<213> ORGANISM: Homo sapiens

<400> SEQUENCE: 5

ctgatgtgta tatcacagac aa                                              22


<210> SEQ ID NO 6
<211> LENGTH: 163
<212> TYPE: PRT
<213> ORGANISM: Chlamydomonas reinhardtii

<400> SEQUENCE: 6

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Ala Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Trp Arg Leu
            100                 105                 110

Pro Ser Ala Lys Glu Ser Pro Asp Lys Phe Leu Glu Val Cys Thr Trp
        115                 120                 125
```

Val Asp Gln Ile Ala Ala Leu Asn Asp Ser Lys Thr Arg Lys Thr Thr
130 135 140

Ser Glu Thr Val Arg Ala Val Leu Asp Ser Leu Ser Glu Lys Lys Lys
145 150 155 160

Ser Ser Pro

<210> SEQ ID NO 7
<211> LENGTH: 9
<212> TYPE: PRT
<213> ORGANISM: Chlamydomonas reinhardtii

<400> SEQUENCE: 7

Leu Ala Gly Leu Ile Asp Ala Asp Gly
1 5

<210> SEQ ID NO 8
<211> LENGTH: 354
<212> TYPE: PRT
<213> ORGANISM: Artificial Sequence
<220> FEATURE:
<223> OTHER INFORMATION: Synthesized

<400> SEQUENCE: 8

Met Asn Thr Lys Tyr Asn Lys Glu Phe Leu Leu Tyr Leu Ala Gly Phe
1 5 10 15

Val Asp Gly Asp Gly Ser Ile Phe Ala Ser Ile Tyr Pro His Gln Arg
20 25 30

Ala Lys Phe Lys His Phe Leu Lys Leu Thr Phe Ala Val Tyr Gln Lys
35 40 45

Thr Gln Arg Arg Trp Phe Leu Asp Lys Leu Val Asp Glu Ile Gly Val
50 55 60

Gly Tyr Val Tyr Asp Ser Gly Ser Val Ser Glu Tyr Arg Leu Ser Glu
65 70 75 80

Ile Lys Pro Leu His Asn Phe Leu Thr Gln Leu Gln Pro Phe Leu Lys
85 90 95

Leu Lys Gln Lys Gln Ala Asn Leu Val Leu Lys Ile Ile Glu Gln Leu
100 105 110

Pro Ser Ala Lys Glu Ser Pro Asp Lys Phe Leu Glu Val Cys Thr Trp
115 120 125

Val Asp Gln Ile Ala Ala Leu Asn Asp Ser Arg Thr Arg Lys Thr Thr
130 135 140

Ser Glu Thr Val Arg Ala Val Leu Asp Ser Leu Pro Gly Ser Val Gly
145 150 155 160

Gly Leu Ser Pro Ser Gln Ala Ser Ser Ala Ala Ser Ser Ala Ser Ser
165 170 175

Ser Pro Gly Ser Gly Ile Ser Glu Ala Leu Arg Ala Gly Ala Gly Ser
180 185 190

Gly Thr Gly Tyr Asn Lys Glu Phe Leu Leu Tyr Leu Ala Gly Phe Val
195 200 205

Asp Gly Asp Gly Ser Ile Tyr Ala Cys Ile Ala Pro Arg Gln Gly Ser
210 215 220

Lys Phe Lys His Arg Leu Lys Leu Gly Phe Ala Val Gly Gln Lys Thr
225 230 235 240

Gln Arg Arg Trp Phe Leu Asp Lys Leu Val Asp Glu Ile Gly Val Gly
245 250 255

Tyr Val Tyr Asp Arg Gly Ser Val Ser Glu Tyr Val Leu Ser Glu Ile
260 265 270

```
Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro


<210> SEQ ID NO 9
<211> LENGTH: 354
<212> TYPE: PRT
<213> ORGANISM: Artificial Sequence
<220> FEATURE:
<223> OTHER INFORMATION: Synthesized

<400> SEQUENCE: 9

Met Asn Thr Lys Tyr Asn Lys Glu Phe Leu Leu Tyr Leu Ala Gly Phe
1               5                   10                  15

Val Asp Gly Asp Gly Ser Ile Phe Ala Ser Ile Tyr Pro His Gln Arg
            20                  25                  30

Ala Lys Phe Lys His Phe Leu Lys Leu Thr Phe Ala Val Tyr Gln Lys
        35                  40                  45

Thr Gln Arg Arg Trp Phe Leu Asp Lys Leu Val Asp Glu Ile Gly Val
    50                  55                  60

Gly Tyr Val Tyr Asp Ser Gly Ser Val Ser Glu Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Arg Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Cys Ile Ala Pro Arg Gln Gly Ser
    210                 215                 220

Lys Phe Lys His Arg Leu Lys Leu Gly Phe Ala Val Gly Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Arg Gly Ser Val Ser Glu Tyr Val Leu Ser Glu Ile
            260                 265                 270
```

-continued

Lys Pro Leu His Asn Phe Leu Thr Gln Leu Gln Pro Phe Leu Lys Leu
275 280 285

Lys Gln Lys Gln Ala Asn Leu Val Leu Lys Ile Ile Glu Gln Leu Pro
290 295 300

Ser Ala Lys Glu Ser Pro Asp Lys Phe Leu Glu Val Cys Thr Trp Val
305 310 315 320

Asp Gln Ile Ala Ala Leu Asn Asp Ser Lys Thr Arg Lys Thr Thr Ser
325 330 335

Glu Thr Val Arg Ala Val Leu Asp Ser Leu Ser Glu Lys Lys Lys Ser
340 345 350

Ser Pro

<210> SEQ ID NO 10
<211> LENGTH: 354
<212> TYPE: PRT
<213> ORGANISM: Artificial Sequence
<220> FEATURE:
<223> OTHER INFORMATION: Synthesized

<400> SEQUENCE: 10

Met Asn Thr Lys Tyr Asn Lys Glu Phe Leu Leu Tyr Leu Ala Gly Phe
1 5 10 15

Val Asp Gly Asp Gly Ser Ile Phe Ala Ser Ile Tyr Pro His Gln Arg
20 25 30

Ala Lys Phe Lys His Phe Leu Lys Leu Thr Phe Ala Val Tyr Gln Lys
35 40 45

Thr Gln Arg Arg Trp Phe Leu Asp Lys Leu Val Asp Glu Ile Gly Val
50 55 60

Gly Tyr Val Tyr Asp Ser Gly Ser Val Ser Glu Tyr Arg Leu Ser Glu
65 70 75 80

Ile Lys Pro Leu His Asn Phe Leu Thr Gln Leu Gln Pro Phe Leu Lys
85 90 95

Leu Lys Gln Lys Gln Ala Asn Leu Val Leu Lys Ile Ile Glu Gln Leu
100 105 110

Pro Ser Ala Lys Glu Ser Pro Asp Lys Phe Leu Glu Val Cys Thr Trp
115 120 125

Val Asp Gln Ile Ala Ala Leu Asn Asp Ser Arg Thr Arg Lys Thr Thr
130 135 140

Ser Glu Thr Val Arg Ala Val Leu Asp Ser Leu Pro Gly Ser Val Gly
145 150 155 160

Gly Leu Ser Pro Ser Gln Ala Ser Ser Ala Ala Ser Ser Ala Ser Ser
165 170 175

Ser Pro Gly Ser Gly Ile Ser Glu Ala Leu Arg Ala Gly Ala Gly Ser
180 185 190

Gly Thr Gly Tyr Asn Lys Glu Phe Leu Leu Tyr Leu Ala Gly Phe Val
195 200 205

Asp Gly Asp Gly Ser Ile Tyr Ala Cys Ile Ala Pro Arg Gln Gly Ser
210 215 220

Lys Phe Lys His Arg Leu Lys Leu Gly Phe Ala Val Gly Gln Lys Thr
225 230 235 240

Gln Arg Arg Trp Phe Leu Asp Lys Leu Val Asp Glu Ile Gly Val Gly
245 250 255

Tyr Val Tyr Asp Arg Gly Ser Val Ser Glu Tyr Val Leu Ser Gln Ile
260 265 270

Lys Pro Leu His Asn Phe Leu Thr Gln Leu Gln Pro Phe Leu Lys Leu

```
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro


<210> SEQ ID NO 11
<211> LENGTH: 354
<212> TYPE: PRT
<213> ORGANISM: Artificial Sequence
<220> FEATURE:
<223> OTHER INFORMATION: Synthesized

<400> SEQUENCE: 11

Met Asn Thr Lys Tyr Asn Lys Glu Phe Leu Leu Tyr Leu Ala Gly Phe
1               5                   10                  15

Val Asp Gly Asp Gly Ser Ile Phe Ala Ser Ile Tyr Pro His Gln Arg
            20                  25                  30

Ala Lys Phe Lys His Phe Leu Lys Leu Thr Phe Ala Val Tyr Gln Lys
        35                  40                  45

Thr Gln Arg Arg Trp Phe Leu Asp Lys Leu Val Asp Glu Ile Gly Val
    50                  55                  60

Gly Tyr Val Tyr Asp Ser Gly Ser Val Ser Glu Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Arg Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Cys Ile Ala Pro Arg Gln Gly Ser
    210                 215                 220

Lys Phe Lys His Arg Leu Lys Leu Gly Phe Ala Val Gly Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Arg Gly Ser Val Ser Glu Tyr Val Leu Ser Gln Ile
            260                 265                 270

Lys Pro Leu His Asn Phe Leu Thr Gln Leu Gln Pro Phe Leu Lys Leu
        275                 280                 285
```

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 12
<211> LENGTH: 354
<212> TYPE: PRT
<213> ORGANISM: Artificial Sequence
<220> FEATURE:
<223> OTHER INFORMATION: Synthesized

<400> SEQUENCE: 12

Met Asn Thr Lys Tyr Asn Lys Glu Phe Leu Leu Tyr Leu Ala Gly Phe
1               5                   10                  15

Val Asp Gly Asp Gly Ser Ile Tyr Ala Cys Ile Tyr Pro His Gln Arg
            20                  25                  30

Ala Lys Phe Lys His Leu Leu Lys Leu Val Phe Ala Val His Gln Lys
        35                  40                  45

Thr Gln Arg Arg Trp Phe Leu Asp Lys Leu Val Asp Glu Ile Gly Val
    50                  55                  60

Gly Tyr Val Tyr Asp Ala Gly Ser Val Ser Glu Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Cys Ile Ala Pro Arg Gln Gly Ser
    210                 215                 220

Lys Phe Lys His Arg Leu Lys Leu Gly Phe Ala Val Gly Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Arg Gly Ser Val Ser Glu Tyr Val Leu Ser Gln Ile
            260                 265                 270

Lys Pro Leu His Asn Phe Leu Thr Gln Leu Gln Pro Phe Leu Lys Leu
        275                 280                 285

```
Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro


<210> SEQ ID NO 13
<211> LENGTH: 354
<212> TYPE: PRT
<213> ORGANISM: Artificial Sequence
<220> FEATURE:
<223> OTHER INFORMATION: Synthesized

<400> SEQUENCE: 13

Met Asn Thr Lys Tyr Asn Lys Glu Phe Leu Leu Tyr Leu Ala Gly Phe
1               5                   10                  15

Val Asp Gly Asp Gly Ser Ile Tyr Ala Cys Ile Tyr Pro Asp Gln Arg
            20                  25                  30

Thr Lys Phe Lys His Gly Leu Arg Leu Asn Phe Ser Val Phe Gln Lys
        35                  40                  45

Thr Gln Arg Arg Trp Phe Leu Asp Lys Leu Val Asp Glu Ile Gly Val
    50                  55                  60

Gly Tyr Val Phe Asp Ala Gly Ser Val Ser Glu Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Cys Ile Ala Pro Arg Gln Gly Ser
    210                 215                 220

Lys Phe Lys His Arg Leu Lys Leu Gly Phe Ala Val Gly Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Arg Gly Ser Val Ser Glu Tyr Val Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
```

```
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro


<210> SEQ ID NO 14
<211> LENGTH: 354
<212> TYPE: PRT
<213> ORGANISM: Artificial Sequence
<220> FEATURE:
<223> OTHER INFORMATION: Synthesized

<400> SEQUENCE: 14

Met Asn Thr Lys Tyr Asn Lys Glu Phe Leu Leu Tyr Leu Ala Gly Phe
1               5                   10                  15

Val Asp Gly Asp Gly Ser Ile Phe Ala Thr Ile His Pro Asp Gln Arg
            20                  25                  30

Ser Lys Phe Lys His Tyr Leu Arg Leu Phe Phe Ser Val Phe Gln Lys
        35                  40                  45

Thr Gln Arg Arg Trp Phe Leu Asp Lys Leu Val Asp Glu Ile Gly Val
    50                  55                  60

Gly Tyr Val Tyr Asp Ala Gly Ser Val Ser Glu Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Thr Ile Ala Pro Cys Gln Arg Ala
    210                 215                 220

Lys Phe Lys His Arg Leu Lys Leu Gly Phe Thr Val Gly Gln Lys Thr
225                 230                 235                 240

Gln Arg Arg Trp Phe Leu Asp Lys Leu Val Asp Glu Ile Gly Val Gly
                245                 250                 255

His Val Tyr Asp Arg Gly Ser Val Ser Glu Tyr Val Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300
```

Ser Ala Lys Glu Ser Pro Asp Lys Phe Leu Glu Val Cys Thr Trp Val
305 310 315 320

Asp Gln Ile Ala Ala Leu Asn Asp Ser Lys Thr Arg Lys Thr Thr Ser
325 330 335

Glu Thr Val Arg Ala Val Leu Asp Ser Leu Ser Glu Lys Lys Lys Ser
340 345 350

Ser Pro

<210> SEQ ID NO 15
<211> LENGTH: 354
<212> TYPE: PRT
<213> ORGANISM: Artificial Sequence
<220> FEATURE:
<223> OTHER INFORMATION: Synthesized

<400> SEQUENCE: 15

Met Asn Thr Lys Tyr Asn Lys Glu Phe Leu Leu Tyr Leu Ala Gly Phe
1 5 10 15

Val Asp Gly Asp Gly Ser Ile Phe Ala Gln Ile Lys Pro Asp Gln Lys
20 25 30

Met Lys Phe Lys His Tyr Leu Ser Leu His Phe Ser Val Phe Gln Lys
35 40 45

Thr Gln Arg Arg Trp Phe Leu Asp Lys Leu Val Asp Glu Ile Gly Val
50 55 60

Gly Tyr Val Tyr Asp Gly Gly Ser Val Ser Glu Tyr Arg Leu Ser Gln
65 70 75 80

Ile Lys Pro Leu His Asn Phe Leu Thr Gln Leu Gln Pro Phe Leu Lys
85 90 95

Leu Lys Gln Lys Gln Ala Asn Leu Val Leu Lys Ile Ile Glu Gln Leu
100 105 110

Pro Ser Ala Lys Glu Ser Pro Asp Lys Phe Leu Glu Val Cys Thr Trp
115 120 125

Val Asp Gln Ile Ala Ala Leu Asn Asp Ser Lys Thr Arg Lys Thr Thr
130 135 140

Ser Glu Thr Val Arg Ala Val Leu Asp Ser Leu Pro Gly Ser Val Gly
145 150 155 160

Gly Leu Ser Pro Ser Gln Ala Ser Ser Ala Ala Ser Ser Ala Ser Ser
165 170 175

Ser Pro Gly Ser Gly Ile Ser Glu Ala Leu Arg Ala Gly Ala Gly Ser
180 185 190

Gly Thr Gly Tyr Asn Lys Glu Phe Leu Leu Tyr Leu Ala Gly Phe Val
195 200 205

Asp Gly Asp Gly Ser Ile Tyr Ala Gln Ile Lys Pro Gln Gln Arg Ala
210 215 220

Lys Phe Lys His Arg Leu Leu Leu Ala Phe Thr Val Ser Gln Lys Thr
225 230 235 240

Gln Arg Arg Trp Phe Leu Asp Lys Leu Val Asp Glu Ile Gly Val Gly
245 250 255

Tyr Val Ile Asp Arg Gly Gly Val Ser Glu Tyr Ile Leu Ser Glu Ile
260 265 270

Lys Pro Leu His Asn Phe Leu Thr Gln Leu Gln Pro Phe Leu Lys Leu
275 280 285

Lys Gln Lys Gln Ala Asn Leu Val Leu Lys Ile Ile Glu Gln Leu Pro
290 295 300

Ser Ala Lys Glu Ser Pro Asp Lys Phe Leu Glu Val Cys Thr Trp Val
305 310 315 320

Asp Gln Ile Ala Ala Leu Asn Asp Ser Lys Thr Arg Lys Thr Thr Ser
325 330 335

Glu Thr Val Arg Ala Val Leu Asp Ser Leu Ser Glu Lys Lys Lys Ser
340 345 350

Ser Pro

<210> SEQ ID NO 16
<211> LENGTH: 354
<212> TYPE: PRT
<213> ORGANISM: Artificial Sequence
<220> FEATURE:
<223> OTHER INFORMATION: Synthesized

<400> SEQUENCE: 16

Met Asn Thr Lys Tyr Asn Lys Glu Phe Leu Leu Tyr Leu Ala Gly Phe
1 5 10 15

Val Asp Gly Asp Gly Ser Ile Phe Ala Ser Ile Asn Pro Asp Gln Arg
20 25 30

Ala Lys Phe Lys His Ser Leu Lys Leu Thr Phe Ser Val Tyr Gln Lys
35 40 45

Thr Gln Arg Arg Trp Phe Leu Asp Lys Leu Val Asp Glu Ile Gly Val
50 55 60

Gly Tyr Val Tyr Asp Thr Gly Ser Val Ser Glu Tyr Arg Leu Ser Gln
65 70 75 80

Ile Lys Pro Leu His Asn Phe Leu Thr Gln Leu Gln Pro Phe Leu Lys
85 90 95

Leu Lys Gln Lys Gln Ala Asn Leu Val Leu Lys Ile Ile Glu Gln Leu
100 105 110

Pro Ser Ala Lys Glu Ser Pro Asp Lys Phe Leu Glu Val Cys Thr Trp
115 120 125

Val Asp Gln Ile Ala Ala Leu Asn Asp Ser Lys Thr Arg Lys Thr Thr
130 135 140

Ser Glu Thr Val Arg Ala Val Leu Asp Ser Leu Pro Gly Ser Val Gly
145 150 155 160

Gly Leu Ser Pro Ser Gln Ala Ser Ser Ala Ala Ser Ser Ala Ser Ser
165 170 175

Ser Pro Gly Ser Gly Ile Ser Glu Ala Leu Arg Ala Gly Ala Gly Ser
180 185 190

Gly Thr Gly Tyr Asn Lys Glu Phe Leu Leu Tyr Leu Ala Gly Phe Val
195 200 205

Asp Gly Asp Gly Ser Ile Tyr Ala Ser Ile Arg Pro Ser Gln Arg Ser
210 215 220

Lys Phe Lys His Lys Leu Gly Leu Gly Phe Ala Val Gly Gln Lys Thr
225 230 235 240

Gln Arg Arg Trp Phe Leu Asp Lys Leu Val Asp Glu Ile Gly Val Gly
245 250 255

Tyr Val Tyr Asp Arg Gly Ser Val Ser Glu Tyr Val Leu Ser Gln Ile
260 265 270

Lys Pro Leu His Asn Phe Leu Thr Gln Leu Gln Pro Phe Leu Lys Leu
275 280 285

Lys Gln Lys Gln Ala Asn Leu Val Leu Lys Ile Ile Glu Gln Leu Pro
290 295 300

Ser Ala Lys Glu Ser Pro Asp Lys Phe Leu Glu Val Cys Thr Trp Val

```
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro


<210> SEQ ID NO 17
<211> LENGTH: 354
<212> TYPE: PRT
<213> ORGANISM: Artificial Sequence
<220> FEATURE:
<223> OTHER INFORMATION: Synthesized

<400> SEQUENCE: 17

Met Asn Thr Lys Tyr Asn Lys Glu Phe Leu Leu Tyr Leu Ala Gly Phe
1               5                   10                  15

Val Asp Gly Asp Gly Ser Ile Phe Ala Ser Ile Tyr Pro His Gln Arg
            20                  25                  30

Ala Lys Phe Lys His Phe Leu Lys Leu Thr Phe Ala Val Tyr Gln Lys
        35                  40                  45

Thr Gln Arg Arg Trp Phe Leu Asp Lys Leu Val Asp Glu Ile Gly Val
    50                  55                  60

Gly Tyr Val Tyr Asp Ser Gly Ser Val Ser Glu Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Arg Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Cys Ile Ala Pro Arg Gln Gly Ser
    210                 215                 220

Lys Phe Lys His Arg Leu Lys Leu Gly Phe Ala Val Gly Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Arg Gly Ser Val Ser Glu Tyr Val Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320
```

```
Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro


<210> SEQ ID NO 18
<211> LENGTH: 354
<212> TYPE: PRT
<213> ORGANISM: Artificial Sequence
<220> FEATURE:
<223> OTHER INFORMATION: Synthesized

<400> SEQUENCE: 18

Met Asn Thr Lys Tyr Asn Lys Glu Phe Leu Leu Tyr Leu Ala Gly Phe
1               5                   10                  15

Val Asp Gly Asp Gly Ser Ile Tyr Ala Cys Ile Ala Pro Asp Gln Arg
            20                  25                  30

Ala Lys Phe Lys His Tyr Leu Arg Leu Gln Phe Ser Val Phe Gln Lys
        35                  40                  45

Thr Gln Arg Arg Trp Phe Leu Asp Lys Leu Val Asp Glu Ile Gly Val
    50                  55                  60

Gly Tyr Val Phe Asp Ala Gly Ser Val Ser Glu Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Cys Ile Ala Pro Arg Gln Gly Ser
    210                 215                 220

Lys Phe Lys His Arg Leu Lys Leu Gly Phe Ala Val Gly Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Arg Gly Ser Val Ser Glu Tyr Val Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320
```

-continued

```
Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro


<210> SEQ ID NO 19
<211> LENGTH: 354
<212> TYPE: PRT
<213> ORGANISM: Artificial Sequence
<220> FEATURE:
<223> OTHER INFORMATION: Synthesized

<400> SEQUENCE: 19

Met Asn Thr Lys Tyr Asn Lys Glu Phe Leu Leu Tyr Leu Ala Gly Phe
1               5                   10                  15

Val Asp Gly Asp Gly Ser Ile Tyr Ala Cys Ile Ala Pro Arg Gln Gly
            20                  25                  30

Ser Lys Phe Lys His Arg Leu Lys Leu Gly Phe Ala Val Gly Gln Lys
        35                  40                  45

Thr Gln Arg Arg Trp Phe Leu Asp Lys Leu Val Asp Glu Ile Gly Val
    50                  55                  60

Gly Tyr Val Tyr Asp Arg Gly Ser Val Ser Glu Tyr Val Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Thr Ile Tyr Pro Asp Gln Arg Ala
    210                 215                 220

Lys Phe Lys His Ala Leu Lys Leu Ile Phe Ser Val Phe Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Gly Gly Ser Val Ser Glu Tyr Arg Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
```

```
                325                 330                 335

Glu Thr Val Arg Ala Val Leu Asp Ser Leu Ser Glu Lys Lys Lys Ser
            340                 345                 350

Ser Pro


<210> SEQ ID NO 20
<211> LENGTH: 354
<212> TYPE: PRT
<213> ORGANISM: Artificial Sequence
<220> FEATURE:
<223> OTHER INFORMATION: Synthesized

<400> SEQUENCE: 20

Met Asn Thr Lys Tyr Asn Lys Glu Phe Leu Leu Tyr Leu Ala Gly Phe
1               5                   10                  15

Val Asp Gly Asp Gly Ser Ile Tyr Ala Thr Ile Arg Pro Ala Gln Arg
            20                  25                  30

Ala Lys Phe Lys His Arg Leu Val Leu Gly Phe Glu Val Gly Gln Lys
        35                  40                  45

Thr Gln Arg Arg Trp Phe Leu Asp Lys Leu Val Asp Glu Ile Gly Val
    50                  55                  60

Gly Tyr Val Tyr Asp Gly Gly Ser Val Ser Lys Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Phe Ala Thr Ile Ala Pro Asp Gln Arg Pro
    210                 215                 220

Lys Phe Lys His Gln Leu Arg Leu Ile Phe Asn Val Cys Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Thr Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335
```

```
Glu Thr Val Arg Ala Val Leu Asp Ser Leu Ser Glu Lys Lys Lys Ser
            340                 345                 350

Ser Pro


<210> SEQ ID NO 21
<211> LENGTH: 354
<212> TYPE: PRT
<213> ORGANISM: Artificial Sequence
<220> FEATURE:
<223> OTHER INFORMATION: Synthesized

<400> SEQUENCE: 21

Met Asn Thr Lys Tyr Asn Lys Glu Phe Leu Leu Tyr Leu Ala Gly Phe
1               5                   10                  15

Val Asp Gly Asp Gly Ser Ile Tyr Ala Cys Ile Ala Pro Arg Gln Gly
            20                  25                  30

Ser Lys Phe Lys His Arg Leu Lys Leu Gly Phe Ala Val Gly Gln Lys
        35                  40                  45

Thr Gln Arg Arg Trp Phe Leu Asp Lys Leu Val Asp Glu Ile Gly Val
    50                  55                  60

Gly Tyr Val Tyr Asp Arg Gly Ser Val Ser Glu Tyr Val Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Phe Ala Ser Ile Tyr Pro His Gln Arg Ala
    210                 215                 220

Lys Phe Lys His Phe Leu Lys Leu Thr Phe Ala Val Tyr Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Ser Gly Ser Val Ser Glu Tyr Arg Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335
```

```
Glu Thr Val Arg Ala Val Leu Asp Ser Leu Ser Glu Lys Lys Lys Ser
            340                 345                 350

Ser Pro


<210> SEQ ID NO 22
<211> LENGTH: 354
<212> TYPE: PRT
<213> ORGANISM: Artificial Sequence
<220> FEATURE:
<223> OTHER INFORMATION: Synthesized

<400> SEQUENCE: 22

Met Asn Thr Lys Tyr Asn Lys Glu Phe Leu Leu Tyr Leu Ala Gly Phe
1               5                   10                  15

Val Asp Gly Asp Gly Ser Ile Tyr Ala Cys Ile Ala Pro Arg Gln Gly
            20                  25                  30

Ser Lys Phe Lys His Arg Leu Lys Leu Gly Phe Ala Val Gly Gln Lys
        35                  40                  45

Thr Gln Arg Arg Trp Phe Leu Asp Lys Leu Val Asp Glu Ile Gly Val
    50                  55                  60

Gly Tyr Val Tyr Asp Arg Gly Ser Val Ser Glu Tyr Val Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Phe Ala Thr Ile Val Pro Glu Gln Arg Ser
    210                 215                 220

Lys Phe Lys His Tyr Leu Lys Leu Thr Phe Ser Val Phe Gln Lys Thr
225                 230                 235                 240

Gln Arg Arg Trp Phe Leu Asp Arg Leu Val Asp Glu Ile Gly Val Gly
                245                 250                 255

Tyr Val Tyr Asp Ala Gly Ser Val Ser Glu Tyr Arg Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
```

```
            340                 345                 350

Ser Pro


<210> SEQ ID NO 23
<211> LENGTH: 354
<212> TYPE: PRT
<213> ORGANISM: Artificial Sequence
<220> FEATURE:
<223> OTHER INFORMATION: Synthesized

<400> SEQUENCE: 23

Met Asn Thr Lys Tyr Asn Lys Glu Phe Leu Leu Tyr Leu Ala Gly Phe
1               5                   10                  15

Val Asp Gly Asp Gly Ser Ile Tyr Ala Cys Ile Ala Pro Arg Gln Gly
            20                  25                  30

Ser Lys Phe Lys His Arg Leu Lys Leu Gly Phe Ala Val Gly Gln Lys
        35                  40                  45

Thr Gln Arg Arg Trp Phe Leu Asp Lys Leu Val Asp Glu Ile Gly Val
    50                  55                  60

Gly Tyr Val Tyr Asp Arg Gly Ser Val Ser Glu Tyr Val Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Phe Ala Thr Ile Phe Pro Asp Gln Arg Met
    210                 215                 220

Lys Phe Lys His Gln Leu Arg Leu His Phe Cys Val His Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Ser Gly Ser Val Ser Glu Tyr Arg Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350
```

Ser Pro

<210> SEQ ID NO 24
<211> LENGTH: 354
<212> TYPE: PRT
<213> ORGANISM: Artificial Sequence
<220> FEATURE:
<223> OTHER INFORMATION: Synthesized

<400> SEQUENCE: 24

```
Met Asn Thr Lys Tyr Asn Lys Glu Phe Leu Leu Tyr Leu Ala Gly Phe
1               5                   10                  15

Val Asp Gly Asp Gly Ser Ile Tyr Ala Thr Ile Ala Pro Cys Gln Arg
            20                  25                  30

Ala Lys Phe Lys His Arg Leu Lys Leu Gly Phe Thr Val Gly Gln Lys
        35                  40                  45

Thr Gln Arg Arg Trp Phe Leu Asp Lys Leu Val Asp Glu Ile Gly Val
    50                  55                  60

Gly His Val Tyr Asp Arg Gly Ser Val Ser Glu Tyr Val Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Phe Ala Ser Ile Tyr Pro His Gln Arg Ala
    210                 215                 220

Lys Phe Lys His Phe Leu Lys Leu Thr Phe Ala Val Tyr Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Ser Gly Ser Val Ser Glu Tyr Arg Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350
```

Ser Pro

<210> SEQ ID NO 25
<211> LENGTH: 354
<212> TYPE: PRT
<213> ORGANISM: Artificial Sequence
<220> FEATURE:
<223> OTHER INFORMATION: Synthesized

<400> SEQUENCE: 25

```
Met Asn Thr Lys Tyr Asn Lys Glu Phe Leu Leu Tyr Leu Ala Gly Phe
1               5                   10                  15

Val Asp Gly Asp Gly Ser Ile Tyr Ala Cys Ile Ala Pro Arg Gln Gly
            20                  25                  30

Ser Lys Phe Lys His Arg Leu Lys Leu Gly Phe Ala Val Gly Gln Lys
        35                  40                  45

Thr Gln Arg Arg Trp Phe Leu Asp Lys Leu Val Asp Glu Ile Gly Val
    50                  55                  60

Gly Tyr Val Tyr Asp Arg Gly Ser Val Ser Glu Tyr Val Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Phe Ala Thr Ile Phe Pro Asp Gln Arg Met
    210                 215                 220

Lys Phe Lys His Gln Leu Arg Leu His Phe Cys Val His Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Ser Gly Ser Val Ser Glu Tyr Arg Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

<210> SEQ ID NO 26
<211> LENGTH: 354
<212> TYPE: PRT
<213> ORGANISM: Artificial Sequence
<220> FEATURE:
<223> OTHER INFORMATION: Synthesized

<400> SEQUENCE: 26

```
Met Asn Thr Lys Tyr Asn Lys Glu Phe Leu Leu Tyr Leu Ala Gly Phe
1               5                   10                  15

Val Asp Gly Asp Gly Ser Ile Tyr Ala Cys Ile Ala Pro Arg Gln Gly
            20                  25                  30

Ser Lys Phe Lys His Arg Leu Lys Leu Gly Phe Ala Val Gly Gln Lys
        35                  40                  45

Thr Gln Arg Arg Trp Phe Leu Asp Lys Leu Val Asp Glu Ile Gly Val
    50                  55                  60

Gly Tyr Val Tyr Asp Arg Gly Ser Val Ser Glu Tyr Val Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Phe Ala Thr Ile Phe Pro Asp Gln Arg Met
    210                 215                 220

Lys Phe Lys His Gln Leu Arg Leu His Phe Cys Val His Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Ser Gly Ser Val Ser Glu Tyr Arg Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

<210> SEQ ID NO 27
<211> LENGTH: 354
<212> TYPE: PRT
<213> ORGANISM: Artificial Sequence
<220> FEATURE:
<223> OTHER INFORMATION: Synthesized

<400> SEQUENCE: 27

```
Met Asn Thr Lys Tyr Asn Lys Glu Phe Leu Leu Tyr Leu Ala Gly Phe
1               5                   10                  15

Val Asp Gly Asp Gly Ser Ile Tyr Ala Cys Ile Ala Pro Gly Gln Gly
            20                  25                  30

Ser Lys Phe Lys His Arg Leu Lys Leu Gly Phe Ala Val Gly Gln Lys
        35                  40                  45

Thr Gln Arg Arg Trp Phe Leu Asp Lys Leu Val Asp Glu Ile Gly Val
    50                  55                  60

Gly Tyr Val Tyr Asp Arg Gly Ser Val Ser Glu Tyr Val Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Phe Ala Thr Ile Phe Pro Asp Gln Arg Met
    210                 215                 220

Lys Phe Lys His Gln Leu Arg Leu Gly Phe Ala Val His Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Arg Gly Ser Val Ser Glu Tyr Arg Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

<210> SEQ ID NO 28
<211> LENGTH: 354
<212> TYPE: PRT
<213> ORGANISM: Artificial Sequence
<220> FEATURE:
<223> OTHER INFORMATION: Synthesized

<400> SEQUENCE: 28

Met Asn Thr Lys Tyr Asn Lys Glu Phe Leu Leu Tyr Leu Ala Gly Phe
1               5                   10                  15

Val Asp Gly Asp Gly Ser Ile Tyr Ala Thr Ile Cys Pro Cys Gln Thr
            20                  25                  30

Leu Lys Phe Lys His Tyr Leu Thr Leu Ser Phe Ser Val Tyr Gln Lys
        35                  40                  45

Thr Gln Arg Arg Trp Phe Leu Asp Lys Leu Val Asp Glu Ile Gly Val
    50                  55                  60

Gly Tyr Val Tyr Asp Gln Gly Ser Val Ser Cys Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile His Ala Cys Ile Gln Pro Gln Gln Asp Val
    210                 215                 220

Lys Phe Lys His Gln Leu His Leu Arg Phe Thr Val His Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Ala Gly Ser Val Ser Thr Tyr Cys Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 29

<211> LENGTH: 354
<212> TYPE: PRT
<213> ORGANISM: Artificial Sequence
<220> FEATURE:
<223> OTHER INFORMATION: Synthesized

<400> SEQUENCE: 29

```
Met Asn Thr Lys Tyr Asn Lys Glu Phe Leu Leu Tyr Leu Ala Gly Phe
1               5                   10                  15

Val Asp Gly Asp Gly Ser Ile Tyr Ala Thr Ile Cys Pro Asp Gln Ala
            20                  25                  30

Leu Lys Phe Lys His Tyr Leu Ser Leu Thr Phe Ala Val Tyr Gln Lys
        35                  40                  45

Thr Gln Arg Arg Trp Phe Leu Asp Lys Leu Val Asp Glu Ile Gly Val
    50                  55                  60

Gly Tyr Val Tyr Asp Gln Gly Ser Val Ser Cys Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile His Ala Cys Ile Gln Pro Met Gln Ser Met
    210                 215                 220

Lys Phe Lys His Tyr Leu His Leu Arg Phe Thr Val His Gln Lys Thr
225                 230                 235                 240

Gln Arg Arg Trp Phe Leu Asp Lys Leu Val Asp Glu Thr Gly Val Gly
                245                 250                 255

Tyr Val Tyr Asp Ala Gly Ser Val Ser Thr Tyr Cys Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

<210> SEQ ID NO 30
<211> LENGTH: 354

<212> TYPE: PRT
<213> ORGANISM: Artificial Sequence
<220> FEATURE:
<223> OTHER INFORMATION: Synthesized

<400> SEQUENCE: 30

Met Asn Thr Lys Tyr Asn Lys Glu Phe Leu Leu Tyr Leu Ala Gly Phe
1 5 10 15

Val Asp Gly Asp Gly Ser Ile Tyr Ala Cys Ile Thr Pro Gln Gln Asp
20 25 30

Met Lys Phe Lys His Arg Leu Gln Leu Arg Phe Cys Val Thr Gln Lys
35 40 45

Thr Gln Arg Arg Trp Phe Leu Asp Lys Leu Val Asp Glu Ile Gly Val
50 55 60

Gly Tyr Val Gln Asp Cys Gly Ser Val Ser Glu Tyr Arg Leu Ser Glu
65 70 75 80

Ile Lys Pro Leu His Asn Phe Leu Thr Gln Leu Gln Pro Phe Leu Lys
85 90 95

Leu Lys Gln Lys Gln Ala Asn Leu Val Leu Lys Ile Ile Glu Gln Leu
100 105 110

Pro Ser Ala Lys Glu Ser Pro Asp Lys Phe Leu Glu Val Cys Thr Trp
115 120 125

Val Asp Gln Ile Ala Ala Leu Asn Asp Ser Lys Thr Arg Lys Thr Thr
130 135 140

Ser Glu Thr Val Arg Ala Val Leu Asp Ser Leu Pro Gly Ser Val Gly
145 150 155 160

Gly Leu Ser Pro Ser Gln Ala Ser Ser Ala Ala Ser Ser Ala Ser Ser
165 170 175

Ser Pro Gly Ser Gly Ile Ser Glu Ala Leu Arg Ala Gly Ala Gly Ser
180 185 190

Gly Thr Gly Tyr Asn Lys Glu Phe Leu Leu Tyr Leu Ala Gly Phe Val
195 200 205

Asp Gly Asp Gly Ser Ile Val Ala Ser Ile Lys Pro Gln Gln Val Ala
210 215 220

Lys Phe Lys His Arg Leu Met Leu Glu Phe Tyr Val Tyr Gln Lys Thr
225 230 235 240

Gln Arg Arg Trp Phe Leu Asp Lys Leu Val Asp Glu Ile Gly Val Gly
245 250 255

Tyr Val Tyr Asp Leu Gly Gly Ala Ser Arg Tyr Val Leu Ser Gln Ile
260 265 270

Lys Pro Leu His Asn Phe Leu Thr Gln Leu Gln Pro Phe Leu Lys Leu
275 280 285

Lys Gln Lys Gln Ala Asn Leu Val Leu Lys Ile Ile Glu Gln Leu Pro
290 295 300

Ser Ala Lys Glu Ser Pro Asp Lys Phe Leu Glu Val Cys Thr Trp Val
305 310 315 320

Asp Gln Ile Ala Ala Leu Asn Asp Ser Lys Thr Arg Lys Thr Thr Ser
325 330 335

Glu Thr Val Arg Ala Val Leu Asp Ser Leu Ser Glu Lys Lys Lys Ser
340 345 350

Ser Pro

<210> SEQ ID NO 31
<211> LENGTH: 354
<212> TYPE: PRT

<213> ORGANISM: Artificial Sequence
<220> FEATURE:
<223> OTHER INFORMATION: Synthesized

<400> SEQUENCE: 31

```
Met Asn Thr Lys Tyr Asn Lys Glu Phe Leu Leu Tyr Leu Ala Gly Phe
1               5                   10                  15

Val Asp Gly Asp Gly Ser Ile Tyr Ala Cys Ile Lys Pro Asp Gln Ala
            20                  25                  30

Ala Lys Phe Lys His Arg Leu Leu Leu Glu Phe Thr Val Cys Gln Lys
        35                  40                  45

Thr Gln Arg Arg Trp Phe Leu Asp Lys Leu Val Asp Glu Ile Gly Val
    50                  55                  60

Gly Tyr Val Val Asp Gln Gly Ser Val Ser Glu Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Cys Ile Thr Pro Gln Gln Asp Met
    210                 215                 220

Lys Phe Lys His Arg Leu Gln Leu Arg Phe Cys Val Thr Gln Lys Thr
225                 230                 235                 240

Gln Arg Arg Trp Phe Leu Asp Lys Leu Val Asp Glu Ile Gly Val Gly
                245                 250                 255

Tyr Val Gln Asp His Gly Gly Ala Ser Glu Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

<210> SEQ ID NO 32
<211> LENGTH: 354
<212> TYPE: PRT
<213> ORGANISM: Artificial Sequence
<220> FEATURE:
<223> OTHER INFORMATION: Synthesized

<400> SEQUENCE: 32

```
Met Asn Thr Lys Tyr Asn Lys Glu Phe Leu Leu Tyr Leu Ala Gly Phe
1               5                   10                  15

Val Asp Gly Asp Gly Ser Ile Trp Ala Ser Ile Arg Pro Thr Gln Leu
            20                  25                  30

Ala Lys Phe Lys His Ala Leu Trp Leu Gly Phe Ala Val Tyr Gln Lys
        35                  40                  45

Thr Gln Arg Arg Trp Phe Leu Asp Lys Leu Val Asp Glu Ile Gly Val
    50                  55                  60

Gly Tyr Val Tyr Asp Ser Gly Ser Val Ser Lys Tyr Thr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Cys Ile Thr Pro Gln Gln Asp Met
    210                 215                 220

Lys Phe Lys His Arg Leu Gln Leu Arg Phe Cys Val Thr Gln Lys Thr
225                 230                 235                 240

Gln Arg Arg Trp Phe Leu Asp Lys Leu Val Asp Glu Ile Gly Val Gly
                245                 250                 255

Tyr Val Gln Asp Lys Gly Ser Ala Ser Glu Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

<210> SEQ ID NO 33
<211> LENGTH: 147
<212> TYPE: PRT
<213> ORGANISM: Artificial Sequence
<220> FEATURE:

<223> OTHER INFORMATION: Synthesized

<400> SEQUENCE: 33

Lys Glu Phe Leu Leu Tyr Leu Ala Gly Phe Val Asp Gly Asp Gly Ser
1 5 10 15

Ile Tyr Ala Cys Ile Ala Pro Arg Gln Gly Ser Lys Phe Lys His Arg
20 25 30

Leu Lys Leu Gly Phe Ala Val Gly Gln Lys Thr Gln Arg Arg Trp Phe
35 40 45

Leu Asp Lys Leu Val Asp Glu Ile Gly Val Gly Tyr Val Tyr Asp Arg
50 55 60

Gly Ser Val Ser Glu Tyr Val Leu Ser Glu Ile Lys Pro Leu His Asn
65 70 75 80

Phe Leu Thr Gln Leu Gln Pro Phe Leu Lys Leu Lys Gln Lys Gln Ala
85 90 95

Asn Leu Val Leu Lys Ile Ile Glu Gln Leu Pro Ser Ala Lys Glu Ser
100 105 110

Pro Asp Lys Phe Leu Glu Val Cys Thr Trp Val Asp Gln Ile Ala Ala
115 120 125

Leu Asn Asp Ser Lys Thr Arg Lys Thr Thr Ser Glu Thr Val Arg Ala
130 135 140

Val Leu Asp
145

<210> SEQ ID NO 34
<211> LENGTH: 147
<212> TYPE: PRT
<213> ORGANISM: Artificial Sequence
<220> FEATURE:
<223> OTHER INFORMATION: Synthesized

<400> SEQUENCE: 34

Lys Glu Phe Leu Leu Tyr Leu Ala Gly Phe Val Asp Gly Asp Gly Ser
1 5 10 15

Ile Tyr Ala Cys Ile Ala Pro Arg Gln Gly Ser Lys Phe Lys His Arg
20 25 30

Leu Lys Leu Gly Phe Ala Val Gly Gln Lys Thr Gln Arg Arg Trp Phe
35 40 45

Leu Asp Lys Leu Val Asp Glu Ile Gly Val Gly Tyr Val Tyr Asp Arg
50 55 60

Gly Ser Val Ser Glu Tyr Val Leu Ser Glu Ile Lys Pro Leu His Asn
65 70 75 80

Phe Leu Thr Gln Leu Gln Pro Phe Leu Lys Leu Lys Gln Lys Gln Ala
85 90 95

Asn Leu Val Leu Lys Ile Ile Glu Gln Leu Pro Ser Ala Lys Glu Ser
100 105 110

Pro Asp Lys Phe Leu Glu Val Cys Thr Trp Val Asp Gln Ile Ala Ala
115 120 125

Leu Asn Asp Ser Lys Thr Arg Lys Thr Thr Ser Glu Thr Val Arg Ala
130 135 140

Val Leu Asp
145

<210> SEQ ID NO 35
<211> LENGTH: 147
<212> TYPE: PRT
<213> ORGANISM: Artificial Sequence
<220> FEATURE:
<223> OTHER INFORMATION: Synthesized

<400> SEQUENCE: 35

Lys Glu Phe Leu Leu Tyr Leu Ala Gly Phe Val Asp Gly Asp Gly Ser
1 5 10 15

Ile Tyr Ala Cys Ile Ala Pro Arg Gln Gly Ser Lys Phe Lys His Arg
20 25 30

Leu Lys Leu Gly Phe Ala Val Gly Gln Lys Thr Gln Arg Arg Trp Phe
35 40 45

Leu Asp Lys Leu Val Asp Glu Ile Gly Val Gly Tyr Val Tyr Asp Arg
50 55 60

Gly Ser Val Ser Glu Tyr Val Leu Ser Gln Ile Lys Pro Leu His Asn
65 70 75 80

Phe Leu Thr Gln Leu Gln Pro Phe Leu Lys Leu Lys Gln Lys Gln Ala
85 90 95

Asn Leu Val Leu Lys Ile Ile Glu Gln Leu Pro Ser Ala Lys Glu Ser
100 105 110

Pro Asp Lys Phe Leu Glu Val Cys Thr Trp Val Asp Gln Ile Ala Ala
115 120 125

Leu Asn Asp Ser Lys Thr Arg Lys Thr Thr Ser Glu Thr Val Arg Ala
130 135 140

Val Leu Asp
145

<210> SEQ ID NO 36
<211> LENGTH: 147
<212> TYPE: PRT
<213> ORGANISM: Artificial Sequence
<220> FEATURE:
<223> OTHER INFORMATION: Synthesized

<400> SEQUENCE: 36

Lys Glu Phe Leu Leu Tyr Leu Ala Gly Phe Val Asp Gly Asp Gly Ser
1 5 10 15

Ile Tyr Ala Cys Ile Ala Pro Arg Gln Gly Ser Lys Phe Lys His Arg
20 25 30

Leu Lys Leu Gly Phe Ala Val Gly Gln Lys Thr Gln Arg Arg Trp Phe
35 40 45

Leu Asp Lys Leu Val Asp Glu Ile Gly Val Gly Tyr Val Tyr Asp Arg
50 55 60

Gly Ser Val Ser Glu Tyr Val Leu Ser Gln Ile Lys Pro Leu His Asn
65 70 75 80

Phe Leu Thr Gln Leu Gln Pro Phe Leu Lys Leu Lys Gln Lys Gln Ala
85 90 95

Asn Leu Val Leu Lys Ile Ile Glu Gln Leu Pro Ser Ala Lys Glu Ser
100 105 110

Pro Asp Lys Phe Leu Glu Val Cys Thr Trp Val Asp Gln Ile Ala Ala
115 120 125

Leu Asn Asp Ser Lys Thr Arg Lys Thr Thr Ser Glu Thr Val Arg Ala
130 135 140

Val Leu Asp
145

<210> SEQ ID NO 37
<211> LENGTH: 147
<212> TYPE: PRT

<213> ORGANISM: Artificial Sequence
<220> FEATURE:
<223> OTHER INFORMATION: Synthesized

<400> SEQUENCE: 37

```
Lys Glu Phe Leu Leu Tyr Leu Ala Gly Phe Val Asp Gly Asp Gly Ser
1               5                   10                  15

Ile Tyr Ala Cys Ile Ala Pro Arg Gln Gly Ser Lys Phe Lys His Arg
            20                  25                  30

Leu Lys Leu Gly Phe Ala Val Gly Gln Lys Thr Gln Arg Arg Trp Phe
        35                  40                  45

Leu Asp Lys Leu Val Asp Glu Ile Gly Val Gly Tyr Val Tyr Asp Arg
    50                  55                  60

Gly Ser Val Ser Glu Tyr Val Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 38
<211> LENGTH: 147
<212> TYPE: PRT
<213> ORGANISM: Artificial Sequence
<220> FEATURE:
<223> OTHER INFORMATION: Synthesized

<400> SEQUENCE: 38

```
Lys Glu Phe Leu Leu Tyr Leu Ala Gly Phe Val Asp Gly Asp Gly Ser
1               5                   10                  15

Ile Tyr Ala Cys Ile Ala Pro Arg Gln Gly Ser Lys Phe Lys His Arg
            20                  25                  30

Leu Lys Leu Gly Phe Ala Val Gly Gln Lys Thr Gln Arg Arg Trp Phe
        35                  40                  45

Leu Asp Lys Leu Val Asp Glu Ile Gly Val Gly Tyr Val Tyr Asp Arg
    50                  55                  60

Gly Ser Val Ser Glu Tyr Val Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 39
<211> LENGTH: 147

<212> TYPE: PRT
<213> ORGANISM: Artificial Sequence
<220> FEATURE:
<223> OTHER INFORMATION: Synthesized

<400> SEQUENCE: 39

Lys Glu Phe Leu Leu Tyr Leu Ala Gly Phe Val Asp Gly Asp Gly Ser
1               5                   10                  15

Ile Tyr Ala Thr Ile Ala Pro Cys Gln Arg Ala Lys Phe Lys His Arg
            20                  25                  30

Leu Lys Leu Gly Phe Thr Val Gly Gln Lys Thr Gln Arg Arg Trp Phe
        35                  40                  45

Leu Asp Lys Leu Val Asp Glu Ile Gly Val Gly His Val Tyr Asp Arg
    50                  55                  60

Gly Ser Val Ser Glu Tyr Val Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 40
<211> LENGTH: 147
<212> TYPE: PRT
<213> ORGANISM: Artificial Sequence
<220> FEATURE:
<223> OTHER INFORMATION: Synthesized

<400> SEQUENCE: 40

Lys Glu Phe Leu Leu Tyr Leu Ala Gly Phe Val Asp Gly Asp Gly Ser
1               5                   10                  15

Ile Tyr Ala Gln Ile Lys Pro Gln Gln Arg Ala Lys Phe Lys His Arg
            20                  25                  30

Leu Leu Leu Ala Phe Thr Val Ser Gln Lys Thr Gln Arg Arg Trp Phe
        35                  40                  45

Leu Asp Lys Leu Val Asp Glu Ile Gly Val Gly Tyr Val Ile Asp Arg
    50                  55                  60

Gly Gly Val Ser Glu Tyr Ile Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 41

-continued

<211> LENGTH: 147
<212> TYPE: PRT
<213> ORGANISM: Artificial Sequence
<220> FEATURE:
<223> OTHER INFORMATION: Synthesized

<400> SEQUENCE: 41

```
Lys Glu Phe Leu Leu Tyr Leu Ala Gly Phe Val Asp Gly Asp Gly Ser
1               5                   10                  15

Ile Tyr Ala Ser Ile Arg Pro Ser Gln Arg Ser Lys Phe Lys His Lys
            20                  25                  30

Leu Gly Leu Gly Phe Ala Val Gly Gln Lys Thr Gln Arg Arg Trp Phe
        35                  40                  45

Leu Asp Lys Leu Val Asp Glu Ile Gly Val Gly Tyr Val Tyr Asp Arg
    50                  55                  60

Gly Ser Val Ser Glu Tyr Val Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 42
<211> LENGTH: 147
<212> TYPE: PRT
<213> ORGANISM: Artificial Sequence
<220> FEATURE:
<223> OTHER INFORMATION: Synthesized

<400> SEQUENCE: 42

```
Lys Glu Phe Leu Leu Tyr Leu Ala Gly Phe Val Asp Gly Asp Gly Ser
1               5                   10                  15

Ile Tyr Ala Cys Ile Ala Pro Arg Gln Gly Ser Lys Phe Lys His Arg
            20                  25                  30

Leu Lys Leu Gly Phe Ala Val Gly Gln Lys Thr Gln Arg Arg Trp Phe
        35                  40                  45

Leu Asp Lys Leu Val Asp Glu Ile Gly Val Gly Tyr Val Tyr Asp Arg
    50                  55                  60

Gly Ser Val Ser Glu Tyr Val Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

-continued

<210> SEQ ID NO 43
<211> LENGTH: 147
<212> TYPE: PRT
<213> ORGANISM: Artificial Sequence
<220> FEATURE:
<223> OTHER INFORMATION: Synthesized

<400> SEQUENCE: 43

```
Lys Glu Phe Leu Leu Tyr Leu Ala Gly Phe Val Asp Gly Asp Gly Ser
1               5                   10                  15

Ile Tyr Ala Cys Ile Ala Pro Arg Gln Gly Ser Lys Phe Lys His Arg
            20                  25                  30

Leu Lys Leu Gly Phe Ala Val Gly Gln Lys Thr Gln Arg Arg Trp Phe
        35                  40                  45

Leu Asp Lys Leu Val Asp Glu Ile Gly Val Gly Tyr Val Tyr Asp Arg
    50                  55                  60

Gly Ser Val Ser Glu Tyr Val Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 44
<211> LENGTH: 147
<212> TYPE: PRT
<213> ORGANISM: Artificial Sequence
<220> FEATURE:
<223> OTHER INFORMATION: Synthesized

<400> SEQUENCE: 44

```
Lys Glu Phe Leu Leu Tyr Leu Ala Gly Phe Val Asp Gly Asp Gly Ser
1               5                   10                  15

Ile Tyr Ala Cys Ile Ala Pro Arg Gln Gly Ser Lys Phe Lys His Arg
            20                  25                  30

Leu Lys Leu Gly Phe Ala Val Gly Gln Lys Thr Gln Arg Arg Trp Phe
        35                  40                  45

Leu Asp Lys Leu Val Asp Glu Ile Gly Val Gly Tyr Val Tyr Asp Arg
    50                  55                  60

Gly Ser Val Ser Glu Tyr Val Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

```
<210> SEQ ID NO 45
<211> LENGTH: 147
<212> TYPE: PRT
<213> ORGANISM: Artificial Sequence
<220> FEATURE:
<223> OTHER INFORMATION: Synthesized

<400> SEQUENCE: 45

Lys Glu Phe Leu Leu Tyr Leu Ala Gly Phe Val Asp Gly Asp Gly Ser
1               5                   10                  15

Ile Tyr Ala Thr Ile Arg Pro Ala Gln Arg Ala Lys Phe Lys His Arg
            20                  25                  30

Leu Val Leu Gly Phe Glu Val Gly Gln Lys Thr Gln Arg Arg Trp Phe
        35                  40                  45

Leu Asp Lys Leu Val Asp Glu Ile Gly Val Gly Tyr Val Tyr Asp Gly
    50                  55                  60

Gly Ser Val Ser Lys Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 46
<211> LENGTH: 147
<212> TYPE: PRT
<213> ORGANISM: Artificial Sequence
<220> FEATURE:
<223> OTHER INFORMATION: Synthesized

<400> SEQUENCE: 46

Lys Glu Phe Leu Leu Tyr Leu Ala Gly Phe Val Asp Gly Asp Gly Ser
1               5                   10                  15

Ile Tyr Ala Cys Ile Ala Pro Arg Gln Gly Ser Lys Phe Lys His Arg
            20                  25                  30

Leu Lys Leu Gly Phe Ala Val Gly Gln Lys Thr Gln Arg Arg Trp Phe
        35                  40                  45

Leu Asp Lys Leu Val Asp Glu Ile Gly Val Gly Tyr Val Tyr Asp Arg
    50                  55                  60

Gly Ser Val Ser Glu Tyr Val Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 47
<211> LENGTH: 147
<212> TYPE: PRT
<213> ORGANISM: Artificial Sequence
<220> FEATURE:
<223> OTHER INFORMATION: Synthesized

<400> SEQUENCE: 47

```
Lys Glu Phe Leu Leu Tyr Leu Ala Gly Phe Val Asp Gly Asp Gly Ser
1               5                   10                  15

Ile Tyr Ala Cys Ile Ala Pro Arg Gln Gly Ser Lys Phe Lys His Arg
            20                  25                  30

Leu Lys Leu Gly Phe Ala Val Gly Gln Lys Thr Gln Arg Arg Trp Phe
        35                  40                  45

Leu Asp Lys Leu Val Asp Glu Ile Gly Val Gly Tyr Val Tyr Asp Arg
    50                  55                  60

Gly Ser Val Ser Glu Tyr Val Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 48
<211> LENGTH: 147
<212> TYPE: PRT
<213> ORGANISM: Artificial Sequence
<220> FEATURE:
<223> OTHER INFORMATION: Synthesized

<400> SEQUENCE: 48

```
Lys Glu Phe Leu Leu Tyr Leu Ala Gly Phe Val Asp Gly Asp Gly Ser
1               5                   10                  15

Ile Tyr Ala Cys Ile Ala Pro Arg Gln Gly Ser Lys Phe Lys His Arg
            20                  25                  30

Leu Lys Leu Gly Phe Ala Val Gly Gln Lys Thr Gln Arg Arg Trp Phe
        35                  40                  45

Leu Asp Lys Leu Val Asp Glu Ile Gly Val Gly Tyr Val Tyr Asp Arg
    50                  55                  60

Gly Ser Val Ser Glu Tyr Val Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
```

145

<210> SEQ ID NO 49
<211> LENGTH: 147
<212> TYPE: PRT
<213> ORGANISM: Artificial Sequence
<220> FEATURE:
<223> OTHER INFORMATION: Synthesized

<400> SEQUENCE: 49

Lys Glu Phe Leu Leu Tyr Leu Ala Gly Phe Val Asp Gly Asp Gly Ser
1 5 10 15

Ile Tyr Ala Thr Ile Ala Pro Cys Gln Arg Ala Lys Phe Lys His Arg
20 25 30

Leu Lys Leu Gly Phe Thr Val Gly Gln Lys Thr Gln Arg Arg Trp Phe
35 40 45

Leu Asp Lys Leu Val Asp Glu Ile Gly Val Gly His Val Tyr Asp Arg
50 55 60

Gly Ser Val Ser Glu Tyr Val Leu Ser Gln Ile Lys Pro Leu His Asn
65 70 75 80

Phe Leu Thr Gln Leu Gln Pro Phe Leu Lys Leu Lys Gln Lys Gln Ala
85 90 95

Asn Leu Val Leu Lys Ile Ile Glu Gln Leu Pro Ser Ala Lys Glu Ser
100 105 110

Pro Asp Lys Phe Leu Glu Val Cys Thr Trp Val Asp Gln Ile Ala Ala
115 120 125

Leu Asn Asp Ser Lys Thr Arg Lys Thr Thr Ser Glu Thr Val Arg Ala
130 135 140

Val Leu Asp
145

<210> SEQ ID NO 50
<211> LENGTH: 147
<212> TYPE: PRT
<213> ORGANISM: Artificial Sequence
<220> FEATURE:
<223> OTHER INFORMATION: Synthesized

<400> SEQUENCE: 50

Lys Glu Phe Leu Leu Tyr Leu Ala Gly Phe Val Asp Gly Asp Gly Ser
1 5 10 15

Ile Tyr Ala Cys Ile Ala Pro Arg Gln Gly Ser Lys Phe Lys His Arg
20 25 30

Leu Lys Leu Gly Phe Ala Val Gly Gln Lys Thr Gln Arg Arg Trp Phe
35 40 45

Leu Asp Lys Leu Val Asp Glu Ile Gly Val Gly Tyr Val Tyr Asp Arg
50 55 60

Gly Ser Val Ser Glu Tyr Val Leu Ser Gln Ile Lys Pro Leu His Asn
65 70 75 80

Phe Leu Thr Gln Leu Gln Pro Phe Leu Lys Leu Lys Gln Lys Gln Ala
85 90 95

Asn Leu Val Leu Lys Ile Ile Glu Gln Leu Pro Ser Ala Lys Glu Ser
100 105 110

Pro Asp Lys Phe Leu Glu Val Cys Thr Trp Val Asp Gln Ile Ala Ala
115 120 125

Leu Asn Asp Ser Lys Thr Arg Lys Thr Thr Ser Glu Thr Val Arg Ala
130 135 140

Val Leu Asp
145

<210> SEQ ID NO 51
<211> LENGTH: 147
<212> TYPE: PRT
<213> ORGANISM: Artificial Sequence
<220> FEATURE:
<223> OTHER INFORMATION: Synthesized

<400> SEQUENCE: 51

Lys Glu Phe Leu Leu Tyr Leu Ala Gly Phe Val Asp Gly Asp Gly Ser
1 5 10 15

Ile Tyr Ala Cys Ile Ala Pro Arg Gln Gly Ser Lys Phe Lys His Arg
20 25 30

Leu Lys Leu Gly Phe Ala Val Gly Gln Lys Thr Gln Arg Arg Trp Phe
35 40 45

Leu Asp Lys Leu Val Asp Glu Ile Gly Val Gly Tyr Val Tyr Asp Arg
50 55 60

Gly Ser Val Ser Glu Tyr Val Leu Ser Glu Ile Lys Pro Leu His Asn
65 70 75 80

Phe Leu Thr Gln Leu Gln Pro Phe Leu Lys Leu Lys Gln Lys Gln Ala
85 90 95

Asn Leu Val Leu Lys Ile Ile Glu Gln Leu Pro Ser Ala Lys Glu Ser
100 105 110

Pro Asp Lys Phe Leu Glu Val Cys Thr Trp Val Asp Gln Ile Ala Ala
115 120 125

Leu Asn Asp Ser Lys Thr Arg Lys Thr Thr Ser Glu Thr Val Arg Ala
130 135 140

Val Leu Asp
145

<210> SEQ ID NO 52
<211> LENGTH: 147
<212> TYPE: PRT
<213> ORGANISM: Artificial Sequence
<220> FEATURE:
<223> OTHER INFORMATION: Synthesized

<400> SEQUENCE: 52

Lys Glu Phe Leu Leu Tyr Leu Ala Gly Phe Val Asp Gly Asp Gly Ser
1 5 10 15

Ile Tyr Ala Cys Ile Ala Pro Gly Gln Gly Ser Lys Phe Lys His Arg
20 25 30

Leu Lys Leu Gly Phe Ala Val Gly Gln Lys Thr Gln Arg Arg Trp Phe
35 40 45

Leu Asp Lys Leu Val Asp Glu Ile Gly Val Gly Tyr Val Tyr Asp Arg
50 55 60

Gly Ser Val Ser Glu Tyr Val Leu Ser Glu Ile Lys Pro Leu His Asn
65 70 75 80

Phe Leu Thr Gln Leu Gln Pro Phe Leu Lys Leu Lys Gln Lys Gln Ala
85 90 95

Asn Leu Val Leu Lys Ile Ile Glu Gln Leu Pro Ser Ala Lys Glu Ser
100 105 110

Pro Asp Lys Phe Leu Glu Val Cys Thr Trp Val Asp Gln Ile Ala Ala
115 120 125

Leu Asn Asp Ser Lys Thr Arg Lys Thr Thr Ser Glu Thr Val Arg Ala
130 135 140

Val Leu Asp
145

<210> SEQ ID NO 53
<211> LENGTH: 147
<212> TYPE: PRT
<213> ORGANISM: Artificial Sequence
<220> FEATURE:
<223> OTHER INFORMATION: Synthesized

<400> SEQUENCE: 53

Lys Glu Phe Leu Leu Tyr Leu Ala Gly Phe Val Asp Gly Asp Gly Ser
1 5 10 15

Ile Tyr Ala Thr Ile Cys Pro Cys Gln Thr Leu Lys Phe Lys His Tyr
20 25 30

Leu Thr Leu Ser Phe Ser Val Tyr Gln Lys Thr Gln Arg Arg Trp Phe
35 40 45

Leu Asp Lys Leu Val Asp Glu Ile Gly Val Gly Tyr Val Tyr Asp Gln
50 55 60

Gly Ser Val Ser Cys Tyr Arg Leu Ser Gln Ile Lys Pro Leu His Asn
65 70 75 80

Phe Leu Thr Gln Leu Gln Pro Phe Leu Lys Leu Lys Gln Lys Gln Ala
85 90 95

Asn Leu Val Leu Lys Ile Ile Glu Gln Leu Pro Ser Ala Lys Glu Ser
100 105 110

Pro Asp Lys Phe Leu Glu Val Cys Thr Trp Val Asp Gln Ile Ala Ala
115 120 125

Leu Asn Asp Ser Lys Thr Arg Lys Thr Thr Ser Glu Thr Val Arg Ala
130 135 140

Val Leu Asp
145

<210> SEQ ID NO 54
<211> LENGTH: 147
<212> TYPE: PRT
<213> ORGANISM: Artificial Sequence
<220> FEATURE:
<223> OTHER INFORMATION: Synthesized

<400> SEQUENCE: 54

Lys Glu Phe Leu Leu Tyr Leu Ala Gly Phe Val Asp Gly Asp Gly Ser
1 5 10 15

Ile Tyr Ala Thr Ile Cys Pro Asp Gln Ala Leu Lys Phe Lys His Tyr
20 25 30

Leu Ser Leu Thr Phe Ala Val Tyr Gln Lys Thr Gln Arg Arg Trp Phe
35 40 45

Leu Asp Lys Leu Val Asp Glu Ile Gly Val Gly Tyr Val Tyr Asp Gln
50 55 60

Gly Ser Val Ser Cys Tyr Arg Leu Ser Gln Ile Lys Pro Leu His Asn
65 70 75 80

Phe Leu Thr Gln Leu Gln Pro Phe Leu Lys Leu Lys Gln Lys Gln Ala
85 90 95

Asn Leu Val Leu Lys Ile Ile Glu Gln Leu Pro Ser Ala Lys Glu Ser
100 105 110

Pro Asp Lys Phe Leu Glu Val Cys Thr Trp Val Asp Gln Ile Ala Ala
115 120 125

Leu Asn Asp Ser Lys Thr Arg Lys Thr Thr Ser Glu Thr Val Arg Ala 130 135 140

Val Leu Asp
145

<210> SEQ ID NO 55
<211> LENGTH: 147
<212> TYPE: PRT
<213> ORGANISM: Artificial Sequence
<220> FEATURE:
<223> OTHER INFORMATION: Synthesized

<400> SEQUENCE: 55

Lys Glu Phe Leu Leu Tyr Leu Ala Gly Phe Val Asp Gly Asp Gly Ser
1 5 10 15

Ile Tyr Ala Cys Ile Thr Pro Gln Gln Asp Met Lys Phe Lys His Arg
20 25 30

Leu Gln Leu Arg Phe Cys Val Thr Gln Lys Thr Gln Arg Arg Trp Phe
35 40 45

Leu Asp Lys Leu Val Asp Glu Ile Gly Val Gly Tyr Val Gln Asp Cys
50 55 60

Gly Ser Val Ser Glu Tyr Arg Leu Ser Glu Ile Lys Pro Leu His Asn
65 70 75 80

Phe Leu Thr Gln Leu Gln Pro Phe Leu Lys Leu Lys Gln Lys Gln Ala
85 90 95

Asn Leu Val Leu Lys Ile Ile Glu Gln Leu Pro Ser Ala Lys Glu Ser
100 105 110

Pro Asp Lys Phe Leu Glu Val Cys Thr Trp Val Asp Gln Ile Ala Ala
115 120 125

Leu Asn Asp Ser Lys Thr Arg Lys Thr Thr Ser Glu Thr Val Arg Ala
130 135 140

Val Leu Asp
145

<210> SEQ ID NO 56
<211> LENGTH: 147
<212> TYPE: PRT
<213> ORGANISM: Artificial Sequence
<220> FEATURE:
<223> OTHER INFORMATION: Synthesized

<400> SEQUENCE: 56

Lys Glu Phe Leu Leu Tyr Leu Ala Gly Phe Val Asp Gly Asp Gly Ser
1 5 10 15

Ile Tyr Ala Cys Ile Thr Pro Gln Gln Asp Met Lys Phe Lys His Arg
20 25 30

Leu Gln Leu Arg Phe Cys Val Thr Gln Lys Thr Gln Arg Arg Trp Phe
35 40 45

Leu Asp Lys Leu Val Asp Glu Ile Gly Val Gly Tyr Val Gln Asp His
50 55 60

Gly Gly Ala Ser Glu Tyr Arg Leu Ser Glu Ile Lys Pro Leu His Asn
65 70 75 80

Phe Leu Thr Gln Leu Gln Pro Phe Leu Lys Leu Lys Gln Lys Gln Ala
85 90 95

Asn Leu Val Leu Lys Ile Ile Glu Gln Leu Pro Ser Ala Lys Glu Ser
100 105 110

Pro Asp Lys Phe Leu Glu Val Cys Thr Trp Val Asp Gln Ile Ala Ala
115 120 125

Leu Asn Asp Ser Lys Thr Arg Lys Thr Thr Ser Glu Thr Val Arg Ala
    130                 135                 140

Val Leu Asp
145

<210> SEQ ID NO 57
<211> LENGTH: 147
<212> TYPE: PRT
<213> ORGANISM: Artificial Sequence
<220> FEATURE:
<223> OTHER INFORMATION: Synthesized

<400> SEQUENCE: 57

Lys Glu Phe Leu Leu Tyr Leu Ala Gly Phe Val Asp Gly Asp Gly Ser
1               5                   10                  15

Ile Tyr Ala Cys Ile Thr Pro Gln Gln Asp Met Lys Phe Lys His Arg
            20                  25                  30

Leu Gln Leu Arg Phe Cys Val Thr Gln Lys Thr Gln Arg Arg Trp Phe
        35                  40                  45

Leu Asp Lys Leu Val Asp Glu Ile Gly Val Gly Tyr Val Gln Asp Lys
    50                  55                  60

Gly Ser Ala Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 58
<211> LENGTH: 147
<212> TYPE: PRT
<213> ORGANISM: Artificial Sequence
<220> FEATURE:
<223> OTHER INFORMATION: Synthesized

<400> SEQUENCE: 58

Lys Glu Phe Leu Leu Tyr Leu Ala Gly Phe Val Asp Gly Asp Gly Ser
1               5                   10                  15

Ile Phe Ala Ser Ile Tyr Pro His Gln Arg Ala Lys Phe Lys His Phe
            20                  25                  30

Leu Lys Leu Thr Phe Ala Val Tyr Gln Lys Thr Gln Arg Arg Trp Phe
        35                  40                  45

Leu Asp Lys Leu Val Asp Glu Ile Gly Val Gly Tyr Val Tyr Asp Ser
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

```
Leu Asn Asp Ser Arg Thr Arg Lys Thr Thr Ser Glu Thr Val Arg Ala
    130                 135                 140

Val Leu Asp
145


<210> SEQ ID NO 59
<211> LENGTH: 147
<212> TYPE: PRT
<213> ORGANISM: Artificial Sequence
<220> FEATURE:
<223> OTHER INFORMATION: Synthesized

<400> SEQUENCE: 59

Lys Glu Phe Leu Leu Tyr Leu Ala Gly Phe Val Asp Gly Asp Gly Ser
1               5                   10                  15

Ile Phe Ala Ser Ile Tyr Pro His Gln Arg Ala Lys Phe Lys His Phe
            20                  25                  30

Leu Lys Leu Thr Phe Ala Val Tyr Gln Lys Thr Gln Arg Arg Trp Phe
        35                  40                  45

Leu Asp Lys Leu Val Asp Glu Ile Gly Val Gly Tyr Val Tyr Asp Ser
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Arg Thr Arg Lys Thr Thr Ser Glu Thr Val Arg Ala
    130                 135                 140

Val Leu Asp
145


<210> SEQ ID NO 60
<211> LENGTH: 147
<212> TYPE: PRT
<213> ORGANISM: Artificial Sequence
<220> FEATURE:
<223> OTHER INFORMATION: Synthesized

<400> SEQUENCE: 60

Lys Glu Phe Leu Leu Tyr Leu Ala Gly Phe Val Asp Gly Asp Gly Ser
1               5                   10                  15

Ile Phe Ala Ser Ile Tyr Pro His Gln Arg Ala Lys Phe Lys His Phe
            20                  25                  30

Leu Lys Leu Thr Phe Ala Val Tyr Gln Lys Thr Gln Arg Arg Trp Phe
        35                  40                  45

Leu Asp Lys Leu Val Asp Glu Ile Gly Val Gly Tyr Val Tyr Asp Ser
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
```

```
        115                 120                 125

Leu Asn Asp Ser Arg Thr Arg Lys Thr Thr Ser Glu Thr Val Arg Ala
    130                 135                 140

Val Leu Asp
145


<210> SEQ ID NO 61
<211> LENGTH: 147
<212> TYPE: PRT
<213> ORGANISM: Artificial Sequence
<220> FEATURE:
<223> OTHER INFORMATION: Synthesized

<400> SEQUENCE: 61

Lys Glu Phe Leu Leu Tyr Leu Ala Gly Phe Val Asp Gly Asp Gly Ser
1               5                   10                  15

Ile Phe Ala Ser Ile Tyr Pro His Gln Arg Ala Lys Phe Lys His Phe
            20                  25                  30

Leu Lys Leu Thr Phe Ala Val Tyr Gln Lys Thr Gln Arg Arg Trp Phe
        35                  40                  45

Leu Asp Lys Leu Val Asp Glu Ile Gly Val Gly Tyr Val Tyr Asp Ser
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Arg Thr Arg Lys Thr Thr Ser Glu Thr Val Arg Ala
    130                 135                 140

Val Leu Asp
145


<210> SEQ ID NO 62
<211> LENGTH: 147
<212> TYPE: PRT
<213> ORGANISM: Artificial Sequence
<220> FEATURE:
<223> OTHER INFORMATION: Synthesized

<400> SEQUENCE: 62

Lys Glu Phe Leu Leu Tyr Leu Ala Gly Phe Val Asp Gly Asp Gly Ser
1               5                   10                  15

Ile Tyr Ala Cys Ile Tyr Pro His Gln Arg Ala Lys Phe Lys His Leu
            20                  25                  30

Leu Lys Leu Val Phe Ala Val His Gln Lys Thr Gln Arg Arg Trp Phe
        35                  40                  45

Leu Asp Lys Leu Val Asp Glu Ile Gly Val Gly Tyr Val Tyr Asp Ala
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110
```

```
Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 63
<211> LENGTH: 147
<212> TYPE: PRT
<213> ORGANISM: Artificial Sequence
<220> FEATURE:
<223> OTHER INFORMATION: Synthesized

<400> SEQUENCE: 63

Lys Glu Phe Leu Leu Tyr Leu Ala Gly Phe Val Asp Gly Asp Gly Ser
1               5                   10                  15

Ile Tyr Ala Cys Ile Tyr Pro Asp Gln Arg Thr Lys Phe Lys His Gly
            20                  25                  30

Leu Arg Leu Asn Phe Ser Val Phe Gln Lys Thr Gln Arg Arg Trp Phe
        35                  40                  45

Leu Asp Lys Leu Val Asp Glu Ile Gly Val Gly Tyr Val Phe Asp Ala
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 64
<211> LENGTH: 147
<212> TYPE: PRT
<213> ORGANISM: Artificial Sequence
<220> FEATURE:
<223> OTHER INFORMATION: Synthesized

<400> SEQUENCE: 64

Lys Glu Phe Leu Leu Tyr Leu Ala Gly Phe Val Asp Gly Asp Gly Ser
1               5                   10                  15

Ile Phe Ala Thr Ile His Pro Asp Gln Arg Ser Lys Phe Lys His Tyr
            20                  25                  30

Leu Arg Leu Phe Phe Ser Val Phe Gln Lys Thr Gln Arg Arg Trp Phe
        35                  40                  45

Leu Asp Lys Leu Val Asp Glu Ile Gly Val Gly Tyr Val Tyr Asp Ala
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110
```

Pro Asp Lys Phe Leu Glu Val Cys Thr Trp Val Asp Gln Ile Ala Ala
115 120 125

Leu Asn Asp Ser Lys Thr Arg Lys Thr Thr Ser Glu Thr Val Arg Ala
130 135 140

Val Leu Asp
145

<210> SEQ ID NO 65
<211> LENGTH: 147
<212> TYPE: PRT
<213> ORGANISM: Artificial Sequence
<220> FEATURE:
<223> OTHER INFORMATION: Synthesized

<400> SEQUENCE: 65

Lys Glu Phe Leu Leu Tyr Leu Ala Gly Phe Val Asp Gly Asp Gly Ser
1 5 10 15

Ile Phe Ala Gln Ile Lys Pro Asp Gln Lys Met Lys Phe Lys His Tyr
20 25 30

Leu Ser Leu His Phe Ser Val Phe Gln Lys Thr Gln Arg Arg Trp Phe
35 40 45

Leu Asp Lys Leu Val Asp Glu Ile Gly Val Gly Tyr Val Tyr Asp Gly
50 55 60

Gly Ser Val Ser Glu Tyr Arg Leu Ser Gln Ile Lys Pro Leu His Asn
65 70 75 80

Phe Leu Thr Gln Leu Gln Pro Phe Leu Lys Leu Lys Gln Lys Gln Ala
85 90 95

Asn Leu Val Leu Lys Ile Ile Glu Gln Leu Pro Ser Ala Lys Glu Ser
100 105 110

Pro Asp Lys Phe Leu Glu Val Cys Thr Trp Val Asp Gln Ile Ala Ala
115 120 125

Leu Asn Asp Ser Lys Thr Arg Lys Thr Thr Ser Glu Thr Val Arg Ala
130 135 140

Val Leu Asp
145

<210> SEQ ID NO 66
<211> LENGTH: 147
<212> TYPE: PRT
<213> ORGANISM: Artificial Sequence
<220> FEATURE:
<223> OTHER INFORMATION: Synthesized

<400> SEQUENCE: 66

Lys Glu Phe Leu Leu Tyr Leu Ala Gly Phe Val Asp Gly Asp Gly Ser
1 5 10 15

Ile Phe Ala Ser Ile Asn Pro Asp Gln Arg Ala Lys Phe Lys His Ser
20 25 30

Leu Lys Leu Thr Phe Ser Val Tyr Gln Lys Thr Gln Arg Arg Trp Phe
35 40 45

Leu Asp Lys Leu Val Asp Glu Ile Gly Val Gly Tyr Val Tyr Asp Thr
50 55 60

Gly Ser Val Ser Glu Tyr Arg Leu Ser Gln Ile Lys Pro Leu His Asn
65 70 75 80

Phe Leu Thr Gln Leu Gln Pro Phe Leu Lys Leu Lys Gln Lys Gln Ala
85 90 95

Asn Leu Val Leu Lys Ile Ile Glu Gln Leu Pro Ser Ala Lys Glu Ser

```
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 67
<211> LENGTH: 147
<212> TYPE: PRT
<213> ORGANISM: Artificial Sequence
<220> FEATURE:
<223> OTHER INFORMATION: Synthesized

<400> SEQUENCE: 67

Lys Glu Phe Leu Leu Tyr Leu Ala Gly Phe Val Asp Gly Asp Gly Ser
1               5                   10                  15

Ile Phe Ala Ser Ile Tyr Pro His Gln Arg Ala Lys Phe Lys His Phe
            20                  25                  30

Leu Lys Leu Thr Phe Ala Val Tyr Gln Lys Thr Gln Arg Arg Trp Phe
        35                  40                  45

Leu Asp Lys Leu Val Asp Glu Ile Gly Val Gly Tyr Val Tyr Asp Ser
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Arg Thr Arg Lys Thr Thr Ser Glu Thr Val Arg Ala
    130                 135                 140

Val Leu Asp
145


<210> SEQ ID NO 68
<211> LENGTH: 147
<212> TYPE: PRT
<213> ORGANISM: Artificial Sequence
<220> FEATURE:
<223> OTHER INFORMATION: Synthesized

<400> SEQUENCE: 68

Lys Glu Phe Leu Leu Tyr Leu Ala Gly Phe Val Asp Gly Asp Gly Ser
1               5                   10                  15

Ile Tyr Ala Cys Ile Ala Pro Asp Gln Arg Ala Lys Phe Lys His Tyr
            20                  25                  30

Leu Arg Leu Gln Phe Ser Val Phe Gln Lys Thr Gln Arg Arg Trp Phe
        35                  40                  45

Leu Asp Lys Leu Val Asp Glu Ile Gly Val Gly Tyr Val Phe Asp Ala
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95
```

```
Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 69
<211> LENGTH: 147
<212> TYPE: PRT
<213> ORGANISM: Artificial Sequence
<220> FEATURE:
<223> OTHER INFORMATION: Synthesized

<400> SEQUENCE: 69

Lys Glu Phe Leu Leu Tyr Leu Ala Gly Phe Val Asp Gly Asp Gly Ser
1               5                   10                  15

Ile Tyr Ala Thr Ile Tyr Pro Asp Gln Arg Ala Lys Phe Lys His Ala
            20                  25                  30

Leu Lys Leu Ile Phe Ser Val Phe Gln Lys Thr Gln Arg Arg Trp Phe
        35                  40                  45

Leu Asp Lys Leu Val Asp Glu Ile Gly Val Gly Tyr Val Tyr Asp Gly
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 70
<211> LENGTH: 147
<212> TYPE: PRT
<213> ORGANISM: Artificial Sequence
<220> FEATURE:
<223> OTHER INFORMATION: Synthesized

<400> SEQUENCE: 70

Lys Glu Phe Leu Leu Tyr Leu Ala Gly Phe Val Asp Gly Asp Gly Ser
1               5                   10                  15

Ile Phe Ala Thr Ile Ala Pro Asp Gln Arg Pro Lys Phe Lys His Gln
            20                  25                  30

Leu Arg Leu Ile Phe Asn Val Cys Gln Lys Thr Gln Arg Arg Trp Phe
        35                  40                  45

Leu Asp Lys Leu Val Asp Glu Ile Gly Val Gly Tyr Val Tyr Asp Thr
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95
```

```
Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 71
<211> LENGTH: 147
<212> TYPE: PRT
<213> ORGANISM: Artificial Sequence
<220> FEATURE:
<223> OTHER INFORMATION: Synthesized

<400> SEQUENCE: 71

Lys Glu Phe Leu Leu Tyr Leu Ala Gly Phe Val Asp Gly Asp Gly Ser
1               5                   10                  15

Ile Phe Ala Ser Ile Tyr Pro His Gln Arg Ala Lys Phe Lys His Phe
            20                  25                  30

Leu Lys Leu Thr Phe Ala Val Tyr Gln Lys Thr Gln Arg Arg Trp Phe
        35                  40                  45

Leu Asp Lys Leu Val Asp Glu Ile Gly Val Gly Tyr Val Tyr Asp Ser
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 72
<211> LENGTH: 147
<212> TYPE: PRT
<213> ORGANISM: Artificial Sequence
<220> FEATURE:
<223> OTHER INFORMATION: Synthesized

<400> SEQUENCE: 72

Lys Glu Phe Leu Leu Tyr Leu Ala Gly Phe Val Asp Gly Asp Gly Ser
1               5                   10                  15

Ile Phe Ala Thr Ile Val Pro Glu Gln Arg Ser Lys Phe Lys His Tyr
            20                  25                  30

Leu Lys Leu Thr Phe Ser Val Phe Gln Lys Thr Gln Arg Arg Trp Phe
        35                  40                  45

Leu Asp Arg Leu Val Asp Glu Ile Gly Val Gly Tyr Val Tyr Asp Ala
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
```

```
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 73
<211> LENGTH: 147
<212> TYPE: PRT
<213> ORGANISM: Artificial Sequence
<220> FEATURE:
<223> OTHER INFORMATION: Synthesized

<400> SEQUENCE: 73

Lys Glu Phe Leu Leu Tyr Leu Ala Gly Phe Val Asp Gly Asp Gly Ser
1               5                   10                  15

Ile Phe Ala Thr Ile Phe Pro Asp Gln Arg Met Lys Phe Lys His Gln
            20                  25                  30

Leu Arg Leu His Phe Cys Val His Gln Lys Thr Gln Arg Arg Trp Phe
        35                  40                  45

Leu Asp Lys Leu Val Asp Glu Ile Gly Val Gly Tyr Val Tyr Asp Ser
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 74
<211> LENGTH: 147
<212> TYPE: PRT
<213> ORGANISM: Artificial Sequence
<220> FEATURE:
<223> OTHER INFORMATION: Synthesized

<400> SEQUENCE: 74

Lys Glu Phe Leu Leu Tyr Leu Ala Gly Phe Val Asp Gly Asp Gly Ser
1               5                   10                  15

Ile Phe Ala Ser Ile Tyr Pro His Gln Arg Ala Lys Phe Lys His Phe
            20                  25                  30

Leu Lys Leu Thr Phe Ala Val Tyr Gln Lys Thr Gln Arg Arg Trp Phe
        35                  40                  45

Leu Asp Lys Leu Val Asp Glu Ile Gly Val Gly Tyr Val Tyr Asp Ser
    50                  55                  60

Gly Ser Val Ser Glu Tyr Arg Leu Ser Gln Ile Lys Pro Leu His Asn
65                  70                  75                  80
```

```
Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 75
<211> LENGTH: 147
<212> TYPE: PRT
<213> ORGANISM: Artificial Sequence
<220> FEATURE:
<223> OTHER INFORMATION: Synthesized

<400> SEQUENCE: 75

Lys Glu Phe Leu Leu Tyr Leu Ala Gly Phe Val Asp Gly Asp Gly Ser
1               5                   10                  15

Ile Phe Ala Thr Ile Phe Pro Asp Gln Arg Met Lys Phe Lys His Gln
            20                  25                  30

Leu Arg Leu His Phe Cys Val His Gln Lys Thr Gln Arg Arg Trp Phe
        35                  40                  45

Leu Asp Lys Leu Val Asp Glu Ile Gly Val Gly Tyr Val Tyr Asp Ser
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 76
<211> LENGTH: 147
<212> TYPE: PRT
<213> ORGANISM: Artificial Sequence
<220> FEATURE:
<223> OTHER INFORMATION: Synthesized

<400> SEQUENCE: 76

Lys Glu Phe Leu Leu Tyr Leu Ala Gly Phe Val Asp Gly Asp Gly Ser
1               5                   10                  15

Ile Phe Ala Thr Ile Phe Pro Asp Gln Arg Met Lys Phe Lys His Gln
            20                  25                  30

Leu Arg Leu His Phe Cys Val His Gln Lys Thr Gln Arg Arg Trp Phe
        35                  40                  45

Leu Asp Lys Leu Val Asp Glu Ile Gly Val Gly Tyr Val Tyr Asp Ser
    50                  55                  60

Gly Ser Val Ser Glu Tyr Arg Leu Ser Gln Ile Lys Pro Leu His Asn
65                  70                  75                  80
```

```
Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 77
<211> LENGTH: 147
<212> TYPE: PRT
<213> ORGANISM: Artificial Sequence
<220> FEATURE:
<223> OTHER INFORMATION: Synthesized

<400> SEQUENCE: 77

Lys Glu Phe Leu Leu Tyr Leu Ala Gly Phe Val Asp Gly Asp Gly Ser
1               5                   10                  15

Ile Phe Ala Thr Ile Phe Pro Asp Gln Arg Met Lys Phe Lys His Gln
            20                  25                  30

Leu Arg Leu Gly Phe Ala Val His Gln Lys Thr Gln Arg Arg Trp Phe
        35                  40                  45

Leu Asp Lys Leu Val Asp Glu Ile Gly Val Gly Tyr Val Tyr Asp Arg
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 78
<211> LENGTH: 147
<212> TYPE: PRT
<213> ORGANISM: Artificial Sequence
<220> FEATURE:
<223> OTHER INFORMATION: Synthesized

<400> SEQUENCE: 78

Lys Glu Phe Leu Leu Tyr Leu Ala Gly Phe Val Asp Gly Asp Gly Ser
1               5                   10                  15

Ile His Ala Cys Ile Gln Pro Gln Gln Asp Val Lys Phe Lys His Gln
            20                  25                  30

Leu His Leu Arg Phe Thr Val His Gln Lys Thr Gln Arg Arg Trp Phe
        35                  40                  45

Leu Asp Lys Leu Val Asp Glu Ile Gly Val Gly Tyr Val Tyr Asp Ala
    50                  55                  60

Gly Ser Val Ser Thr Tyr Cys Leu Ser Gln Ile Lys Pro Leu His Asn
```

```
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 79
<211> LENGTH: 147
<212> TYPE: PRT
<213> ORGANISM: Artificial Sequence
<220> FEATURE:
<223> OTHER INFORMATION: Synthesized

<400> SEQUENCE: 79

Lys Glu Phe Leu Leu Tyr Leu Ala Gly Phe Val Asp Gly Asp Gly Ser
1               5                   10                  15

Ile His Ala Cys Ile Gln Pro Met Gln Ser Met Lys Phe Lys His Tyr
            20                  25                  30

Leu His Leu Arg Phe Thr Val His Gln Lys Thr Gln Arg Arg Trp Phe
        35                  40                  45

Leu Asp Lys Leu Val Asp Glu Thr Gly Val Gly Tyr Val Tyr Asp Ala
    50                  55                  60

Gly Ser Val Ser Thr Tyr Cys Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 80
<211> LENGTH: 147
<212> TYPE: PRT
<213> ORGANISM: Artificial Sequence
<220> FEATURE:
<223> OTHER INFORMATION: Synthesized

<400> SEQUENCE: 80

Lys Glu Phe Leu Leu Tyr Leu Ala Gly Phe Val Asp Gly Asp Gly Ser
1               5                   10                  15

Ile Val Ala Ser Ile Lys Pro Gln Gln Val Ala Lys Phe Lys His Arg
            20                  25                  30

Leu Met Leu Glu Phe Tyr Val Tyr Gln Lys Thr Gln Arg Arg Trp Phe
        35                  40                  45

Leu Asp Lys Leu Val Asp Glu Ile Gly Val Gly Tyr Val Tyr Asp Leu
    50                  55                  60
```

```
Gly Gly Ala Ser Arg Tyr Val Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 81
<211> LENGTH: 147
<212> TYPE: PRT
<213> ORGANISM: Artificial Sequence
<220> FEATURE:
<223> OTHER INFORMATION: Synthesized

<400> SEQUENCE: 81

Lys Glu Phe Leu Leu Tyr Leu Ala Gly Phe Val Asp Gly Asp Gly Ser
1               5                   10                  15

Ile Tyr Ala Cys Ile Lys Pro Asp Gln Ala Ala Lys Phe Lys His Arg
            20                  25                  30

Leu Leu Leu Glu Phe Thr Val Cys Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 82
<211> LENGTH: 147
<212> TYPE: PRT
<213> ORGANISM: Artificial Sequence
<220> FEATURE:
<223> OTHER INFORMATION: Synthesized

<400> SEQUENCE: 82

Lys Glu Phe Leu Leu Tyr Leu Ala Gly Phe Val Asp Gly Asp Gly Ser
1               5                   10                  15

Ile Trp Ala Ser Ile Arg Pro Thr Gln Leu Ala Lys Phe Lys His Ala
            20                  25                  30

Leu Trp Leu Gly Phe Ala Val Tyr Gln Lys Thr Gln Arg Arg Trp Phe
        35                  40                  45

Leu Asp Lys Leu Val Asp Glu Ile Gly Val Gly Tyr Val Tyr Asp Ser
    50                  55                  60
```

Gly Ser Val Ser Lys Tyr Thr Leu Ser Glu Ile Lys Pro Leu His Asn
65 70 75 80

Phe Leu Thr Gln Leu Gln Pro Phe Leu Lys Leu Lys Gln Lys Gln Ala
85 90 95

Asn Leu Val Leu Lys Ile Ile Glu Gln Leu Pro Ser Ala Lys Glu Ser
100 105 110

Pro Asp Lys Phe Leu Glu Val Cys Thr Trp Val Asp Gln Ile Ala Ala
115 120 125

Leu Asn Asp Ser Lys Thr Arg Lys Thr Thr Ser Glu Thr Val Arg Ala
130 135 140

Val Leu Asp
145

<210> SEQ ID NO 83
<211> LENGTH: 22
<212> TYPE: DNA
<213> ORGANISM: Homo sapiens

<400> SEQUENCE: 83
accggacctc gttgtttaga ct 22

<210> SEQ ID NO 84
<211> LENGTH: 22
<212> TYPE: DNA
<213> ORGANISM: Homo sapiens

<400> SEQUENCE: 84
tgtttacaca gtgtttcatt cc 22

<210> SEQ ID NO 85
<211> LENGTH: 22
<212> TYPE: DNA
<213> ORGANISM: Homo sapiens

<400> SEQUENCE: 85
gactacacat atagtgtctg tt 22

<210> SEQ ID NO 86
<211> LENGTH: 72
<212> TYPE: DNA
<213> ORGANISM: Homo sapiens

<400> SEQUENCE: 86
atggacttca agagcaacag tgctgtggcc tggagcaaca aatctgactt tgcatgtgca 60
aacgccttca ac 72

<210> SEQ ID NO 87
<211> LENGTH: 69
<212> TYPE: DNA
<213> ORGANISM: Artificial Sequence
<220> FEATURE:
<223> OTHER INFORMATION: Synthesized

<400> SEQUENCE: 87
atggacttca agagcaacag tgctgtggcc tggagcaaat ctgactttgc atgtgcaaac 60
gccttcaac 69

<210> SEQ ID NO 88
<211> LENGTH: 55
<212> TYPE: DNA

<213> ORGANISM: Artificial Sequence
<220> FEATURE:
<223> OTHER INFORMATION: Synthesized

<400> SEQUENCE: 88
atggacttca agagcaacaa acaaatctga ctttgcatgt gcaaacgcct tcaac 55

<210> SEQ ID NO 89
<211> LENGTH: 67
<212> TYPE: DNA
<213> ORGANISM: Artificial Sequence
<220> FEATURE:
<223> OTHER INFORMATION: Synthesized

<400> SEQUENCE: 89
atggacttca agagcaacag tgctgtggcc tggagaatct gactttgcat gtgcaaacgc 60
cttcaac 67

<210> SEQ ID NO 90
<211> LENGTH: 65
<212> TYPE: DNA
<213> ORGANISM: Artificial Sequence
<220> FEATURE:
<223> OTHER INFORMATION: Synthesized

<400> SEQUENCE: 90
atggacttca agagcaacag tgctgtggcc tggagtctga ctttgcatgt gcaaacgcct 60
tcaac 65

<210> SEQ ID NO 91
<211> LENGTH: 52
<212> TYPE: DNA
<213> ORGANISM: Artificial Sequence
<220> FEATURE:
<223> OTHER INFORMATION: Synthesized

<400> SEQUENCE: 91
atggacttca agagcaaaca aatctgactt tgcatgtgca aacgccttca ac 52

<210> SEQ ID NO 92
<211> LENGTH: 70
<212> TYPE: DNA
<213> ORGANISM: Artificial Sequence
<220> FEATURE:
<223> OTHER INFORMATION: Synthesized

<400> SEQUENCE: 92
atggacttca agagcaacag tgctgtggcc tggagacaaa tctgactttg catgtgcaaa 60
cgccttcaac 70

<210> SEQ ID NO 93
<211> LENGTH: 68
<212> TYPE: DNA
<213> ORGANISM: Artificial Sequence
<220> FEATURE:
<223> OTHER INFORMATION: Synthesized

<400> SEQUENCE: 93
atggacttca agagcaacag tgctgtggcc tggagcaatc tgactttgca tgtgcaaacg 60
ccttcaac 68

<210> SEQ ID NO 94
<211> LENGTH: 77

<212> TYPE: DNA
<213> ORGANISM: Artificial Sequence
<220> FEATURE:
<223> OTHER INFORMATION: Synthesized

<400> SEQUENCE: 94
atggacttca agagcaacag tgctgtggcc tggagcaacg caacaaatct gactttgcat 60
gtgcaaacgc cttcaac 77

<210> SEQ ID NO 95
<211> LENGTH: 76
<212> TYPE: DNA
<213> ORGANISM: Artificial Sequence
<220> FEATURE:
<223> OTHER INFORMATION: Synthesized

<400> SEQUENCE: 95
atggacttca agagcaacag tgctgtggcc tggagcaaag aacaaatctg actttgcatg 60
tgcaaacgcc ttcaac 76

<210> SEQ ID NO 96
<211> LENGTH: 70
<212> TYPE: DNA
<213> ORGANISM: Artificial Sequence
<220> FEATURE:
<223> OTHER INFORMATION: Synthesized

<400> SEQUENCE: 96
atggacttca agagcaacag tgctgtggcc tggcaacaaa tctgactttg catgtgcaaa 60
cgccttcaac 70

<210> SEQ ID NO 97
<211> LENGTH: 62
<212> TYPE: DNA
<213> ORGANISM: Artificial Sequence
<220> FEATURE:
<223> OTHER INFORMATION: Synthesized

<400> SEQUENCE: 97
atggacttca agagcaacag tgctgtggca aatctgactt tgcatgtgca aacgccttca 60
ac 62

<210> SEQ ID NO 98
<211> LENGTH: 68
<212> TYPE: DNA
<213> ORGANISM: Artificial Sequence
<220> FEATURE:
<223> OTHER INFORMATION: Synthesized

<400> SEQUENCE: 98
atggacttca agagcaacag tgctgtggcc tggacaaatc tgactttgca tgtgcaaacg 60
ccttcaac 68

<210> SEQ ID NO 99
<211> LENGTH: 69
<212> TYPE: DNA
<213> ORGANISM: Artificial Sequence
<220> FEATURE:
<223> OTHER INFORMATION: Synthesized

<400> SEQUENCE: 99
atggacttca agagcaacag tgctgtggcc tggagcaaat ctgactttgc atgtgcaaac 60
gccttcaac 69

<210> SEQ ID NO 100
<211> LENGTH: 56
<212> TYPE: DNA
<213> ORGANISM: Artificial Sequence
<220> FEATURE:
<223> OTHER INFORMATION: Synthesized

<400> SEQUENCE: 100
atggacttca agagcaacag tgctgtggcc tggagcaatg tgcaaacgcc ttcaac 56

<210> SEQ ID NO 101
<211> LENGTH: 69
<212> TYPE: DNA
<213> ORGANISM: Artificial Sequence
<220> FEATURE:
<223> OTHER INFORMATION: Synthesized

<400> SEQUENCE: 101
atggacttca agagcaacag tgctgtggcc tggaacaaat ctgactttgc atgtgcaaac 60
gccttcaac 69

<210> SEQ ID NO 102
<211> LENGTH: 71
<212> TYPE: DNA
<213> ORGANISM: Artificial Sequence
<220> FEATURE:
<223> OTHER INFORMATION: Synthesized

<400> SEQUENCE: 102
atggacttca agagcaacag tgctgtggcc tggagcacaa atctgacttt gcatgtgcaa 60
acgccttcaa c 71

<210> SEQ ID NO 103
<211> LENGTH: 56
<212> TYPE: DNA
<213> ORGANISM: Artificial Sequence
<220> FEATURE:
<223> OTHER INFORMATION: Synthesized

<400> SEQUENCE: 103
atggacttca agagcaacag tgctgtggcc tggagcaatg tgcaaacgcc ttcaac 56

<210> SEQ ID NO 104
<211> LENGTH: 36
<212> TYPE: DNA
<213> ORGANISM: Artificial Sequence
<220> FEATURE:
<223> OTHER INFORMATION: Synthesized

<400> SEQUENCE: 104
atcaaatctg actttgcatg tgcaaacgcc ttcaac 36

<210> SEQ ID NO 105
<211> LENGTH: 34
<212> TYPE: DNA
<213> ORGANISM: Homo sapiens

<400> SEQUENCE: 105
gtgctgtggc ctggagcaac aaatctgact ttgc 34

<210> SEQ ID NO 106
<211> LENGTH: 62

<212> TYPE: DNA
<213> ORGANISM: Artificial Sequence
<220> FEATURE:
<223> OTHER INFORMATION: Synthesized

<400> SEQUENCE: 106
gtgctgtggc ctggagcaag aattcatgcg gccgcaatct agagcaacaa atctgacttt 60
gc 62

<210> SEQ ID NO 107
<211> LENGTH: 6053
<212> TYPE: DNA
<213> ORGANISM: Artificial Sequence
<220> FEATURE:
<223> OTHER INFORMATION: Synthesized

<400> SEQUENCE: 107
cagcagctgg cgtaatagcg aagaggcccg caccgatcgc ccttcccaac agttgcgcag 60
cctgaatggc gaatggaatt ccagacgatt gagcgtcaaa atgtaggtat ttccatgagc 120
gtttttcctg ttgcaatggc tggcggtaat attgttctgg atattaccag caaggccgat 180
agtttgagtt cttctactca ggcaagtgat gttattacta atcaaagaag tattgcgaca 240
acggttaatt tgcgtgatgg acagactctt ttactcggtg gcctcactga ttataaaaac 300
acttctcagg attctggcgt accgttcctg tctaaaatcc ctttaatcgg cctcctgttt 360
agctcccgct ctgattctaa cgaggaaagc acgttatacg tgctcgtcaa agcaaccata 420
gtacgcgccc tgtagcggcg cattaagcgc ggcgggtgtg gtggttacgc gcagcgtgac 480
cgctacactt gccagcgccc tagcgcccgc tcctttcgct ttcttccctt cctttctcgc 540
cacgttcgcc ggctttcccc gtcaagctct aaatcggggg ctccctttag ggttccgatt 600
tagtgcttta cggcacctcg accccaaaaa acttgattag ggtgatggtt cacgtagtgg 660
gccatcgccc tgatagacgg tttttcgccc tttgacgttg gagtccacgt tctttaatag 720
tggactcttg ttccaaactg gaacaacact caaccctatc tcggtctatt cttttgattt 780
ataagggatt ttgccgattt cggcctattg gttaaaaaat gagctgattt aacaaaaatt 840
taacgcgaat tttaacaaaa tattaacgtt tacaatttaa atatttgctt atacaatctt 900
cctgtttttg gggcttttct gattatcaac cggggtacat atgattgaca tgctagtttt 960
acgattaccg ttcatcgccc tgcgcgctcg ctcgctcact gaggccgccc gggcaaagcc 1020
cgggcgtcgg gcgacctttg gtcgcccggc ctcagtgagc gagcgagcgc gcagagaggg 1080
agtggaattc acgcgtggat cttaatagta atcaattacg gggtcattag ttcatagccc 1140
atatatggag ttccgcgtta cataacttac ggtaaatggc ccgcctggct gaccgcccaa 1200
cgacccccgc ccattgacgt caataatgac gtatgttccc atagtaacgc caatagggac 1260
tttccattga cgtcaatggg tggagtattt acggtaaact gcccacttgg cagtacatca 1320
agtgtatcat atgccaagtc cgccccctat tgacgtcaat gacggtaaat ggcccgcctg 1380
gcattatgcc cagtacatga ccttacggga ctttcctact tggcagtaca tctacgtatt 1440
agtcatcgct attaccatgg tgatgcggtt ttggcagtac accaatgggc gtggatagcg 1500
gtttgactca cggggatttc caagtctcca ccccattgac gtcaatggga gtttgttttg 1560
gcaccaaaat caacgggact ttccaaaatg tcgtaataac cccgccccgt tgacgcaaat 1620
gggcggtagg cgtgtacggt gggaggtcta tataagcaga gctcgtttag tgaaccgtca 1680
gatcactaga agctttctgg gcacacccct catctgactt tttaattcct ccacttcaac 1740

-continued

```
acctggtgca ttcatgtgcc ggcacaatca gtgattggtg ggttaatgag tgactgcgtg   1800
agactgactt agtgagctgg gaaagatttt ttggcagaca gggagaaata aggagaggca   1860
acttggagaa ggggcttaga atgaggccta gaagagcagt aaggggcaaa cagtctgagc   1920
aaaggcaggc aggcaggaac tcagttggag agactgaggc tgggccacgt gccctctcct   1980
gccaccttct cttcatctgc ttttttcccg tgtcattctc tggactgcca gaacaaggct   2040
cactgtttct tagtaaaaag agggttttgg tggcaatgga taaggccgag accaccaatc   2100
agaggagttt tagacatcat tgaccagagc tctgggcaga acctggccat tcctgaagca   2160
aggaaacagc ctgcgaaggc accaaagctg cccttacctg ggctggggaa gaaggtgtct   2220
tctggaataa tgctgttgtt gaaggcgttt gcacatgcaa agtcagattt gttgctctag   2280
attgcggccg catgaattct tgctccaggc cacagcactg ttgctcttga agtccataga   2340
cctcatgtct agcacagttt tgtctgtgat atacacatca gaatccttac tttgtgacac   2400
atttgtttga gaatcaaaat cggtgaatag gcagacagac ttgtcactgg atttagagtc   2460
tctcagctgg tacacggcag ggtcagggtt ctggatatct gtgggacaag aggatcaggg   2520
ttaggacatg atctcatttc cctctttgcc ccaacccagg ctggagtcca gatgccagtg   2580
atggacaagg gcggggctct gtggggctgg caagtcacgg tctcatgctt tatacgggaa   2640
atagcatctt agaaaccagc tgctcgtgat ggactgggac tcagggacag gcacaagcta   2700
tcaatcttgg ccaagaggcc atgatttcag tgaacgttca cggccaggcc tggcctgcca   2760
ctcaaggaaa cctgaaatgc agggctactt aataatactg cttattcttt tatttaatag   2820
gatcttcttc aaaaccccag caatataact ctggcagagt aaaggcaggc atgggaaaaa   2880
ggcccagcaa agcaaactgt acatcttgga atctggagtg gtctccccaa cttaggctgg   2940
gcattagcag aatgggaggt ttatggtatg ttggcattaa gttgggaaat ctatcacatt   3000
accaggagat tgctctctca ttgatagagg ttttgaacta taaatcagaa cacctgcgtc   3060
taagccccag cgcaattgtt gttgttaact tgtttattgc agcttataat ggttacaaat   3120
aaagcaatag catcacaaat ttcacaaata aagcattttt ttcactgcat tctagttgtg   3180
gtttgtccaa actcatcaat gtatcttaag gcgggaattg atctaggaac ccctagtgat   3240
ggagttggcc actccctctc tgcgcgctcg ctcgctcact gaggccgccc gggcaaagcc   3300
cgggcgtcgg gcgacctttg gtcgcccggc ctcagtgagc gagcgagcgc gcagagaggg   3360
agtggccaac cccccccccc ccccccggc gattctcttg tttgctccag actctcaggc   3420
aatgacctga tagcctttgt agagacctct caaaaatagc taccctctcc ggcatgaatt   3480
tatcagctag aacggttgaa tatcatattg atggtgattt gactgtctcc ggcctttctc   3540
acccgtttga atctttacct acacattact caggcattgc atttaaaata tatgagggtt   3600
ctaaaaattt ttatccttgc gttgaaataa aggcttctcc cgcaaaagta ttacagggtc   3660
ataatgtttt tggtacaacc gatttagctt tatgctctga ggctttattg cttaattttg   3720
ctaattcttt gccttgcctg tatgatttat tggatgttgg aattcctgat gcggtatttt   3780
ctccttacgc atctgtgcgg tatttcacac cgcatatggt gcactctcag tacaatctgc   3840
tctgatgccg catagttaag ccagccccga cacccgccaa cacccgctga cgcgccctga   3900
cgggcttgtc tgctcccggc atccgcttac agacaagctg tgaccgtctc cgggagctgc   3960
atgtgtcaga ggttttcacc gtcatcaccg aaacgcgcga gacgaaaggg cctcgtgata   4020
cgcctatttt tataggttaa tgtcatgata ataatggttt cttagacgtc aggtggcact   4080
tttcggggaa atgtgcgcgg aacccctatt tgtttatttt tctaaataca ttcaaatatg   4140
```

```
tatccgctca tgagacaata accctgataa atgcttcaat aatattgaaa aaggaagagt   4200

atgagtattc aacatttccg tgtcgccctt attccctttt ttgcggcatt ttgccttcct   4260

gtttttgctc acccagaaac gctggtgaaa gtaaaagatg ctgaagatca gttgggtgca   4320

cgagtgggtt acatcgaact ggatctcaac agcggtaaga tccttgagag ttttcgcccc   4380

gaagaacgtt ttccaatgat gagcactttt aaagttctgc tatgtggcgc ggtattatcc   4440

cgtattgacg ccgggcaaga gcaactcggt cgccgcatac actattctca gaatgacttg   4500

gttgagtact caccagtcac agaaaagcat cttacggatg gcatgacagt aagagaatta   4560

tgcagtgctg ccataaccat gagtgataac actgcggcca acttacttct gacaacgatc   4620

ggaggaccga aggagctaac cgcttttttg cacaacatgg gggatcatgt aactcgcctt   4680

gatcgttggg aaccggagct gaatgaagcc ataccaaacg acgagcgtga caccacgatg   4740

cctgtagcaa tggcaacaac gttgcgcaaa ctattaactg gcgaactact tactctagct   4800

tcccggcaac aattaataga ctggatggag gcggataaag ttgcaggacc acttctgcgc   4860

tcggcccttc cggctggctg gtttattgct gataaatctg gagccggtga gcgtgggtct   4920

cgcggtatca ttgcagcact ggggccagat ggtaagccct cccgtatcgt agttatctac   4980

acgacgggga gtcaggcaac tatggatgaa cgaaatagac agatcgctga gataggtgcc   5040

tcactgatta agcattggta actgtcagac caagtttact catatatact ttagattgat   5100

ttaaaacttc atttttaatt taaaaggatc taggtgaaga tcctttttga taatctcatg   5160

accaaaatcc cttaacgtga gttttcgttc cactgagcgt cagaccccgt agaaaagatc   5220

aaaggatctt cttgagatcc tttttttctg cgcgtaatct gctgcttgca aacaaaaaaa   5280

ccaccgctac cagcggtggt ttgtttgccg gatcaagagc taccaactct ttttccgaag   5340

gtaactggct tcagcagagc gcagatacca aatactgtcc ttctagtgta gccgtagtta   5400

ggccaccact tcaagaactc tgtagcaccg cctacatacc tcgctctgct aatcctgtta   5460

ccagtggctg ctgccagtgg cgataagtcg tgtcttaccg ggttggactc aagacgatag   5520

ttaccggata aggcgcagcg gtcgggctga acggggggtt cgtgcacaca gcccagcttg   5580

gagcgaacga cctacaccga actgagatac ctacagcgtg agctatgaga aagcgccacg   5640

cttcccgaag ggagaaaggc ggacaggtat ccggtaagcg gcagggtcgg aacaggagag   5700

cgcacgaggg agcttccagg gggaaacgcc tggtatcttt atagtcctgt cgggtttcgc   5760

cacctctgac ttgagcgtcg atttttgtga tgctcgtcag gggggcggag cctatggaaa   5820

aacgccagca acgcggcctt tttacggttc ctggcctttt gctggccttt tgctcacatg   5880

ttctttcctg cgttatcccc tgattctgtg gataaccgta ttaccgcctt tgagtgagct   5940

gataccgctc gccgcagccg aacgaccgag cgcagcgagt cagtgagcga ggaagcggaa   6000

gagcgcccaa tacgcaaacc gcctctcccc gcgcgttggc cgattcatta atg          6053
```

<210> SEQ ID NO 108
<211> LENGTH: 5458
<212> TYPE: DNA
<213> ORGANISM: Artificial Sequence
<220> FEATURE:
<223> OTHER INFORMATION: Synthesized

<400> SEQUENCE: 108

```
cagcagctgg cgtaatagcg aagaggcccg caccgatcgc ccttcccaac agttgcgcag     60

cctgaatggc gaatggaatt ccagacgatt gagcgtcaaa atgtaggtat ttccatgagc    120
```

-continued

```
gtttttcctg ttgcaatggc tggcggtaat attgttctgg atattaccag caaggccgat    180
agtttgagtt cttctactca ggcaagtgat gttattacta atcaaagaag tattgcgaca    240
acggttaatt tgcgtgatgg acagactctt ttactcggtg gcctcactga ttataaaaac    300
acttctcagg attctggcgt accgttcctg tctaaaatcc ctttaatcgg cctcctgttt    360
agctcccgct ctgattctaa cgaggaaagc acgttatacg tgctcgtcaa agcaaccata    420
gtacgcgccc tgtagcggcg cattaagcgc ggcgggtgtg gtggttacgc gcagcgtgac    480
cgctacactt gccagcgccc tagcgcccgc tcctttcgct ttcttccctt cctttctcgc    540
cacgttcgcc ggctttcccc gtcaagctct aaatcggggg ctccctttag ggttccgatt    600
tagtgcttta cggcacctcg accccaaaaa acttgattag ggtgatggtt cacgtagtgg    660
gccatcgccc tgatagacgg tttttcgccc tttgacgttg gagtccacgt tctttaatag    720
tggactcttg ttccaaactg gaacaacact caaccctatc tcggtctatt cttttgattt    780
ataagggatt ttgccgattt cggcctattg gttaaaaaat gagctgattt aacaaaaatt    840
taacgcgaat tttaacaaaa tattaacgtt tacaatttaa atatttgctt atacaatctt    900
cctgtttttg gggcttttct gattatcaac cggggtacat atgattgaca tgctagtttt    960
acgattaccg ttcatcgccc tgcgcgctcg ctcgctcact gaggccgccc gggcaaagcc   1020
cgggcgtcgg gcgacctttg gtcgcccggc ctcagtgagc gagcgagcgc gcagagaggg   1080
agtggaattc acgcgtgctt tctgggcaca cccctcatct gactttttaa ttcctccact   1140
tcaacacctg gtgcattcat gtgccggcac aatcagtgat tggtgggtta atgagtgact   1200
gcgtgagact gacttagtga gctgggaaag attttttggc agacagggag aaataaggag   1260
aggcaacttg gagaaggggc ttagaatgag gcctagaaga gcagtaaggg gcaaacagtc   1320
tgagcaaagg caggcaggca ggaactcagt tggagagact gaggctgggc cacgtgccct   1380
ctcctgccac cttctcttca tctgcttttt tcccgtgtca ttctctggac tgccagaaca   1440
aggctcactg tttcttagta aaaagagggt tttggtggca atggataagg ccgagaccac   1500
caatcagagg agttttagac atcattgacc agagctctgg gcagaacctg gccattcctg   1560
aagcaaggaa acagcctgcg aaggcaccaa agctgccctt acctgggctg gggaagaagg   1620
tgtcttctgg aataatgctg ttgttgaagg cgtttgcaca tgcaaagtca gatttgttgc   1680
tctagattgc ggccgcatga attcttgctc caggccacag cactgttgct cttgaagtcc   1740
atagacctca tgtctagcac agttttgtct gtgatataca catcagaatc cttactttgt   1800
gacacatttg tttgagaatc aaaatcggtg aataggcaga cagacttgtc actggattta   1860
gagtctctca gctggtacac ggcagggtca gggttctgga tatctgtggg acaagaggat   1920
cagggttagg acatgatctc atttccctct ttgccccaac ccaggctgga gtccagatgc   1980
cagtgatgga caagggcggg gctctgtggg gctggcaagt cacggtctca tgctttatac   2040
gggaaatagc atcttagaaa ccagctgctc gtgatggact gggactcagg gacaggcaca   2100
agctatcaat cttggccaag aggccatgat ttcagtgaac gttcacggcc aggcctggcc   2160
tgccactcaa ggaaacctga aatgcagggc tacttaataa tactgcttat tcttttattt   2220
aataggatct tcttcaaaac cccagcaata taactctggc agagtaaagg caggcatggg   2280
aaaaaggccc agcaaagcaa actgtacatc ttggaatctg gagtggtctc cccaacttag   2340
gctgggcatt agcagaatgg gaggtttatg gtatgttggc attaagttgg gaaatctatc   2400
acattaccag gagattgctc tctcattgat agaggttttg aactataaat cagaacacct   2460
gcgtctaagc cccagcgcaa ttgttgttgt taacttgttt attgcagctt ataatggtta   2520
```

```
caaataaagc aatagcatca caaatttcac aaataaagca tttttttcac tgcattctag   2580
ttgtggtttg tccaaactca tcaatgtatc ttaaggcggg aattgatcta ggaaccccta   2640
gtgatggagt tggccactcc ctctctgcgc gctcgctcgc tcactgaggc cgcccgggca   2700
aagcccgggc gtcgggcgac ctttggtcgc ccggcctcag tgagcgagcg agcgcgcaga   2760
gagggagtgg ccaacccccc cccccccccc ccggcgattc tcttgtttgc tccagactct   2820
caggcaatga cctgatagcc tttgtagaga cctctcaaaa atagctaccc tctccggcat   2880
gaatttatca gctagaacgg ttgaatatca tattgatggt gatttgactg tctccggcct   2940
ttctcacccg tttgaatctt tacctacaca ttactcaggc attgcattta aaatatatga   3000
gggttctaaa aatttttatc cttgcgttga aataaaggct tctcccgcaa aagtattaca   3060
gggtcataat gtttttggta caaccgattt agctttatgc tctgaggctt tattgcttaa   3120
ttttgctaat tctttgcctt gcctgtatga tttattggat gttggaattc ctgatgcggt   3180
attttctcct tacgcatctg tgcggtattt cacaccgcat atggtgcact ctcagtacaa   3240
tctgctctga tgccgcatag ttaagccagc cccgacaccc gccaacaccc gctgacgcgc   3300
cctgacgggc ttgtctgctc ccggcatccg cttacagaca agctgtgacc gtctccggga   3360
gctgcatgtg tcagaggttt tcaccgtcat caccgaaacg cgcgagacga aagggcctcg   3420
tgatacgcct atttttatag gttaatgtca tgataataat ggtttcttag acgtcaggtg   3480
gcacttttcg gggaaatgtg cgcggaaccc ctatttgttt atttttctaa atacattcaa   3540
atatgtatcc gctcatgaga caataaccct gataaatgct tcaataatat tgaaaaagga   3600
agagtatgag tattcaacat ttccgtgtcg cccttattcc cttttttgcg gcattttgcc   3660
ttcctgtttt tgctcaccca gaaacgctgg tgaaagtaaa agatgctgaa gatcagttgg   3720
gtgcacgagt gggttacatc gaactggatc tcaacagcgg taagatcctt gagagttttc   3780
gccccgaaga acgttttcca atgatgagca cttttaaagt tctgctatgt ggcgcggtat   3840
tatcccgtat tgacgccggg caagagcaac tcggtcgccg catacactat tctcagaatg   3900
acttggttga gtactcacca gtcacagaaa agcatcttac ggatggcatg acagtaagag   3960
aattatgcag tgctgccata accatgagtg ataacactgc ggccaactta cttctgacaa   4020
cgatcggagg accgaaggag ctaaccgctt ttttgcacaa catgggggat catgtaactc   4080
gccttgatcg ttgggaaccg gagctgaatg aagccatacc aaacgacgag cgtgacacca   4140
cgatgcctgt agcaatggca acaacgttgc gcaaactatt aactggcgaa ctacttactc   4200
tagcttcccg gcaacaatta atagactgga tggaggcgga taaagttgca ggaccacttc   4260
tgcgctcggc ccttccggct ggctggttta ttgctgataa atctggagcc ggtgagcgtg   4320
ggtctcgcgg tatcattgca gcactggggc cagatggtaa gccctcccgt atcgtagtta   4380
tctacacgac ggggagtcag gcaactatgg atgaacgaaa tagacagatc gctgagatag   4440
gtgcctcact gattaagcat tggtaactgt cagaccaagt ttactcatat atactttaga   4500
ttgatttaaa acttcatttt taatttaaaa ggatctaggt gaagatcctt tttgataatc   4560
tcatgaccaa aatcccttaa cgtgagtttt cgttccactg agcgtcagac cccgtagaaa   4620
agatcaaagg atcttcttga gatccttttt ttctgcgcgt aatctgctgc ttgcaaacaa   4680
aaaaaccacc gctaccagcg gtggtttgtt tgccggatca agagctacca actctttttc   4740
cgaaggtaac tggcttcagc agagcgcaga taccaaatac tgtccttcta gtgtagccgt   4800
agttaggcca ccacttcaag aactctgtag caccgcctac atacctcgct ctgctaatcc   4860
```

-continued

```
tgttaccagt ggctgctgcc agtggcgata agtcgtgtct taccgggttg gactcaagac   4920

gatagttacc ggataaggcg cagcggtcgg gctgaacggg gggttcgtgc acacagccca   4980

gcttggagcg aacgacctac accgaactga gatacctaca gcgtgagcta tgagaaagcg   5040

ccacgcttcc cgaagggaga aaggcggaca ggtatccggt aagcggcagg gtcggaacag   5100

gagagcgcac gagggagctt ccagggggaa acgcctggta tctttatagt cctgtcgggt   5160

ttcgccacct ctgacttgag cgtcgatttt tgtgatgctc gtcagggggg cggagcctat   5220

ggaaaaacgc cagcaacgcg gcctttttac ggttcctggc cttttgctgg ccttttgctc   5280

acatgttctt tcctgcgtta tcccctgatt ctgtggataa ccgtattacc gcctttgagt   5340

gagctgatac cgctcgccgc agccgaacga ccgagcgcag cgagtcagtg agcgaggaag   5400

cggaagagcg cccaatacgc aaaccgcctc tccccgcgcg ttggccgatt cattaatg     5458
```

<210> SEQ ID NO 109
<211> LENGTH: 6082
<212> TYPE: DNA
<213> ORGANISM: Artificial Sequence
<220> FEATURE:
<223> OTHER INFORMATION: Synthesized

<400> SEQUENCE: 109

```
cagcagctgg cgtaatagcg aagaggcccg caccgatcgc ccttcccaac agttgcgcag     60

cctgaatggc gaatggaatt ccagacgatt gagcgtcaaa atgtaggtat ttccatgagc    120

gtttttcctg ttgcaatggc tggcggtaat attgttctgg atattaccag caaggccgat    180

agtttgagtt cttctactca ggcaagtgat gttattacta atcaaagaag tattgcgaca    240

acggttaatt tgcgtgatgg acagactctt ttactcggtg gcctcactga ttataaaaac    300

acttctcagg attctggcgt accgttcctg tctaaaatcc ctttaatcgg cctcctgttt    360

agctcccgct ctgattctaa cgaggaaagc acgttatacg tgctcgtcaa agcaaccata    420

gtacgcgccc tgtagcggcg cattaagcgc ggcgggtgtg gtggttacgc gcagcgtgac    480

cgctacactt gccagcgccc tagcgcccgc tcctttcgct ttcttccctt cctttctcgc    540

cacgttcgcc ggctttcccc gtcaagctct aaatcggggg ctccctttag ggttccgatt    600

tagtgcttta cggcacctcg accccaaaaa acttgattag ggtgatggtt cacgtagtgg    660

gccatcgccc tgatagacgg tttttcgccc tttgacgttg gagtccacgt tctttaatag    720

tggactcttg ttccaaactg gaacaacact caaccctatc tcggtctatt cttttgattt    780

ataagggatt ttgccgattt cggcctattg gttaaaaaat gagctgattt aacaaaaatt    840

taacgcgaat tttaacaaaa tattaacgtt tacaatttaa atatttgctt atacaatctt    900

cctgtttttg gggcttttct gattatcaac cggggtacat atgattgaca tgctagtttt    960

acgattaccg ttcatcgccc tgcgcgctcg ctcgctcact gaggccgccc gggcaaagcc   1020

cgggcgtcgg gcgacctttg gtcgcccggc ctcagtgagc gagcgagcgc gcagagaggg   1080

agtggaattc acgcgtactg gcatctggac tccagcctgg gttggggcaa agagggaaat   1140

gagatcatgt cctaaccctg atcctcttgt cccacagata tccagaaccc tgaccctgcc   1200

gtgtaccagc tgagagactc taaatccagt gacaagtctg tctgcctatt caccgatttt   1260

gattctcaaa caaatgtgtc acaaagtaag gattctgatg tgtatatcac agacaaaact   1320

gtgctagaca tgaggtctat ggacttcaag agcaacagtg ctgtggcctg gagcaactag   1380

tgggcagagc gcacatcgcc cacagtcccc gagaagttgg ggggaggggt cggcaattga   1440

accggtgcct agagaaggtg gcgcggggta aactgggaaa gtgatgtcgt gtactggctc   1500
```

```
cgcctttttc ccgagggtgg gggagaaccg tatataagtg cagtagtcgc cgtgaacgtt   1560
ctttttcgca acgggtttgc cgccagaaca cagctagcac catggcgctc ccagtgacag   1620
ccttactttt acctctggcg ttattattgc acgcggctcg tcctgacata cagatgactc   1680
agactacctc ttccctatct gcttctttag gcgaccgagt aacaatatct tgccgggcca   1740
gccaggacat ctcaaaatac ttaaactggt atcagcagaa gccggacgga acagttaagt   1800
tgctcattta ccacacgtcg agattacact caggcgttcc tagccgattt tcgggttccg   1860
gttccggtac ggactacagc ctgacaatca gtaaccttga gcaggaggac atcgccacct   1920
acttctgtca gcagggcaac acgctcccgt acacattcgg tggggaact aagctggaga   1980
ttaccggagg cggtggcagc ggtggcggcg gcagcggggg tggcggctcg gaggtcaagt   2040
tacaggagag cggaccgggc ttggtcgcac ctagccagag cctctcagtc acgtgcactg   2100
tgtctggagt cagtctccca gactacgggg tatcatggat acgacagccg cctagaaagg   2160
gcttagagtg gctgggggtt atctggggaa gtgaaaccac atactacaac tcagctctca   2220
agagccgcct caccatcatt aaggacaaca gtaagtcgca ggttttctta aagatgaact   2280
ctctccagac tgacgacacc gctatttact actgcgcgaa gcactactac tacggcggga   2340
gttacgcaat ggactactgg ggtcagggca cttctgtgac cgtatccagc actactaccc   2400
cagccccacg tccccccacg ccagctccaa cgatagcaag tcagccctta tctcttcgcc   2460
ctgaggcttg caggcccgcg gcgggcggcg ccgttcacac gcgaggacta gacttcgcct   2520
gcgacatcta catctgggca ccactagccg ggacttgcgg agtgttgttg ttgagcttgg   2580
taataacgct ctactgcaag cgtgggagaa agaagctctt gtacattttc aagcagccat   2640
tcatgcgtcc cgttcagacg actcaggagg aggacggctg ctcgtgccga ttcccggagg   2700
aggaggaggg cggttgcgaa ctcagagtga agttctctcg ctccgcggac gcacccgctt   2760
accagcaggg tcagaaccag ctatacaacg agttaaacct ggggcgccgg gaggagtacg   2820
acgtgttaga caagcgtaga ggtagggacc cggagatggg aggcaagcct cggagaaaga   2880
acccccagga gggcctgtac aacgaactcc agaaggacaa gatggctgag gcgtactcgg   2940
agattggtat gaagggcgag agacgtcgcg gaaagggaca cgacggctta taccaggggc   3000
tttccaccgc gaccaaggac acatacgacg cgctgcacat gcaagcctta ccacctcgat   3060
gataagatac attgatgagt ttggacaaac cacaactaga atgcagtgaa aaaaatgctt   3120
tatttgtgaa atttgtgatg ctattgcttt atttgtaacc attataagct gcaataaaca   3180
agttctagag caacaaatct gactttgcat gtgcaaacgc cttcaacaac agcattattc   3240
cagaagacac cttcttcccc agcccaggta agggcagctt tggtgccttc aattgcctct   3300
ctgcgcgctc gctcgctcac tgaggccgcc cgggcaaagc ccgggcgtcg ggcgaccttt   3360
ggtcgcccgg cctcagtgag cgagcgagcg cgcagagagg gagtggccaa ccccggcgat   3420
tctcttgttt gctccagact ctcaggcaat gacctgatag cctttgtacc tgcaggtctc   3480
aaaaatagct accctctccg gcatgaattt atcagctaga acggttgaat atcatattga   3540
tggtgatttg actgtctccg gcctttctca cccgtttgaa tctttaccta cacattactc   3600
aggcattgca tttaaaatat atgagggttc taaaaatttt tatccttgcg ttgaaataaa   3660
ggcttctccc gcaaaagtat tacagggtca taatgttttt ggtacaaccg atttagcttt   3720
atgctctgag gctttattgc ttaattttgc taattctttg ccttgcctgt atgatttatt   3780
ggatgttgga attcctgatg cggtattttc tccttacgca tctgtgcggt atttcacacc   3840
```

-continued gcatatggtg cactctcagt acaatctgct ctgatgccgc atagttaagc cagccccgac 3900
acccgccaac acccgctgac gcgccctgac gggcttgtct gctcccggca tccgcttaca 3960
gacaagctgt gaccgtctcc gggagctgca tgtgtcagag gttttcaccg tcatcaccga 4020
aacgcgcgag acgaaagggc ctcgtgatac gcctattttt ataggttaat gtcatgataa 4080
taatggtttc ttagacgtca ggtggcactt ttcggggaaa tgtgcgcgga acccctattt 4140
gtttattttt ctaaatacat tcaaatatgt atccgctcat gagacaataa ccctgataaa 4200
tgcttcaata atattgaaaa aggaagagta tgagtattca acatttccgt gtcgccctta 4260
ttcccttttt tgcggcattt tgccttcctg tttttgctca cccagaaacg ctggtgaaag 4320
taaaagatgc tgaagatcag ttgggtgcac gagtgggtta catcgaactg gatctcaaca 4380
gcggtaagat ccttgagagt tttcgccccg aagaacgttt tccaatgatg agcactttta 4440
aagttctgct atgtggcgcg gtattatccc gtattgacgc cgggcaagag caactcggtc 4500
gccgcataca ctattctcag aatgacttgg ttgagtactc accagtcaca gaaaagcatc 4560
ttacggatgg catgacagta agagaattat gcagtgctgc cataaccatg agtgataaca 4620
ctgcggccaa cttacttctg acaacgatcg gaggaccgaa ggagctaacc gcttttttgc 4680
acaacatggg ggatcatgta actcgccttg atcgttggga accggagctg aatgaagcca 4740
taccaaacga cgagcgtgac accacgatgc ctgtagcaat ggcaacaacg ttgcgcaaac 4800
tattaactgg cgaactactt actctagctt cccggcaaca attaatagac tggatggagg 4860
cggataaagt tgcaggacca cttctgcgct cggcccttcc ggctggctgg tttattgctg 4920
ataaatctgg agccggtgag cgtgggtctc gcggtatcat tgcagcactg gggccagatg 4980
gtaagccctc ccgtatcgta gttatctaca cgacggggag tcaggcaact atggatgaac 5040
gaaatagaca gatcgctgag ataggtgcct cactgattaa gcattggtaa ctgtcagacc 5100
aagtttactc atatatactt tagattgatt taaaacttca tttttaattt aaaaggatct 5160
aggtgaagat cctttttgat aatctcatga ccaaaatccc ttaacgtgag ttttcgttcc 5220
actgagcgtc agaccccgta gaaaagatca aaggatcttc ttgagatcct ttttttctgc 5280
gcgtaatctg ctgcttgcaa acaaaaaaac caccgctacc agcggtggtt tgtttgccgg 5340
atcaagagct accaactctt tttccgaagg taactggctt cagcagagcg cagataccaa 5400
atactgtcct tctagtgtag ccgtagttag gccaccactt caagaactct gtagcaccgc 5460
ctacatacct cgctctgcta atcctgttac cagtggctgc tgccagtggc gataagtcgt 5520
gtcttaccgg gttggactca agacgatagt taccggataa ggcgcagcgg tcgggctgaa 5580
cggggggttc gtgcacacag cccagcttgg agcgaacgac ctacaccgaa ctgagatacc 5640
tacagcgtga gctatgagaa agcgccacgc ttcccgaagg gagaaaggcg gacaggtatc 5700
cggtaagcgg cagggtcgga acaggagagc gcacgaggga gcttccaggg ggaaacgcct 5760
ggtatcttta tagtcctgtc gggtttcgcc acctctgact tgagcgtcga tttttgtgat 5820
gctcgtcagg ggggcggagc ctatggaaaa acgccagcaa cgcggccttt ttacggttcc 5880
tggccttttg ctggcctttt gctcacatgt tctttcctgc gttatcccct gattctgtgg 5940
ataaccgtat taccgccttt gagtgagctg ataccgctcg ccgcagccga acgaccgagc 6000
gcagcgagtc agtgagcgag gaagcggaag agcgcccaat acgcaaaccg cctctccccg 6060
cgcgttggcc gattcattaa tg 6082

<210> SEQ ID NO 110
<211> LENGTH: 7887

<212> TYPE: DNA
<213> ORGANISM: Artificial Sequence
<220> FEATURE:
<223> OTHER INFORMATION: Synthesized

<400> SEQUENCE: 110
cagcagctgg cgtaatagcg aagaggcccg caccgatcgc ccttcccaac agttgcgcag 60
cctgaatggc gaatggaatt ccagacgatt gagcgtcaaa atgtaggtat ttccatgagc 120
gtttttcctg ttgcaatggc tggcggtaat attgttctgg atattaccag caaggccgat 180
agtttgagtt cttctactca ggcaagtgat gttattacta atcaaagaag tattgcgaca 240
acggttaatt tgcgtgatgg acagactctt ttactcggtg gcctcactga ttataaaaac 300
acttctcagg attctggcgt accgttcctg tctaaaatcc ctttaatcgg cctcctgttt 360
agctcccgct ctgattctaa cgaggaaagc acgttatacg tgctcgtcaa agcaaccata 420
gtacgcgccc tgtagcggcg cattaagcgc ggcgggtgtg gtggttacgc gcagcgtgac 480
cgctacactt gccagcgccc tagcgcccgc tcctttcgct ttcttccctt cctttctcgc 540
cacgttcgcc ggctttcccc gtcaagctct aaatcggggg ctccctttag ggttccgatt 600
tagtgcttta cggcacctcg accccaaaaa acttgattag ggtgatggtt cacgtagtgg 660
gccatcgccc tgatagacgg tttttcgccc tttgacgttg gagtccacgt tctttaatag 720
tggactcttg ttccaaactg gaacaacact caaccctatc tcggtctatt cttttgattt 780
ataagggatt ttgccgattt cggcctattg gttaaaaaat gagctgattt aacaaaaatt 840
taacgcgaat tttaacaaaa tattaacgtt tacaatttaa atatttgctt atacaatctt 900
cctgtttttg gggcttttct gattatcaac cggggtacat atgattgaca tgctagtttt 960
acggcgcgcc gggttggcca ctccctctct gcgcgctcgc tcgctcactg aggccgggcg 1020
accaaaggtc gcccgacgcc cgggctttgc ccgggcggcc tcagtgagcg agcgagcgcg 1080
cagagaggga gtggccaact ccatcactag gggttcctac gcgtagatct catattctgg 1140
cagggtcagt ggctccaact aacatttgtt tggtacttta cagtttatta aatagatgtt 1200
tatatggaga agctctcatt tctttctcag aagagcctgg ctaggaaggt ggatgaggca 1260
ccatattcat tttgcaggtg aaattcctga gatgtaagga gctgctgtga cttgctcaag 1320
gccttatatc aagtaaacgg tagcgctggg gcttagacgc aggtgttctg atttatagtt 1380
caaaacctct atcaatgaga gagcaatctc ctggtaatgt gatagatttc ccaacttaat 1440
gccaacatac cataaacctc ccattctgct aatgcccagc ctaagttggg gagaccactc 1500
cagattccaa gatgtacagt ttgctttgct gggccttttt cccatgcctg cctttactct 1560
gccagagtta tattgctggg gttttgaaga agatcctatt aaataaaaga ataagcagta 1620
ttattaagta gccctgcatt tcaggtttcc ttgagtggca ggccaggcct ggccgtgaac 1680
gttcactgaa atcatggcct cttggccaag attgatagct tgtgcctgtc cctgagtccc 1740
agtccatcac gagcagctgg tttctaagat gctatttccc gtataaagca tgagaccgtg 1800
acttgccagc cccacagagc cccgcccttg tccatcactg gcatctggac tccagcctgg 1860
gttggggcaa agagggaaat gagatcatgt cctaaccctg atcctcttgt cccacagata 1920
tccagaaccc tgaccctgcc gtgtaccagc tgagagactc taaatccagt gacaagtctg 1980
tctgcctatt caccgatttt gattctcaaa caaatgtgtc acaaagtaag gattctgatg 2040
tgtatatcac agacaaaact gtgctagaca tgaggtctat ggacttcaag agcaacagtg 2100
ctgtggcctg gagcaactag tggatctgcg atcgctccgg tgcccgtcag tgggcagagc 2160
gcacatcgcc cacagtcccc gagaagttgg ggggaggggt cggcaattga acgggtgcct 2220
agagaaggtg gcgcggggta aactgggaaa gtgatgtcgt gtactggctc cgcctttttc 2280
ccgagggtgg gggagaaccg tatataagtg cagtagtcgc cgtgaacgtt ctttttcgca 2340
acgggtttgc cgccagaaca cagctgaagc ttcgaggggc tcgcatctct ccttcacgcg 2400
cccgccgccc tacctgaggc cgccatccac gccggttgag tcgcgttctg ccgcctcccg 2460
cctgtggtgc ctcctgaact gcgtccgccg tctaggtaag tttaaagctc aggtcgagac 2520
cgggcctttg tccggcgctc ccttggagcc tacctagact cagccggctc tccacgcttt 2580
gcctgaccct gcttgctcaa ctctacgtct ttgtttcgtt ttctgttctg cgccgttaca 2640
gatccaagct gtgaccggcg cctactctag agctagcgca gtcagtgctt ctgacacaac 2700
agtctcgaac ttaactagca ccatggcgct cccagtgaca gccttacttt tacctctggc 2760
gttattattg cacgcggctc gtcctgacat acagatgact cagactacct cttccctatc 2820
tgcttcttta ggcgaccgag taacaatatc ttgccgggcc agccaggaca tctcaaaata 2880
cttaaactgg tatcagcaga agccggacgg aacagttaag ttgctcattt accacacgtc 2940
gagattacac tcaggcgttc ctagccgatt ttcgggttcc ggttccggta cggactacag 3000
cctgacaatc agtaaccttg agcaggagga catcgccacc tacttctgtc agcagggcaa 3060
cacgctcccg tacacattcg gtgggggaac taagctggag attaccggag gcggtggcag 3120
cggtggcggc ggcagcgggg gtggcggctc ggaggtcaag ttacaggaga gcggaccggg 3180
cttggtcgca cctagccaga gcctctcagt cacgtgcact gtgtctggag tcagtctccc 3240
agactacggg gtatcatgga tacgacagcc gcctagaaag ggcttagagt ggctgggggt 3300
tatctgggga agtgaaacca catactacaa ctcagctctc aagagccgcc tcaccatcat 3360
taaggacaac agtaagtcgc aggttttctt aaagatgaac tctctccaga ctgacgacac 3420
cgctatttac tactgcgcga agcactacta ctacggcggg agttacgcaa tggactactg 3480
gggtcagggc acttctgtga ccgtatccag cactactacc ccagccccac gtcccccac 3540
gccagctcca acgatagcaa gtcagccctt atctcttcgc cctgaggctt gcaggcccgc 3600
ggcgggcggc gccgttcaca cgcgaggact agacttcgcc tgcgacatct acatctgggc 3660
accactagcc gggacttgcg gagtgttgtt gttgagcttg gtaataacgc tctactgcaa 3720
gcgtgggaga aagaagctct tgtacatttt caagcagcca ttcatgcgtc ccgttcagac 3780
gactcaggag gaggacggct gctcgtgccg attcccggag gaggaggagg gcggttgcga 3840
actcagagtg aagttctctc gctccgcgga cgcacccgct taccagcagg gtcagaacca 3900
gctatacaac gagttaaacc tggggcgccg ggaggagtac gacgtgttag acaagcgtag 3960
aggtagggac ccggagatgg gaggcaagcc tcggagaaag aacccccagg agggcctgta 4020
caacgaactc cagaaggaca agatggctga ggcgtactcg gagattggta tgaagggcga 4080
gagacgtcgc ggaaagggac acgacggctt ataccagggg ctttccaccg cgaccaagga 4140
cacatacgac gcgctgcaca tgcaagcctt accacctcga tgaggtacca gcggccgctt 4200
cgagcagaca tgataagata cattgatgag tttggacaaa ccacaactag aatgcagtga 4260
aaaaaatgct ttatttgtga aatttgtgat gctattgctt tatttgtaac cattataagc 4320
tgcaataaac aagttaacaa caacaattcg aatttaaatc ggatccgcaa caaatctgac 4380
tttgcatgtg caaacgcctt caacaacagc attattccag aagacacctt cttccccagc 4440
ccaggtaagg gcagctttgg tgccttcgca ggctgtttcc ttgcttcagg aatggccagg 4500
ttctgcccag agctctggtc aatgatgtct aaaactcctc tgattggtgg tctcggcctt 4560

```
atccattgcc accaaaaccc tctttttact aagaaacagt gagccttgtt ctggcagtcc   4620
agagaatgac acgggaaaaa agcagatgaa gagaaggtgg caggagaggg cacgtggccc   4680
agcctcagtc tctccaactg agttcctgcc tgcctgcctt tgctcagact gtttgcccct   4740
tactgctctt ctaggcctca ttctaagccc cttctccaag ttgcctctcc ttatttctcc   4800
ctgtctgcca aaaaatcttt cccagctcac taagtcagtc tcacgcagtc actcattaac   4860
ccaccaatca ctgattgtgc cggcacatga atgcaccagg tgttgaagtg gaggaattaa   4920
aaagtcagat gaggggtgtg cccagaggaa gcaccattct agttgggga gcccatctgt   4980
cagctgggaa aagtccaaat aacttcagat tggaatgtgt tttaactcag ggttgagaaa   5040
acagccacct tcaggacaaa agtcagggaa gggctctctg aagaaatgct acttgaagat   5100
accagcccta ccaagggcag ggagaggacc aattgatgga gttggccact ccctctctgc   5160
gcgctcgctc gctcactgag gccgcccggg caaagcccgg gcgtcgggcg acctttggtc   5220
gcccggcctc agtgagcgag cgagcgcgca gagagggagt ggccaacggc gcgcctgcag   5280
gtctcaaaaa tagctaccct ctccggcatg aatttatcag ctagaacggt tgaatatcat   5340
attgatggtg atttgactgt ctccggcctt tctcacccgt ttgaatcttt acctacacat   5400
tactcaggca ttgcatttaa aatatatgag ggttctaaaa atttttatcc ttgcgttgaa   5460
ataaaggctt ctcccgcaaa agtattacag ggtcataatg tttttggtac aaccgattta   5520
gctttatgct ctgaggcttt attgcttaat tttgctaatt ctttgccttg cctgtatgat   5580
ttattggatg ttggaattcc tgatgcggta ttttctcctt acgcatctgt gcggtatttc   5640
acaccgcata tggtgcactc tcagtacaat ctgctctgat gccgcatagt taagccagcc   5700
ccgacacccg ccaacacccg ctgacgcgcc ctgacgggct tgtctgctcc cggcatccgc   5760
ttacagacaa gctgtgaccg tctccgggag ctgcatgtgt cagaggtttt caccgtcatc   5820
accgaaacgc gcgagacgaa agggcctcgt gatacgccta tttttatagg ttaatgtcat   5880
gataataatg gtttcttaga cgtcaggtgg cacttttcgg ggaaatgtgc gcggaacccc   5940
tatttgttta tttttctaaa tacattcaaa tatgtatccg ctcatgagac aataaccctg   6000
ataaatgctt caataatatt gaaaaaggaa gagtatgagt attcaacatt tccgtgtcgc   6060
ccttattccc ttttttgcgg cattttgcct tcctgttttt gctcacccag aaacgctggt   6120
gaaagtaaaa gatgctgaag atcagttggg tgcacgagtg ggttacatcg aactggatct   6180
caacagcggt aagatccttg agagttttcg ccccgaagaa cgttttccaa tgatgagcac   6240
ttttaaagtt ctgctatgtg gcgcggtatt atcccgtatt gacgccgggc aagagcaact   6300
cggtcgccgc atacactatt ctcagaatga cttggttgag tactcaccag tcacagaaaa   6360
gcatcttacg gatggcatga cagtaagaga attatgcagt gctgccataa ccatgagtga   6420
taacactgcg gccaacttac ttctgacaac gatcggagga ccgaaggagc taaccgcttt   6480
tttgcacaac atgggggatc atgtaactcg ccttgatcgt tgggaaccgg agctgaatga   6540
agccatacca aacgacgagc gtgacaccac gatgcctgta gcaatggcaa caacgttgcg   6600
caaactatta actggcgaac tacttactct agcttcccgg caacaattaa tagactggat   6660
ggaggcggat aaagttgcag gaccacttct gcgctcggcc cttccggctg gctggtttat   6720
tgctgataaa tctggagccg gtgagcgtgg gtctcgcggt atcattgcag cactggggcc   6780
agatggtaag ccctcccgta tcgtagttat ctacacgacg gggagtcagg caactatgga   6840
tgaacgaaat agacagatcg ctgagatagg tgcctcactg attaagcatt ggtaactgtc   6900
```

agaccaagtt tactcatata tactttagat tgatttaaaa cttcattttt aatttaaaag 6960
gatctaggtg aagatccttt ttgataatct catgaccaaa atcccttaac gtgagttttc 7020
gttccactga gcgtcagacc ccgtagaaaa gatcaaagga tcttcttgag atcctttttt 7080
tctgcgcgta atctgctgct tgcaaacaaa aaaaccaccg ctaccagcgg tggtttgttt 7140
gccggatcaa gagctaccaa ctctttttcc gaaggtaact ggcttcagca gagcgcagat 7200
accaaatact gtccttctag tgtagccgta gttaggccac cacttcaaga actctgtagc 7260
accgcctaca tacctcgctc tgctaatcct gttaccagtg gctgctgcca gtggcgataa 7320
gtcgtgtctt accgggttgg actcaagacg atagttaccg gataaggcgc agcggtcggg 7380
ctgaacgggg ggttcgtgca cacagcccag cttggagcga acgacctaca ccgaactgag 7440
atacctacag cgtgagctat gagaaagcgc cacgcttccc gaagggagaa aggcggacag 7500
gtatccggta agcggcaggg tcggaacagg agagcgcacg agggagcttc caggggggaaa 7560 cgcctggtat ctttatagtc ctgtcgggtt tcgccacctc tgacttgagc gtcgattttt 7620
gtgatgctcg tcaggggggc ggagcctatg gaaaaacgcc agcaacgcgg cctttttacg 7680
gttcctggcc ttttgctggc cttttgctca catgttcttt cctgcgttat cccctgattc 7740
tgtggataac cgtattaccg cctttgagtg agctgatacc gctcgccgca gccgaacgac 7800
cgagcgcagc gagtcagtga gcgaggaagc ggaagagcgc ccaatacgca aaccgcctct 7860
ccccgcgcgt tggccgattc attaatg 7887

<210> SEQ ID NO 111
<211> LENGTH: 486
<212> TYPE: PRT
<213> ORGANISM: Artificial Sequence
<220> FEATURE:
<223> OTHER INFORMATION: Synthesized

<400> SEQUENCE: 111

Met Ala Leu Pro Val Thr Ala Leu Leu Leu Pro Leu Ala Leu Leu Leu
1 5 10 15

His Ala Ala Arg Pro Asp Ile Gln Met Thr Gln Thr Thr Ser Ser Leu
20 25 30

Ser Ala Ser Leu Gly Asp Arg Val Thr Ile Ser Cys Arg Ala Ser Gln
35 40 45

Asp Ile Ser Lys Tyr Leu Asn Trp Tyr Gln Gln Lys Pro Asp Gly Thr
50 55 60

Val Lys Leu Leu Ile Tyr His Thr Ser Arg Leu His Ser Gly Val Pro
65 70 75 80

Ser Arg Phe Ser Gly Ser Gly Ser Gly Thr Asp Tyr Ser Leu Thr Ile
85 90 95

Ser Asn Leu Glu Gln Glu Asp Ile Ala Thr Tyr Phe Cys Gln Gln Gly
100 105 110

Asn Thr Leu Pro Tyr Thr Phe Gly Gly Gly Thr Lys Leu Glu Ile Thr
115 120 125

Gly Gly Gly Gly Ser Gly Gly Gly Gly Ser Gly Gly Gly Ser Glu
130 135 140

Val Lys Leu Gln Glu Ser Gly Pro Gly Leu Val Ala Pro Ser Gln Ser
145 150 155 160

Leu Ser Val Thr Cys Thr Val Ser Gly Val Ser Leu Pro Asp Tyr Gly
165 170 175

Val Ser Trp Ile Arg Gln Pro Pro Arg Lys Gly Leu Glu Trp Leu Gly
180 185 190

```
Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485


<210> SEQ ID NO 112
<211> LENGTH: 242
<212> TYPE: PRT
<213> ORGANISM: Artificial Sequence
<220> FEATURE:
<223> OTHER INFORMATION: Synthesized

<400> SEQUENCE: 112

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60
```

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asn Thr Leu Pro Tyr
85 90 95

Thr Phe Gly Gly Gly Thr Lys Leu Glu Ile Thr Gly Gly Gly Gly Ser
100 105 110

Gly Gly Gly Gly Ser Gly Gly Gly Gly Ser Glu Val Lys Leu Gln Glu
115 120 125

Ser Gly Pro Gly Leu Val Ala Pro Ser Gln Ser Leu Ser Val Thr Cys
130 135 140

Thr Val Ser Gly Val Ser Leu Pro Asp Tyr Gly Val Ser Trp Ile Arg
145 150 155 160

Gln Pro Pro Arg Lys Gly Leu Glu Trp Leu Gly Val Ile Trp Gly Ser
165 170 175

Glu Thr Thr Tyr Tyr Asn Ser Ala Leu Lys Ser Arg Leu Thr Ile Ile
180 185 190

Lys Asp Asn Ser Lys Ser Gln Val Phe Leu Lys Met Asn Ser Leu Gln
195 200 205

Thr Asp Asp Thr Ala Ile Tyr Tyr Cys Ala Lys His Tyr Tyr Tyr Gly
210 215 220

Gly Ser Tyr Ala Met Asp Tyr Trp Gly Gln Gly Thr Ser Val Thr Val
225 230 235 240

Ser Ser

<210> SEQ ID NO 113
<211> LENGTH: 112
<212> TYPE: PRT
<213> ORGANISM: Artificial Sequence
<220> FEATURE:
<223> OTHER INFORMATION: Synthesized

<400> SEQUENCE: 113

Arg Val Lys Phe Ser Arg Ser Ala Asp Ala Pro Ala Tyr Gln Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 114
<211> LENGTH: 42
<212> TYPE: PRT
<213> ORGANISM: Artificial Sequence
<220> FEATURE:
<223> OTHER INFORMATION: Synthesized

<400> SEQUENCE: 114

Lys Arg Gly Arg Lys Lys Leu Leu Tyr Ile Phe Lys Gln Pro Phe Met
1 5 10 15

Arg Pro Val Gln Thr Thr Gln Glu Glu Asp Gly Cys Ser Cys Arg Phe
20 25 30

Pro Glu Glu Glu Glu Gly Gly Cys Glu Leu
35 40

<210> SEQ ID NO 115
<211> LENGTH: 21
<212> TYPE: PRT
<213> ORGANISM: Artificial Sequence
<220> FEATURE:
<223> OTHER INFORMATION: Synthesized

<400> SEQUENCE: 115

Met Ala Leu Pro Val Thr Ala Leu Leu Leu Pro Leu Ala Leu Leu Leu
1 5 10 15

His Ala Ala Arg Pro
20

<210> SEQ ID NO 116
<211> LENGTH: 45
<212> TYPE: PRT
<213> ORGANISM: Artificial Sequence
<220> FEATURE:
<223> OTHER INFORMATION: Synthesized

<400> SEQUENCE: 116

Thr Thr Thr Pro Ala Pro Arg Pro Pro Thr Pro Ala Pro Thr Ile Ala
1 5 10 15

Ser Gln Pro Leu Ser Leu Arg Pro Glu Ala Cys Arg Pro Ala Ala Gly
20 25 30

Gly Ala Val His Thr Arg Gly Leu Asp Phe Ala Cys Asp
35 40 45

<210> SEQ ID NO 117
<211> LENGTH: 24
<212> TYPE: PRT
<213> ORGANISM: Artificial Sequence
<220> FEATURE:
<223> OTHER INFORMATION: Synthesized

<400> SEQUENCE: 117

Ile Tyr Ile Trp Ala Pro Leu Ala Gly Thr Cys Gly Val Leu Leu Leu
1 5 10 15

Ser Leu Val Ile Thr Leu Tyr Cys
20

<210> SEQ ID NO 118
<211> LENGTH: 493
<212> TYPE: DNA
<213> ORGANISM: Artificial Sequence
<220> FEATURE:
<223> OTHER INFORMATION: Synthesized

<400> SEQUENCE: 118
gggcagagcg cacatcgccc acagtccccg agaagttggg gggaggggtc ggcaattgaa 60
cgggtgccta gagaaggtgg cgcggggtaa actgggaaag tgatgtcgtg tactggctcc 120
gcctttttcc cgagggtggg ggagaaccgt atataagtgc agtagtcgcc gtgaacgttc 180
tttttcgcaa cgggtttgcc gccagaacac agctgaagct tcgaggggct cgcatctctc 240
cttcacgcgc ccgccgccct acctgaggcc gccatccacg ccggttgagt cgcgttctgc 300
cgcctcccgc ctgtggtgcc tcctgaactg cgtccgccgt ctaggtaagt ttaaagctca 360
ggtcgagacc gggcctttgt ccggcgctcc cttggagcct acctagactc agccggctct 420
ccacgctttg cctgaccctg cttgctcaac tctacgtctt tgtttcgttt tctgttctgc 480
gccgttacag atc 493

<210> SEQ ID NO 119
<211> LENGTH: 2184
<212> TYPE: DNA
<213> ORGANISM: Artificial Sequence
<220> FEATURE:
<223> OTHER INFORMATION: Synthesized

<400> SEQUENCE: 119
gggcagagcg cacatcgccc acagtccccg agaagttggg gggaggggtc ggcaattgaa 60
cgggtgccta gagaaggtgg cgcggggtaa actgggaaag tgatgtcgtg tactggctcc 120
gcctttttcc cgagggtggg ggagaaccgt atataagtgc agtagtcgcc gtgaacgttc 180
tttttcgcaa cgggtttgcc gccagaacac agctgaagct tcgaggggct cgcatctctc 240
cttcacgcgc ccgccgccct acctgaggcc gccatccacg ccggttgagt cgcgttctgc 300
cgcctcccgc ctgtggtgcc tcctgaactg cgtccgccgt ctaggtaagt ttaaagctca 360
ggtcgagacc gggcctttgt ccggcgctcc cttggagcct acctagactc agccggctct 420
ccacgctttg cctgaccctg cttgctcaac tctacgtctt tgtttcgttt tctgttctgc 480
gccgttacag atccaagctg tgaccggcgc ctactctaga gctagcgcag tcagtgcttc 540
tgacacaaca gtctcgaact taactagcac catggcgctc ccagtgacag ccttactttt 600
acctctggcg ttattattgc acgcggctcg tcctgacata cagatgactc agactacctc 660
ttccctatct gcttctttag gcgaccgagt aacaatatct tgccgggcca gccaggacat 720
ctcaaaatac ttaaactggt atcagcagaa gccggacgga acagttaagt tgctcattta 780
ccacacgtcg agattacact caggcgttcc tagccgattt tcgggttccg gttccggtac 840
ggactacagc ctgacaatca gtaaccttga gcaggaggac atcgccacct acttctgtca 900
gcagggcaac acgctcccgt acacattcgg tgggggaact aagctggaga ttaccggagg 960
cggtggcagc ggtggcggcg gcagcggggg tggcggctcg gaggtcaagt tacaggagag 1020
cggaccgggc ttggtcgcac ctagccagag cctctcagtc acgtgcactg tgtctggagt 1080
cagtctccca gactacgggg tatcatggat acgacagccg cctagaaagg gcttagagtg 1140
gctgggggtt atctggggaa gtgaaaccac atactacaac tcagctctca agagccgcct 1200
caccatcatt aaggacaaca gtaagtcgca ggttttctta aagatgaact ctctccagac 1260
tgacgacacc gctatttact actgcgcgaa gcactactac tacggcggga gttacgcaat 1320
ggactactgg ggtcagggca cttctgtgac cgtatccagc actactaccc cagcccccacg 1380 tccccccacg ccagctccaa cgatagcaag tcagccctta tctcttcgcc ctgaggcttg 1440
caggcccgcg gcgggcggcg ccgttcacac gcgaggacta gacttcgcct gcgacatcta 1500
catctgggca ccactagccg ggacttgcgg agtgttgttg ttgagcttgg taataacgct 1560
ctactgcaag cgtgggagaa agaagctctt gtacattttc aagcagccat tcatgcgtcc 1620
cgttcagacg actcaggagg aggacggctg ctcgtgccga ttcccggagg aggaggaggg 1680
cggttgcgaa ctcagagtga agttctctcg ctccgcggac gcacccgctt accagcaggg 1740
tcagaaccag ctatacaacg agttaaacct ggggcgccgg gaggagtacg acgtgttaga 1800
caagcgtaga ggtagggacc cggagatggg aggcaagcct cggagaaaga acccccagga 1860
gggcctgtac aacgaactcc agaaggacaa gatggctgag gcgtactcgg agattggtat 1920
gaagggcgag agacgtcgcg gaaagggaca cgacggctta taccaggggc tttccaccgc 1980
gaccaaggac acatacgacg cgctgcacat gcaagcctta ccacctcgat gaggtaccag 2040
cggccgcttc gagcagacat gataagatac attgatgagt ttggacaaac cacaactaga 2100
atgcagtgaa aaaaatgctt tatttgtgaa atttgtgatg ctattgcttt atttgtaacc 2160
attataagct gcaataaaca agtt 2184

<210> SEQ ID NO 120
<211> LENGTH: 6811
<212> TYPE: DNA
<213> ORGANISM: Artificial Sequence
<220> FEATURE:
<223> OTHER INFORMATION: Synthesized

<400> SEQUENCE: 120
atatccagaa ccctgaccct gccgtgtacc agctgagaga ctctaaatcc agtgacaagt 60
ctgtctgcct attcaccgat tttgattctc aaacaaatgt gtcacaaagt aaggattctg 120
atgtgtatat cacagacaaa actgtgctag acatgaggtc tatggacttc aagagcaaca 180
gtgctgtggc ctggagcaag ggcagagcgc acatcgccca cagtccccga gaagttgggg 240
ggaggggtcg gcaattgaac gggtgcctag agaaggtggc gcggggtaaa ctgggaaagt 300
gatgtcgtgt actggctccg cctttttccc gagggtgggg gagaaccgta tataagtgca 360
gtagtcgccg tgaacgttct ttttcgcaac gggtttgccg ccagaacaca gctgaagctt 420
cgaggggctc gcatctctcc ttcacgcgcc cgccgcccta cctgaggccg ccatccacgc 480
cggttgagtc gcgttctgcc gcctcccgcc tgtggtgcct cctgaactgc gtccgccgtc 540
taggtaagtt taaagctcag gtcgagaccg ggcctttgtc cggcgctccc ttggagccta 600
cctagactca gccggctctc cacgctttgc ctgaccctgc ttgctcaact ctacgtcttt 660
gtttcgtttt ctgttctgcg ccgttacaga tccaagctgt gaccggcgcc tactctagag 720
ctagcgcagt cagtgcttct gacacaacag tctcgaactt aactagcacc atggcgctcc 780
cagtgacagc cttactttta cctctggcgt tattattgca cgcggctcgt cctgacatac 840
agatgactca gactacctct tccctatctg cttctttagg cgaccgagta acaatatctt 900
gccgggccag ccaggacatc tcaaaatact taaactggta tcagcagaag ccggacggaa 960
cagttaagtt gctcatttac cacacgtcga gattacactc aggcgttcct agccgatttt 1020
cgggttccgg ttccggtacg gactacagcc tgacaatcag taaccttgag caggaggaca 1080
tcgccaccta cttctgtcag cagggcaaca cgctcccgta cacattcggt gggggaacta 1140
agctggagat taccggaggc ggtggcagcg gtggcggcgg cagcgggggt ggcggctcgg 1200
aggtcaagtt acaggagagc ggaccgggct tggtcgcacc tagccagagc ctctcagtca 1260
cgtgcactgt gtctggagtc agtctcccag actacggggt atcatggata cgacagccgc 1320
ctagaaaggg cttagagtgg ctgggggtta tctggggaag tgaaaccaca tactacaact 1380
cagctctcaa gagccgcctc accatcatta aggacaacag taagtcgcag gttttcttaa 1440
agatgaactc tctccagact gacgacaccg ctatttacta ctgcgcgaag cactactact 1500
acggcgggag ttacgcaatg gactactggg gtcagggcac ttctgtgacc gtatccagca 1560
ctactacccc agccccacgt ccccccacgc cagctccaac gatagcaagt cagcccttat 1620
ctcttcgccc tgaggcttgc aggcccgcgg cgggcggcgc cgttcacacg cgaggactag 1680
acttcgcctg cgacatctac atctgggcac cactagccgg gacttgcgga gtgttgttgt 1740

-continued tgagcttggt aataacgctc tactgcaagc gtgggagaaa gaagctcttg tacattttca 1800
agcagccatt catgcgtccc gttcagacga ctcaggagga ggacggctgc tcgtgccgat 1860
tcccggagga ggaggagggc ggttgcgaac tcagagtgaa gttctctcgc tccgcggacg 1920
cacccgctta ccagcagggt cagaaccagc tatacaacga gttaaacctg ggcgcccggg 1980
aggagtacga cgtgttagac aagcgtagag gtagggaccc ggagatggga ggcaagcctc 2040
ggagaaagaa cccccaggag ggcctgtaca acgaactcca gaaggacaag atggctgagg 2100
cgtactcgga gattggtatg aagggcgaga gacgtcgcgg aaagggacac gacggcttat 2160
accaggggct ttccaccgcg accaaggaca catacgacgc gctgcacatg caagccttac 2220
cacctcgatg aggtaccagc ggccgcttcg agcagacatg ataagataca ttgatgagtt 2280
tggacaaacc acaactagaa tgcagtgaaa aaaatgcttt atttgtgaaa tttgtgatgc 2340
tattgcttta tttgtaacca ttataagctg caataaacaa gttcaaatct gactttgcat 2400
gtgcaaacgc cttcaacaac agcattattc cagaagacac cttcttcccc agcccaggta 2460
agggcagctt tggtgccttc gcaggctgtt tccttgcttc aggaatggcc aggttctgcc 2520
cagagctctg gtcaatgatg tctaaaactc ctctgattgg tggtctcggc cttatccatt 2580
gccaccaaaa ccctcttttt actaagaaac agtgagcctt gttctggcag tccagagaat 2640
gacacgggaa aaaagcagat gaagagaagg tggcaggaga gggcacgtgg cccagcctca 2700
gtctctccaa ctgagttcct gcctgcctgc ctttgctcag actgtttgcc ccttactgct 2760
cttctaggcc tcattctaag ccccttctcc aagttgcctc tccttatttc tccctgtctg 2820
ccaaaaaatc tttcccagct cactaagtca gtctcacgca gtcactcatt aacccaccaa 2880
tcactgattg tgccggcaca tgaatgcacc aggtgttgaa gtggaggaat taaaaagtca 2940
gatgaggggt gtgcccagag gaagcaccat tctagttggg ggagcccatc tgtcagctgg 3000
gaaaagtcca aataacttca gattggaatg tgttttaact cagggttgag aaaacagcta 3060
ccttcaggac aaaagtcagg gaagggctct ctgaagaaat gctacttgaa gataccagcc 3120
ctaccaaggg cagggagagg accctataga ggcctgggac aggagctcaa tgagaaagga 3180
gaagagcagc aggcatgagt tgaatgaagg aggcagggcc gggtcacagg gccttctagg 3240
ccatgagagg gtagacagta ttctaaggac gccagaaagc tgttgatcgg cttcaagcag 3300
gggagggaca cctaatttgc ttttcttttt tttttttttt tttttttttt tttttgagat 3360
ggagttttgc tcttgttgcc caggctggag tgcaatggtg catcttggct cactgcaacc 3420
tccgcctccc aggttcaagt gattctcctg cctcagcctc ccgagtagct gagattacag 3480
gcacccgcca ccatgcctgg ctaatttttt gtatttttag tagagacagg gtttcactat 3540
gttggccagg ctggtctcga actcctgacc tcaggtgatc cacccgcttc agcctcccaa 3600
agtgctggga ttacaggcgt gagccaccac acccggcctg cttttcttaa agatcaatct 3660
gagtgctgta cggagagtgg gttgtaagcc aagagtagaa gcagaaaggg agcagttgca 3720
gcagagagat gatggaggcc tgggcagggt ggtggcaggg aggtaaccaa caccattcag 3780
gtttcaaagg tagaaccatg cagggatgag aaagcaaaga ggggatcaag gaaggcagct 3840
ggattttggc ctgagcagct gagtcaatga tagtgccgtt tactaagaag aaaccaagga 3900
aaaaatttgg ggtgcaggga tcaaaacttt ttggaacata tgaaagtacg tgtttatact 3960
ctttatggcc cttgtcacta tgtatgcctc gctgcctcca ttggactcta gaatgaagcc 4020
aggcaagagc agggtctatg tgtgatggca catgtggcca gggtcatgca acatgtactt 4080

-continued

```
tgtacaaaca gtgtatattg agtaaataga aatggtgtcc aggagccgag gtatcggtcc   4140
tgccagggcc aggggctctc cctagcaggt gctcatatgc tgtaagttcc ctccagatct   4200
ctccacaagg aggcatggaa aggctgtagt tgttcacctg cccaagaact aggaggtctg   4260
gggtgggaga gtcagcctgc tctggatgct gaaagaatgt ctgtttttcc ttttagaaag   4320
ttcctgtgat gtcaagctgg tcgagaaaag ctttgaaaca ggtaagacag gggtctagcc   4380
tgggtttgca caggattgcg gaagtgatga acccgcaata accctgcctg gatgagggag   4440
tgggaagaaa ttagtagatg tgggaatgaa tgatgaggaa tggaaacagc ggttcaagac   4500
ctgcccagag ctgggtgggg tctctcctga atccctctca ccatctctga ctttccattc   4560
taagcacttt gaggatgagt ttctagcttc aatagaccaa ggactctctc ctaggcctct   4620
gtattccttt caacagctcc actgtcaaga gagccagaga gagcttctgg gtggcccagc   4680
tgtgaaattt ctgagtccct tagggatagc cctaaacgaa ccagatcatc ctgaggacag   4740
ccaagaggtt ttgccttctt tcaagacaag caacagtact cacataggct gtgggcaatg   4800
gtcctgtctc tcaagaatcc cctgccactc ctcacaccca ccctgggccc atattcattt   4860
ccatttgagt tgttcttatt gagtcatcct tcctgtggta gcggaactca ctaaggggcc   4920
catctggacc cgaggtattg tgatgataaa ttctgagcac ctaccccatc cccagaaggg   4980
ctcagaaata aaataagagc caagtctagt cggtgtttcc tgtcttgaaa cacaatactg   5040
ttggccctgg aagaatgcac agaatctgtt tgtaagggga tatgcacaga agctgcaagg   5100
gacaggaggt gcaggagctg caggcctccc ccacccagcc tgctctgcct tggggaaaac   5160
cgtgggtgtg tcctgcaggc catgcaggcc tgggacatgc aagcccataa ccgctgtggc   5220
ctcttggttt tacagatacg aacctaaact ttcaaaacct gtcagtgatt gggttccgaa   5280
tcctcctcct gaaagtggcc gggtttaatc tgctcatgac gctgcggctg tggtccagct   5340
gaggtgaggg gccttgaagc tgggagtggg gtttagggac gcgggtctct gggtgcatcc   5400
taagctctga gagcaaacct ccctgcaggg tcttgctttt aagtccaaag cctgagccca   5460
ccaaactctc ctacttcttc ctgttacaaa ttcctcttgt gcaataataa tggcctgaaa   5520
cgctgtaaaa tatcctcatt tcagccgcct cagttgcact tctcccctat gaggtaggaa   5580
gaacagttgt ttagaaacga agaaactgag gccccacagc taatgagtgg aggaagagag   5640
acacttgtgt acaccacatg ccttgtgttg tacttctctc accgtgtaac ctcctcatgt   5700
cctctctccc cagtacggct ctcttagctc agtagaaaga agacattaca ctcatattac   5760
accccaatcc tggctagagt ctccgcaccc tcctccccca gggtccccag tcgtcttgct   5820
gacaactgca tcctgttcca tcaccatcaa aaaaaaactc caggctgggt gcgggggctc   5880
acacctgtaa tcccagcact ttgggaggca gaggcaggag gagcacagga gctggagacc   5940
agcctgggca acacagggag accccgcctc tacaaaaagt gaaaaaatta accaggtgtg   6000
gtgctgcaca cctgtagtcc cagctactta agaggctgag atgggaggat cgcttgagcc   6060
ctggaatgtt gaggctacaa tgagctgtga ttgcgtcact gcactccagc ctggaagaca   6120
aagcaagatc ctgtctcaaa taataaaaaa aataagaact ccagggtaca tttgctccta   6180
gaactctacc acatagcccc aaacagagcc atcaccatca catccctaac agtcctgggt   6240
cttcctcagt gtccagcctg acttctgttc ttcctcattc cagatctgca agattgtaag   6300
acagcctgtg ctccctcgct ccttcctctg cattgcccct cttctccctc tccaaacaga   6360
gggaactctc ctacccccaa ggaggtgaaa gctgctacca cctctgtgcc cccccggcaa   6420
tgccaccaac tggatcctac ccgaatttat gattaagatt gctgaagagc tgccaaacac   6480
```

tgctgccacc ccctctgttc ccttattgct gcttgtcact gcctgacatt cacggcagag 6540
gcaaggctgc tgcagcctcc cctggctgtg cacattccct cctgctcccc agagactgcc 6600
tccgccatcc cacagatgat ggatcttcag tgggttctct tgggctctag gtcctgcaga 6660
atgttgtgag ggtttattt ttttttaata gtgttcataa agaaatacat agtattcttc 6720
ttctcaagac gtgggggaa attatctcat tatcgaggcc ctgctatgct gtgtatctgg 6780
gcgtgttgta tgtcctgctg ccgatgcctt c 6811

<210> SEQ ID NO 121
<211> LENGTH: 6811
<212> TYPE: DNA
<213> ORGANISM: Artificial Sequence
<220> FEATURE:
<223> OTHER INFORMATION: Synthesized

<400> SEQUENCE: 121
atatccagaa ccctgaccct gccgtgtacc agctgagaga ctctaaatcc agtgacaagt 60
ctgtctgcct attcaccgat tttgattctc aaacaaatgt gtcacgggca gagcgcacat 120
cgcccacagt ccccgagaag ttgggggag gggtcggcaa ttgaacgggt gcctagagaa 180
ggtggcgcgg ggtaaactgg gaaagtgatg tcgtgtactg gctccgcctt tttcccgagg 240
gtgggggaga accgtatata agtgcagtag tcgccgtgaa cgttcttttt cgcaacgggt 300
ttgccgccag aacacagctg aagcttcgag gggctcgcat ctctccttca cgcgcccgcc 360
gccctacctg aggccgccat ccacgccggt tgagtcgcgt tctgccgcct cccgcctgtg 420
gtgcctcctg aactgcgtcc gccgtctagg taagtttaaa gctcaggtcg agaccgggcc 480
tttgtccggc gctcccttgg agcctaccta gactcagccg gctctccacg ctttgcctga 540
ccctgcttgc tcaactctac gtctttgttt cgttttctgt tctgcgccgt tacagatcca 600
agctgtgacc ggcgcctact ctagagctag cgcagtcagt gcttctgaca caacagtctc 660
gaacttaact agcaccatgg cgctcccagt gacagcctta cttttacctc tggcgttatt 720
attgcacgcg gctcgtcctg acatacagat gactcagact acctcttccc tatctgcttc 780
tttaggcgac cgagtaacaa tatcttgccg ggccagccag gacatctcaa aatacttaaa 840
ctggtatcag cagaagccgg acggaacagt taagttgctc atttaccaca cgtcgagatt 900
acactcaggc gttcctagcc gattttcggg ttccggttcc ggtacggact acagcctgac 960
aatcagtaac cttgagcagg aggacatcgc cacctacttc tgtcagcagg gcaacacgct 1020
cccgtacaca ttcggtgggg gaactaagct ggagattacc ggaggcggtg gcagcggtgg 1080
cggcggcagc gggggtggcg gctcggaggt caagttacag gagagcggac cgggcttggt 1140
cgcacctagc cagagcctct cagtcacgtg cactgtgtct ggagtcagtc tcccagacta 1200
cggggtatca tggatacgac agccgcctag aaagggctta gagtggctgg gggttatctg 1260
gggaagtgaa accacatact acaactcagc tctcaagagc cgcctcacca tcattaagga 1320
caacagtaag tcgcaggttt tcttaaagat gaactctctc cagactgacg acaccgctat 1380
ttactactgc gcgaagcact actactacgg cgggagttac gcaatggact actggggtca 1440
gggcacttct gtgaccgtat ccagcactac taccccagcc ccacgtcccc ccacgccagc 1500
tccaacgata gcaagtcagc ccttatctct tcgccctgag gcttgcaggc ccgcggcggg 1560
cggcgccgtt cacacgcgag gactagactt cgcctgcgac atctacatct gggcaccact 1620
agccgggact tgcggagtgt tgttgttgag cttggtaata acgctctact gcaagcgtgg 1680
gagaaagaag ctcttgtaca ttttcaagca gccattcatg cgtcccgttc agacgactca 1740
ggaggaggac ggctgctcgt gccgattccc ggaggaggag gagggcggtt gcgaactcag 1800
agtgaagttc tctcgctccg cggacgcacc cgcttaccag cagggtcaga accagctata 1860
caacgagtta aacctggggc gccgggagga gtacgacgtg ttagacaagc gtagaggtag 1920
ggacccggag atgggaggca agcctcggag aaagaacccc caggagggcc tgtacaacga 1980
actccagaag gacaagatgg ctgaggcgta ctcggagatt ggtatgaagg gcgagagacg 2040
tcgcggaaag ggacacgacg gcttatacca ggggctttcc accgcgacca aggacacata 2100
cgacgcgctg cacatgcaag ccttaccacc tcgatgaggt accagcggcc gcttcgagca 2160
gacatgataa gatacattga tgagtttgga caaaccacaa ctagaatgca gtgaaaaaaa 2220
tgctttattt gtgaaatttg tgatgctatt gctttatttg taaccattat aagctgcaat 2280
aaacaagtta aagtaaggat tctgatgtgt atatcacaga caaaactgtg ctagacatga 2340
ggtctatgga cttcaagagc aacagtgctg tggcctggag caacaaatct gactttgcat 2400
gtgcaaacgc cttcaacaac agcattattc cagaagacac cttcttcccc agcccaggta 2460
agggcagctt tggtgccttc gcaggctgtt tccttgcttc aggaatggcc aggttctgcc 2520
cagagctctg gtcaatgatg tctaaaactc ctctgattgg tggtctcggc cttatccatt 2580
gccaccaaaa ccctcttttt actaagaaac agtgagcctt gttctggcag tccagagaat 2640
gacacgggaa aaaagcagat gaagagaagg tggcaggaga gggcacgtgg cccagcctca 2700
gtctctccaa ctgagttcct gcctgcctgc ctttgctcag actgtttgcc ccttactgct 2760
cttctaggcc tcattctaag ccccttctcc aagttgcctc tccttatttc tccctgtctg 2820
ccaaaaaatc tttcccagct cactaagtca gtctcacgca gtcactcatt aacccaccaa 2880
tcactgattg tgccggcaca tgaatgcacc aggtgttgaa gtggaggaat taaaaagtca 2940
gatgaggggt gtgcccagag gaagcaccat tctagttggg ggagcccatc tgtcagctgg 3000
gaaaagtcca aataacttca gattggaatg tgttttaact cagggttgag aaaacagcta 3060
ccttcaggac aaaagtcagg gaagggctct ctgaagaaat gctacttgaa gataccagcc 3120
ctaccaaggg cagggagagg accctataga ggcctgggac aggagctcaa tgagaaagga 3180
gaagagcagc aggcatgagt tgaatgaagg aggcagggcc gggtcacagg gccttctagg 3240
ccatgagagg gtagacagta ttctaaggac gccagaaagc tgttgatcgg cttcaagcag 3300
gggagggaca cctaatttgc ttttcttttt tttttttttt tttttttttt tttttgagat 3360
ggagttttgc tcttgttgcc caggctggag tgcaatggtg catcttggct cactgcaacc 3420
tccgcctccc aggttcaagt gattctcctg cctcagcctc ccgagtagct gagattacag 3480
gcacccgcca ccatgcctgg ctaatttttt gtatttttag tagagacagg gtttcactat 3540
gttggccagg ctggtctcga actcctgacc tcaggtgatc cacccgcttc agcctcccaa 3600
agtgctggga ttacaggcgt gagccaccac acccggcctg cttttcttaa agatcaatct 3660
gagtgctgta cggagagtgg gttgtaagcc aagagtagaa gcagaaaggg agcagttgca 3720
gcagagagat gatggaggcc tgggcagggt ggtggcaggg aggtaaccaa caccattcag 3780
gtttcaaagg tagaaccatg cagggatgag aaagcaaaga ggggatcaag gaaggcagct 3840
ggattttggc ctgagcagct gagtcaatga tagtgccgtt tactaagaag aaaccaagga 3900
aaaaatttgg ggtgcaggga tcaaaacttt ttggaacata tgaaagtacg tgtttatact 3960
ctttatggcc cttgtcacta tgtatgcctc gctgcctcca ttggactcta gaatgaagcc 4020
aggcaagagc agggtctatg tgtgatggca catgtggcca gggtcatgca acatgtactt 4080

-continued

```
tgtacaaaca gtgtatattg agtaaataga aatggtgtcc aggagccgag gtatcggtcc   4140
tgccagggcc aggggctctc cctagcaggt gctcatatgc tgtaagttcc ctccagatct   4200
ctccacaagg aggcatggaa aggctgtagt tgttcacctg cccaagaact aggaggtctg   4260
gggtgggaga gtcagcctgc tctggatgct gaaagaatgt ctgtttttcc ttttagaaag   4320
ttcctgtgat gtcaagctgg tcgagaaaag ctttgaaaca ggtaagacag gggtctagcc   4380
tgggtttgca caggattgcg gaagtgatga acccgcaata accctgcctg gatgagggag   4440
tgggaagaaa ttagtagatg tgggaatgaa tgatgaggaa tggaaacagc ggttcaagac   4500
ctgcccagag ctgggtgggg tctctcctga atccctctca ccatctctga ctttccattc   4560
taagcacttt gaggatgagt ttctagcttc aatagaccaa ggactctctc ctaggcctct   4620
gtattccttt caacagctcc actgtcaaga gagccagaga gagcttctgg gtggcccagc   4680
tgtgaaattt ctgagtccct tagggatagc cctaaacgaa ccagatcatc ctgaggacag   4740
ccaagaggtt ttgccttctt tcaagacaag caacagtact cacataggct gtgggcaatg   4800
gtcctgtctc tcaagaatcc cctgccactc ctcacaccca ccctgggccc atattcattt   4860
ccatttgagt tgttcttatt gagtcatcct tcctgtggta gcggaactca ctaaggggcc   4920
catctggacc cgaggtattg tgatgataaa ttctgagcac ctaccccatc cccagaaggg   4980
ctcagaaata aaataagagc caagtctagt cggtgtttcc tgtcttgaaa cacaatactg   5040
ttggccctgg aagaatgcac agaatctgtt tgtaagggga tatgcacaga agctgcaagg   5100
gacaggaggt gcaggagctg caggcctccc ccacccagcc tgctctgcct tggggaaaac   5160
cgtgggtgtg tcctgcaggc catgcaggcc tgggacatgc aagcccataa ccgctgtggc   5220
ctcttggttt tacagatacg aacctaaact ttcaaaacct gtcagtgatt gggttccgaa   5280
tcctcctcct gaaagtggcc gggtttaatc tgctcatgac gctgcggctg tggtccagct   5340
gaggtgaggg gccttgaagc tgggagtggg gtttagggac gcgggtctct gggtgcatcc   5400
taagctctga gagcaaacct ccctgcaggg tcttgctttt aagtccaaag cctgagccca   5460
ccaaactctc ctacttcttc ctgttacaaa ttcctcttgt gcaataataa tggcctgaaa   5520
cgctgtaaaa tatcctcatt tcagccgcct cagttgcact tctcccctat gaggtaggaa   5580
gaacagttgt ttagaaacga agaaactgag gccccacagc taatgagtgg aggaagagag   5640
acacttgtgt acaccacatg ccttgtgttg tacttctctc accgtgtaac ctcctcatgt   5700
cctctctccc cagtacggct ctcttagctc agtagaaaga agacattaca ctcatattac   5760
accccaatcc tggctagagt ctccgcaccc tcctccccca gggtccccag tcgtcttgct   5820
gacaactgca tcctgttcca tcaccatcaa aaaaaaactc caggctgggt gcgggggctc   5880
acacctgtaa tcccagcact ttgggaggca gaggcaggag gagcacagga gctggagacc   5940
agcctgggca acacagggag accccgcctc tacaaaaagt gaaaaaatta accaggtgtg   6000
gtgctgcaca cctgtagtcc cagctactta agaggctgag atgggaggat cgcttgagcc   6060
ctggaatgtt gaggctacaa tgagctgtga ttgcgtcact gcactccagc ctggaagaca   6120
aagcaagatc ctgtctcaaa taataaaaaa aataagaact ccagggtaca tttgctccta   6180
gaactctacc acatagcccc aaacagagcc atcaccatca catccctaac agtcctgggt   6240
cttcctcagt gtccagcctg acttctgttc ttcctcattc cagatctgca agattgtaag   6300
acagcctgtg ctccctcgct ccttcctctg cattgcccct cttctccctc tccaaacaga   6360
gggaactctc ctacccccaa ggaggtgaaa gctgctacca cctctgtgcc cccccggcaa   6420
```

```
tgccaccaac tggatcctac ccgaatttat gattaagatt gctgaagagc tgccaaacac   6480

tgctgccacc ccctctgttc ccttattgct gcttgtcact gcctgacatt cacggcagag   6540

gcaaggctgc tgcagcctcc cctggctgtg cacattccct cctgctcccc agagactgcc   6600

tccgccatcc cacagatgat ggatcttcag tgggttctct tgggctctag gtcctgcaga   6660

atgttgtgag ggtttattt tttttaata gtgttcataa agaaatacat agtattcttc   6720

ttctcaagac gtggggggaa attatctcat tatcgaggcc ctgctatgct gtgtatctgg   6780

gcgtgttgta tgtcctgctg ccgatgcctt c                                  6811
```

<210> SEQ ID NO 122
<211> LENGTH: 6811
<212> TYPE: DNA
<213> ORGANISM: Artificial Sequence
<220> FEATURE:
<223> OTHER INFORMATION: Synthesized

<400> SEQUENCE: 122

```
atatccagaa ccctgaccct gccgtgtacc agctgagaga ctctaaatcc agtgacaagt     60

ctgtctgcct attcaccgat tttgattctc aaacaaatgt gtcacaaagt aaggattctg    120

atgtgtatat gggcagagcg cacatcgccc acagtccccg agaagttggg gggaggggtc    180

ggcaattgaa cgggtgccta gagaaggtgg cgcggggtaa actgggaaag tgatgtcgtg    240

tactggctcc gcctttttcc cgagggtggg ggagaaccgt atataagtgc agtagtcgcc    300

gtgaacgttc tttttcgcaa cgggtttgcc gccagaacac agctgaagct tcgaggggct    360

cgcatctctc cttcacgcgc ccgccgccct acctgaggcc gccatccacg ccggttgagt    420

cgcgttctgc cgcctcccgc ctgtggtgcc tcctgaactg cgtccgccgt ctaggtaagt    480

ttaaagctca ggtcgagacc gggcctttgt ccggcgctcc cttggagcct acctagactc    540

agccggctct ccacgctttg cctgaccctg cttgctcaac tctacgtctt tgtttcgttt    600

tctgttctgc gccgttacag atccaagctg tgaccggcgc ctactctaga gctagcgcag    660

tcagtgcttc tgacacaaca gtctcgaact taactagcac catggcgctc ccagtgacag    720

ccttactttt acctctggcg ttattattgc acgcggctcg tcctgacata cagatgactc    780

agactacctc ttccctatct gcttctttag gcgaccgagt aacaatatct tgccgggcca    840

gccaggacat ctcaaaatac ttaaactggt atcagcagaa gccggacgga acagttaagt    900

tgctcattta ccacacgtcg agattacact caggcgttcc tagccgattt tcgggttccg    960

gttccggtac ggactacagc ctgacaatca gtaaccttga gcaggaggac atcgccacct   1020

acttctgtca gcagggcaac acgctcccgt acacattcgg tgggggaact aagctggaga   1080

ttaccggagg cggtggcagc ggtggcggcg gcagcggggg tggcggctcg gaggtcaagt   1140

tacaggagag cggaccgggc ttggtcgcac ctagccagag cctctcagtc acgtgcactg   1200

tgtctggagt cagtctccca gactacgggg tatcatggat acgacagccg cctagaaagg   1260

gcttagagtg gctgggggtt atctggggaa gtgaaaccac atactacaac tcagctctca   1320

agagccgcct caccatcatt aaggacaaca gtaagtcgca ggttttctta aagatgaact   1380

ctctccagac tgacgacacc gctatttact actgcgcgaa gcactactac tacggcggga   1440

gttacgcaat ggactactgg ggtcagggca cttctgtgac cgtatccagc actactaccc   1500

cagccccacg tccccccacg ccagctccaa cgatagcaag tcagccctta tctcttcgcc   1560

ctgaggcttg caggcccgcg gcgggcggcg ccgttcacac gcgaggacta gacttcgcct   1620

gcgacatcta catctgggca ccactagccg ggacttgcgg agtgttgttg ttgagcttgg   1680
```

```
taataacgct ctactgcaag cgtgggagaa agaagctctt gtacattttc aagcagccat   1740
tcatgcgtcc cgttcagacg actcaggagg aggacggctg ctcgtgccga ttcccggagg   1800
aggaggaggg cggttgcgaa ctcagagtga agttctctcg ctccgcggac gcacccgctt   1860
accagcaggg tcagaaccag ctatacaacg agttaaacct ggggcgccgg gaggagtacg   1920
acgtgttaga caagcgtaga ggtagggacc cggagatggg aggcaagcct cggagaaaga   1980
acccccagga gggcctgtac aacgaactcc agaaggacaa gatggctgag gcgtactcgg   2040
agattggtat gaagggcgag agacgtcgcg gaaagggaca cgacggctta taccaggggc   2100
tttccaccgc gaccaaggac acatacgacg cgctgcacat gcaagcctta ccacctcgat   2160
gaggtaccag cggccgcttc gagcagacat gataagatac attgatgagt ttggacaaac   2220
cacaactaga atgcagtgaa aaaaatgctt tatttgtgaa atttgtgatg ctattgcttt   2280
atttgtaacc attataagct gcaataaaca agttcacaga caaaactgtg ctagacatga   2340
ggtctatgga cttcaagagc aacagtgctg tggcctggag caacaaatct gactttgcat   2400
gtgcaaacgc cttcaacaac agcattattc cagaagacac cttcttcccc agcccaggta   2460
agggcagctt tggtgccttc gcaggctgtt tccttgcttc aggaatggcc aggttctgcc   2520
cagagctctg gtcaatgatg tctaaaactc ctctgattgg tggtctcggc cttatccatt   2580
gccaccaaaa ccctcttttt actaagaaac agtgagcctt gttctggcag tccagagaat   2640
gacacgggaa aaaagcagat gaagagaagg tggcaggaga gggcacgtgg cccagcctca   2700
gtctctccaa ctgagttcct gcctgcctgc ctttgctcag actgtttgcc ccttactgct   2760
cttctaggcc tcattctaag ccccttctcc aagttgcctc tccttatttc tccctgtctg   2820
ccaaaaaatc tttcccagct cactaagtca gtctcacgca gtcactcatt aacccaccaa   2880
tcactgattg tgccggcaca tgaatgcacc aggtgttgaa gtggaggaat taaaaagtca   2940
gatgaggggt gtgcccagag gaagcaccat tctagttggg ggagcccatc tgtcagctgg   3000
gaaaagtcca aataacttca gattggaatg tgttttaact cagggttgag aaaacagcta   3060
ccttcaggac aaaagtcagg gaagggctct ctgaagaaat gctacttgaa gataccagcc   3120
ctaccaaggg cagggagagg accctataga ggcctgggac aggagctcaa tgagaaagga   3180
gaagagcagc aggcatgagt tgaatgaagg aggcagggcc gggtcacagg gccttctagg   3240
ccatgagagg gtagacagta ttctaaggac gccagaaagc tgttgatcgg cttcaagcag   3300
gggagggaca cctaatttgc ttttcttttt tttttttttt tttttttttt tttttgagat   3360
ggagttttgc tcttgttgcc caggctggag tgcaatggtg catcttggct cactgcaacc   3420
tccgcctccc aggttcaagt gattctcctg cctcagcctc ccgagtagct gagattacag   3480
gcacccgcca ccatgcctgg ctaatttttt gtatttttag tagagacagg gtttcactat   3540
gttggccagg ctggtctcga actcctgacc tcaggtgatc cacccgcttc agcctcccaa   3600
agtgctggga ttacaggcgt gagccaccac acccggcctg cttttcttaa agatcaatct   3660
gagtgctgta cggagagtgg gttgtaagcc aagagtagaa gcagaaaggg agcagttgca   3720
gcagagagat gatggaggcc tgggcagggt ggtggcaggg aggtaaccaa caccattcag   3780
gtttcaaagg tagaaccatg cagggatgag aaagcaaaga ggggatcaag gaaggcagct   3840
ggattttggc ctgagcagct gagtcaatga tagtgccgtt tactaagaag aaaccaagga   3900
aaaaatttgg ggtgcaggga tcaaaacttt ttggaacata tgaaagtacg tgtttatact   3960
ctttatggcc cttgtcacta tgtatgcctc gctgcctcca ttggactcta gaatgaagcc   4020
```

-continued

```
aggcaagagc agggtctatg tgtgatggca catgtggcca gggtcatgca acatgtactt   4080
tgtacaaaca gtgtatattg agtaaataga aatggtgtcc aggagccgag gtatcggtcc   4140
tgccagggcc aggggctctc cctagcaggt gctcatatgc tgtaagttcc ctccagatct   4200
ctccacaagg aggcatggaa aggctgtagt tgttcacctg cccaagaact aggaggtctg   4260
gggtgggaga gtcagcctgc tctggatgct gaaagaatgt ctgtttttcc ttttagaaag   4320
ttcctgtgat gtcaagctgg tcgagaaaag ctttgaaaca ggtaagacag ggtctagcc    4380
tgggtttgca caggattgcg gaagtgatga acccgcaata accctgcctg gatgagggag   4440
tgggaagaaa ttagtagatg tgggaatgaa tgatgaggaa tggaaacagc ggttcaagac   4500
ctgcccagag ctgggtgggg tctctcctga atccctctca ccatctctga ctttccattc   4560
taagcacttt gaggatgagt ttctagcttc aatagaccaa ggactctctc ctaggcctct   4620
gtattccttt caacagctcc actgtcaaga gagccagaga gagcttctgg gtggcccagc   4680
tgtgaaattt ctgagtccct tagggatagc cctaaacgaa ccagatcatc ctgaggacag   4740
ccaagaggtt ttgccttctt tcaagacaag caacagtact cacataggct gtgggcaatg   4800
gtcctgtctc tcaagaatcc cctgccactc ctcacaccca ccctgggccc atattcattt   4860
ccatttgagt tgttcttatt gagtcatcct tcctgtggta gcggaactca ctaaggggcc   4920
catctggacc cgaggtattg tgatgataaa ttctgagcac ctaccccatc cccagaaggg   4980
ctcagaaata aaataagagc caagtctagt cggtgtttcc tgtcttgaaa cacaatactg   5040
ttggccctgg aagaatgcac agaatctgtt tgtaagggga tatgcacaga agctgcaagg   5100
gacaggaggt gcaggagctg caggcctccc ccacccagcc tgctctgcct tggggaaaac   5160
cgtgggtgtg tcctgcaggc catgcaggcc tgggacatgc aagcccataa ccgctgtggc   5220
ctcttggttt tacagatacg aacctaaact ttcaaaacct gtcagtgatt gggttccgaa   5280
tcctcctcct gaaagtggcc gggtttaatc tgctcatgac gctgcggctg tggtccagct   5340
gaggtgaggg gccttgaagc tgggagtggg gtttagggac gcgggtctct gggtgcatcc   5400
taagctctga gagcaaacct ccctgcaggg tcttgctttt aagtccaaag cctgagccca   5460
ccaaactctc ctacttcttc ctgttacaaa ttcctcttgt gcaataataa tggcctgaaa   5520
cgctgtaaaa tatcctcatt tcagccgcct cagttgcact tctcccctat gaggtaggaa   5580
gaacagttgt ttagaaacga agaaactgag gccccacagc taatgagtgg aggaagagag   5640
acacttgtgt acaccacatg ccttgtgttg tacttctctc accgtgtaac ctcctcatgt   5700
cctctctccc cagtacggct ctcttagctc agtagaaaga agacattaca ctcatattac   5760
accccaatcc tggctagagt ctccgcaccc tcctccccca gggtccccag tcgtcttgct   5820
gacaactgca tcctgttcca tcaccatcaa aaaaaaactc caggctgggt gcgggggctc   5880
acacctgtaa tcccagcact ttgggaggca gaggcaggag gagcacagga gctggagacc   5940
agcctgggca acacagggag accccgcctc tacaaaaagt gaaaaaatta accaggtgtg   6000
gtgctgcaca cctgtagtcc cagctactta agaggctgag atgggaggat cgcttgagcc   6060
ctggaatgtt gaggctacaa tgagctgtga ttgcgtcact gcactccagc ctggaagaca   6120
aagcaagatc ctgtctcaaa taataaaaaa aataagaact ccagggtaca tttgctccta   6180
gaactctacc acatagcccc aaacagagcc atcaccatca catccctaac agtcctgggt   6240
cttcctcagt gtccagcctg acttctgttc ttcctcattc cagatctgca agattgtaag   6300
acagcctgtg ctccctcgct ccttcctctg cattgcccct cttctccctc tccaaacaga   6360
gggaactctc ctacccccaa ggaggtgaaa gctgctacca cctctgtgcc cccccggcaa   6420
```

tgccaccaac tggatcctac ccgaatttat gattaagatt gctgaagagc tgccaaacac 6480
tgctgccacc ccctctgttc ccttattgct gcttgtcact gcctgacatt cacggcagag 6540
gcaaggctgc tgcagcctcc cctggctgtg cacattccct cctgctcccc agagactgcc 6600
tccgccatcc cacagatgat ggatcttcag tgggttctct tgggctctag gtcctgcaga 6660
atgttgtgag ggtttattt ttttttaata gtgttcataa agaaatacat agtattcttc 6720
ttctcaagac gtggggggaa attatctcat tatcgaggcc ctgctatgct gtgtatctgg 6780
gcgtgttgta tgtcctgctg ccgatgcctt c 6811

<210> SEQ ID NO 123
<211> LENGTH: 6040
<212> TYPE: DNA
<213> ORGANISM: Artificial Sequence
<220> FEATURE:
<223> OTHER INFORMATION: Synthesized

<400> SEQUENCE: 123
cagcagctgg cgtaatagcg aagaggcccg caccgatcgc ccttcccaac agttgcgcag 60
cctgaatggc gaatggaatt ccagacgatt gagcgtcaaa atgtaggtat ttccatgagc 120
gtttttcctg ttgcaatggc tggcggtaat attgttctgg atattaccag caaggccgat 180
agtttgagtt cttctactca ggcaagtgat gttattacta atcaaagaag tattgcgaca 240
acggttaatt tgcgtgatgg acagactctt ttactcggtg gcctcactga ttataaaaac 300
acttctcagg attctggcgt accgttcctg tctaaaatcc ctttaatcgg cctcctgttt 360
agctcccgct ctgattctaa cgaggaaagc acgttatacg tgctcgtcaa agcaaccata 420
gtacgcgccc tgtagcggcg cattaagcgc ggcgggtgtg gtggttacgc gcagcgtgac 480
cgctacactt gccagcgccc tagcgcccgc tcctttcgct ttcttccctt cctttctcgc 540
cacgttcgcc ggctttcccc gtcaagctct aaatcggggg ctccctttag ggttccgatt 600
tagtgcttta cggcacctcg accccaaaaa acttgattag ggtgatggtt cacgtagtgg 660
gccatcgccc tgatagacgg tttttcgccc tttgacgttg gagtccacgt tctttaatag 720
tggactcttg ttccaaactg gaacaacact caaccctatc tcggtctatt cttttgattt 780
ataagggatt ttgccgattt cggcctattg gttaaaaaat gagctgattt aacaaaaatt 840
taacgcgaat tttaacaaaa tattaacgct tacaatttaa atatttgctt atacaatctt 900
cctgtttttg gggcttttct gattatcaac cggggtacat atgattgaca tgctagtttt 960
acgattaccg ttcatcgccc tgcgcgctcg ctcgctcact gaggccgccc gggcaaagcc 1020
cgggcgtcgg gcgacctttg gtcgcccggc ctcagtgagc gagcgagcgc gcagagaggg 1080
agtggaattc acgcgtgata tccagaaccc tgaccctgcc gtgtaccagc tgagagactc 1140
taaatccagt gacaagtctg tctgcctatt caccgatttt gattctcaaa caaatgtgtc 1200
acaaagtaag gattctgatg tgcatatcac agacaaaact gtgctagaca tgaggtctat 1260
ggacttcaag agcaacagtg ctgtggcctg gagcaactag tgggcggagt tagggcggag 1320
ccaatcagcg tgcgccgttc cgaaagttgc cttttatggc tgggcggaga atgggcggtg 1380
aacgccgatg attatataag gacgcgccgg gtgtggcaca gctagttccg tcgcagccgg 1440
gatttgggtc gcggttcttg tttgttccgg aaagccacca tggcgctccc agtgacagcc 1500
ttacttttac ctctggcgtt attattgcac gcggctcgtc ctgacataca gatgactcag 1560
actacctctt ccctatctgc ttctttaggc gaccgagtaa caatatcttg ccgggccagc 1620

-continued

```
caggacatct caaaatactt aaactggtat cagcagaagc cggacggaac agttaagttg   1680
ctcatttacc acacgtcgag attacactca ggcgttccta gccgattttc gggttccggt   1740
tccggtacgg actacagcct gacaatcagt aaccttgagc aggaggacat cgccacctac   1800
ttctgtcagc agggcaacac gctcccgtac acattcggtg ggggaactaa gctggagatt   1860
accggaggcg gtggcagcgg tggcggcggc agcgggggtg gcggctcgga ggtcaagtta   1920
caggagagcg gaccgggctt ggtcgcacct agccagagcc tctcagtcac gtgcactgtg   1980
tctggagtca gtctcccaga ctacggggta tcatggatac gacagccgcc tagaaagggc   2040
ttagagtggc tgggggttat ctggggaagt gaaaccacat actacaactc agctctcaag   2100
agccgcctca ccatcattaa ggacaacagt aagtcgcagg ttttcttaaa gatgaactct   2160
ctccagactg acgacaccgc tatttactac tgcgcgaagc actactacta cggcgggagt   2220
tacgcaatgg actactgggg tcagggcact tctgtgaccg tatccagcac tactacccca   2280
gccccacgtc cccccacgcc agctccaacg atagcaagtc agcccttatc tcttcgccct   2340
gaggcttgca ggcccgcggc gggcggcgcc gttcacacgc gaggactaga cttcgcctgc   2400
gacatctaca tctgggcacc actagccggg acttgcggag tgttgttgtt gagcttggta   2460
ataacgctct actgcaagcg tgggagaaag aagctcttgt acattttcaa gcagccattc   2520
atgcgtcccg ttcagacgac tcaggaggag gacggctgct cgtgccgatt cccggaggag   2580
gaggagggcg gttgcgaact cagagtgaag ttctctcgct ccgcggacgc acccgcttac   2640
cagcagggtc agaaccagct atacaacgag ttaaacctgg ggcgccggga ggagtacgac   2700
gtgttagaca agcgtagagg tagggacccg gagatgggag gcaagcctcg gagaaagaac   2760
ccccaggagg gcctgtacaa cgaactccag aaggacaaga tggctgaggc gtactcggag   2820
attggtatga agggcgagag acgtcgcgga aagggacacg acggcttata ccaggggctt   2880
tccaccgcga ccaaggacac atacgacgcg ctgcacatgc aagccttacc acctcgatga   2940
taagatacat tgatgagttt ggacaaacca caactagaat gcagtgaaaa aaatgcttta   3000
tttgtgaaat ttgtgatgct attgctttat ttgtaaccat tataagctgc aataaacaag   3060
ttctagagca acaaatctga ctttgcatgt gcaaacgcct tcaacaacag cattattcca   3120
gaagacacct tcttccccag cccaggtaag ggcagctttg gtgccttcgc aggctgtttc   3180
cttgcttcag gaatggccag gttctgccca gagctctggt caatgatgtc taaaactcct   3240
ctgattgcaa ttgcctctct gcgcgctcgc tcgctcactg aggccgcccg ggcaaagccc   3300
gggcgtcggg cgacctttgg tcgcccggcc tcagtgagcg agcgagcgcg cagagaggga   3360
gtggccaacc ccggcgattc tcttgtttgc tccagactct caggcaatga cctgatagcc   3420
tttgtacctg caggtctcaa aaatagctac cctctccggc atgaatttat cagctagaac   3480
ggttgaatat catattgatg gtgatttgac tgtctccggc ctttctcacc cgtttgaatc   3540
tttacctaca cattactcag gcattgcatt taaaatatat gagggttcta aaaattttta   3600
tccttgcgtt gaaataaagg cttctcccgc aaaagtatta cagggtcata atgtttttgg   3660
tacaaccgat ttagctttat gctctgaggc tttattgctt aattttgcta attctttgcc   3720
ttgcctgtat gatttattgg atgttggaat tcctgatgcg gtattttctc cttacgcatc   3780
tgtgcggtat ttcacaccgc atatggtgca ctctcagtac aatctgctct gatgccgcat   3840
agttaagcca gccccgacac ccgccaacac ccgctgacgc gccctgacgg gcttgtctgc   3900
tcccggcatc cgcttacaga caagctgtga ccgtctccgg gagctgcatg tgtcagaggt   3960
tttcaccgtc atcaccgaaa cgcgcgagac gaaagggcct cgtgatacgc ctatttttat   4020
```

aggttaatgt catgataata atggtttctt agacgtcagg tggcactttt cggggaaatg 4080
tgcgcggaac ccctatttgt ttatttttct aaatacattc aaatatgtat ccgctcatga 4140
gacaataacc ctgataaatg cttcaataat attgaaaaag gaagagtatg agtattcaac 4200
atttccgtgt cgcccttatt cccttttttg cggcattttg ccttcctgtt tttgctcacc 4260
cagaaacgct ggtgaaagta aaagatgctg aagatcagtt gggtgcacga gtgggttaca 4320
tcgaactgga tctcaacagc ggtaagatcc ttgagagttt tcgccccgaa gaacgttttc 4380
caatgatgag cacttttaaa gttctgctat gtggcgcggt attatcccgt attgacgccg 4440
ggcaagagca actcggtcgc cgcatacact attctcagaa tgacttggtt gagtactcac 4500
cagtcacaga aaagcatctt acggatggca tgacagtaag agaattatgc agtgctgcca 4560
taaccatgag tgataacact gcggccaact tacttctgac aacgatcgga ggaccgaagg 4620
agctaaccgc ttttttgcac aacatggggg atcatgtaac tcgccttgat cgttgggaac 4680
cggagctgaa tgaagccata ccaaacgacg agcgtgacac cacgatgcct gtagcaatgg 4740
caacaacgtt gcgcaaacta ttaactggcg aactacttac tctagcttcc cggcaacaat 4800
taatagactg gatggaggcg gataaagttg caggaccact tctgcgctcg gcccttccgg 4860
ctggctggtt tattgctgat aaatctggag ccggtgagcg tgggtctcgc ggtatcattg 4920
cagcactggg gccagatggt aagccctccc gtatcgtagt tatctacacg acggggagtc 4980
aggcaactat ggatgaacga aatagacaga tcgctgagat aggtgcctca ctgattaagc 5040
attggtaact gtcagaccaa gtttactcat atatacttta gattgattta aaacttcatt 5100
tttaatttaa aaggatctag gtgaagatcc tttttgataa tctcatgacc aaaatccctt 5160
aacgtgagtt ttcgttccac tgagcgtcag accccgtaga aaagatcaaa ggatcttctt 5220
gagatccttt ttttctgcgc gtaatctgct gcttgcaaac aaaaaaacca ccgctaccag 5280
cggtggtttg tttgccggat caagagctac caactctttt tccgaaggta actggcttca 5340
gcagagcgca gataccaaat actgtccttc tagtgtagcc gtagttaggc caccacttca 5400
agaactctgt agcaccgcct acatacctcg ctctgctaat cctgttacca gtggctgctg 5460
ccagtggcga taagtcgtgt cttaccgggt tggactcaag acgatagtta ccggataagg 5520
cgcagcggtc gggctgaacg gggggttcgt gcacacagcc cagcttggag cgaacgacct 5580
acaccgaact gagataccta cagcgtgagc tatgagaaag cgccacgctt cccgaaggga 5640
gaaaggcgga caggtatccg gtaagcggca gggtcggaac aggagagcgc acgagggagc 5700
ttccaggggg aaacgcctgg tatctttata gtcctgtcgg gtttcgccac ctctgacttg 5760
agcgtcgatt tttgtgatgc tcgtcagggg ggcggagcct atggaaaaac gccagcaacg 5820
cggccttttt acggttcctg gccttttgct ggccttttgc tcacatgttc tttcctgcgt 5880
tatcccctga ttctgtggat aaccgtatta ccgcctttga gtgagctgat accgctcgcc 5940
gcagccgaac gaccgagcgc agcgagtcag tgagcgagga agcggaagag cgcccaatac 6000
gcaaaccgcc tctccccgcg cgttggccga ttcattaatg 6040

<210> SEQ ID NO 124
<211> LENGTH: 8342
<212> TYPE: DNA
<213> ORGANISM: Artificial Sequence
<220> FEATURE:
<223> OTHER INFORMATION: Synthesized

<400> SEQUENCE: 124

```
cagcagctgg cgtaatagcg aagaggcccg caccgatcgc ccttcccaac agttgcgcag     60
cctgaatggc gaatggaatt ccagacgatt gagcgtcaaa atgtaggtat ttccatgagc    120
gtttttcctg ttgcaatggc tggcggtaat attgttctgg atattaccag caaggccgat    180
agtttgagtt cttctactca ggcaagtgat gttattacta atcaaagaag tattgcgaca    240
acggttaatt tgcgtgatgg acagactctt ttactcggtg gcctcactga ttataaaaac    300
acttctcagg attctggcgt accgttcctg tctaaaatcc ctttaatcgg cctcctgttt    360
agctcccgct ctgattctaa cgaggaaagc acgttatacg tgctcgtcaa agcaaccata    420
gtacgcgccc tgtagcggcg cattaagcgc ggcgggtgtg gtggttacgc gcagcgtgac    480
cgctacactt gccagcgccc tagcgcccgc tcctttcgct ttcttccctt cctttctcgc    540
cacgttcgcc ggctttcccc gtcaagctct aaatcggggg ctccctttag ggttccgatt    600
tagtgcttta cggcacctcg accccaaaaa acttgattag ggtgatggtt cacgtagtgg    660
gccatcgccc tgatagacgg tttttcgccc tttgacgttg gagtccacgt tctttaatag    720
tggactcttg ttccaaactg gaacaacact caaccctatc tcggtctatt cttttgattt    780
ataagggatt ttgccgattt cggcctattg gttaaaaaat gagctgattt aacaaaaatt    840
taacgcgaat tttaacaaaa tattaacgtt tacaatttaa atatttgctt atacaatctt    900
cctgtttttg gggcttttct gattatcaac cggggtacat atgattgaca tgctagtttt    960
acggcgcgcc gggttggcca ctccctctct gcgcgctcgc tcgctcactg aggccgggcg   1020
accaaaggtc gcccgacgcc cgggctttgc ccgggcggcc tcagtgagcg agcgagcgcg   1080
cagagaggga gtggccaact ccatcactag gggttcctac gcgtagatct catattctgg   1140
cagggtcagt ggctccaact aacatttgtt tggtacttta cagtttatta aatagatgtt   1200
tatatggaga agctctcatt tctttctcag aagagcctgg ctaggaaggt ggatgaggca   1260
ccatattcat tttgcaggtg aaattcctga gatgtaagga gctgctgtga cttgctcaag   1320
gccttatatc gagtaaacgg tagcgctggg gcttagacgc aggtgttctg atttatagtt   1380
caaaacctct atcaatgaga gagcaatctc ctggtaatgt gatagatttc ccaacttaat   1440
gccaacatac cataaacctc ccattctgct aatgcccagc ctaagttggg gagaccactc   1500
cagattccaa gatgtacagt ttgctttgct gggccttttt cccatgcctg cctttactct   1560
gccagagtta tattgctggg gttttgaaga agatcctatt aaataaaaga ataagcagta   1620
ttattaagta gccctgcatt tcaggtttcc ttgagtggca ggccaggcct ggccgtgaac   1680
gttcactgaa atcatggcct cttggccaag attgatagct tgtgcctgtc cctgagtccc   1740
agtccatcac gagcagctgg tttctaagat gctatttccc gtataaagca tgagaccgtg   1800
acttgccagc cccacagagc cccgcccttg tccatcactg gcatctggac tccagcctgg   1860
gttggggcaa agagggaaat gagatcatgt cctaaccctg atcctcttgt cccacagata   1920
tccagaaccc tgaccctgcc gtgtaccagc tgagagactc taaatccagt gacaagtctg   1980
tctgcctatt caccgatttt gattctcaaa caaatgtgtc acaaagtaag gattctgatg   2040
tgtatatcac agacaaaact gtgctagaca tgaggtctat ggacttcaag agcaacagtg   2100
ctgtggcctg gagcaactag tcaatattgg ccattagcca tattattcat tggttatata   2160
gcataaatca atattggcta ttggccattg catacgttgt atctatatca taatatgtac   2220
atttatattg gctcatgtcc aatatgaccg ccatgttggc attgattatt gaccagttat   2280
taatagtaat caattacggg gtcattagtt catagcccat atatggagtt ccgcgttaca   2340
taacttacgg taaatggccc gcctggctga ccgcccaacg acccccgccc attgacgtca   2400
```

```
ataatgacgt atgttcccat agtaacgcca atagggactt tccattgacg tcaatgggtg   2460
gagtatttac ggtaaactgc ccacttggca gtacatcaag tgtatcataa tccaagtccg   2520
ccccctattg acgtcaatga cggtaaatgg cccgcctggc attatgccca gtacatgacc   2580
ttacgggact ttcctacttg gcagtacatc tacgtattag tcatcgctat taccatgatg   2640
atgcggtttt ggcagtacac caatgggcgt ggatagcggt ttgactcacg gggatttcca   2700
agtctccacc ccattgacgt caatgggagt ttgttttggc accaaaatca acgggacttt   2760
ccaaaatgtc gtaataaccc cgccccgttg acgcaaatgg gcggtaggcg tgtacggtgg   2820
gaggtctata taagcagagc tcgtttagtg aaccgtcaga tcactagaag ctttattgcg   2880
gtagtttatc acagttaaat tgctaacgca gtcagtgctt ctgacacaac agtctcgaac   2940
ttaagctgca gaagttggtc gtgaggcact gggcaggtaa gtatcaaggt tacaagacag   3000
gtttaaggag accaatagaa actgggcttg tcgagacaga gaagactctt gcgtttctga   3060
taggcaccta ttggtcttac tgacatccac tttgcctttc tctccacagg tgtccactcc   3120
cagttcaatt acagctctta aggctagagt acttaatacg actcactata ggccaccatg   3180
gcgctcccag tgacagcctt acttttacct ctggcgttat tattgcacgc ggctcgtcct   3240
gacatacaga tgactcagac tacctcttcc ctatctgctt ctttaggcga ccgagtaaca   3300
atatcttgcc gggccagcca ggacatctca aaatacttaa actggtatca gcagaagccg   3360
gacggaacag ttaagttgct catttaccac acgtcgagat tacactcagg cgttcctagc   3420
cgattttcgg gttccggttc cggtacggac tacagcctga caatcagtaa ccttgagcag   3480
gaggacatcg ccacctactt ctgtcagcag ggcaacacgc tcccgtacac attcggtggg   3540
ggaactaagc tggagattac cggaggcggt ggcagcggtg gcggcggcag cgggggtggc   3600
ggctcggagg tcaagttaca ggagagcgga ccgggcttgg tcgcacctag ccagagcctc   3660
tcagtcacgt gcactgtgtc tggagtcagt ctcccagact acggggtatc atggatacga   3720
cagccgccta gaaagggctt agagtggctg gggttatct ggggaagtga aaccacatac   3780
tacaactcag ctctcaagag ccgcctcacc atcattaagg acaacagtaa gtcgcaggtt   3840
ttcttaaaga tgaactctct ccagactgac gacaccgcta tttactactg cgcgaagcac   3900
tactactacg gcgggagtta cgcaatggac tactggggtc agggcacttc tgtgaccgta   3960
tccagcacta ctaccccagc cccacgtccc cccacgccag ctccaacgat agcaagtcag   4020
cccttatctc ttcgccctga ggcttgcagg cccgcggcgg gcggcgccgt tcacacgcga   4080
ggactagact tcgcctgcga catctacatc tgggcaccac tagccgggac ttgcggagtg   4140
ttgttgttga gcttggtaat aacgctctac tgcaagcgtg ggagaaagaa gctcttgtac   4200
attttcaagc agccattcat gcgtcccgtt cagacgactc aggaggagga cggctgctcg   4260
tgccgattcc cggaggagga ggagggcggt tgcgaactca gagtgaagtt ctctcgctcc   4320
gcggacgcac ccgcttacca gcagggtcag aaccagctat acaacgagtt aaacctgggg   4380
cgccgggagg agtacgacgt gttagacaag cgtagaggta gggacccgga gatgggaggc   4440
aagcctcgga gaaagaaccc ccaggagggc ctgtacaacg aactccagaa ggacaagatg   4500
gctgaggcgt actcggagat tggtatgaag ggcgagagac gtcgcggaaa gggacacgac   4560
ggcttatacc aggggctttc caccgcgacc aaggacacat acgacgcgct gcacatgcaa   4620
gccttaccac ctcgatgagg taccagcggc cgcttcgagc agacatgata agatacattg   4680
atgagtttgg acaaaccaca actagaatgc agtgaaaaaa atgctttatt tgtgaaattt   4740
```

```
gtgatgctat tgctttattt gtaaccatta taagctgcaa taaacaagtt aacaacaaca   4800
attcgaattt aaatcggatc cgcaacaaat ctgactttgc atgtgcaaac gccttcaaca   4860
acagcattat tccagaagac accttcttcc ccagcccagg taagggcagc tttggtgcct   4920
tcgcaggctg tttccttgct tcaggaatgg ccaggttctg cccagagctc tggtcaatga   4980
tgtctaaaac tcctctgatt ggtggtctcg gccttatcca ttgccaccaa aaccctcttt   5040
ttactaagaa acagtgagcc ttgttctggc agtccagaga atgacacggg aaaaaagcag   5100
atgaagagaa ggtggcagga gagggcacgt ggcccagcct cagtctctcc aactgagttc   5160
ctgcctgcct gcctttgctc agactgtttg ccccttactg ctcttctagg cctcattcta   5220
agccccttct ccaagttgcc tctccttatt tctccctgtc tgccaaaaaa tctttcccag   5280
ctcactaagt cagtctcacg cagtcactca ttaacccacc aatcactgat tgtgccggca   5340
catgaatgca ccaggtgttg aagtggagga attaaaaagt cagatgaggg gtgtgcccag   5400
aggaagcacc attctagttg gggagcccca tctgtcagct gggaaaagtc caaataactt   5460
cagattggaa tgtgttttaa ctcagggttg agaaaacagc caccttcagg acaaaagtca   5520
gggaagggct ctctgaagaa atgctacttg aagataccag ccctaccaag ggcagggaga   5580
ggaccaattg atggagttgg ccactccctc tctgcgcgct cgctcgctca ctgaggccgc   5640
ccgggcaaag cccgggcgtc gggcgacctt tggtcgcccg gcctcagtga gcgagcgagc   5700
gcgcagagag ggagtggcca acggcgcgcc tgcaggtctc aaaaatagct accctctccg   5760
gcatgaattt atcagctaga acggttgaat atcatattga tggtgatttg actgtctccg   5820
gcctttctca cccgtttgaa tctttaccta cacattactc aggcattgca tttaaaatat   5880
atgagggttc taaaaatttt tatccttgcg ttgaaataaa ggcttctccc gcaaaagtat   5940
tacagggtca taatgttttt ggtacaaccg atttagcttt atgctctgag gctttattgc   6000
ttaattttgc taattctttg ccttgcctgt atgatttatt ggatgttgga attcctgatg   6060
cggtattttc tccttacgca tctgtgcggt atttcacacc gcatatggtg cactctcagt   6120
acaatctgct ctgatgccgc atagttaagc cagccccgac acccgccaac acccgctgac   6180
gcgccctgac gggcttgtct gctcccggca tccgcttaca gacaagctgt gaccgtctcc   6240
gggagctgca tgtgtcagag gttttcaccg tcatcaccga aacgcgcgag acgaaagggc   6300
ctcgtgatac gcctattttt ataggttaat gtcatgataa taatggtttc ttagacgtca   6360
ggtggcactt ttcggggaaa tgtgcgcgga acccctattt gtttattttt ctaaatacat   6420
tcaaatatgt atccgctcat gagacaataa ccctgataaa tgcttcaata atattgaaaa   6480
aggaagagta tgagtattca acatttccgt gtcgccctta ttcccttttt tgcggcattt   6540
tgccttcctg tttttgctca cccagaaacg ctggtgaaag taaaagatgc tgaagatcag   6600
ttgggtgcac gagtgggtta catcgaactg gatctcaaca gcggtaagat ccttgagagt   6660
tttcgccccg aagaacgttt tccaatgatg agcactttta aagttctgct atgtggcgcg   6720
gtattatccc gtattgacgc cgggcaagag caactcggtc gccgcataca ctattctcag   6780
aatgacttgg ttgagtactc accagtcaca gaaaagcatc ttacggatgg catgacagta   6840
agagaattat gcagtgctgc cataaccatg agtgataaca ctgcggccaa cttacttctg   6900
acaacgatcg gaggaccgaa ggagctaacc gcttttttgc acaacatggg ggatcatgta   6960
actcgccttg atcgttggga accggagctg aatgaagcca taccaaacga cgagcgtgac   7020
accacgatgc ctgtagcaat ggcaacaacg ttgcgcaaac tattaactgg cgaactactt   7080
actctagctt cccggcaaca attaatagac tggatggagg cggataaagt tgcaggacca   7140
```

cttctgcgct cggcccttcc ggctggctgg tttattgctg ataaatctgg agccggtgag 7200
cgtgggtctc gcggtatcat tgcagcactg gggccagatg gtaagccctc ccgtatcgta 7260
gttatctaca cgacggggag tcaggcaact atggatgaac gaaatagaca gatcgctgag 7320
ataggtgcct cactgattaa gcattggtaa ctgtcagacc aagtttactc atatatactt 7380
tagattgatt taaaacttca tttttaattt aaaaggatct aggtgaagat cctttttgat 7440
aatctcatga ccaaaatccc ttaacgtgag ttttcgttcc actgagcgtc agaccccgta 7500
gaaaagatca aaggatcttc ttgagatcct ttttttctgc gcgtaatctg ctgcttgcaa 7560
acaaaaaaac caccgctacc agcggtggtt tgtttgccgg atcaagagct accaactctt 7620
tttccgaagg taactggctt cagcagagcg cagataccaa atactgtcct tctagtgtag 7680
ccgtagttag gccaccactt caagaactct gtagcaccgc ctacatacct cgctctgcta 7740
atcctgttac cagtggctgc tgccagtggc gataagtcgt gtcttaccgg gttggactca 7800
agacgatagt taccggataa ggcgcagcgg tcgggctgaa cggggggttc gtgcacacag 7860
cccagcttgg agcgaacgac ctacaccgaa ctgagatacc tacagcgtga gctatgagaa 7920
agcgccacgc ttcccgaagg gagaaaggcg gacaggtatc cggtaagcgg cagggtcgga 7980
acaggagagc gcacgaggga gcttccaggg ggaaacgcct ggtatcttta tagtcctgtc 8040
gggtttcgcc acctctgact tgagcgtcga tttttgtgat gctcgtcagg ggggcggagc 8100
ctatggaaaa acgccagcaa cgcggccttt ttacggttcc tggccttttg ctggcctttt 8160
gctcacatgt tctttcctgc gttatcccct gattctgtgg ataaccgtat taccgccttt 8220
gagtgagctg ataccgctcg ccgcagccga acgaccgagc gcagcgagtc agtgagcgag 8280
gaagcggaag agcgcccaat acgcaaaccg cctctccccg cgcgttggcc gattcattaa 8340
tg 8342

<210> SEQ ID NO 125
<211> LENGTH: 7464
<212> TYPE: DNA
<213> ORGANISM: Artificial Sequence
<220> FEATURE:
<223> OTHER INFORMATION: Synthesized

<400> SEQUENCE: 125
cagcagctgg cgtaatagcg aagaggcccg caccgatcgc ccttcccaac agttgcgcag 60
cctgaatggc gaatggaatt ccagacgatt gagcgtcaaa atgtaggtat ttccatgagc 120
gtttttcctg ttgcaatggc tggcggtaat attgttctgg atattaccag caaggccgat 180
agtttgagtt cttctactca ggcaagtgat gttattacta atcaaagaag tattgcgaca 240
acggttaatt tgcgtgatgg acagactctt ttactcggtg gcctcactga ttataaaaac 300
acttctcagg attctggcgt accgttcctg tctaaaatcc ctttaatcgg cctcctgttt 360
agctcccgct ctgattctaa cgaggaaagc acgttatacg tgctcgtcaa agcaaccata 420
gtacgcgccc tgtagcggcg cattaagcgc ggcgggtgtg gtggttacgc gcagcgtgac 480
cgctacactt gccagcgccc tagcgcccgc tcctttcgct ttcttccctt cctttctcgc 540
cacgttcgcc ggctttcccc gtcaagctct aaatcggggg ctccctttag ggttccgatt 600
tagtgcttta cggcacctcg accccaaaaa acttgattag ggtgatggtt cacgtagtgg 660
gccatcgccc tgatagacgg tttttcgccc tttgacgttg gagtccacgt tctttaatag 720
tggactcttg ttccaaactg gaacaacact caaccctatc tcggtctatt cttttgattt 780

```
ataagggatt ttgccgattt cggcctattg gttaaaaaat gagctgattt aacaaaaatt    840
taacgcgaat tttaacaaaa tattaacgtt tacaatttaa atatttgctt atacaatctt    900
cctgtttttg gggcttttct gattatcaac cggggtacat atgattgaca tgctagtttt    960
acggcgcgcc gggttggcca ctccctctct gcgcgctcgc tcgctcactg aggccgggcg   1020
accaaaggtc gcccgacgcc cgggctttgc ccgggcggcc tcagtgagcg agcgagcgcg   1080
cagagaggga gtggccaact ccatcactag gggttcctac gcgtagatct catattctgg   1140
cagggtcagt ggctccaact aacatttgtt tggtacttta cagtttatta aatagatgtt   1200
tatatggaga agctctcatt tctttctcag aagagcctgg ctaggaaggt ggatgaggca   1260
ccatattcat tttgcaggtg aaattcctga gatgtaagga gctgctgtga cttgctcaag   1320
gccttatatc gagtaaacgg tagcgctggg gcttagacgc aggtgttctg atttatagtt   1380
caaaacctct atcaatgaga gagcaatctc ctggtaatgt gatagatttc ccaacttaat   1440
gccaacatac cataaacctc ccattctgct aatgcccagc ctaagttggg gagaccactc   1500
cagattccaa gatgtacagt ttgctttgct gggccttttt cccatgcctg cctttactct   1560
gccagagtta tattgctggg gttttgaaga agatcctatt aaataaaaga ataagcagta   1620
ttattaagta gccctgcatt tcaggtttcc ttgagtggca ggccaggcct ggccgtgaac   1680
gttcactgaa atcatggcct cttggccaag attgatagct tgtgcctgtc cctgagtccc   1740
agtccatcac gagcagctgg tttctaagat gctatttccc gtataaagca tgagaccgtg   1800
acttgccagc cccacagagc cccgcccttg tccatcactg gcatctggac tccagcctgg   1860
gttggggcaa agagggaaat gagatcatgt cctaaccctg atcctcttgt cccacagata   1920
tccagaaccc tgaccctgcc gtgtaccagc tgagagactc taaatccagt gacaagtctg   1980
tctgcctatt caccgatttt gattctcaaa caaatgtgtc acaaagtaag gattctgatg   2040
tgtatatcac agacaaaact gtgctagaca tgaggtctat ggacttcaag agcaacagtg   2100
ctgtggcctg gagcaactag tgggcggagt tagggcggag ccaatcagcg tgcgccgttc   2160
cgaaagttgc cttttatggc tgggcggaga atgggcggtg aacgccgatg attatataag   2220
gacgcgccgg gtgtggcaca gctagttccg tcgcagccgg gatttgggtc gcggttcttg   2280
tttgttccgg aaagccacca tggcgctccc agtgacagcc ttacttttac ctctggcgtt   2340
attattgcac gcggctcgtc ctgacataca gatgactcag actacctctt ccctatctgc   2400
ttctttaggc gaccgagtaa caatatcttg ccgggccagc caggacatct caaaatactt   2460
aaactggtat cagcagaagc cggacggaac agttaagttg ctcatttacc acacgtcgag   2520
attacactca ggcgttccta gccgattttc gggttccggt tccggtacgg actacagcct   2580
gacaatcagt aaccttgagc aggaggacat cgccacctac ttctgtcagc agggcaacac   2640
gctcccgtac acattcggtg gggaactaa gctggagatt accggaggcg gtggcagcgg   2700
tggcggcggc agcgggggtg gcggctcgga ggtcaagtta caggagagcg gaccgggctt   2760
ggtcgcacct agccagagcc tctcagtcac gtgcactgtg tctggagtca gtctcccaga   2820
ctacggggta tcatggatac gacagccgcc tagaaagggc ttagagtggc tgggggttat   2880
ctggggaagt gaaaccacat actacaactc agctctcaag agccgcctca ccatcattaa   2940
ggacaacagt aagtcgcagg ttttcttaaa gatgaactct ctccagactg acgacaccgc   3000
tatttactac tgcgcgaagc actactacta cggcgggagt tacgcaatgg actactgggg   3060
tcagggcact tctgtgaccg tatccagcac tactacccca gccccacgtc cccccacgcc   3120
agctccaacg atagcaagtc agcccttatc tcttcgccct gaggcttgca ggcccgcggc   3180
```

gggcggcgcc gttcacacgc gaggactaga cttcgcctgc gacatctaca tctgggcacc 3240
actagccggg acttgcggag tgttgttgtt gagcttggta ataacgctct actgcaagcg 3300
tgggagaaag aagctcttgt acattttcaa gcagccattc atgcgtcccg ttcagacgac 3360
tcaggaggag gacggctgct cgtgccgatt cccggaggag gaggagggcg gttgcgaact 3420
cagagtgaag ttctctcgct ccgcggacgc acccgcttac cagcagggtc agaaccagct 3480
atacaacgag ttaaacctgg ggcgccggga ggagtacgac gtgttagaca agcgtagagg 3540
tagggacccg gagatgggag gcaagcctcg gagaaagaac ccccaggagg gcctgtacaa 3600
cgaactccag aaggacaaga tggctgaggc gtactcggag attggtatga agggcgagag 3660
acgtcgcgga aagggacacg acggcttata ccaggggctt tccaccgcga ccaaggacac 3720
atacgacgcg ctgcacatgc aagccttacc acctcgatga ggtaccagcg gccgcttcga 3780
gcagacatga taagatacat tgatgagttt ggacaaacca caactagaat gcagtgaaaa 3840
aaatgcttta tttgtgaaat ttgtgatgct attgctttat ttgtaaccat tataagctgc 3900
aataaacaag ttaacaacaa caattcgaat ttaaatcgga tccgcaacaa atctgacttt 3960
gcatgtgcaa acgccttcaa caacagcatt attccagaag acaccttctt ccccagccca 4020
ggtaagggca gctttggtgc cttcgcaggc tgtttccttg cttcaggaat ggccaggttc 4080
tgcccagagc tctggtcaat gatgtctaaa actcctctga ttggtggtct cggccttatc 4140
cattgccacc aaaaccctct ttttactaag aaacagtgag ccttgttctg gcagtccaga 4200
gaatgacacg ggaaaaaagc agatgaagag aaggtggcag gagagggcac gtggcccagc 4260
ctcagtctct ccaactgagt tcctgcctgc ctgcctttgc tcagactgtt tgccccttac 4320
tgctcttcta ggcctcattc taagcccctt ctccaagttg cctctcctta tttctccctg 4380
tctgccaaaa aatctttccc agctcactaa gtcagtctca cgcagtcact cattaaccca 4440
ccaatcactg attgtgccgg cacatgaatg caccaggtgt tgaagtggag gaattaaaaa 4500
gtcagatgag gggtgtgccc agaggaagca ccattctagt tgggggagcc catctgtcag 4560
ctgggaaaag tccaaataac ttcagattgg aatgtgtttt aactcagggt tgagaaaaca 4620
gccaccttca ggacaaaagt cagggaaggg ctctctgaag aaatgctact tgaagatacc 4680
agccctacca agggcaggga gaggaccaat tgatggagtt ggccactccc tctctgcgcg 4740
ctcgctcgct cactgaggcc gcccgggcaa agcccgggcg tcgggcgacc tttggtcgcc 4800
cggcctcagt gagcgagcga gcgcgcagag agggagtggc caacggcgcg cctgcaggtc 4860
tcaaaaatag ctaccctctc cggcatgaat ttatcagcta gaacggttga atatcatatt 4920
gatggtgatt tgactgtctc cggcctttct cacccgtttg aatctttacc tacacattac 4980
tcaggcattg catttaaaat atatgagggt tctaaaaatt tttatccttg cgttgaaata 5040
aaggcttctc ccgcaaaagt attacagggt cataatgttt ttggtacaac cgatttagct 5100
ttatgctctg aggctttatt gcttaatttt gctaattctt tgccttgcct gtatgattta 5160
ttggatgttg gaattcctga tgcggtattt tctccttacg catctgtgcg gtatttcaca 5220
ccgcatatgg tgcactctca gtacaatctg ctctgatgcc gcatagttaa gccagccccg 5280
acacccgcca acacccgctg acgcgccctg acgggcttgt ctgctcccgg catccgctta 5340
cagacaagct gtgaccgtct ccgggagctg catgtgtcag aggttttcac cgtcatcacc 5400
gaaacgcgcg agacgaaagg gcctcgtgat acgcctattt ttataggtta atgtcatgat 5460
aataatggtt tcttagacgt caggtggcac ttttcgggga aatgtgcgcg gaacccctat 5520

-continued

```
ttgtttattt ttctaaatac attcaaatat gtatccgctc atgagacaat aaccctgata   5580
aatgcttcaa taatattgaa aaaggaagag tatgagtatt caacatttcc gtgtcgccct   5640
tattcccttt tttgcggcat tttgccttcc tgtttttgct cacccagaaa cgctggtgaa   5700
agtaaaagat gctgaagatc agttgggtgc acgagtgggt tacatcgaac tggatctcaa   5760
cagcggtaag atccttgaga gttttcgccc cgaagaacgt tttccaatga tgagcacttt   5820
taaagttctg ctatgtggcg cggtattatc ccgtattgac gccgggcaag agcaactcgg   5880
tcgccgcata cactattctc agaatgactt ggttgagtac tcaccagtca cagaaaagca   5940
tcttacggat ggcatgacag taagagaatt atgcagtgct gccataacca tgagtgataa   6000
cactgcggcc aacttacttc tgacaacgat cggaggaccg aaggagctaa ccgctttttt   6060
gcacaacatg ggggatcatg taactcgcct tgatcgttgg gaaccggagc tgaatgaagc   6120
cataccaaac gacgagcgtg acaccacgat gcctgtagca atggcaacaa cgttgcgcaa   6180
actattaact ggcgaactac ttactctagc ttcccggcaa caattaatag actggatgga   6240
ggcggataaa gttgcaggac cacttctgcg ctcggccctt ccggctggct ggtttattgc   6300
tgataaatct ggagccggtg agcgtgggtc tcgcggtatc attgcagcac tggggccaga   6360
tggtaagccc tcccgtatcg tagttatcta cacgacgggg agtcaggcaa ctatggatga   6420
acgaaataga cagatcgctg agataggtgc ctcactgatt aagcattggt aactgtcaga   6480
ccaagtttac tcatatatac tttagattga tttaaaactt catttttaat ttaaaaggat   6540
ctaggtgaag atcctttttg ataatctcat gaccaaaatc ccttaacgtg agttttcgtt   6600
ccactgagcg tcagaccccg tagaaaagat caaaggatct tcttgagatc cttttttct    6660
gcgcgtaatc tgctgcttgc aaacaaaaaa accaccgcta ccagcggtgg tttgtttgcc   6720
ggatcaagag ctaccaactc tttttccgaa ggtaactggc ttcagcagag cgcagatacc   6780
aaatactgtc cttctagtgt agccgtagtt aggccaccac ttcaagaact ctgtagcacc   6840
gcctacatac ctcgctctgc taatcctgtt accagtggct gctgccagtg gcgataagtc   6900
gtgtcttacc gggttggact caagacgata gttaccggat aaggcgcagc ggtcgggctg   6960
aacggggggt tcgtgcacac agcccagctt ggagcgaacg acctacaccg aactgagata   7020
cctacagcgt gagctatgag aaagcgccac gcttcccgaa gggagaaagg cggacaggta   7080
tccggtaagc ggcagggtcg gaacaggaga gcgcacgagg gagcttccag ggggaaacgc   7140
ctggtatctt tatagtcctg tcgggtttcg ccacctctga cttgagcgtc gatttttgtg   7200
atgctcgtca ggggggcgga gcctatggaa aaacgccagc aacgcggcct ttttacggtt   7260
cctggccttt tgctggcctt ttgctcacat gttctttcct gcgttatccc ctgattctgt   7320
ggataaccgt attaccgcct ttgagtgagc tgataccgct cgccgcagcc gaacgaccga   7380
gcgcagcgag tcagtgagcg aggaagcgga agagcgccca atacgcaaac cgcctctccc   7440
cgcgcgttgg ccgattcatt aatg                                          7464
```

GENETICALLY-MODIFIED CELLS COMPRISING A MODIFIED HUMAN T CELL RECEPTOR ALPHA CONSTANT REGION GENE

CROSS REFERENCE TO RELATED APPLICATIONS

This application is a continuation of U.S. application Ser. No. 15/607,059, filed May 26, 2017, which claims priority to International Patent Application No. PCT/US2016/055492, filed Oct. 5, 2016, which claims priority to U.S. Provisional Application No. 62/297,426, entitled "Genetically-Modified Cells Comprising a Modified Human T Cell Receptor Alpha Constant Region Gene," filed Feb. 19, 2016, and U.S. Provisional Application No. 62/237,394, entitled "Genetically-Modified Cells Comprising a Modified Human T Cell Receptor Alpha Constant Region Gene," filed Oct. 5, 2015, the disclosures of which are hereby incorporated by reference in their entireties.

FIELD OF THE INVENTION

The invention relates to the fields of oncology, cancer immunotherapy, molecular biology and recombinant nucleic acid technology. In particular, the invention relates to a genetically-modified cell comprising in its genome a modified human T cell receptor alpha constant region gene, wherein the cell has reduced cell-surface expression of the endogenous T cell receptor. The invention further relates to methods for producing such a genetically-modified cell, and to methods of using such a cell for treating a disease, including cancer, in a subject.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Jan. 8, 2018, is named P109070014US06-SEQ-MJT.txt, and is 264,046 bytes in size.

BACKGROUND OF THE INVENTION

T cell adoptive immunotherapy is a promising approach for cancer treatment. This strategy utilizes isolated human T cells that have been genetically-modified to enhance their specificity for a specific tumor associated antigen. Genetic modification may involve the expression of a chimeric antigen receptor or an exogenous T cell receptor to graft antigen specificity onto the T cell. By contrast to exogenous T cell receptors, chimeric antigen receptors derive their specificity from the variable domains of a monoclonal antibody. Thus, T cells expressing chimeric antigen receptors (CAR T cells) induce tumor immunoreactivity in a major histocompatibility complex non-restricted manner. To date, T cell adoptive immunotherapy has been utilized as a clinical therapy for a number of cancers, including B cell malignancies (e.g., acute lymphoblastic leukemia (ALL), B cell non-Hodgkin lymphoma (NHL), and chronic lymphocytic leukemia), multiple myeloma, neuroblastoma, glioblastoma, advanced gliomas, ovarian cancer, mesothelioma, melanoma, and pancreatic cancer.

Despite its potential usefulness as a cancer treatment, adoptive immunotherapy with CAR T cells has been limited, in part, by expression of the endogenous T cell receptor on the cell surface. CAR T cells expressing an endogenous T cell receptor may recognize major and minor histocompatibility antigens following administration to an allogeneic patient, which can lead to the development of graft-versus-host-disease (GVHD). As a result, clinical trials have largely focused on the use of autologous CAR T cells, wherein a patient's T cells are isolated, genetically-modified to incorporate a chimeric antigen receptor, and then re-infused into the same patient. An autologous approach provides immune tolerance to the administered CAR T cells; however, this approach is constrained by both the time and expense necessary to produce patient-specific CAR T cells after a patient's cancer has been diagnosed.

Thus, it would be advantageous to develop "off the shelf" CAR T cells, prepared using T cells from a third party donor, that have reduced expression of the endogenous T cell receptor and do not initiate GVHD upon administration. Such products could be generated and validated in advance of diagnosis, and could be made available to patients as soon as necessary. Therefore, a need exists for the development of allogeneic CAR T cells that lack an endogenous T cell receptor in order to prevent the occurrence of GVHD.

Genetic modification of genomic DNA can be performed using site-specific, rare-cutting endonucleases that are engineered to recognize DNA sequences in the locus of interest. Methods for producing engineered, site-specific endonucleases are known in the art. For example, zinc-finger nucleases (ZFNs) can be engineered to recognize and cut pre-determined sites in a genome. ZFNs are chimeric proteins comprising a zinc finger DNA-binding domain fused to the nuclease domain of the FokI restriction enzyme. The zinc finger domain can be redesigned through rational or experimental means to produce a protein that binds to a pre-determined DNA sequence ~18 basepairs in length. By fusing this engineered protein domain to the FokI nuclease, it is possible to target DNA breaks with genome-level specificity. ZFNs have been used extensively to target gene addition, removal, and substitution in a wide range of eukaryotic organisms (reviewed in Dural et al. (2005), *Nucleic Acids Res* 33, 5978). Likewise, TAL-effector nucleases (TALENs) can be generated to cleave specific sites in genomic DNA. Like a ZFN, a TALEN comprises an engineered, site-specific DNA-binding domain fused to the FokI nuclease domain (reviewed in Mak et al. (2013), *Curr Opin Struct Biol.* 23:93-9). In this case, however, the DNA binding domain comprises a tandem array of TAL-effector domains, each of which specifically recognizes a single DNA basepair. A limitation that ZFNs and TALENs have for the practice of the current invention is that they are heterodimeric, so that the production of a single functional nuclease in a cell requires co-expression of two protein monomers.

Compact TALENs have an alternative endonuclease architecture that avoids the need for dimerization (Beurdeley et al. (2013), *Nat Commun.* 4:1762). A Compact TALEN comprises an engineered, site-specific TAL-effector DNA-binding domain fused to the nuclease domain from the I-TevI homing endonuclease. Unlike FokI, I-TevI does not need to dimerize to produce a double-strand DNA break so a Compact TALEN is functional as a monomer.

Engineered endonucleases based on the CRISPR/Cas9 system are also know in the art (Ran et al. (2013), *Nat Protoc.* 8:2281-2308; Mali et al. (2013), *Nat Methods* 10:957-63). A CRISPR endonuclease comprises two components: (1) a caspase effector nuclease, typically microbial Cas9; and (2) a short "guide RNA" comprising a ~20 nucleotide targeting sequence that directs the nuclease to a location of interest in the genome. By expressing multiple guide RNAs in the same cell, each having a different targeting sequence, it is possible to target DNA breaks simultaneously to multiple sites in the genome. Thus, CRISPR/Cas9 nucleases are suitable for the present invention. The primary drawback of the CRISPR/Cas9 system is its reported high frequency of off-target DNA breaks, which could limit the utility of the system for treating human patients (Fu et al. (2013), *Nat Biotechnol.* 31:822-6).

Homing endonucleases are a group of naturally-occurring nucleases that recognize 15-40 base-pair cleavage sites commonly found in the genomes of plants and fungi. They are frequently associated with parasitic DNA elements, such as group 1 self-splicing introns and inteins. They naturally promote homologous recombination or gene insertion at specific locations in the host genome by producing a double-stranded break in the chromosome, which recruits the cellular DNA-repair machinery (Stoddard (2006), *Q. Rev. Biophys.* 38: 49-95). Homing endonucleases are commonly grouped into four families: the LAGLIDADG (SEQ ID NO:7) family, the GIY-YIG family, the His-Cys box family and the HNH family. These families are characterized by structural motifs, which affect catalytic activity and recognition sequence. For instance, members of the LAGLIDADG (SEQ ID NO:7) family are characterized by having either one or two copies of the conserved LAGLIDADG (SEQ ID NO:7) motif (see Chevalier et al. (2001), *Nucleic Acids Res.* 29(18): 3757-3774). The LAGLIDADG (SEQ ID NO:7) homing endonucleases with a single copy of the LAGLIDADG (SEQ ID NO:7) motif form homodimers, whereas members with two copies of the LAGLIDADG (SEQ ID NO:7) motif are found as monomers.

I-CreI (SEQ ID NO: 6) is a member of the LAGLIDADG (SEQ ID NO:7) family of homing endonucleases that recognizes and cuts a 22 basepair recognition sequence in the chloroplast chromosome of the algae *Chlamydomonas reinhardtii*. Genetic selection techniques have been used to modify the wild-type I-CreI cleavage site preference (Sussman et al. (2004), *J. Mol. Biol.* 342: 31-41; Chames et al. (2005), *Nucleic Acids Res.* 33: e178; Seligman et al. (2002), *Nucleic Acids Res.* 30: 3870-9, Arnould et al. (2006), *J. Mol. Biol.* 355: 443-58). More recently, a method of rationally-designing mono-LAGLIDADG (SEQ ID NO:7) homing endonucleases was described that is capable of comprehensively redesigning I-CreI and other homing endonucleases to target widely-divergent DNA sites, including sites in mammalian, yeast, plant, bacterial, and viral genomes (WO 2007/047859).

As first described in WO 2009/059195, I-CreI and its engineered derivatives are normally dimeric but can be fused into a single polypeptide using a short peptide linker that joins the C-terminus of a first subunit to the N-terminus of a second subunit (Li et al. (2009), *Nucleic Acids Res.* 37:1650-62; Grizot et al. (2009), *Nucleic Acids Res.* 37:5405-19). Thus, a functional “single-chain” meganuclease can be expressed from a single transcript.

The use of engineered meganucleases for cleaving DNA targets in the human T cell receptor alpha constant region was previously disclosed in International Publication WO 2014/191527. The ’527 publication discloses variants of the I-OnuI meganuclease that are engineered to target a recognition sequence (SEQ ID NO:3 of the ’527 publication) within exon 1 of the TCR alpha constant region gene. Although the ’527 publication discusses that a chimeric antigen receptor can be expressed in TCR knockout cells, the authors do not disclose the insertion of the chimeric antigen receptor coding sequence into the meganuclease cleavage site in the TCR alpha constant region gene.

The use of other nucleases and mechanisms for disrupting expression of the endogenous TCR have also been disclosed. For example, the use of zinc finger nucleases for disrupting TCR genes in human T cells was described by U.S. Pat. No. 8,956,828 and by U.S. Patent Application Publication No. US2014/0349402. U.S. Publication No. US2014/0301990 describes the use of zinc finger nucleases and transcription-activator like effector nucleases (TALENs), and a CRISPR/Cas system with an engineered single guide RNA for targeting TCR genes in an isolated T cell. U.S. Patent Application Publication No. US2012/0321667 discloses the use of small-hairpin RNAs that target nucleic acids encoding specific TCRs and/or CD3 chains in T cells.

However, the present invention improves upon the teachings of the prior art. The present inventors are the first to teach genetically-modified cells that comprise an exogenous polynucleotide sequence (e.g., a chimeric antigen receptor or exogenous TCR coding sequence) inserted into the human TCR alpha constant region gene, which simultaneously disrupts expression of the endogenous T cell receptor at the cell surface. Further, the prior art does not teach the meganucleases or the recognition sequences described herein, or their use for producing such genetically-modified cells.

SUMMARY OF THE INVENTION

The present invention provides a genetically-modified cell comprising in its genome a modified T cell receptor (TCR) alpha constant region gene. Such a cell is a genetically-modified human T cell, or a genetically-modified cell derived from a human T cell. Further, such a cell has reduced cell-surface expression of the endogenous TCR when compared to an unmodified control cell. The present invention also provides a method for producing the genetically-modified cell. The present invention further provides a method of immunotherapy for treating cancer by administering the genetically-modified cell.

Thus, in one aspect, the invention provides a genetically-modified cell comprising in its genome a modified human TCR alpha constant region gene, wherein the modified human TCR alpha constant region gene comprises from 5' to 3': (a) a 5' region of the human TCR alpha constant region gene; (b) an exogenous polynucleotide; and (c) a 3' region of the human TCR alpha constant region gene. The genetically-modified cell is a genetically-modified human T cell or a genetically-modified cell derived from a human T cell. Further, the genetically-modified cell has reduced cell-surface expression of the endogenous TCR when compared to an unmodified control cell.

In one embodiment, the exogenous polynucleotide comprises a nucleic acid sequence encoding a chimeric antigen receptor, wherein the chimeric antigen receptor comprises an extracellular ligand-binding domain and one or more intracellular signaling domains.

In one such embodiment, the chimeric antigen receptor comprises an extracellular ligand-binding domain having at least 80%, at least 85%, at least 90%, at least 95%, or up to 100% sequence identity to SEQ ID NO:112, wherein the extracellular ligand-binding domain binds to CD19.

In another such embodiment, the chimeric antigen receptor comprises an intracellular cytoplasmic signaling domain having at least 80%, at least 85%, at least 90%, at least 95%, or up to 100% sequence identity to SEQ ID NO:113.

In another such embodiment, the chimeric antigen receptor comprises an intracellular co-stimulatory signaling domain having at least 80%, at least 85%, at least 90%, at least 95%, or up to 100% sequence identity to SEQ ID NO:114.

In another such embodiment, the chimeric antigen receptor further comprises a signal peptide. In some embodiments, the signal peptide can have at least 80%, at least 85%, at least 90%, at least 95%, or up to 100% sequence identity to SEQ ID NO:115.

In another such embodiment, the chimeric antigen receptor further comprises a hinge domain. In some embodiments, the hinge domain has at least 80%, at least 85%, at least 90%, at least 95%, or up to 100% sequence identity to SEQ ID NO:116.

In another such embodiment, the chimeric antigen receptor further comprises a transmembrane domain. In some embodiments, the transmembrane domain has at least 80%, at least 85%, at least 90%, at least 95%, or up to 100% sequence identity to SEQ ID NO:117.

In another such embodiment, the chimeric antigen receptor has at least 80%, at least 85%, at least 90%, at least 95%, or up to 100% sequence identity to SEQ ID NO:111.

In another embodiment, the exogenous polynucleotide comprises a promoter sequence that drives expression of the exogenous polynucleotide. In one such embodiment, the promoter sequence has at least 80%, at least 85%, at least 90%, at least 95%, or up to 100% sequence identity to SEQ ID NO:118.

In another embodiment, the nucleic acid sequence of the exogenous polynucleotide has at least 80%, at least 85%, at least 90%, at least 95%, or up to 100% sequence identity to SEQ ID NO:119.

In another embodiment, the exogenous polynucleotide is inserted into the TCR gene at a position within a recognition sequence comprising SEQ ID NO:3. In one such embodiment, the modified human TCR alpha constant region gene comprises a nucleic acid sequence having at least 80%, at least 85%, at least 90%, at least 95%, or up to 100% sequence identity to SEQ ID NO:120.

In another embodiment, the exogenous polynucleotide is inserted into the TCR alpha constant region gene at a position within a recognition sequence comprising SEQ ID NO:4. In one such embodiment, the modified human TCR alpha constant region gene comprises a nucleic acid sequence having at least 80%, at least 85%, at least 90%, at least 95%, or up to 100% sequence identity to SEQ ID NO:121.

In another embodiment, the exogenous polynucleotide is inserted into the TCR alpha constant region gene at a position within a recognition sequence comprising SEQ ID NO:5. In one such embodiment, the modified human TCR alpha constant region gene comprises a nucleic acid sequence having at least 80%, at least 85%, at least 90%, at least 95%, or up to 100% sequence identity to SEQ ID NO:122.

In another aspect, the invention provides a pharmaceutical composition comprising a genetically-modified cell, as described herein, and a pharmaceutically acceptable carrier.

In another aspect, the invention provides a genetically-modified cell, as described herein, for use as a medicament. The invention further provides the use of a genetically-modified cell, as described herein, in the manufacture of a medicament for treating a disease in a subject in need thereof. In one such aspect, the medicament is useful in the treatment of cancer. In some embodiments, the treatment of cancer is immunotherapy.

In another aspect, the invention provides a method for producing a genetically-modified cell comprising a modified human TCR alpha constant region gene, the method comprising: (a) introducing into a cell: (i) a first nucleic acid sequence encoding an engineered nuclease; or (ii) an engineered nuclease protein; wherein the engineered nuclease produces a cleavage site at a recognition sequence within the human TCR alpha constant region gene; and (b) introducing into the cell a second nucleic acid sequence comprising an exogenous polynucleotide. In such a method, the cell is a human T cell or is derived from a human T cell. Additionally, the sequence of the exogenous polynucleotide is inserted into the human TCR alpha constant region gene at the cleavage site. Further, the genetically-modified cell has reduced cell-surface expression of the endogenous TCR when compared to an unmodified control cell.

In various embodiments of the method, the first nucleic acid sequence or the engineered nuclease protein can be introduced into the cell prior to introducing the second nucleic acid, or subsequent to introducing the second nucleic acid.

In one embodiment of the method, the second nucleic acid sequence comprises from 5' to 3': (a) a 5' homology arm that is homologous to the 5' upstream sequence flanking the cleavage site; (b) the exogenous polynucleotide; and (c) a 3' homology arm that is homologous to the 3' downstream sequence flanking the cleavage site. In such an embodiment, the sequence of the exogenous polynucleotide is inserted into the human TCR alpha constant region gene at the cleavage site by homologous recombination.

In another embodiment of the method, the second nucleic acid lacks substantial homology to the cleavage site, and the sequence of the exogenous polynucleotide is inserted into the human TCR alpha constant region gene by non-homologous end-joining.

In another embodiment of the method, the exogenous polynucleotide comprises a nucleic acid sequence encoding a chimeric antigen receptor.

In another embodiment of the method, the exogenous polynucleotide comprises a first promoter sequence that drives expression of the exogenous polynucleotide.

In another embodiment of the method, the first nucleic acid encoding the engineered nuclease is introduced into the cell using an mRNA. In some embodiments, the mRNA can be a polycistronic mRNA comprising a coding sequence for at least one engineered nuclease described herein and a coding sequence for at least one additional protein (e.g., a second nuclease). In particular embodiments, a polycistronic mRNA can encode two or more engineered nucleases described herein that target different recognition sequences within the same gene (e.g., the T cell receptor alpha constant region gene). In other embodiments, a polycistronic mRNA can encode an engineered nuclease described herein and a second nuclease that recognizes and cleaves a different recognition sequence within the same gene (e.g., the T cell receptor alpha constant region gene) or, alternatively, recognizes and cleaves a different recognition sequence within another gene of interest in the genome. In such embodiments, genetically-modified cells produced using such polycistronic mRNA can have multiple genes knocked out simultaneously. In additional embodiments, a polycistronic mRNA can encode at least one engineered nuclease described herein and one additional protein that is beneficial to the cell, improves efficiency of insertion of an exogenous sequence of interest into a cleavage site, and/or is beneficial in the treatment of a disease.

In another embodiment of the method, at least the second nucleic acid sequence is introduced into the cell by contacting the cell with a viral vector comprising the second nucleic acid sequence. In some embodiments, both the first nucleic acid sequence and the second nucleic acid sequence are introduced by contacting the cell with a single viral vector comprising both the first nucleic acid sequence and the second nucleic acid sequence. Alternatively, the cell can be contacted with a first viral vector comprising the first nucleic acid sequence and a second viral vector comprising the second nucleic acid sequence.

In such an embodiment of the method, wherein the second nucleic acid sequence is introduced by a viral vector, the second nucleic acid can further comprise a second promoter sequence positioned 5' upstream of the 5' homology arm or, alternatively, positioned 3' downstream of the 3' homology arm. In embodiments where the second promoter is positioned 3' downstream of the 3' homology arm, the promoter may be inverted.

In another particular embodiment of the method, at least the second nucleic acid sequence is introduced into the cell by contacting the cell with a recombinant adeno-associated virus (AAV) vector comprising the second nucleic acid sequence. In some embodiments, both the first nucleic acid sequence and the second nucleic acid sequence are introduced by contacting the cell with a single recombinant AAV comprising both the first nucleic acid sequence and the second nucleic acid sequence. Alternatively, the cell can be contacted with a first recombinant AAV comprising the first nucleic acid sequence and a second recombinant AAV comprising the second nucleic acid sequence.

In such an embodiment of the method, wherein the second nucleic acid sequence is introduced by a recombinant AAV vector, the second nucleic acid can further comprise a second promoter sequence positioned 5' upstream of the 5' homology arm or, alternatively, positioned 3' downstream of the 3' homology arm. In embodiments where the second promoter is positioned 3' downstream of the 3' homology arm, the promoter may be inverted.

In another such embodiment of the method, the recombinant AAV vector is a self-complementary AAV vector.

In another such embodiment of the method, the recombinant AAV vector can have any serotype. In a particular embodiment of the method, the recombinant AAV vector has a serotype of AAV2. In another particular embodiment of the method, the recombinant AAV vector has a serotype of AAV6.

In another embodiment of the method, at least the second nucleic acid sequence is introduced into the cell using a single-stranded DNA template.

In a particular embodiment of the method, the first nucleic acid sequence encoding a engineered nuclease described herein is introduced into the cell by an mRNA, and the second nucleic acid sequence comprising an exogenous polynucleotide is introduced into the cell using a viral vector, preferably a recombinant AAV vector, wherein the cell is a human T cell, and wherein the sequence of interest encodes a chimeric antigen receptor. In such an embodiment, the method produces a genetically-modified T cell comprising a chimeric antigen receptor and reduced cell-surface expression of the endogenous T cell receptor when compared to a control cell.

In another embodiment of the method, the engineered nuclease is a recombinant meganuclease, a recombinant zinc-finger nuclease (ZFN), a recombinant transcription activator-like effector nuclease (TALEN), a CRISPR/Cas nuclease, or a megaTAL nuclease. In a particular embodiment of the method, the engineered nuclease is a recombinant meganuclease.

In such an embodiment of the method, the recombinant meganuclease recognizes and cleaves a recognition sequence within residues 93-208 of the human T cell receptor alpha constant region (SEQ ID NO:1). Such a recombinant meganuclease comprises a first subunit and a second subunit, wherein the first subunit binds to a first recognition half-site of the recognition sequence and comprises a first hypervariable (HVR1) region, and wherein the second subunit binds to a second recognition half-site of the recognition sequence and comprises a second hypervariable (HVR2) region.

In one such embodiment of the method, the recognition sequence comprises SEQ ID NO:3 (i.e., the TRC 1-2 recognition sequence).

In another such embodiment of the method, the first meganuclease subunit comprises an amino acid sequence having at least 80%, at least 85%, at least 90%, or at least 95% sequence identity to residues 198-344 of any one of SEQ ID NOs:8-18 or residues 7-153 of any one of SEQ ID NOs:19-27, and the second meganuclease subunit comprises an amino acid sequence having at least 80%, at least 85%, at least 90%, or at least 95% sequence identity to residues 7-153 of any one of SEQ ID NOs:8-18 or residues 198-344 of any one of SEQ ID NOs:19-27.

In another such embodiment of the method, the HVR1 region comprises Y at a position corresponding to: (a) position 215 of any one of SEQ ID NOs:8-18; or (b) position 24 of any one of SEQ ID NOs:19-27. In another such embodiment, the HVR1 region comprises G at a position corresponding to: (a) position 233 of any one of SEQ ID NOs:8-18; or (b) position 42 of any one of SEQ ID NOs: 19-27. In another such embodiment, the HVR1 region comprises one or more of Y and G at positions corresponding to (a) positions 215 and 233, respectively, of any one of SEQ ID NOs:8-18; or (b) positions 24 and 42, respectively, of any one of SEQ ID NOs:19-27.

In another such embodiment of the method, the HVR2 region comprises T at a position corresponding to: (a) position 26 of any one of SEQ ID NOs:8-18; or (b) position 217 of any one of SEQ ID NOs:19-27. In another such embodiment, the HVR2 region comprises F or Y at a position corresponding to: (a) position 28 of any one of SEQ ID NOs:8-18; or (b) position 219 of any one of SEQ ID NOs:19-27. In another such embodiment, the HVR2 region comprises F at a position corresponding to: (a) position 38 of any one of SEQ ID NOs:8-18; or (b) position 229 of any one of SEQ ID NOs:19-27. In another such embodiment, the HVR2 region comprises S at a position corresponding to: (a) position 44 of any one of SEQ ID NOs:8-18; or (b) position 235 of any one of SEQ ID NOs:19-27. In another such embodiment, the HVR2 region comprises F or Y at a position corresponding to: (a) position 46 of any one of SEQ ID NOs:8-18; or (b) position 237 of any one of SEQ ID NOs:19-27. In another such embodiment, the HVR2 region comprises one or more of T, F or Y, F, S, and F or Y, and R at positions corresponding to: (a) positions 26, 28, 38, 44, and 46, respectively, of any one of SEQ ID NOs:8-18; or (b) positions 217, 219, 229, 235, and 237, respectively, of any one of SEQ ID NOs:19-27.

In another such embodiment of the method, the HVR1 region comprises residues 215-270 of any one of SEQ ID NOs:8-18 or residues 24-79 of any one of SEQ ID NOs: 19-27. In another such embodiment, the HVR2 region comprises residues 24-79 of any one of SEQ ID NOs:8-18 or residues 215-270 of any one of SEQ ID NOs:19-27.

In another such embodiment of the method, the first meganuclease subunit comprises residues 198-344 of any one of SEQ ID NOs:8-18 or residues 7-153 of any one of SEQ ID NOs:19-27. In another such embodiment, the second meganuclease subunit comprises residues 7-153 of any one of SEQ ID NOs:8-18 or residues 198-344 of any one of SEQ ID NOs:19-27.

In another such embodiment of the method, the recombinant meganuclease is a single-chain meganuclease comprising a linker, wherein the linker covalently joins the first subunit and the second subunit.

In another such embodiment of the method, the recombinant meganuclease comprises the amino acid sequence of any one of SEQ ID NOs:8-27.

In a further embodiment of the method, the recognition sequence comprises SEQ ID NO:4 (i.e., the TRC 3-4 recognition sequence).

In one such embodiment of the method, the first meganuclease subunit comprises an amino acid sequence having at least 80%, at least 85%, at least 90%, or at least 95% sequence identity to residues 7-153 of SEQ ID NO:28 or 29, and the second meganuclease subunit comprises an amino acid sequence having at least 80%, at least 85%, at least 90%, or at least 95% sequence identity to residues 198-344 of SEQ ID NO:28 or 29.

In another such embodiment of the method, the HVR1 region comprises Y at a position corresponding to position 24 of SEQ ID NO:28 or 29. In another such embodiment, the HVR1 region comprises T at a position corresponding to position 26 of SEQ ID NO:30 or 31. In another such embodiment, the HVR1 region comprises Y at a position corresponding to position 46 of SEQ ID NO:28 or 29. In another such embodiment, the HVR1 region comprises one or more of Y, T, and Y at positions corresponding to positions 24, 26, and 46, respectively, of SEQ ID NO:28 or 29.

In another such embodiment of the method, the HVR2 region comprises H at a position corresponding to position 215 of SEQ ID NO:28 or 29. In another such embodiment, the HVR2 region comprises T at a position corresponding to position 266 of SEQ ID NO:28 or 29. In another such embodiment, the HVR2 region comprises C at a position corresponding to position 268 of SEQ ID NO:28 or 29. In another such embodiment, the HVR2 region comprises one or more of H, T, and C at positions corresponding to positions 215, 266, and 268 of SEQ ID NOs:28 or 29.

In another such embodiment of the method, the HVR1 region comprises residues 24-79 of SEQ ID NO:28 or 29. In another such embodiment, the HVR2 region comprises residues 215-270 of SEQ ID NO:28 or 29.

In another such embodiment of the method, the first meganuclease subunit comprises residues 7-153 of SEQ ID NO:28 or 29. In another such embodiment, the second meganuclease subunit comprises residues 198-344 of SEQ ID NO:28 or 29.

In another such embodiment of the method, the recombinant meganuclease is a single-chain meganuclease comprising a linker, wherein the linker covalently joins the first subunit and the second subunit.

In another such embodiment of the method, the recombinant meganuclease comprises the amino acid sequence of SEQ ID NO:28 or 29.

In a further embodiment of the method, the recognition sequence comprises SEQ ID NO:5 (i.e., the TRC 7-8 recognition sequence).

In one such embodiment of the method, the first meganuclease subunit comprises an amino acid sequence having at least 80%, at least 85%, at least 90%, or at least 95% sequence identity to residues 7-153 of SEQ ID NO:30 or residues 198-344 of SEQ ID NO:31 or 32, and the second meganuclease subunit comprises an amino acid sequence having at least 80%, at least 85%, at least 90%, or at least 95% sequence identity to residues 198-344 of SEQ ID NO:30 or residues 7-153 of SEQ ID NO:31 or 32.

In another such embodiment of the method, the HVR1 region comprises Y at a position corresponding to: (a) position 24 of SEQ ID NO:30; or (b) position 215 of SEQ ID NO:31 or 32.

In another such embodiment of the method, the HVR2 region comprises Y or W at a position corresponding to: (a) position 215 of SEQ ID NO:30; or (b) position 24 of SEQ ID NO:31 or 32. In another such embodiment, the HVR2 region comprises M, L, or W at a position corresponding to: (a) position 231 of SEQ ID NO:30; or (b) position 40 of SEQ ID NO:31 or 32. In another such embodiment, the HVR2 region comprises Y at a position corresponding to: (a) position 237 of SEQ ID NO:30; or (b) position 46 of SEQ ID NO:31 or 32. In another such embodiment, the HVR2 region comprises one or more of Y or W, M, L, or W, and Y at positions corresponding to: (a) positions 215, 231, and 237, respectively, of SEQ ID NO:30; or (b) positions 24, 40, and 46, respectively, of SEQ ID NO:31 or 32.

In another such embodiment of the method, the HVR1 region comprises residues 24-79 of SEQ ID NO:30 or residues 215-270 of SEQ ID NO:31 or 32. In another such embodiment, the HVR2 region comprises residues 215-270 of SEQ ID NO:30 or residues 24-79 of SEQ ID NO:31 or 32.

In another such embodiment of the method, the first meganuclease subunit comprises residues 7-153 of SEQ ID NO:30 or residues 198-344 of SEQ ID NO:31 or 32. In another such embodiment, the second meganuclease subunit comprises residues 198-344 of SEQ ID NO:30 or residues 7-153 of SEQ ID NO:31 or 32.

In another such embodiment of the method, the recombinant meganuclease is a single-chain meganuclease comprising a linker, wherein the linker covalently joins the first subunit and the second subunit.

In another such embodiment of the method, the recombinant meganuclease comprises the amino acid sequence of any one of SEQ ID NOs:30-32.

In another aspect, the invention provides a method of immunotherapy for treating cancer in a subject in need thereof. In some embodiments, the method comprises administering to the subject a pharmaceutical composition comprising a genetically-modified cell, as described herein, and a pharmaceutically acceptable carrier. In some embodiments, the method comprises administering to the subject a pharmaceutical composition comprising a genetically-modified cell produced according to the methods described herein, and a pharmaceutically acceptable carrier.

In another embodiment of the method, the cancer to be treated is selected from the group consisting of a cancer of B-cell origin, breast cancer, gastric cancer, neuroblastoma, osteosarcoma, lung cancer, melanoma, prostate cancer, colon cancer, renal cell carcinoma, ovarian cancer, rhabdomyo sarcoma, leukemia, and Hodgkin's lymphoma.

In another embodiment of the method, the cancer of B-cell origin is selected from the group consisting of B-lineage acute lymphoblastic leukemia, B-cell chronic lymphocytic leukemia, and B-cell non-Hodgkin's lymphoma.

In some embodiments, the CAR comprises an extracellular antigen-binding domain. In some embodiments, the extracellular ligand-binding domain or moiety can be in the form of a single-chain variable fragment (scFv) derived from a monoclonal antibody, which provides specificity for a particular epitope or antigen (e.g., an epitope or antigen preferentially present on the surface of a cell, such as a cancer cell or other disease-causing cell or particle). The scFv can be attached via a linker sequence. The extracellular ligand-binding domain can be specific for any antigen or epitope of interest. In some embodiments, the scFv can be humanized. The extracellular domain of a chimeric antigen receptor can also comprise an autoantigen (see, Payne et al. (2016), *Science* 353(6295): 179-184), which can be recognized by autoantigen-specific B cell receptors on B lymphocytes, thus directing T cells to specifically target and kill autoreactive B lymphocytes in antibody-mediated autoimmune diseases. Such CARs can be referred to as chimeric autoantibody receptors (CAARs), and their use is encompassed by the invention.

The foregoing and other aspects and embodiments of the present invention can be more fully understood by reference to the following detailed description and claims. Certain features of the invention, which are, for clarity, described in the context of separate embodiments, may also be provided in combination in a single embodiment. All combinations of the embodiments are specifically embraced by the present invention and are disclosed herein just as if each and every combination was individually and explicitly disclosed. Conversely, various features of the invention, which are, for brevity, described in the context of a single embodiment, may also be provided separately or in any suitable sub-combination. All sub-combinations of features listed in the embodiments are also specifically embraced by the present invention and are disclosed herein just as if each and every such sub-combination was individually and explicitly disclosed herein. Embodiments of each aspect of the present invention disclosed herein apply to each other aspect of the invention mutatis mutandis.

BRIEF DESCRIPTION OF THE FIGURES

FIG. 1. TRC recognition sequences in the human TRC alpha constant region gene. A) Each recognition sequence targeted by a recombinant meganuclease of the invention comprises two recognition half-sites. Each recognition half-site comprises 9 base pairs, separated by a 4 base pair central sequence. The TRC 1-2 recognition sequence (SEQ ID NO:3) spans nucleotides 187-208 of the human T cell alpha constant region (SEQ ID NO:1), and comprises two recognition half-sites referred to as TRC1 and TRC2. The TRC 3-4 recognition sequence (SEQ ID NO:4) spans nucleotides 93-114 of the human T cell alpha constant region (SEQ ID NO:1), and comprises two recognition half-sites referred to as TRC3 and TRC4. The TRC 7-8 recognition sequence (SEQ ID NO:5) spans nucleotides 118-139 of the human T cell alpha constant region (SEQ ID NO:1), and comprises two recognition half-sites referred to as TRC7 and TRC8. B) The recombinant meganucleases of the invention comprise two subunits, wherein the first subunit comprising the HVR1 region binds to a first recognition half-site (e.g., TRC1, TRC3, or TRC7) and the second subunit comprising the HVR2 region binds to a second recognition half-site (e.g., TRC2, TRC4, or TRC8). In embodiments where the recombinant meganuclease is a single-chain meganuclease, the first subunit comprising the HVR1 region can be positioned as either the N-terminal or C-terminal subunit. Likewise, the second subunit comprising the HVR2 region can be positioned as either the N-terminal or C-terminal subunit.

FIG. 2A-B. Amino acid alignment of TRC1-binding subunits. A-B) Some recombinant meganucleases encompassed by the invention comprise one subunit that binds the 9 base pair TRC1 recognition half-site of SEQ ID NO:3. Amino acid sequence alignments are provided for the TRC1-binding subunits (SEQ ID NOs:33-52) of the recombinant meganucleases set forth in SEQ ID NOs:8-27. As shown, the TRC1-binding subunit of SEQ ID NOs:8-18 comprises residues 198-344, whereas the TRC1-binding subunit of SEQ ID NOs:19-27 comprises residues 7-153. Each TRC1-binding subunit comprises a 56 amino acid hypervariable region as indicated. Variable residues within the hypervariable region are shaded, with the most frequent amino acids at each position further highlighted; the most prevalent residues are bolded, whereas the second most prevalent are bolded and italicized. Residues outside of the hypervariable region are identical in each subunit, with the exception of a Q or E residue at position 80 or position 271 (see, U.S. Pat. No. 8,021,867). All TRC1-binding subunits provided in FIG. 2 share at least 90% sequence identity to the TRC1-binding subunit (residues 198-344) of the TRC 1-2x.87 EE meganuclease (SEQ ID NO:33). Residue numbers shown are those of SEQ ID NOs:8-27.

FIG. 3A-B. Amino acid alignment of TRC2-binding subunits. A-B) Some recombinant meganucleases encompassed by the invention comprise one subunit that binds the 9 base pair TRC2 recognition half-site of SEQ ID NO:3. Amino acid sequence alignments are provided for the TRC2-binding subunits (SEQ ID NOs:58-77) of the recombinant meganucleases set forth in SEQ ID NOs:8-27. As shown, the TRC2-binding subunit of SEQ ID NOs:8-18 comprises residues 7-153, whereas the TRC2-binding subunit of SEQ ID NOs:19-27 comprises residues 198-344. Each TRC2-binding subunit comprises a 56 amino acid hypervariable region as indicated. Variable residues within the hypervariable region are shaded, with the most frequent amino acids at each position further highlighted; the most prevalent residues are bolded, whereas the second most prevalent are bolded and italicized. Residues outside of the hypervariable region are identical in each subunit, with the exceptions of a Q or E residue at position 80 or position 271 (see, U.S. Pat. No. 8,021,867), and an R residue at position 139 of meganucleases TRC 1-2x.87 EE, TRC 1-2x.87 QE, TRC 1-2x.87 EQ, TRC 1-2x.87, and TRC 1-2x.163 (shaded grey and underlined). All TRC2-binding subunits provided in FIG. 3 share at least 90% sequence identity to the TRC2-binding subunit (residues 7-153) of the TRC 1-2x.87 EE meganuclease (SEQ ID NO:58). Residue numbers shown are those of SEQ ID NOs:8-27.

FIG. 4. Amino acid alignment of TRC3-binding subunits. Some recombinant meganucleases encompassed by the invention comprise one subunit that binds the 9 base pair TRC3 recognition half-site of SEQ ID NO:4. Amino acid sequence alignments are provided for the TRC3-binding subunits (SEQ ID NOs:53 and 54) of the recombinant meganucleases set forth in SEQ ID NOs:28 and 29. As shown, the TRC3-binding subunit of SEQ ID NOs:28 and 29 comprises residues 7-153. Each TRC3-binding subunit comprises a 56 amino acid hypervariable region as indicated. Variable residues within the hypervariable region are shaded. Residues outside of the hypervariable region are identical in each subunit, with the exceptions of a Q or E residue at position 80 (see, U.S. Pat. No. 8,021,867). The TRC3-binding subunits of the TRC 3-4x.3 and TRC 3-4x.19 meganucleases share 97% sequence identity. Residue numbers shown are those of SEQ ID NOs:28 and 29.

Figure 8:
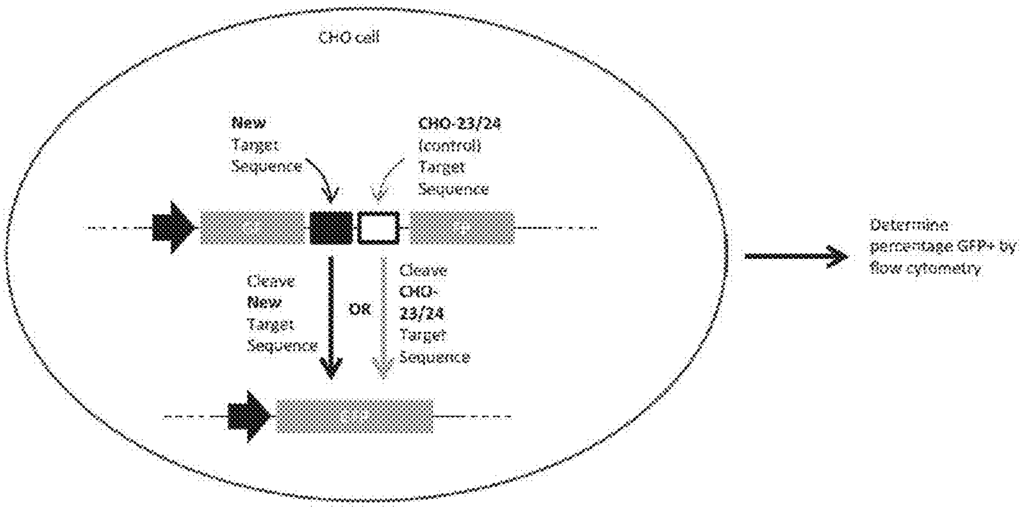

FIG. 5. Amino acid alignment of TRC4-binding subunits. Some recombinant meganucleases encompassed by the invention comprise one subunit that binds the 9 base pair TRC4 recognition half-site of SEQ ID NO:4. Amino acid sequence alignments are provided for the TRC4-binding subunits (SEQ ID NOs:78 and 79) of the recombinant meganucleases set forth in SEQ ID NOs:28 and 29. As shown, the TRC4-binding subunit of SEQ ID NOs:28 and 29 comprises residues 198-344. Each TRC4-binding subunit comprises a 56 amino acid hypervariable region as indicated. Variable residues within the hypervariable region are shaded. Residues outside of the hypervariable region are identical in each subunit, with the exceptions of a Q or E residue at position 80 (see, U.S. Pat. No. 8,021,867). The TRC4-binding subunits of the TRC 3-4x.3 and TRC 3-4x.19 meganucleases share 97% sequence identity. Residue numbers shown are those of SEQ ID NOs:28 and 29.

FIG. 6A-B. Amino acid alignment of TRC7-binding subunits. A-B) Some recombinant meganucleases encompassed by the invention comprise one subunit that binds the 9 base pair TRC7 recognition half-site of SEQ ID NO:5. Amino acid sequence alignments are provided for the TRC7-binding subunits (SEQ ID NOs:55-57) of the recombinant meganucleases set forth in SEQ ID NOs:30-32. As shown, the TRC7-binding subunit of SEQ ID NO:30 comprises residues 7-153, whereas the TRC7-binding subunit of SEQ ID NOs:31 and 32 comprises residues 198-344. Each TRC7-binding subunit comprises a 56 amino acid hypervariable region as indicated. Variable residues within the hypervariable region are shaded, with the most frequent amino acids at each position further highlighted; the most prevalent residues are bolded, whereas the second most prevalent are bolded and italicized. Residues outside of the hypervariable region are identical in each subunit, with the exception of a Q or E residue at position 80 or position 271 (see, U.S. Pat. No. 8,021,867). All TRC7-binding subunits provided in FIG. 6 share at least 90% sequence identity to the TRC7-binding subunit (residues 7-153) of the TRC 7-8x.7 meganuclease (SEQ ID NO:55). Residue numbers shown are those of SEQ ID NOs:30-32.

FIG. 7A-B. Amino acid alignment of TRC8-binding subunits. A-B) Some recombinant meganucleases encompassed by the invention comprise one subunit that binds the 9 base pair TRC8 recognition half-site of SEQ ID NO:5. Amino acid sequence alignments are provided for the TRC8-binding subunits (SEQ ID NOs:80-82) of the recombinant meganucleases set forth in SEQ ID NOs:30-32. As shown, the TRC8-binding subunit of SEQ ID NO:30 comprises residues 198-344, whereas the TRC8-binding subunit of SEQ ID NOs:31 and 32 comprises residues 7-153. Each TRC8-binding subunit comprises a 56 amino acid hypervariable region as indicated. Variable residues within the hypervariable region are shaded, with the most frequent amino acids at each position further highlighted; the most prevalent residues are bolded, whereas the second most prevalent are bolded and italicized. Residues outside of the hypervariable region are identical in each subunit, with the exception of a Q or E residue at position 80 or position 271 (see, U.S. Pat. No. 8,021,867). All TRC8-binding subunits provided in FIG. 7 share at least 90% sequence identity to the TRC8-binding subunit (residues 198-344) of the TRC 7-8x.7 meganuclease (SEQ ID NO:80). Residue numbers shown are those of SEQ ID NOs:30-32.

FIG. 8. Schematic of reporter assay in CHO cells for evaluating recombinant meganucleases targeting recognition sequences found in the T cell receptor alpha constant region (SEQ ID NO:1). For the recombinant meganucleases described herein, a CHO cell line was produced in which a reporter cassette was integrated stably into the genome of the cell. The reporter cassette comprised, in 5' to 3' order: an SV40 Early Promoter; the 5' 2/3 of the GFP gene; the recognition sequence for an engineered meganuclease of the invention (e.g., the TRC 1-2 recognition sequence, the TRC 3-4 recognition sequence, or the TRC 7-8 recognition sequence); the recognition sequence for the CHO-23/24 meganuclease (WO/2012/167192); and the 3' 2/3 of the GFP gene. Cells stably transfected with this cassette did not express GFP in the absence of a DNA break-inducing agent. Meganucleases were introduced by transduction of plasmid DNA or mRNA encoding each meganuclease. When a DNA break was induced at either of the meganuclease recognition sequences, the duplicated regions of the GFP gene recombined with one another to produce a functional GFP gene. The percentage of GFP-expressing cells could then be determined by flow cytometry as an indirect measure of the frequency of genome cleavage by the meganucleases.

Figure 9:
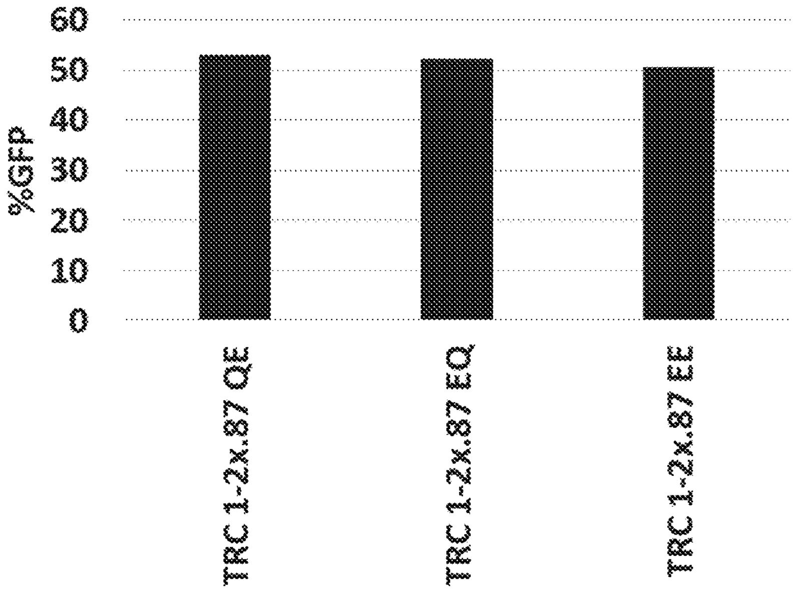

FIG. 9. Efficiency of recombinant meganucleases for recognizing and cleaving recognition sequences in the human T cell receptor alpha constant region (SEQ ID NO:1) in a CHO cell reporter assay. Each of the recombinant meganucleases set forth in SEQ ID NOs:8-32 were engineered to target the TRC 1-2 recognition sequence (SEQ ID NO:3), the TRC 3-4 recognition sequence (SEQ ID NO:4), or the TRC 7-8 recognition sequence (SEQ ID NO:5), and were screened for efficacy in the CHO cell reporter assay. The results shown provide the percentage of GFP-expressing cells observed in each assay, which indicates the efficacy of each meganuclease for cleaving a TRC target recognition sequence or the CHO-23/24 recognition sequence. A negative control (RHO 1-2 bs) was further included in each assay. A)-C) Meganucleases targeting the TRC 1-2 recognition sequence. D) Meganucleases targeting the TRC 3-4 recognition sequence. E)-F) Meganucleases targeting the TRC 7-8 recognition sequence. G) Variants of the TRC 1-2x.87 meganuclease, wherein the Q at position 271 is substituted with E (TRC 1-2x.87 QE), the Q at position 80 is substituted with E (TRC 1-2x.87 EQ), or the Q at position 80 and the Q at position 271 are both substituted with E (TRC 1-2x.87 EE).

Figure 10:
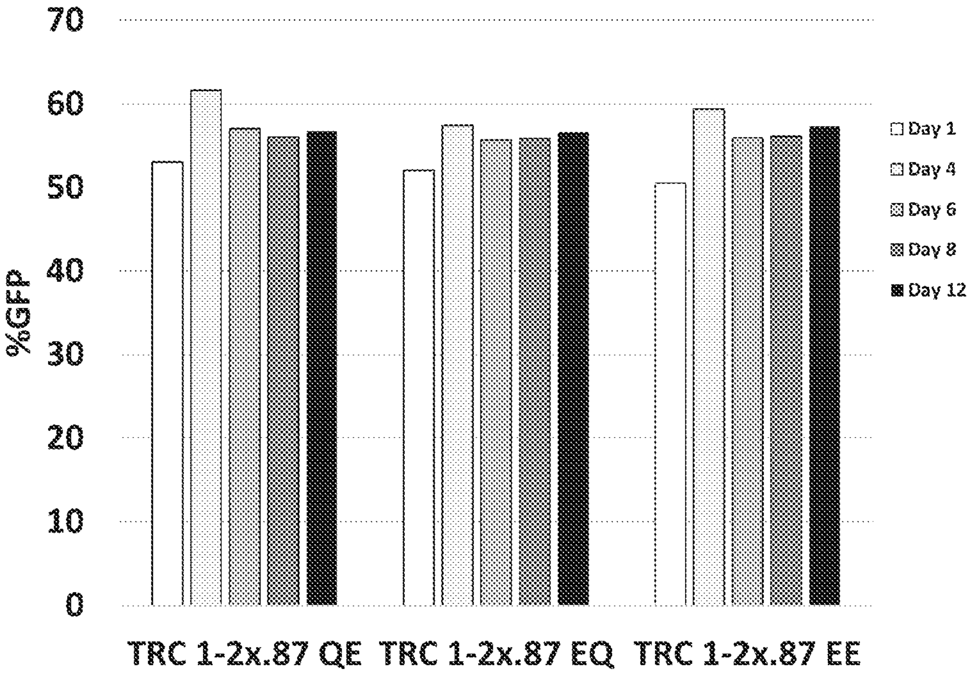

FIG. 10. Time course of recombinant meganuclease efficacy in CHO cell reporter assay. The TRC 1-2x.87 QE, TRC 1-2x.87 EQ, and TRC 1-2x.87 EE meganucleases were evaluated in the CHO reporter assay, with the percentage of GFP-expressing cells determined 1, 4, 6, 8, and 12 days after introduction of meganuclease-encoding mRNA into the CHO reporter cells.

FIG. 11. Analysis of Jurkat cell genomic DNA following transfection with TRC 1-2 meganucleases. At 72 hours post-transfection with mRNA encoding TRC 1-2 meganucleases, genomic DNA was harvested and a T7 endonuclease assay was performed to estimate genetic modification at the endogenous TRC 1-2 recognition sequence.

Figure 12:
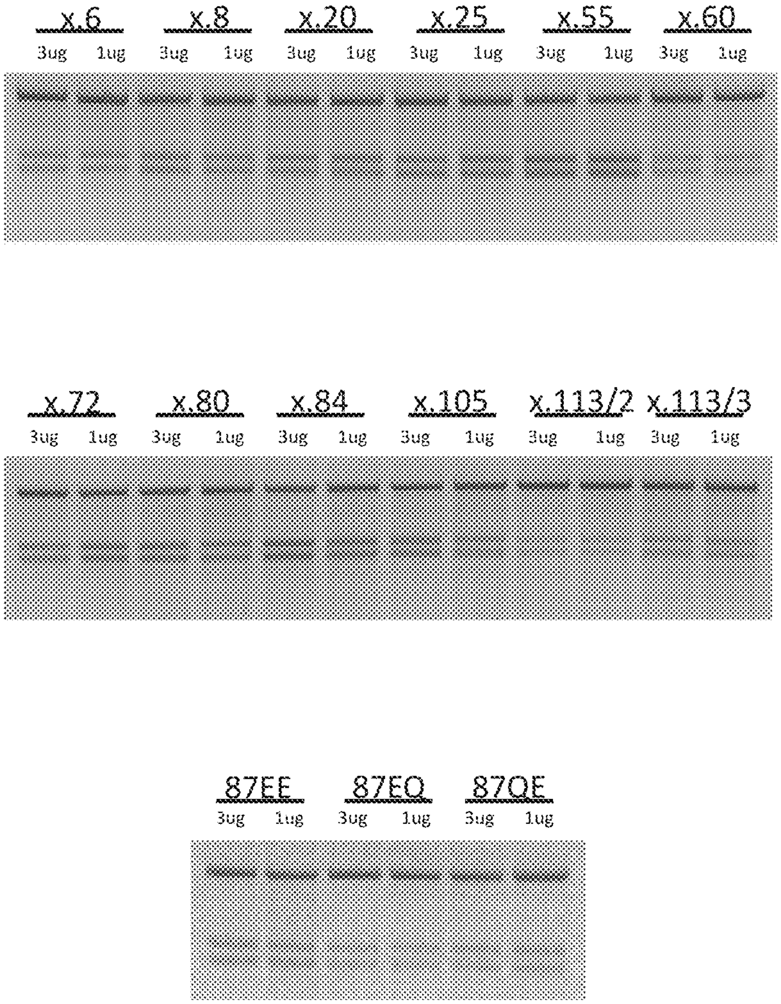

FIG. 12. Dose-response of TRC 1-2 meganuclease expression in Jurkat cells on genetic modification at the endogenous TRC 1-2 recognition sequence. Jurkat cells were transfected with either 3 μg or 1 μg of a given TRC 1-2 meganuclease mRNA. At 96 hours, genomic DNA was analyzed using a T7 endonuclease assay.

Figure 13:
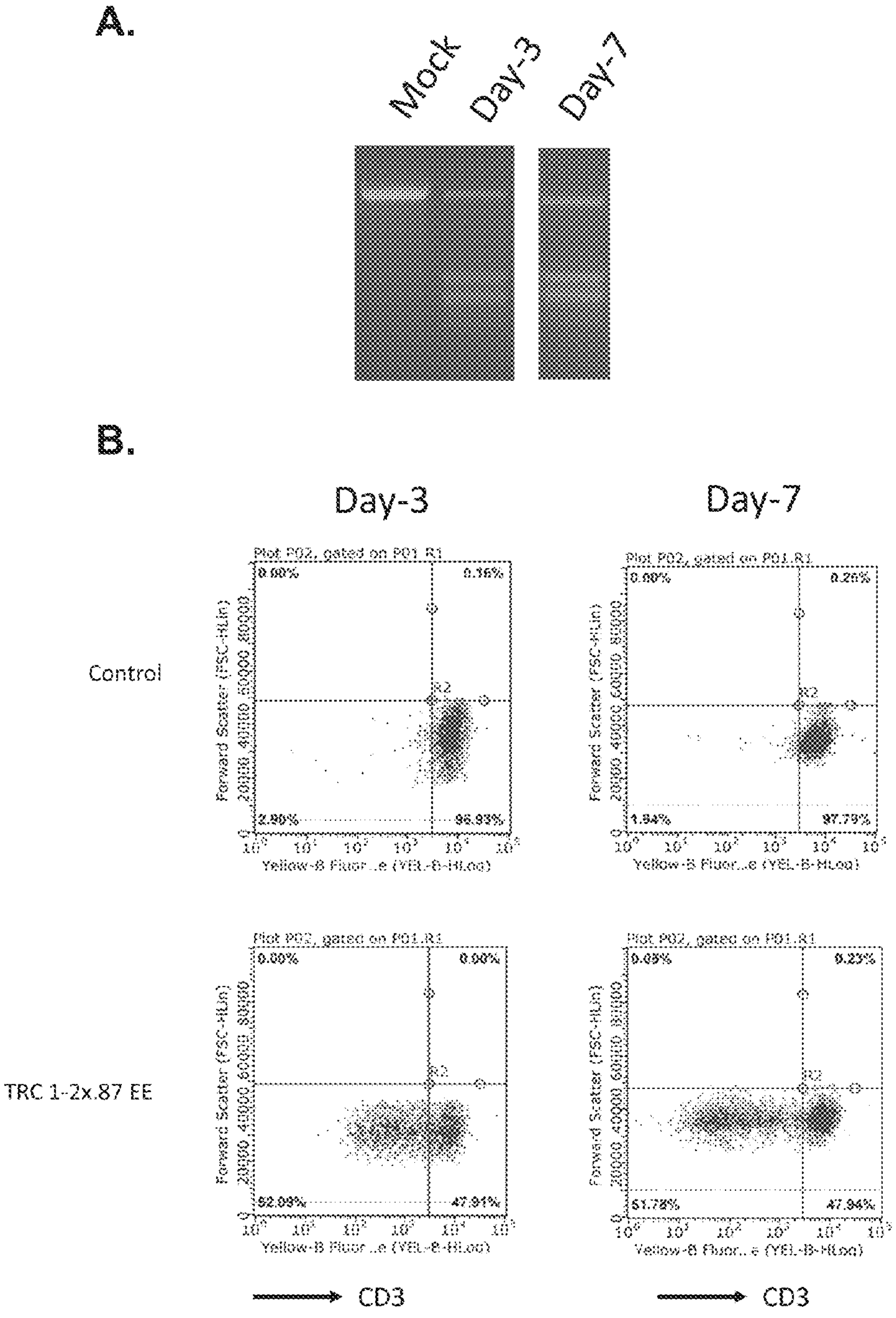

FIG. 13. Cleavage of TRC 1-2 recognition sequence in human T cells. A) CD3+ T cells were stimulated with anti-CD3 and anti-CD28 antibodies for 3 days, then electroporated with mRNA encoding the TRC 1-2x.87 EE meganuclease. Genomic DNA was harvested at 3 days and 7 days post-transfection, and analyzed using a T7 endonuclease assay. B) To determine whether mutations at the endogenous TRC 1-2 recognition sequence were sufficient to eliminate surface expression of the T cell receptor, cells were analyzed by flow cytometry using an anti-CD3 antibody. Control cells (transfected with water) and TRC 1-2x.87 EE-transfected cells were analyzed at day 3 and day 7 post-transfection, and the percentage of CD3-positive and CD3-negative T cells was determined.

FIG. 14. Nucleic acid sequences of representative deletions that were observed at the TRC 1-2 recognition sequence in human T cells following expression of TRC 1-2 meganucleases.

Figure 15:
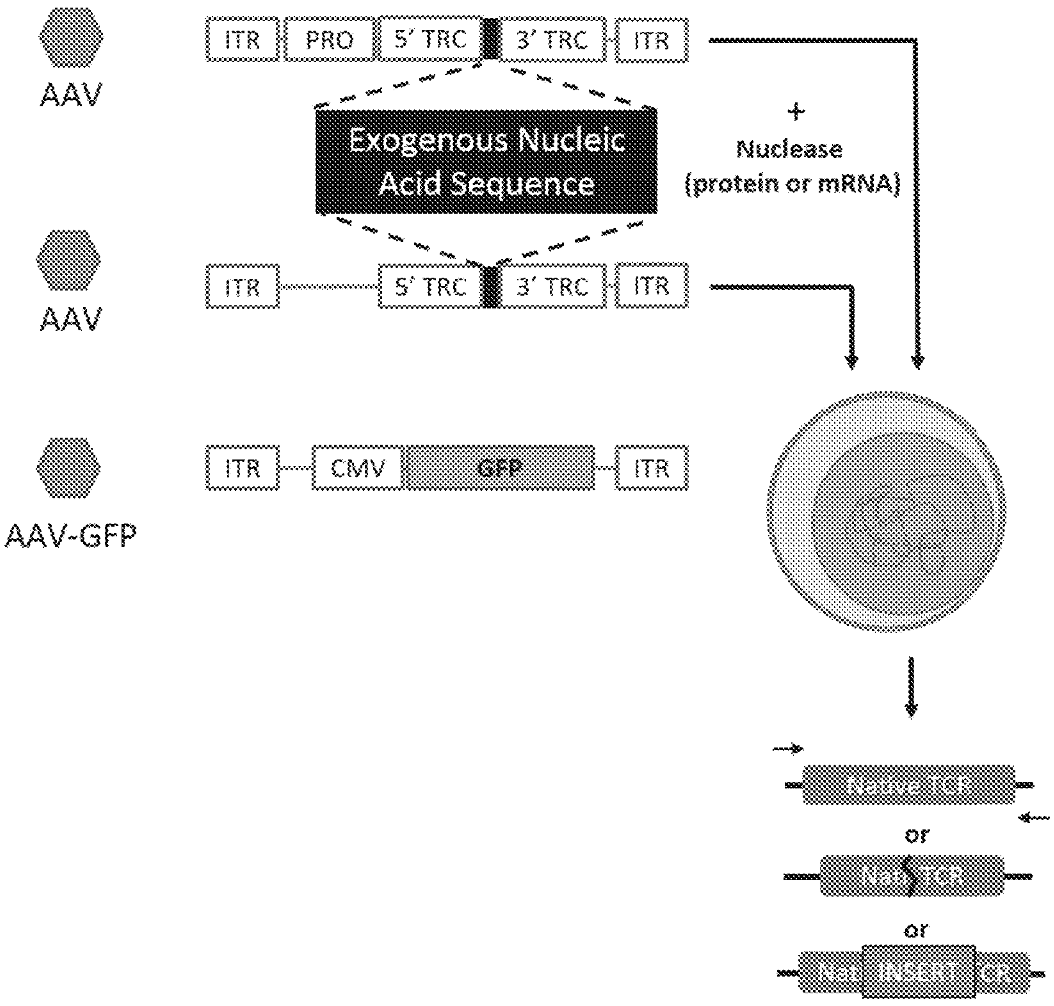

FIG. 15. Diagram illustrating sequence elements of recombinant AAV vectors and their use in combination with an engineered nuclease to insert an exogenous nucleic acid sequence into the endogenous TCR alpha constant region gene.

Figure 16:
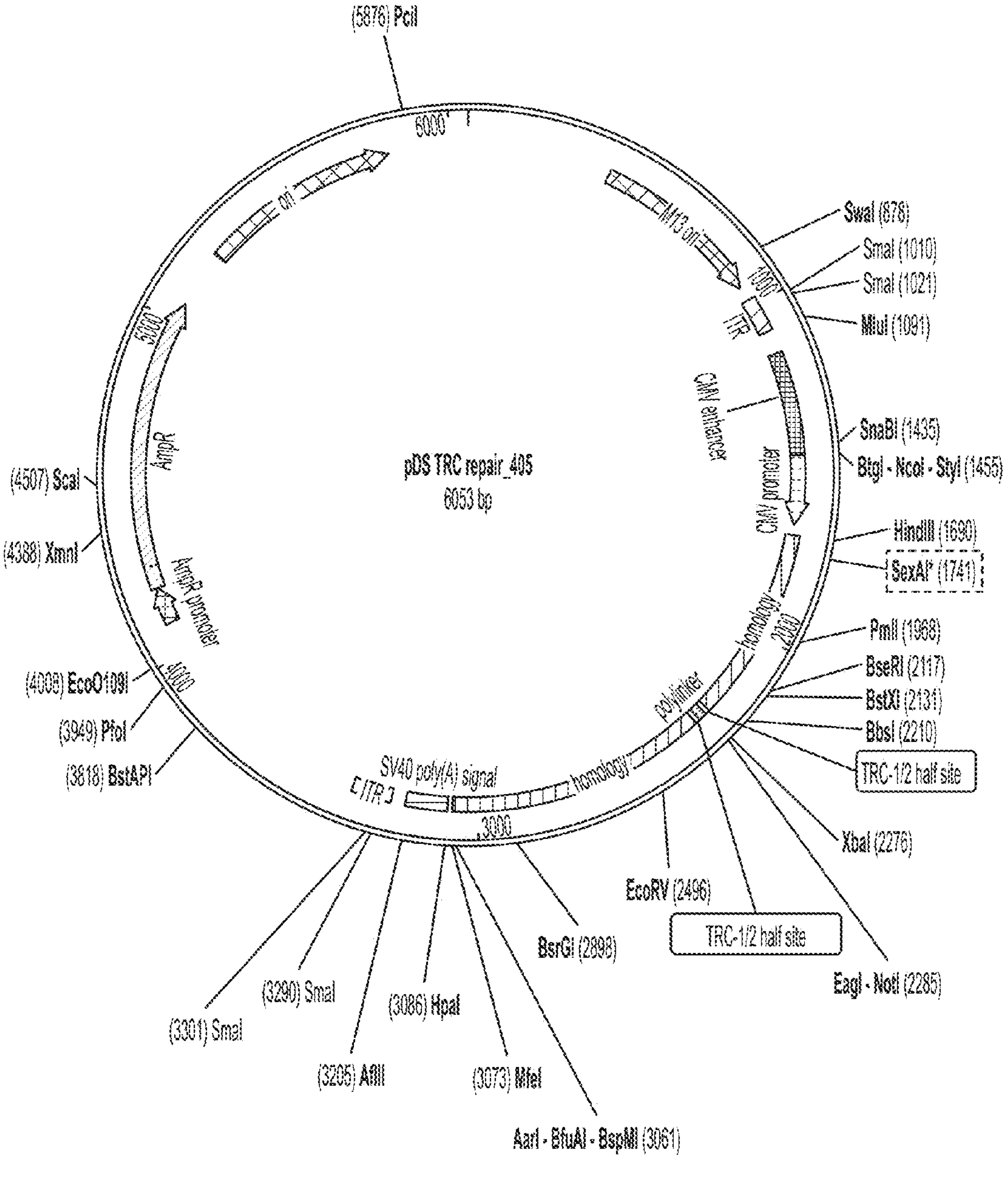

FIG. 16. Map of plasmid used to produce the AAV405 vector.

Figure 17:
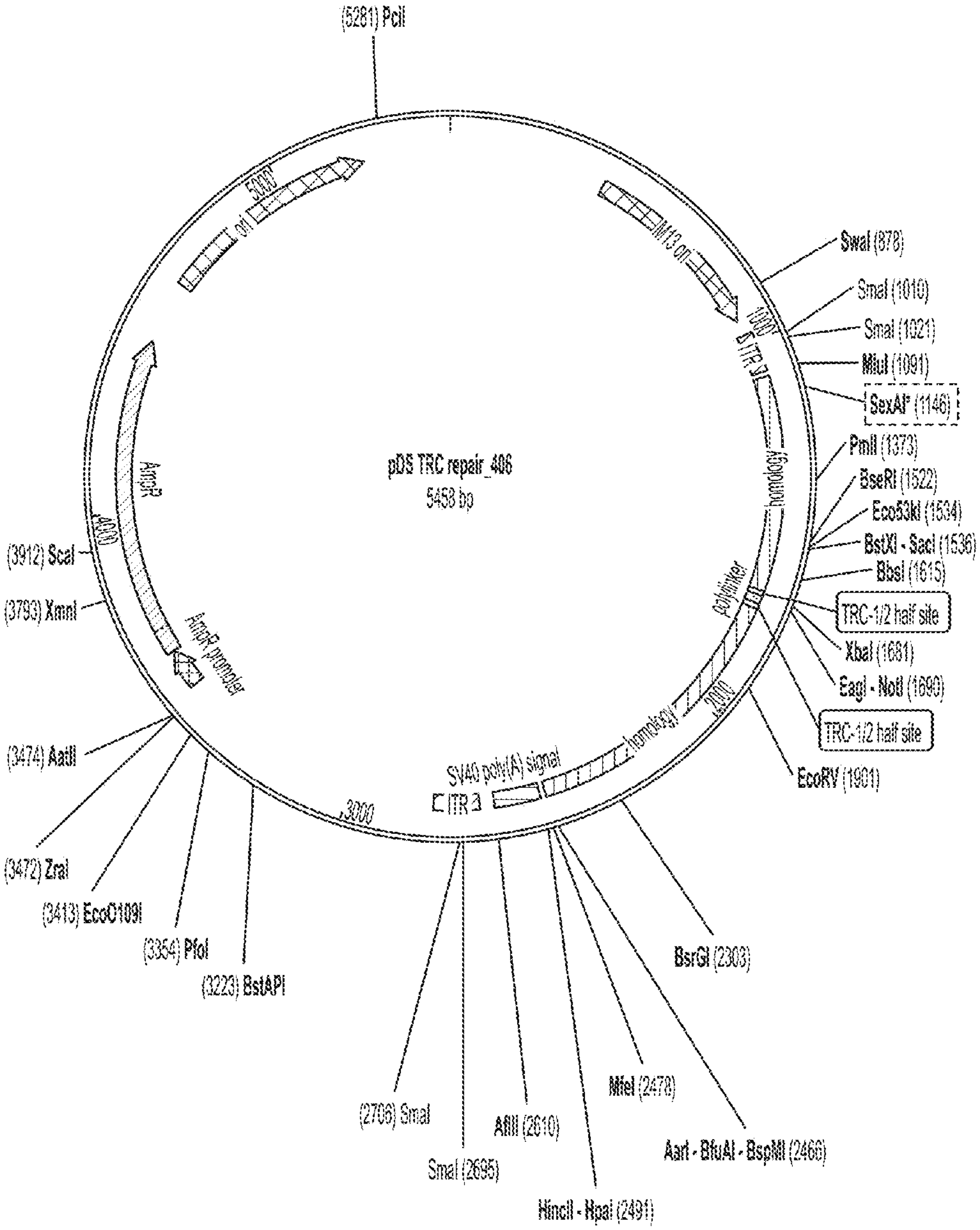

FIG. 17. Map of plasmid used to produce the AAV406 vector.

Figure 18:
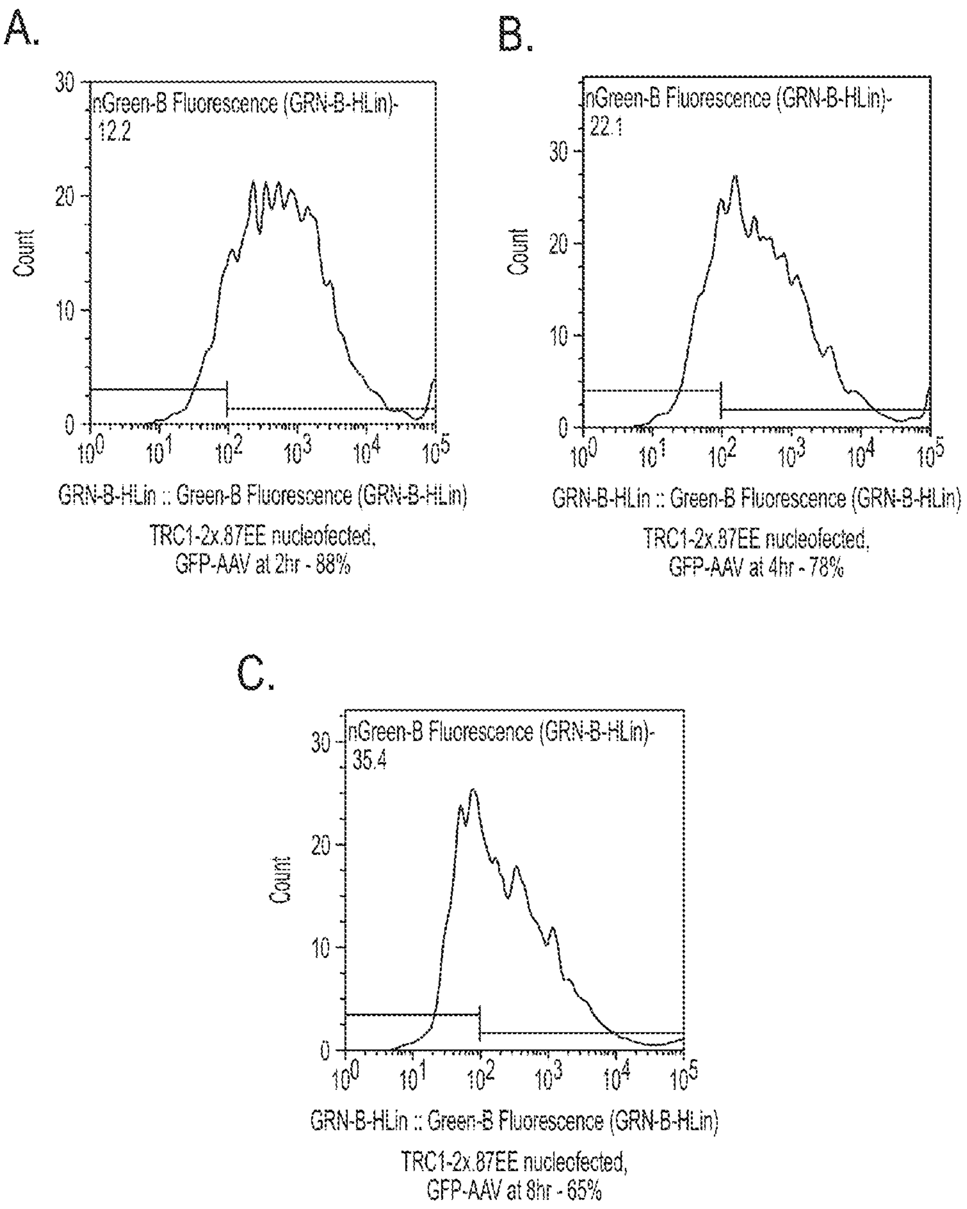

FIG. 18. Determining the timing of meganuclease mRNA transfection and recombinant AAV transduction to enhance AAV transduction efficiency. Human CD3+ T cells were electroporated with mRNA encoding the TRC 1-2x.87 EE meganuclease and at 2, 4, or 8 hours post-transfection, cells were transduced with a recombinant AAV vector encoding GFP (GFP-AAV). T cells were analyzed by flow cytometry for GFP expression at 72 hours post-transduction to determine transduction efficiency.

Figure 19:
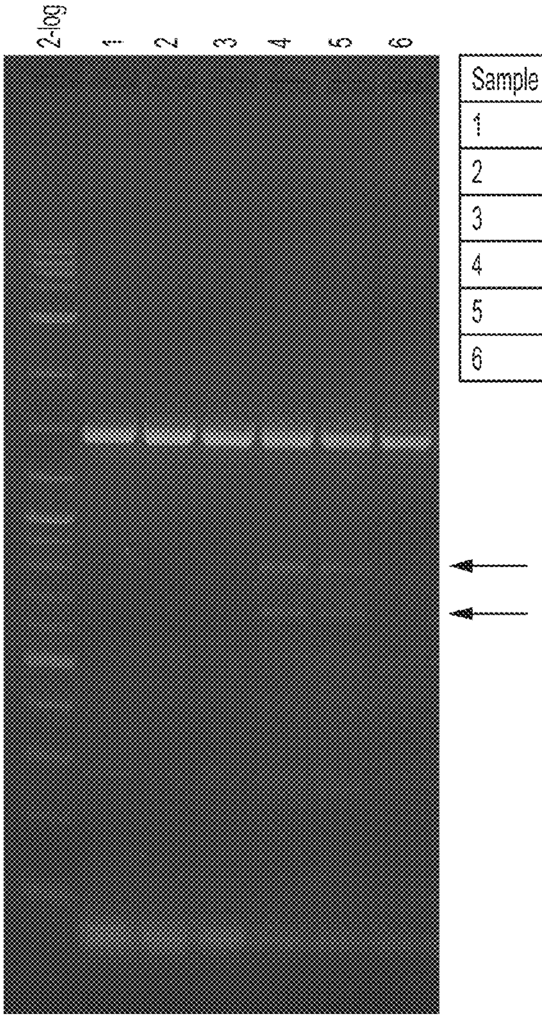

FIG. 19. Analyzing human T cells for insertion of an exogenous nucleic acid sequence using recombinant AAV vectors. CD3+ T cells transfected with TRC 1-2x.87 EE mRNA and subsequently transduced (2 hours post-transfection) with AAV405 or AAV406. Transduction-only controls were mock transfected (with water) and transduced with either AAV405 or AAV406. Meganuclease-only controls were transfected with TRC 1-2x.87 EE and then mock transduced (with water) at 2 hours post-transfection. Genomic DNA was harvested from T cells and the TRC 1-2 locus was amplified by PCR using primers that recognized sequences beyond the region of homology in the AAV vectors. PCR primers outside of the homology regions only allowed for amplification of the T cell genome, not from the AAV vectors. PCR products were purified and digested with EagI. PCR products were then analyzed for cleavage.

FIG. 20. Characterization of EagI insertion into the TRC 1-2 recognition sequence of human T cells using AAV405. A) Undigested PCR product generated from previous experiments was cloned into a pCR-blunt vector. Colony PCR was performed using M13 forward and reverse primers and a portion of PCR products from cells transfected with TRC 1-2x.87 EE and AAV405 was analyzed by gel electrophoresis. Analysis shows a mix of full-length PCR products (approximately 1600 bp), smaller inserts, and empty plasmids (approximately 300 bp). B) In parallel, another portion of PCR products were digested with EagI to determine the percent of clones that contain the EagI recognition site inserted in the TRC 1-2 recognition sequence. PCR products cleaved with EagI generated expected fragments of approximately 700 and 800 bp.

FIG. 21. Characterization of EagI insertion into the TRC 1-2 recognition sequence of human T cells using AAV406. A) Undigested PCR product generated from previous experiments was cloned into a pCR-blunt vector. Colony PCR was performed using M13 forward and reverse primers and a portion of PCR products from cells transfected with TRC 1-2x.87 EE and AAV406 was analyzed by gel electrophoresis. Analysis shows a mix of full-length PCR products (approximately 1600 bp), smaller inserts, and empty plasmids (approximately 300 bp). B) In parallel, another portion of PCR products were digested with EagI to determine the percent of clones that contain the EagI recognition site inserted in the TRC 1-2 recognition sequence. PCR products cleaved with EagI generated expected fragments of approximately 700 and 800 bp.

FIG. 22. A) Nucleic acid sequences of representative deletions and insertions (i.e., indels) that were observed at the TRC 1-2 recognition sequence in human T cells following expression of TRC 1-2 meganucleases. B) Nucleic acid sequence of the TRC 1-2 recognition sequence confirming insertion of the exogenous nucleic acid sequence comprising the EagI restriction site.

Figure 23:
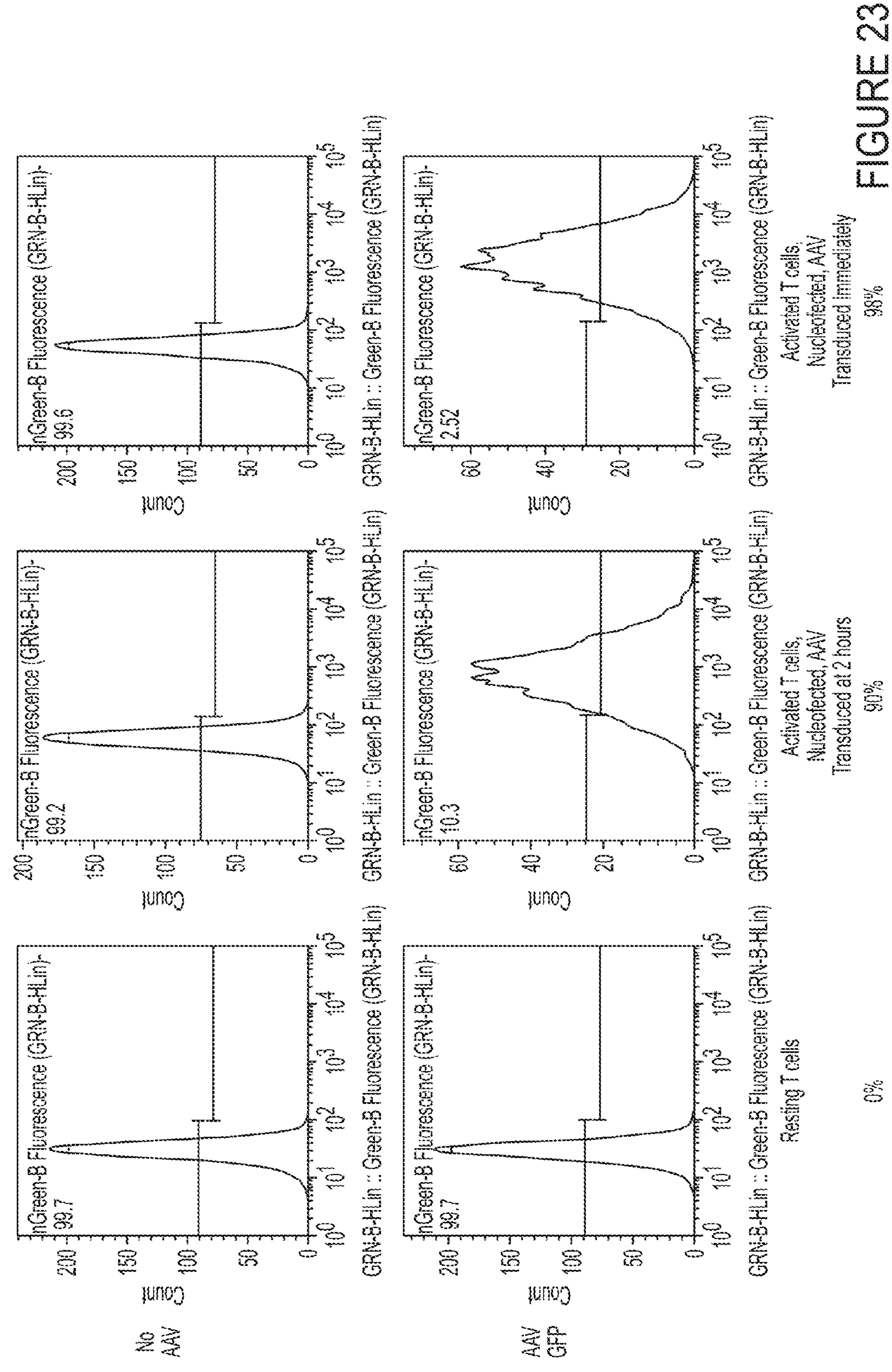

FIG. 23. Enhancement of recombinant AAV transduction efficiency. Transduction efficiency was further analyzed by optimizing the timing of meganuclease mRNA transfection and subsequent AAV transduction. Human CD3+ T cells were electroporated with mRNA encoding the TRC 1-2x.87 EE meganuclease and subsequently transduced with GFP-AAV immediately after transfection or 2 hours post-transfection. Additionally, non-stimulated resting T cells were transduced with GFP-AAV. Mock transduced cells were also analyzed. At 72 hours post-transduction, cells were analyzed by flow cytometry for GFP expression to determine AAV transduction efficiency.

Figure 24:
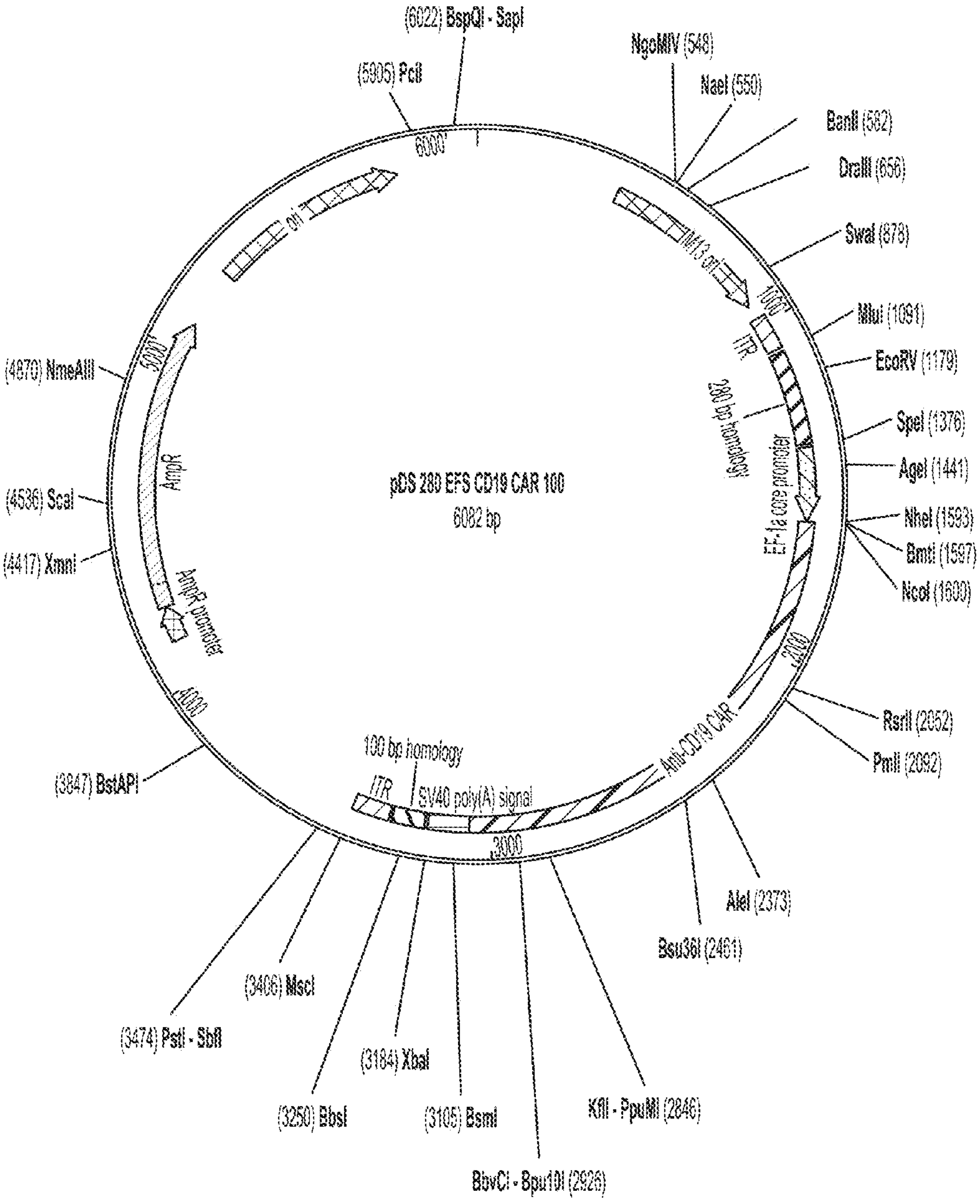

FIG. 24. Map of plasmid used to produce the AAV-CAR100 (AAV408) vector.

Figure 25:
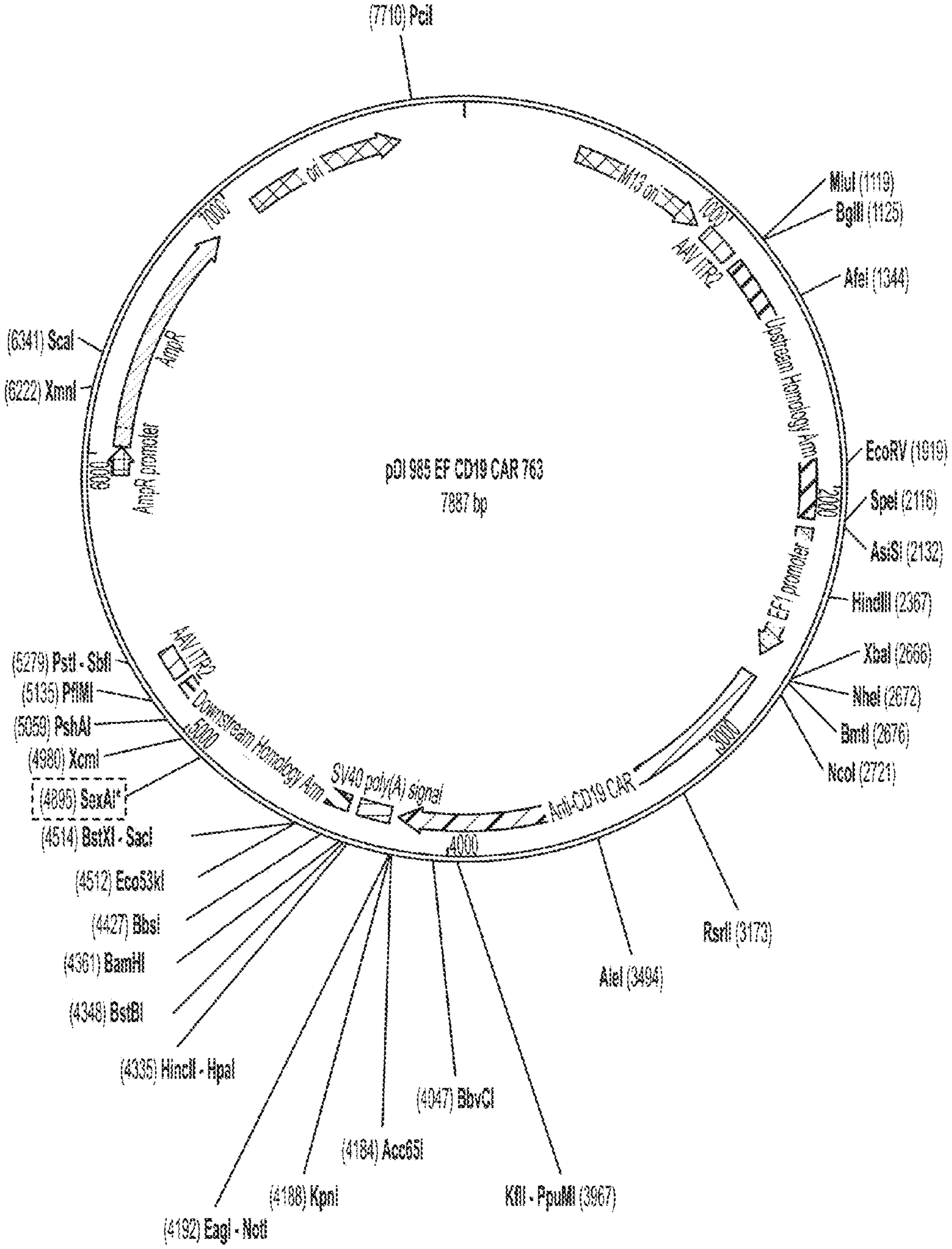

FIG. 25. Map of plasmid used to produce the AAV-CAR763 (AAV412) vector.

Figure 26:
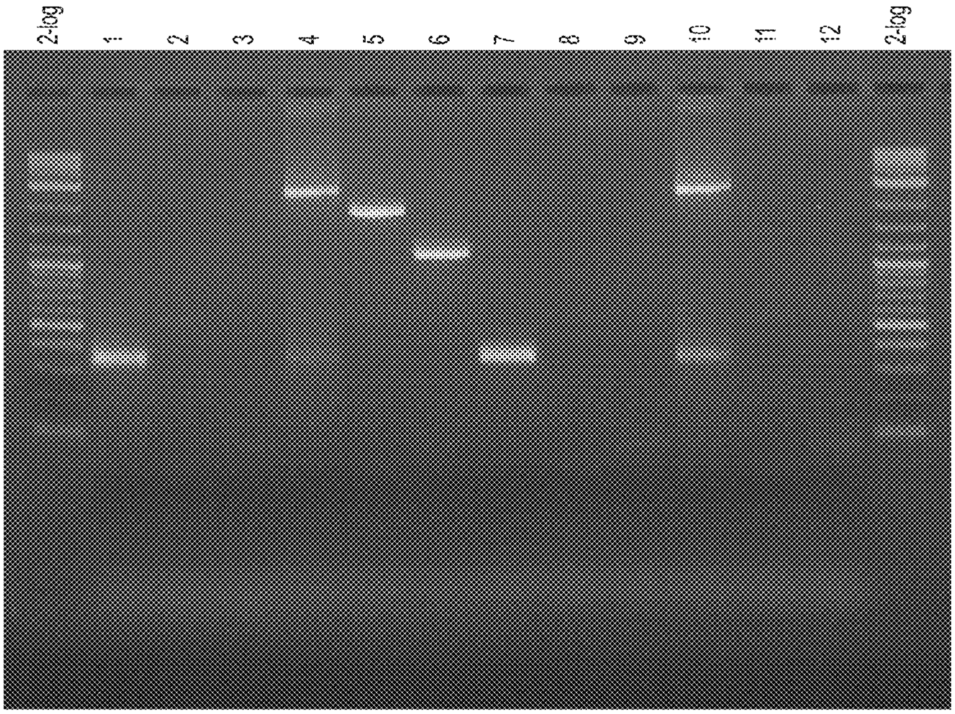

FIG. 26. Insertion of chimeric antigen receptor coding sequence at TRC 1-2 recognition site in human T cells. A PCR-based assay was developed to determine whether the AAV412 HDR template was utilized to repair double-strand breaks at the TRC 1-2 recognition sequence.

FIG. 27. Insertion of chimeric antigen receptor coding sequence at TRC 1-2 recognition site in human T cells. A PCR-based assay was developed to determine whether the AAV408 HDR template was utilized to repair double-strand breaks at the TRC 1-2 recognition sequence. A) PCR products generated using a primer pair that only amplifies a product on the 5' end of the TRC 1-2 recognition sequence locus if the CAR gene has been inserted into that locus. B) PCR products generated using a primer pair that only amplifies a product on the 3' end of the TRC 1-2 recognition sequence locus if the CAR gene has been inserted into that locus.

Figure 28:
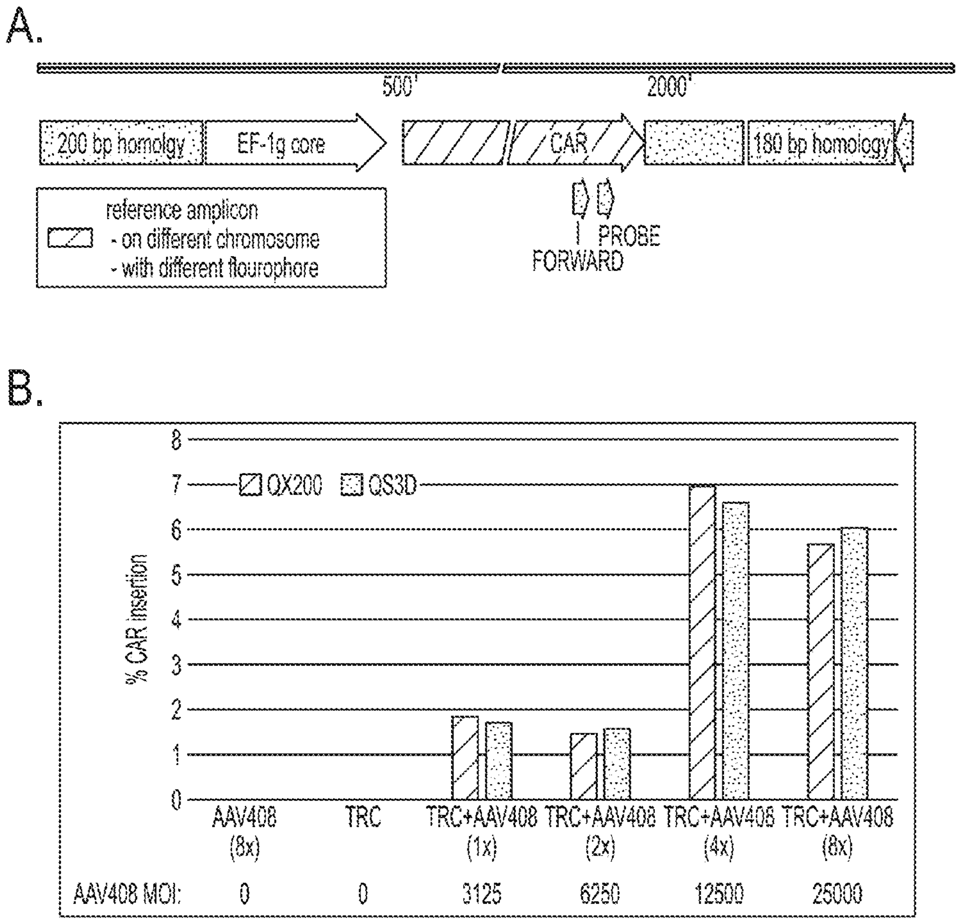

FIG. 28. Digital PCR. A) Schematic of a digital PCR assay developed to quantitatively determine insertion efficiency of the chimeric antigen receptor coding sequence into the TRC 1-2 recognition site in human T cells. B) Results of digital PCR on genomic DNA from human T cells electroporated with a TRC 1-2x.87EE meganuclease mRNA and/or increasing amounts of AAV408.

Figure 29:
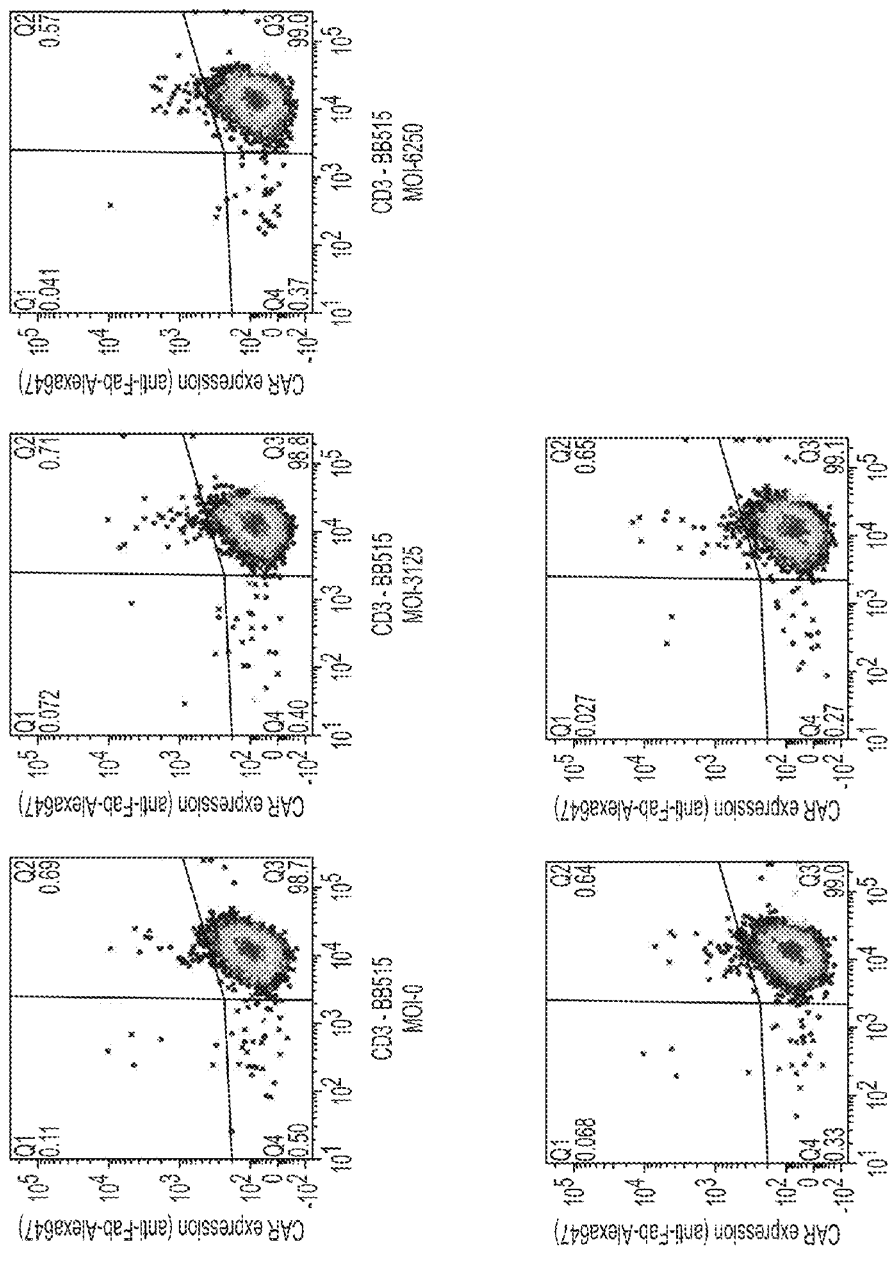
Figure 29:
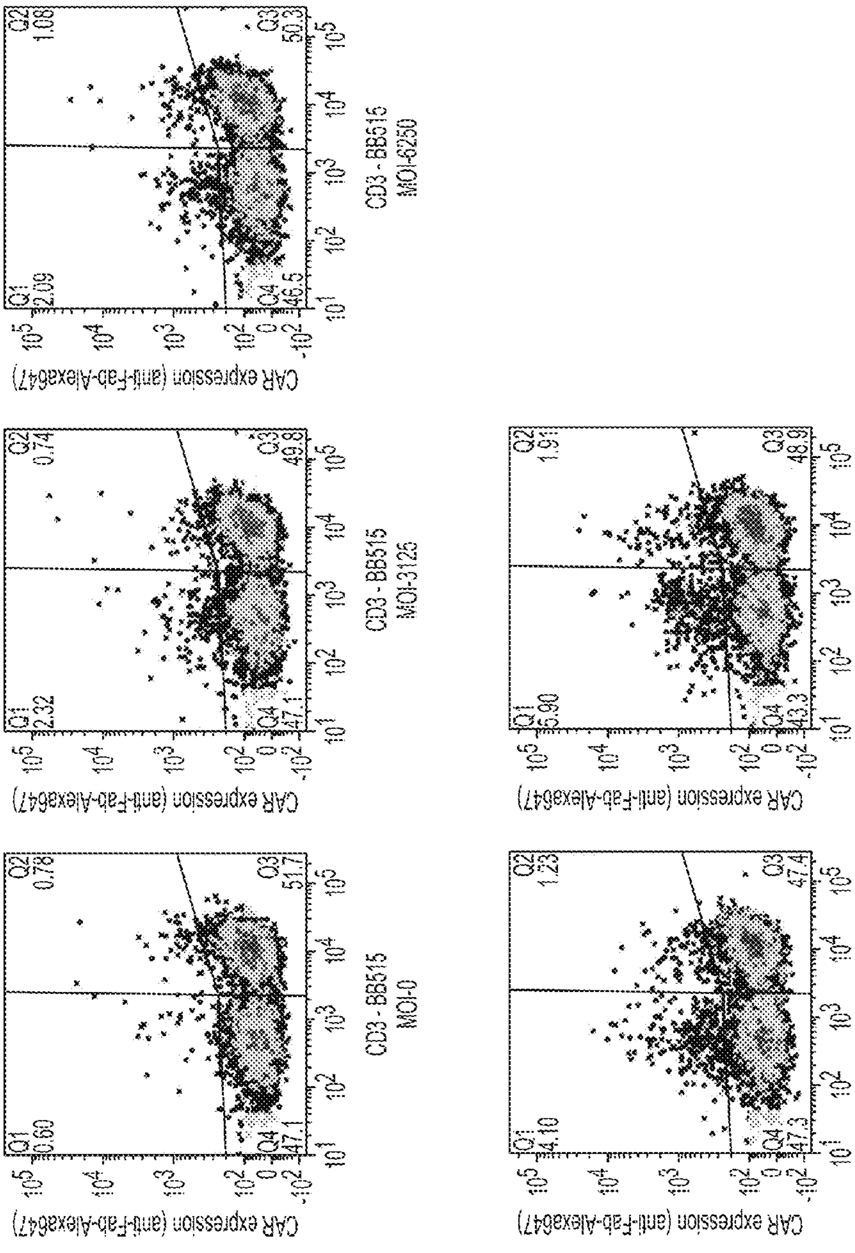

FIG. 29. Cell-surface expression of CD19 chimeric antigen receptor on human T cells. The expression level of the anti-CD19 chimeric antigen receptor was determined in cells that had the CAR gene inserted into the TRC 1-2 recognition sequence using AAV408 as the HDR template. Cell-surface expression was analyzed by flow cytometry. A) Cells that were mock electroporated and mock transduced (MOI—0), and cells that were mock electroporated and transduced with increasing amounts of AAV408. B) Cells that were electroporated with TRC 1-2x.87EE and mock transduced (MOI—0), and cells that were electroporated with TRC 1-2x.87EE and transduced with increasing amounts of AAV408.

Figure 30:
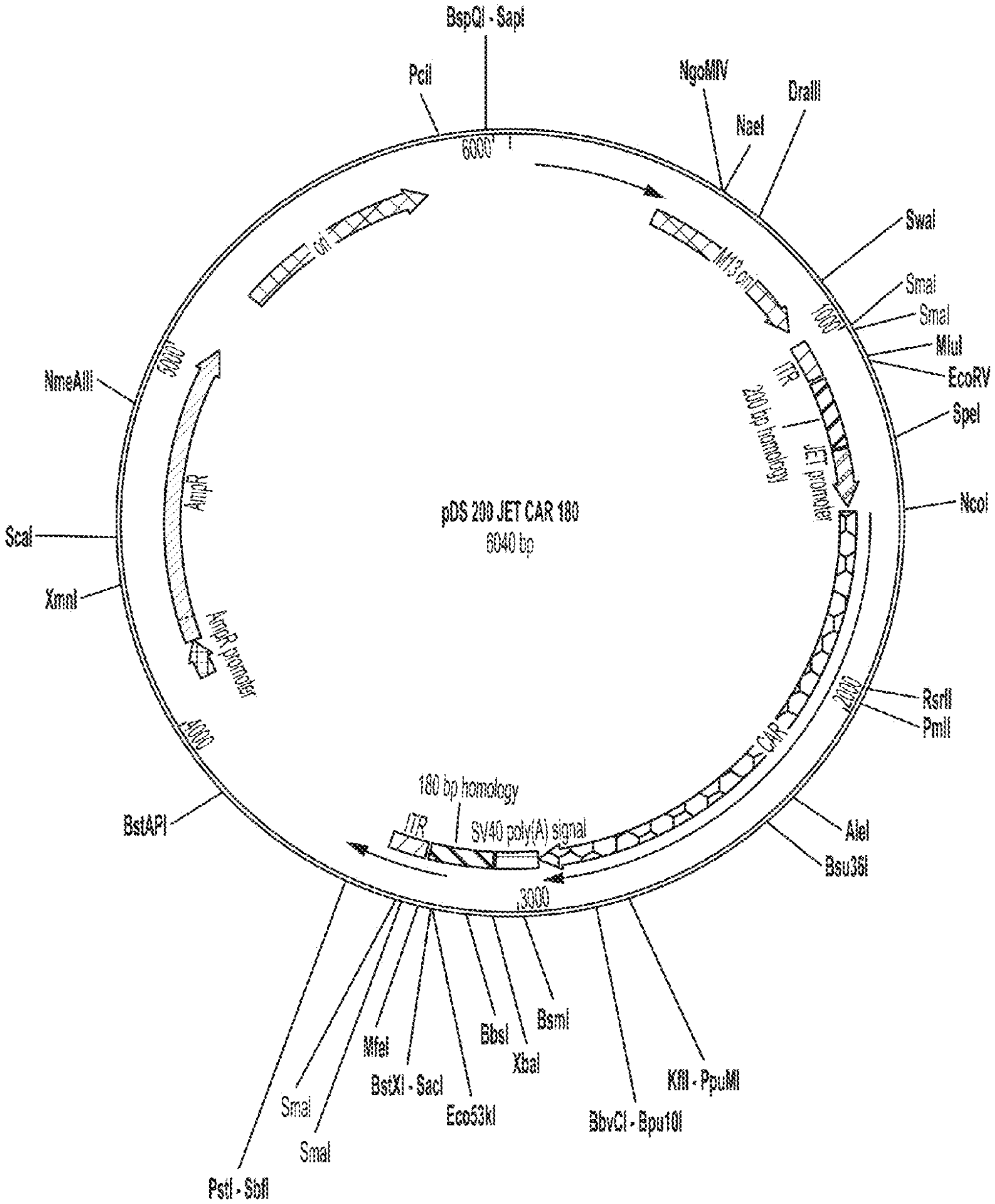

FIG. 30. Map of plasmid used to produce the AAV421 vector.

Figure 31:
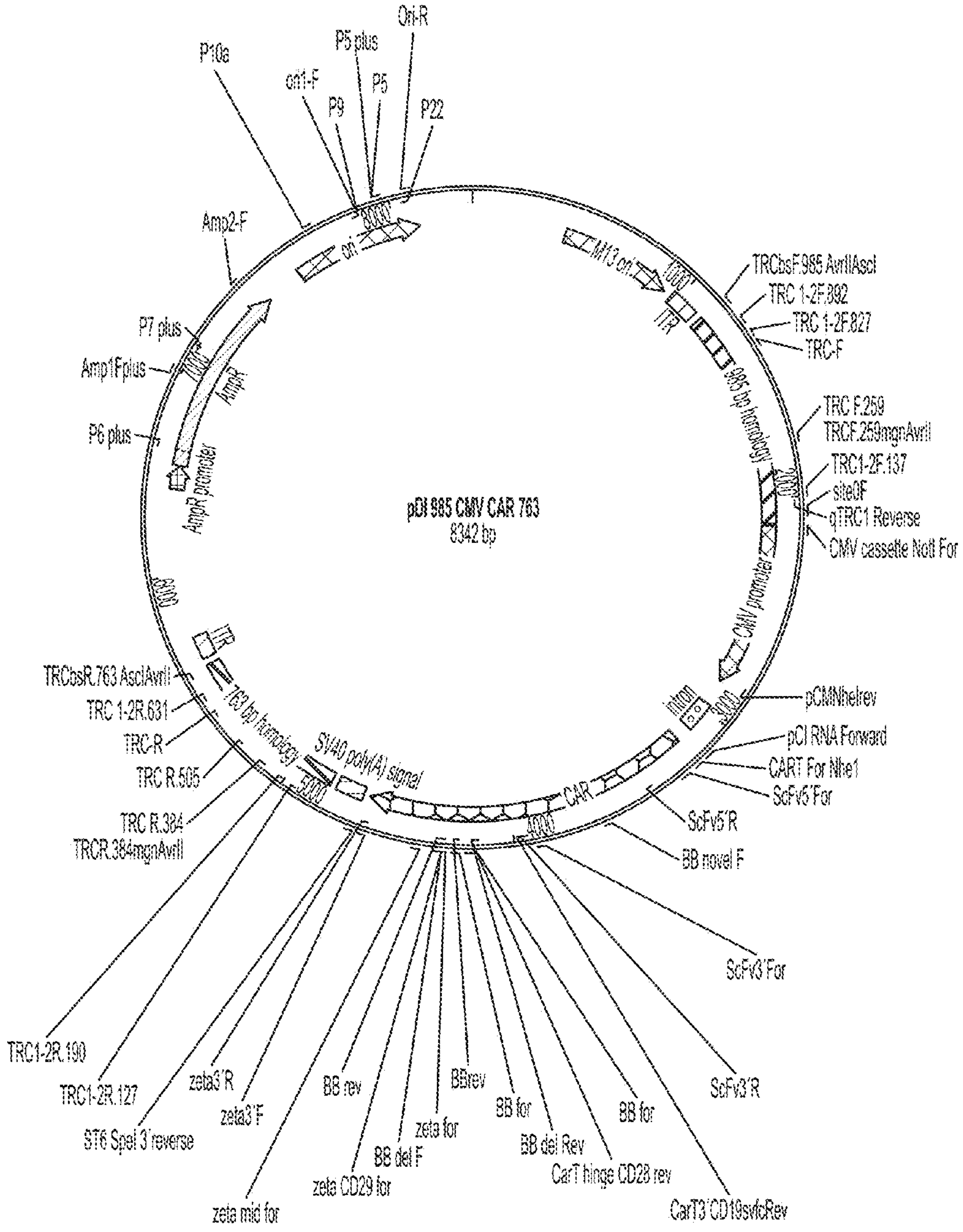

FIG. 31. Map of plasmid used to produce the AAV422 vector.

Figure 32:
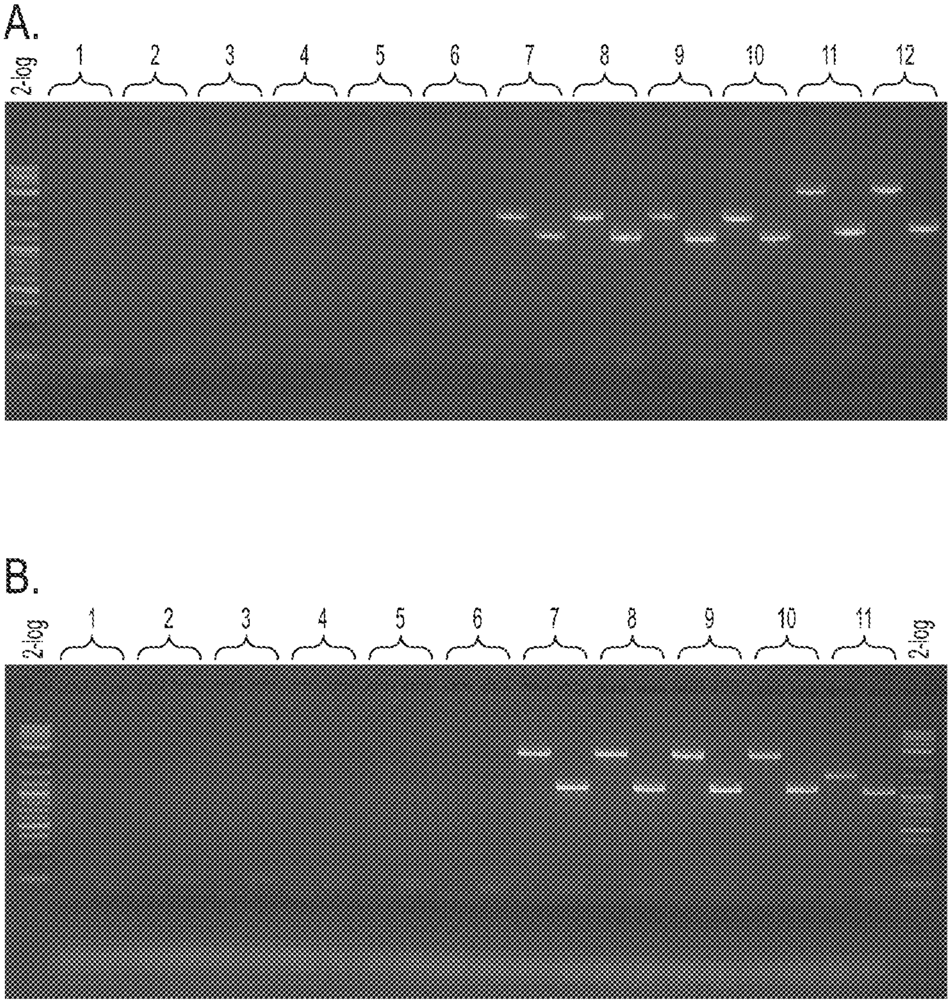

FIG. 32. Insertion of chimeric antigen receptor coding sequence. PCR methods were used to determine if the chimeric antigen receptor coding sequence introduced by AAV421 or AAV422 inserted at the TRC 1-2 recognition site cleaved by the TRC 1-2x.87EE meganuclease. A) Analysis of insertion following transduction with AAV421. B) Analysis of insertion following transduction with AAV422.

Figure 33:
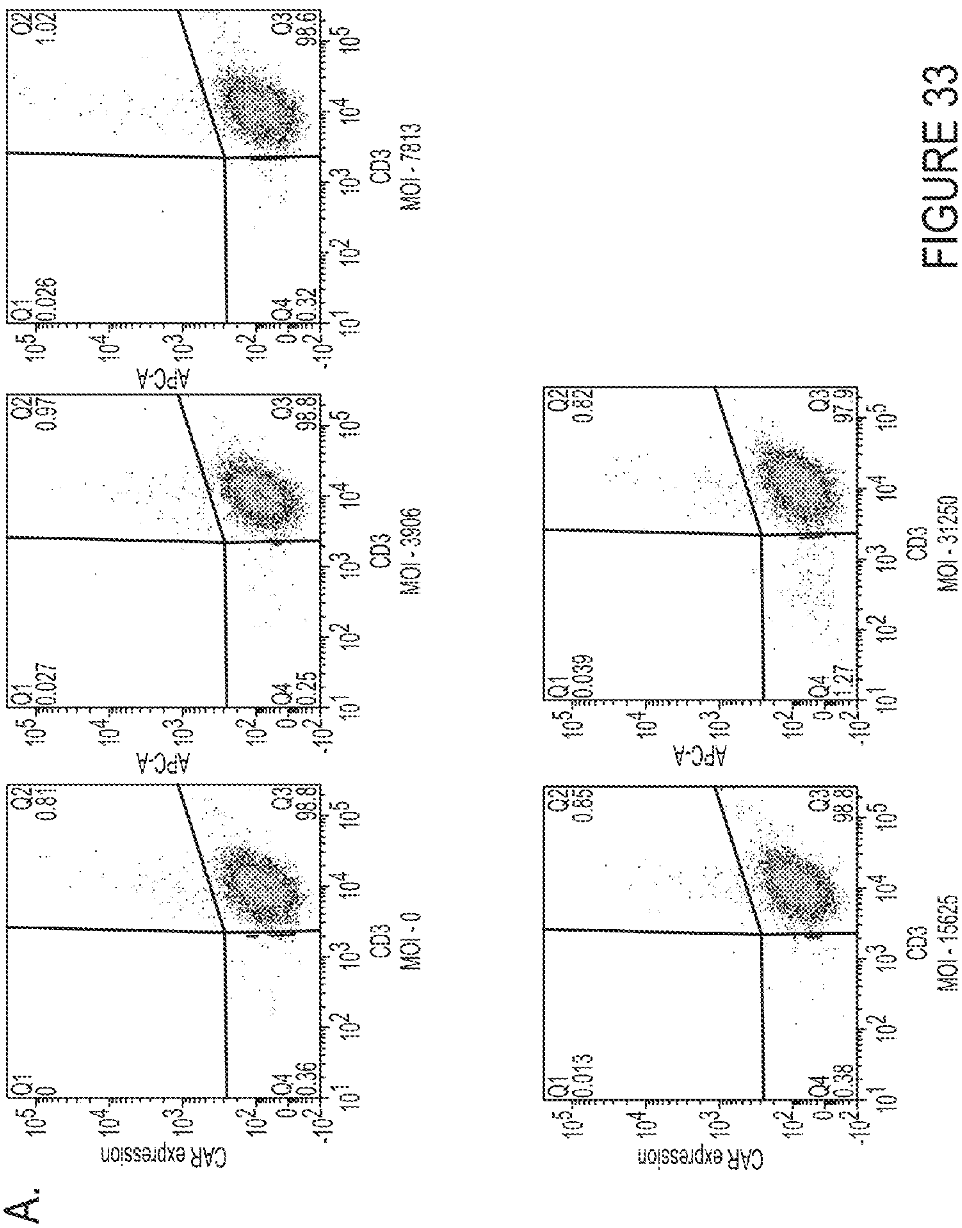
Figure 33:
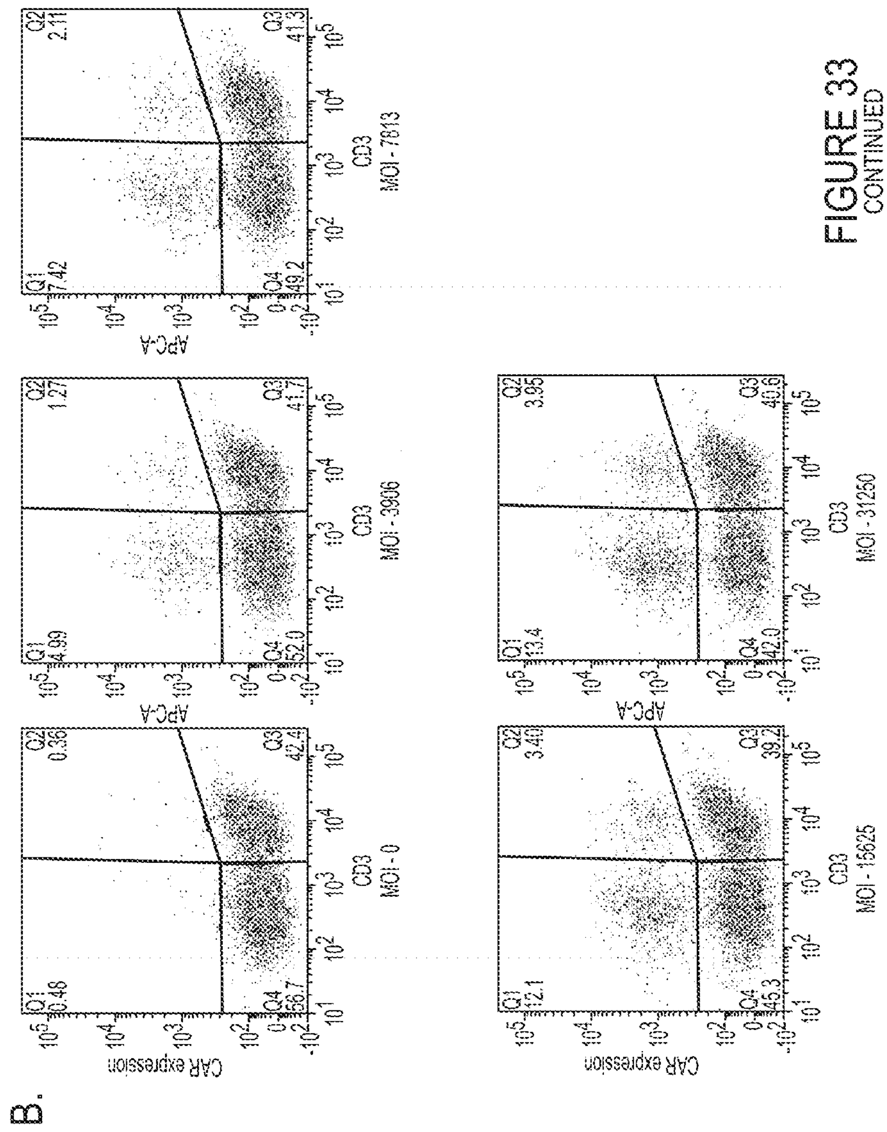

FIG. 33. Cell-surface expression of CD19 chimeric antigen receptor on human T cells. The expression level of the anti-CD19 chimeric antigen receptor was determined in cells that had the CAR gene inserted into the TRC 1-2 recognition sequence using AAV421 as the HDR template. Cell-surface expression was analyzed by flow cytometry. A) Cells that were mock electroporated and mock transduced (MOI—0), and cells that were mock electroporated and transduced with increasing amounts of AAV421. B) Cells that were electroporated with TRC 1-2x.87EE and mock transduced (MOI—0), and cells that were electroporated with TRC 1-2x.87EE and transduced with increasing amounts of AAV421.

Figure 34:
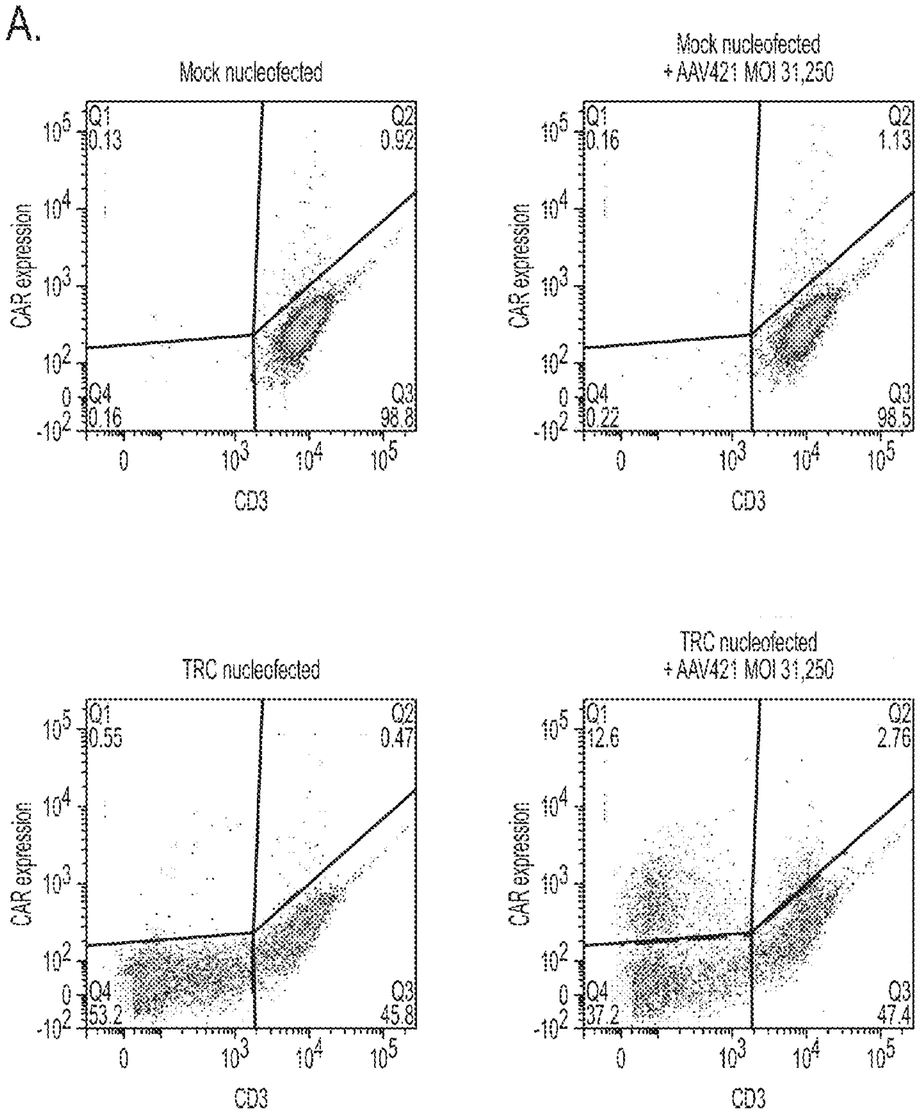
Figure 34:
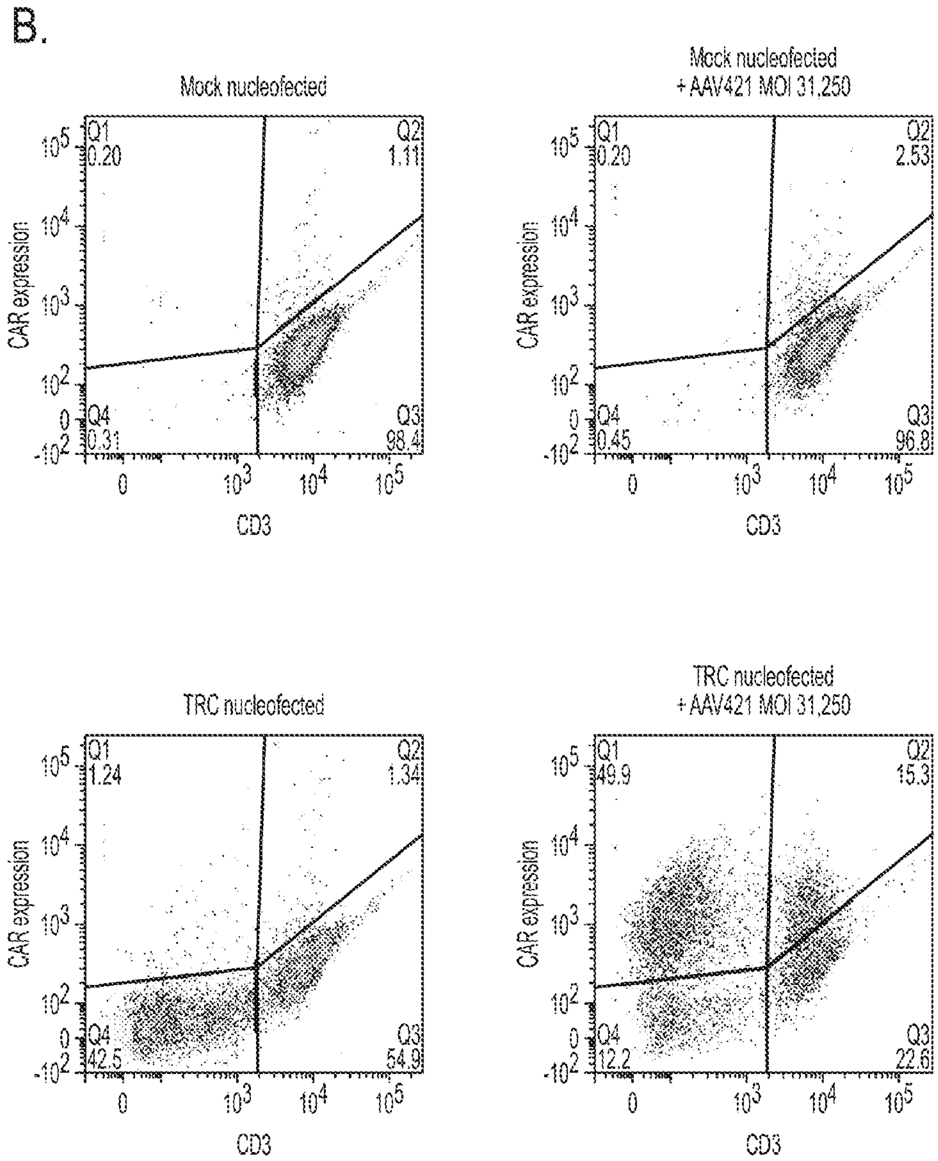
Figure 34:
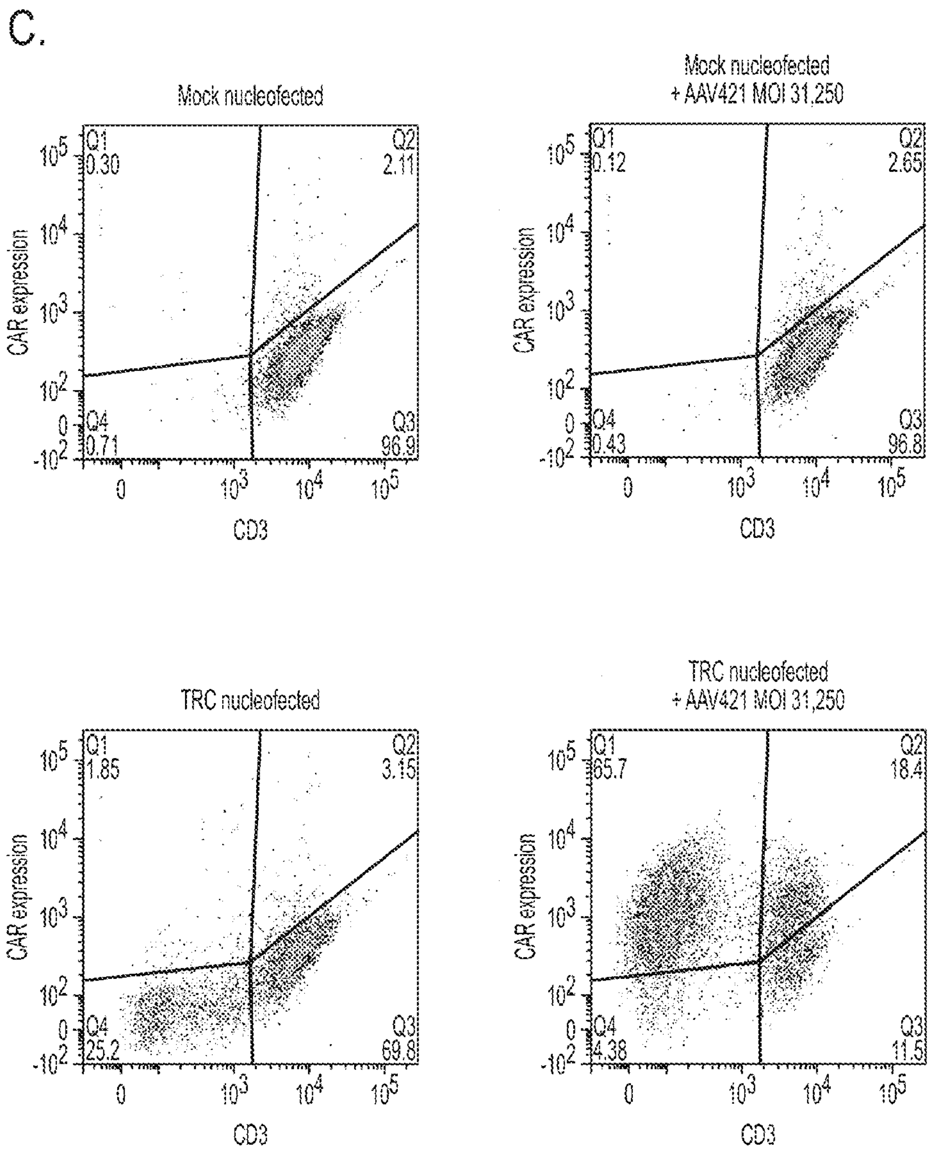

FIG. 34. Expansion of human T cells expressing a cell-surface chimeric antigen receptor. Methods were determined for preferentially expanding and enriching a $CD3^-/CAR^+$ T cell population following electroporation with mRNA for the TRC 1-2x.87EE meganuclease and transduction with AAV421. A) Supplementation with IL-7 (10 ng/mL) and IL-15 (10 ng/mL). B) Supplementation with IL-7 (10 ng/mL) and IL-15 (10 ng/mL), and incubation with mitomycin C-inactivated IM-9 cells. C) Supplementation with IL-7 (10 ng/mL) and IL-15 (10 ng/mL), and two incubations with mitomycin C-inactivated IM-9 cells.

Figure 35:
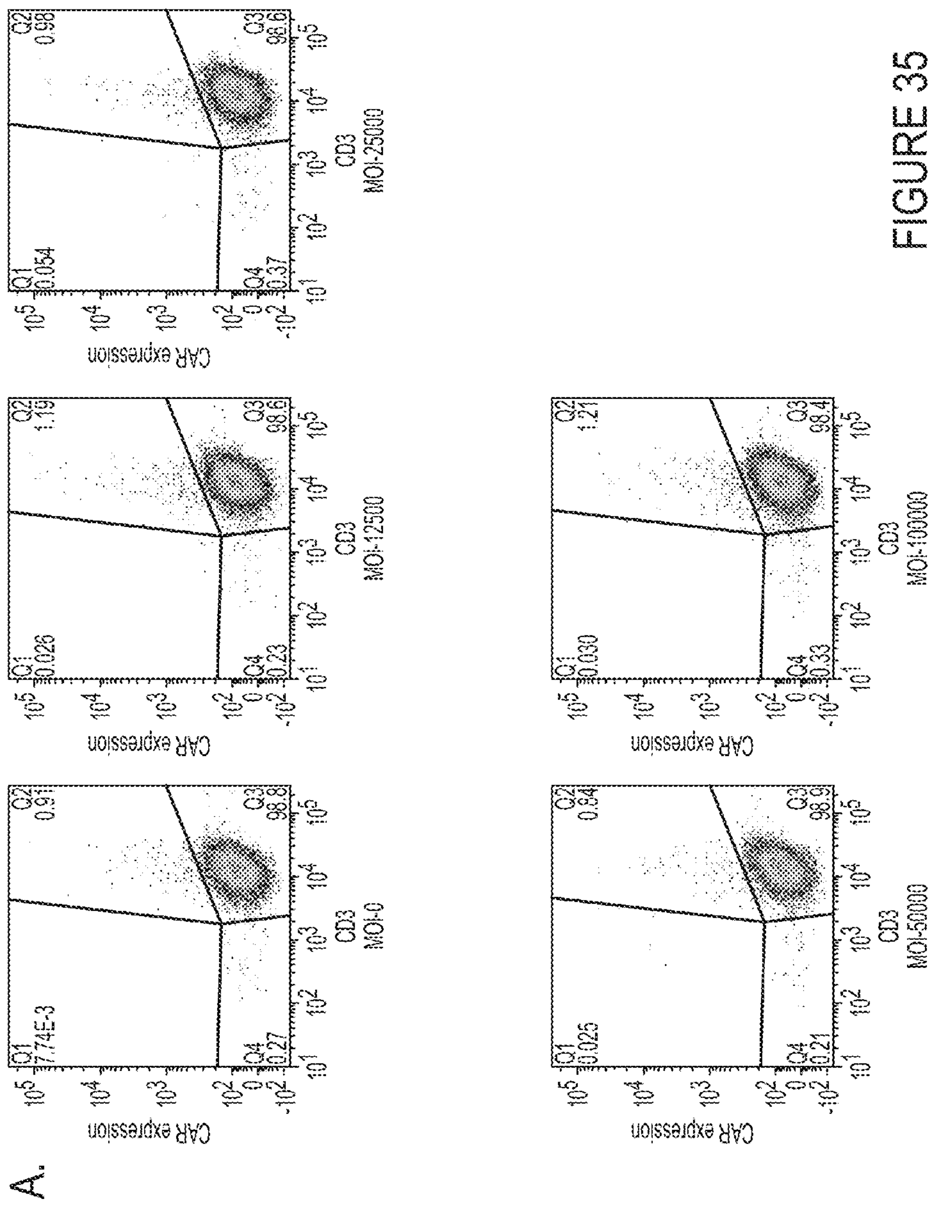
Figure 35:
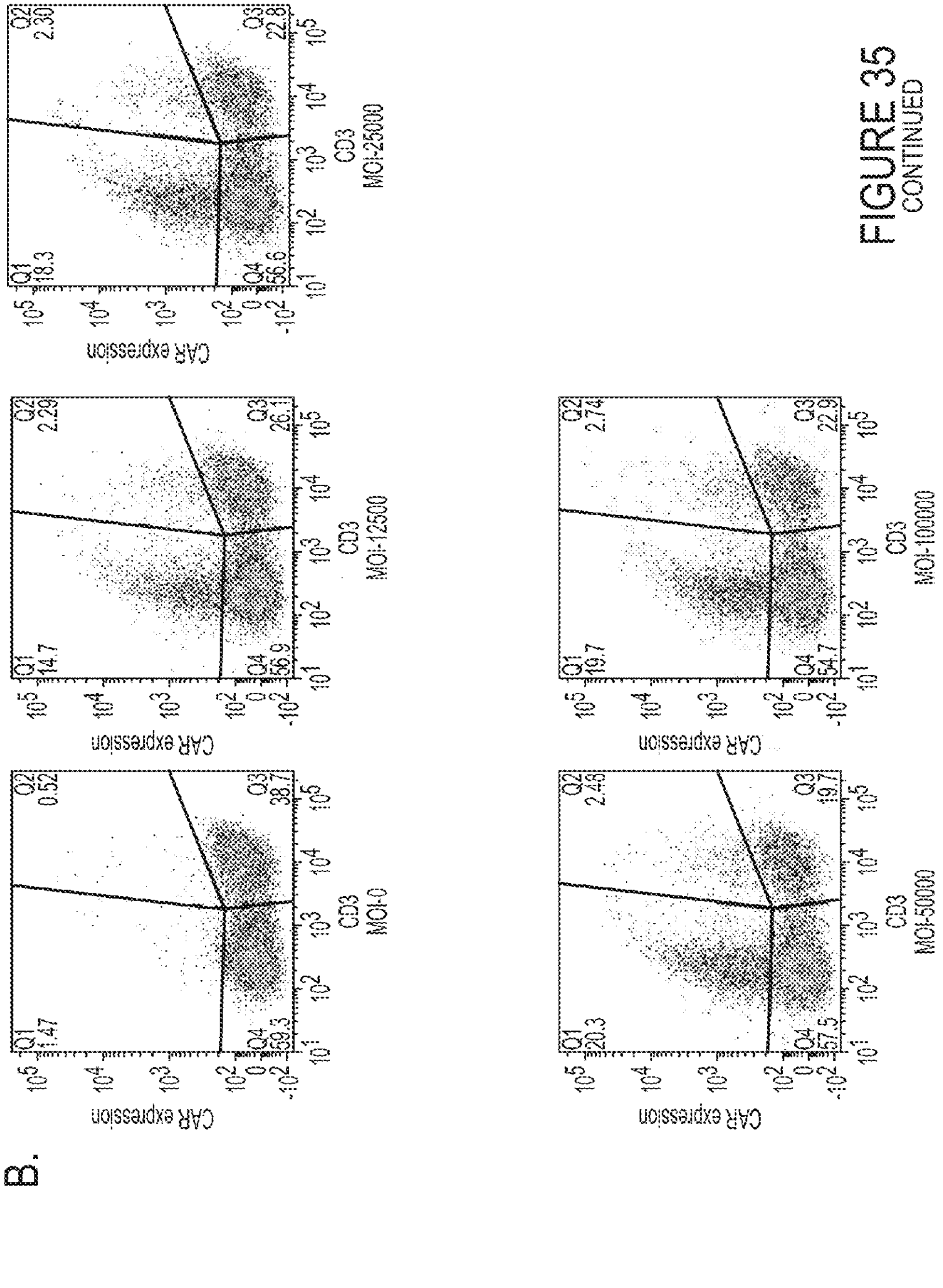

FIG. 35. Cell-surface expression of CD19 chimeric antigen receptor on human T cells. The expression level of the anti-CD19 chimeric antigen receptor was determined in cells that had the CAR gene inserted into the TRC 1-2 recognition sequence using AAV422 as the HDR template. Cell-surface expression was analyzed by flow cytometry. A) Cells that were mock electroporated and mock transduced (MOI—0), and cells that were mock electroporated and transduced with increasing amounts of AAV422. B) Cells that were electroporated with TRC 1-2x.87EE and mock transduced (MOI—0), and cells that were electroporated with TRC 1-2x.87EE and transduced with increasing amounts of AAV422.

Figure 36:
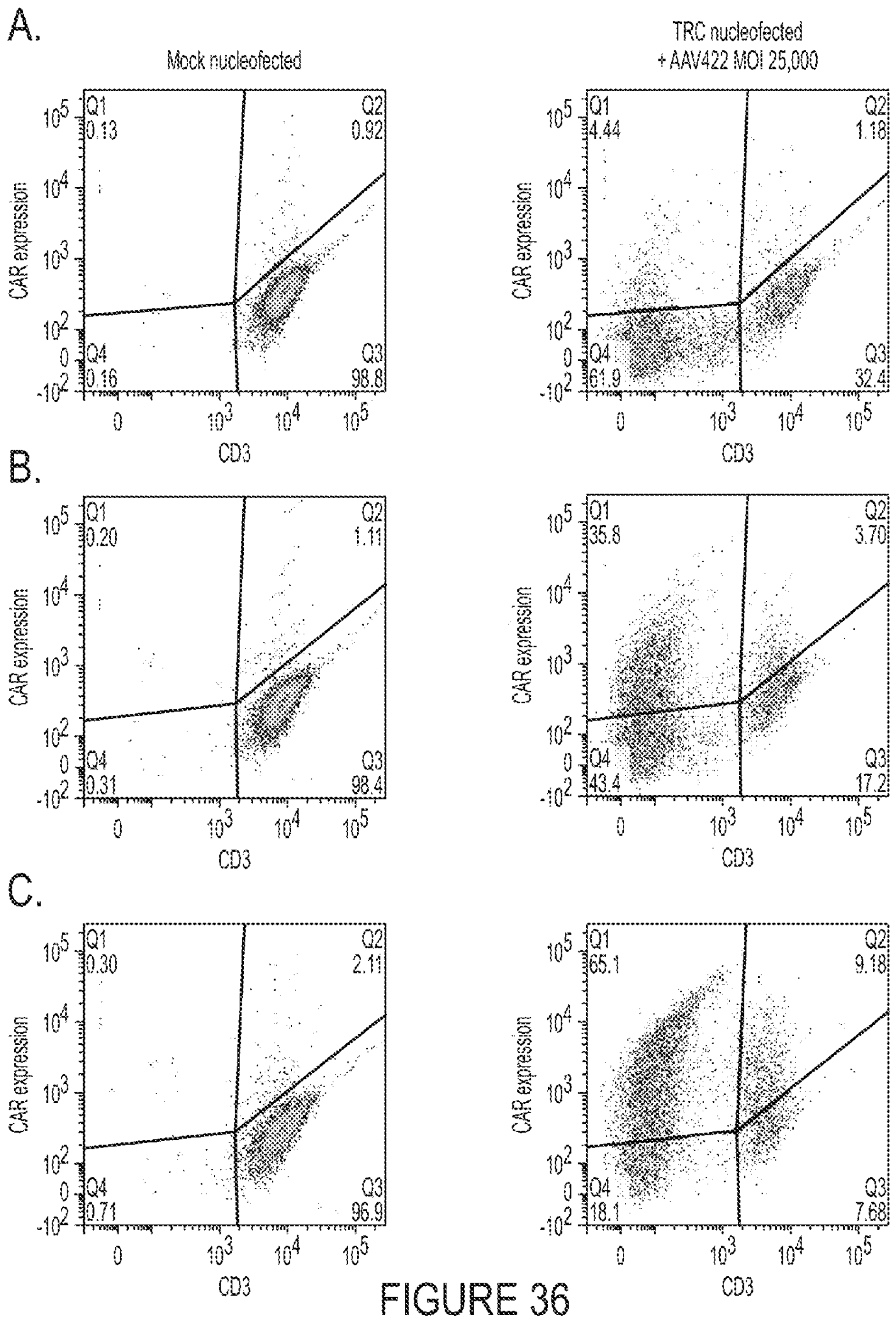

FIG. 36. Expansion of human T cells expressing a cell-surface chimeric antigen receptor. Methods were determined for preferentially expanding and enriching a $CD3^-/CAR^+$ T cell population following electroporation with mRNA for the TRC 1-2x.87EE meganuclease and transduction with AAV422. A) Supplementation with IL-7 (10 ng/mL) and IL-15 (10 ng/mL). B) Supplementation with IL-7 (10 ng/mL) and IL-15 (10 ng/mL), and incubation with mitomycin C-inactivated IM-9 cells. C) Supplementation with IL-7 (10 ng/mL) and IL-15 (10 ng/mL), and two incubations with mitomycin C-inactivated IM-9 cells.

Figure 37:
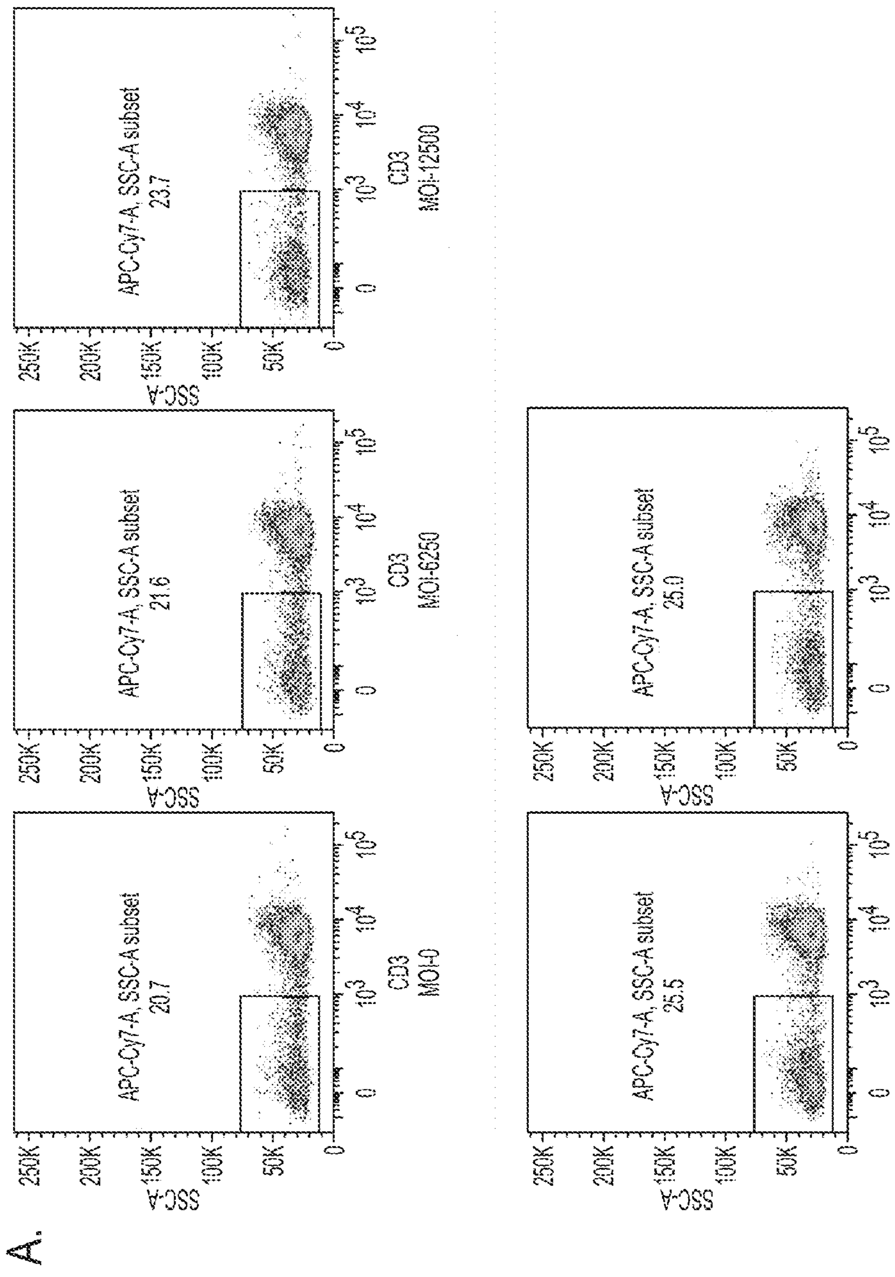
Figure 37:
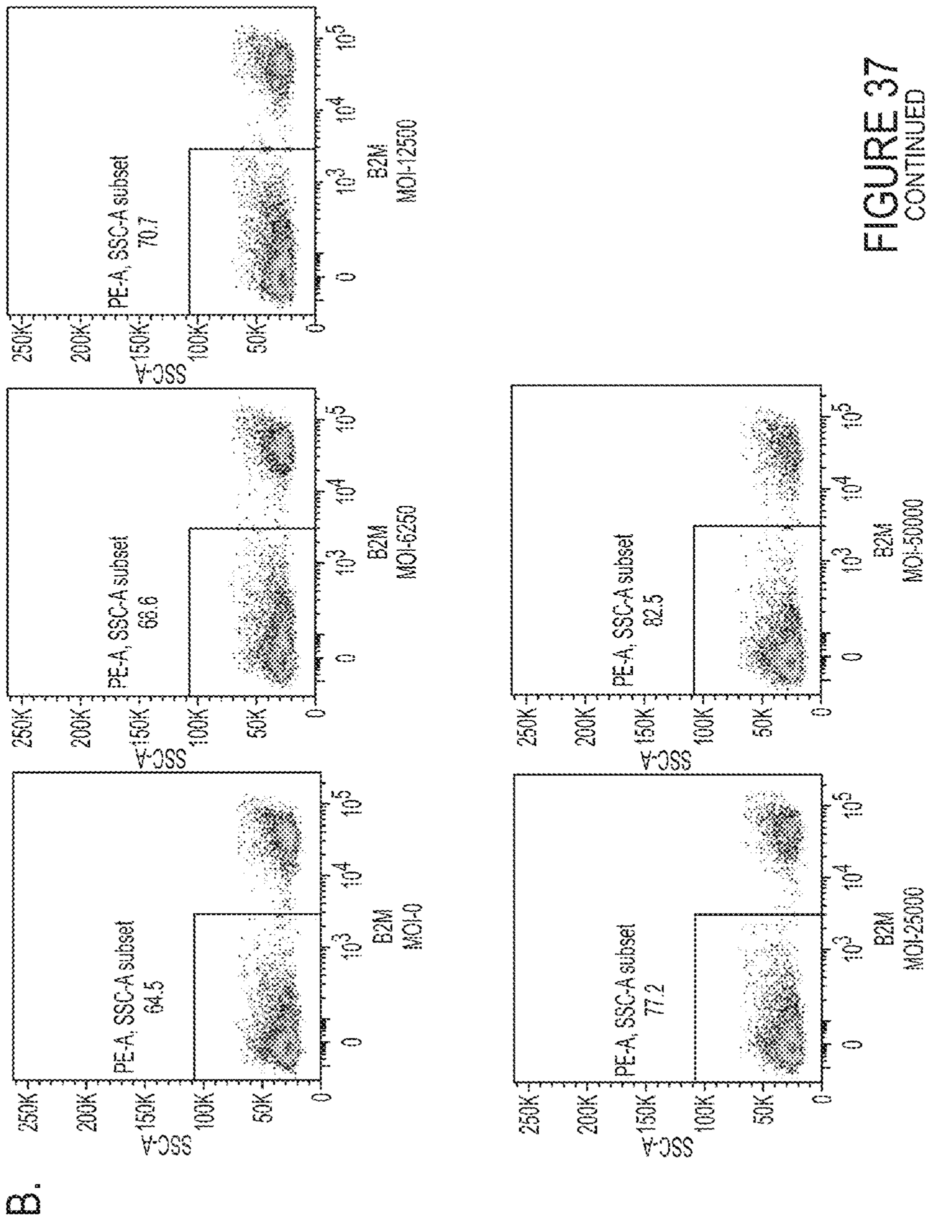
Figure 37:
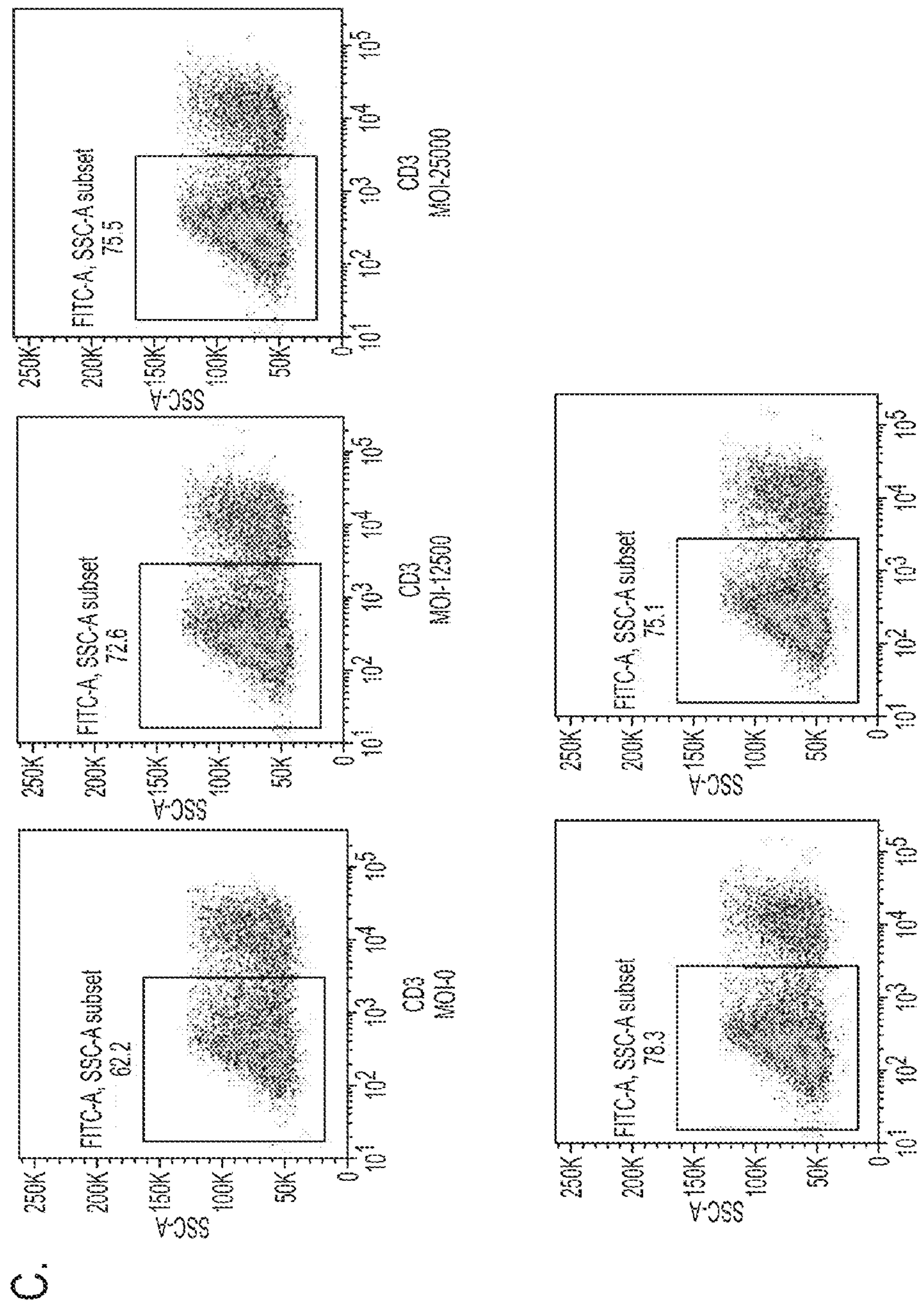

FIG. 37. Meganuclease knockout efficiency using single-strand AAV. Experiments were conducted to examine the knockout efficiency of two meganucleases in human T cells when simultaneously transduced with a single-stranded AAV vector. A) Cells electroporated with mRNA for TRC 1-2x.87EE and transduced with increasing amounts of the single-stranded AAV412. B) Cells electroporated with mRNA for a meganuclease targeting the beta-2 microglobulin gene and transduced with increasing amounts of the single-stranded AAV412. C) Cells electroporated with mRNA for TRC 1-2x.87EE and transduced with increasing amounts of the single-stranded AAV422.

Figure 38:
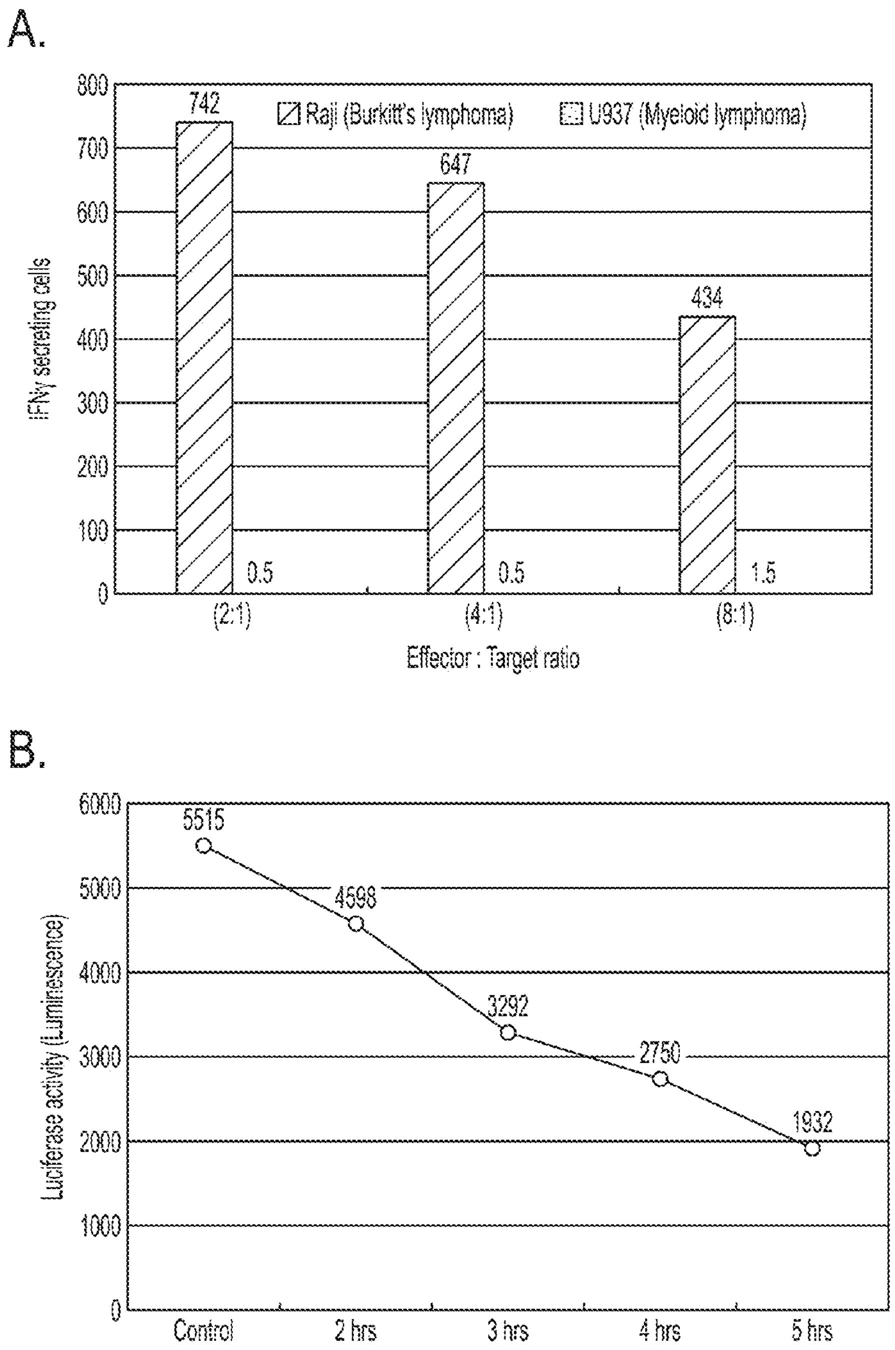

FIG. 38. Functional activity of anti-CD19 CAR T cells. A) IFN-gamma ELISPOT assay, in which either $CD19^+$ Raji cells or $CD19^-$ U937 cells were the target population. B) Cell killing assay in which luciferase-labeled $CD19^+$ Raji cells were the target.

Figure 39:
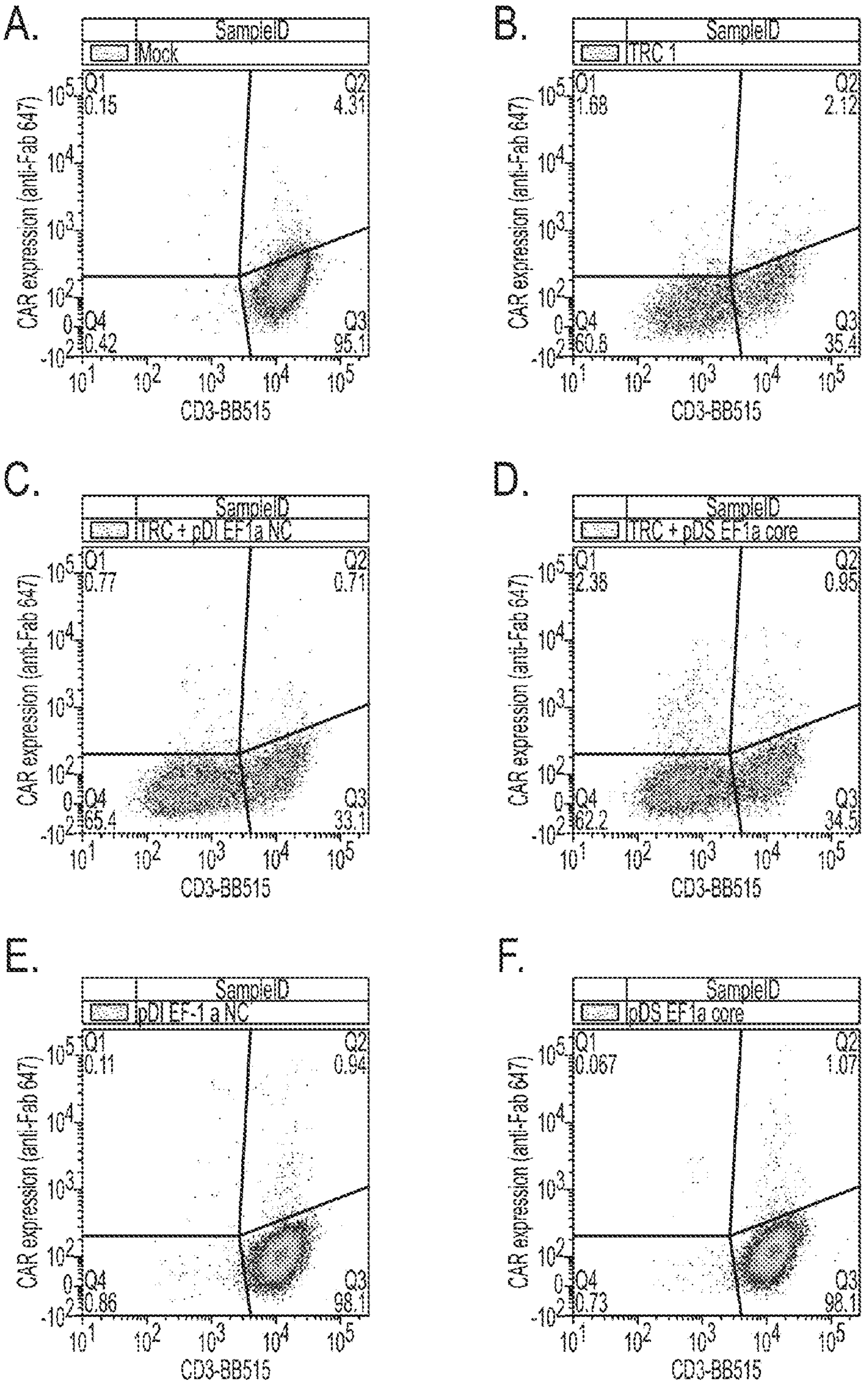
Figure 39:
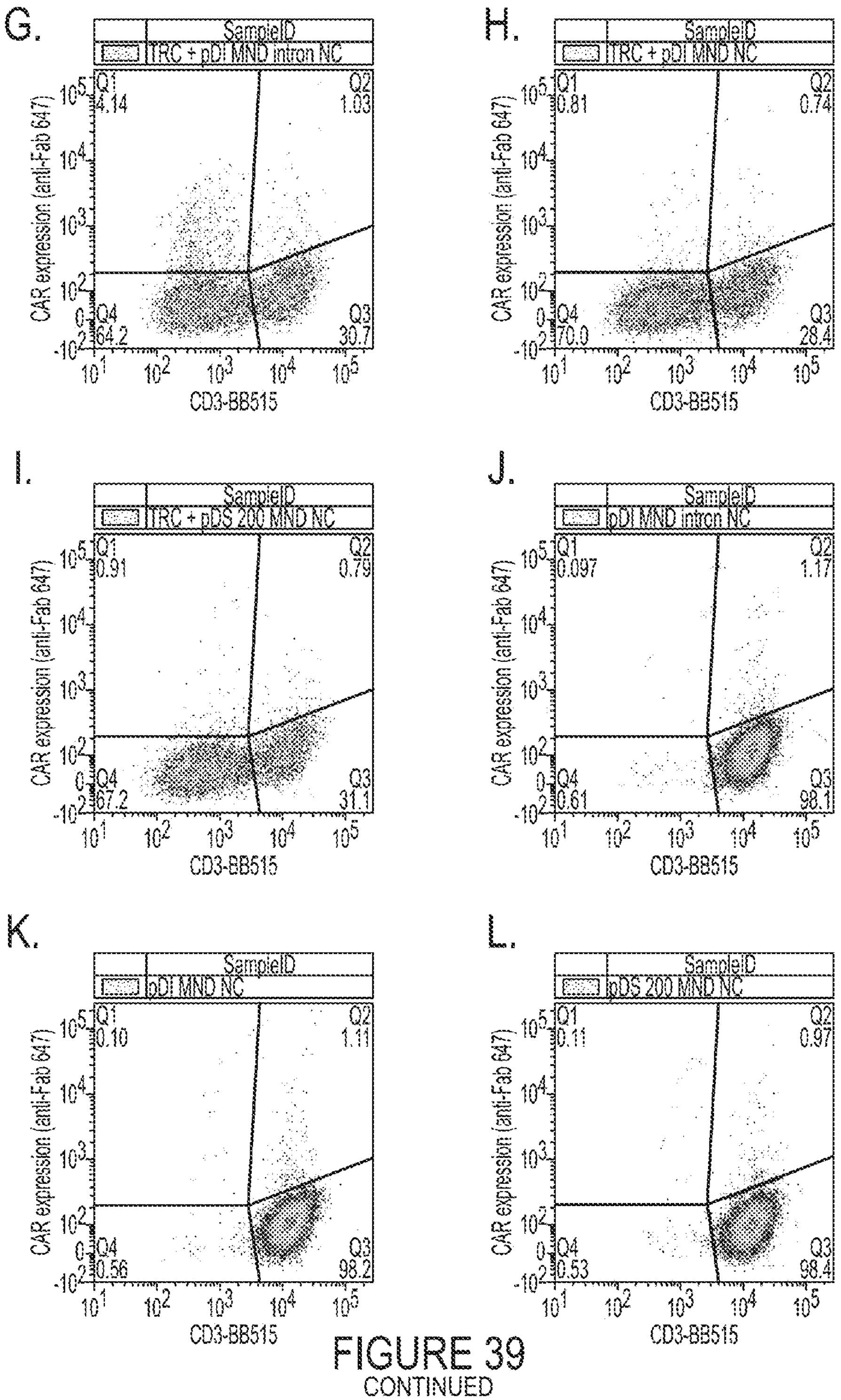
Figure 39:
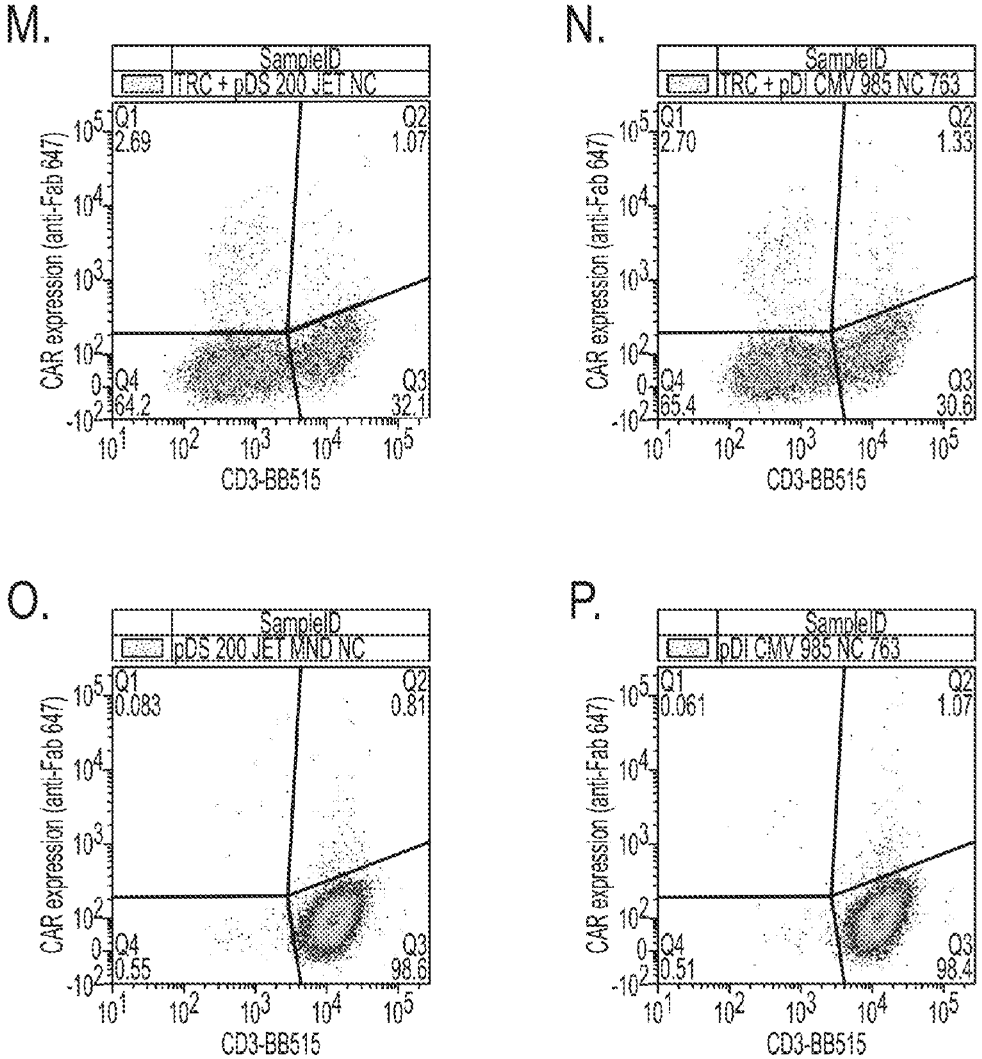

FIG. 39. Expression of chimeric antigen receptors following transduction with linearized DNA donor templates. These experiments generated plasmids that contain an anti-CD19 CAR gene flanked by homology arms that are homologous to the TRC 1-2 recognition sequence locus. Different promoters were used in some plasmids, and homology arms were either “short” (200 bp on the 5' homology arm and 180 bp on the 3' homology arm) or “long” (985 bp on the 5' homology arm and 763 bp on the 3' homology arm). CAR donor plasmids were linearized at a restriction site in the vector backbone and gel purified. A) Background $CD3^-/CAR^+$ staining. B) Cells electroporated with TRC 1-2x.87EE mRNA alone. C) Cells co-electroporated with TRC 1-2x.87EE mRNA and a long homology arm vector with an EF1α core promoter with an HTLV enhancer. D) Cells co-electroporated with TRC 1-2x.87EE mRNA and a short homology arm vector with EF1α core promoter (with no enhancer). E) Cells electroporated with a long homology arm vector with an EF1α core promoter with an HTLV enhancer in the absence of TRC 1-2x.87EE mRNA. F) Cells electroporated with a short homology arm vector with EF1α core promoter (with no enhancer) in the absence of TRC 1-2x.87EE mRNA. G) Cells electroporated with a long homology arm construct that contains an MND promoter driving expression of the CAR and an intron in the 5' end of the CAR gene, as well as TRC 1-2x.87EE mRNA. H) Cells electroporated with a long homology arm construct that contains an MND promoter driving expression of the CAR and no intron, as well as TRC 1-2x.87EE mRNA. I) Cells electroporated with a short homology arm plasmid with the MND promoter and no intron, as well as TRC 1-2x.87EE mRNA. J) Cells electroporated with a long homology arm construct that contains an MND promoter driving expression of the CAR and an intron in the 5' end of the CAR gene, but no TRC 1-2x.87EE mRNA. K) Cells electroporated with a long homology arm construct that contains an MND promoter driving expression of the CAR and no intron, but no TRC 1-2x.87EE mRNA. L) Cells electroporated with a short homology arm plasmid with the MND promoter and no intron, but no TRC 1-2x.87EE mRNA. M) Cells electroporated with a short homology arm construct that contained a JeT promoter, as well as TRC 1-2x.87EE mRNA. N) Cells electroporated with a long homology arm construct that contained a CMV promoter, as well as TRC 1-2x.87EE mRNA. O) Cells electroporated with a short homology arm construct that contained a JeT promoter, but no TRC 1-2x.87EE mRNA. P) Cells electroporated with a long homology arm construct that contained a CMV promoter, but no TRC 1-2x.87EE mRNA.

FIG. 40. PCR analysis to determine whether the chimeric antigen receptor coding region delivered by linearized DNA constructs was inserted into the TRC 1-2 recognition sequence in human T cells.

Figure 41:
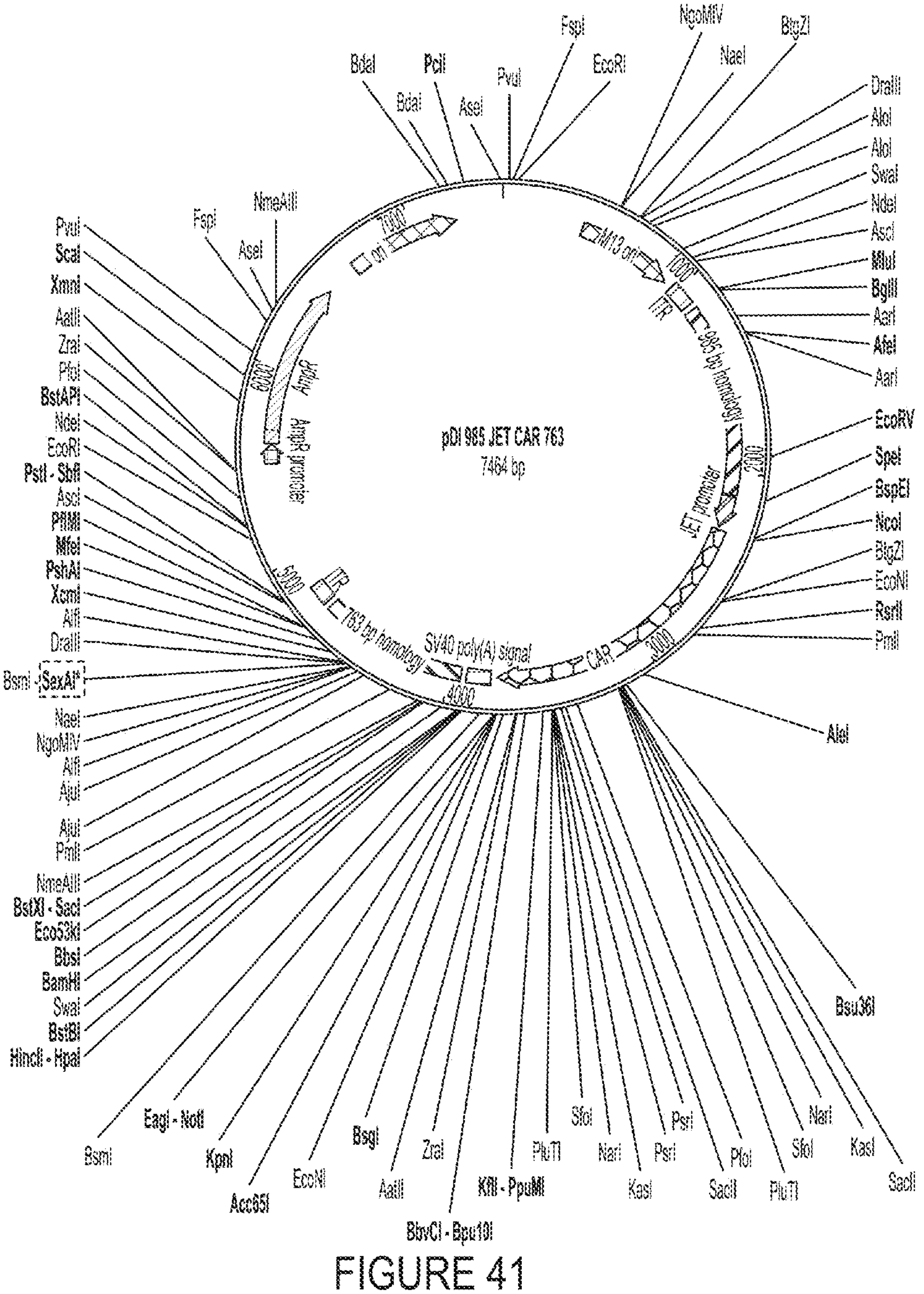

FIG. 41. Map of plasmid used to produce the AAV423 vector.

Figure 42:
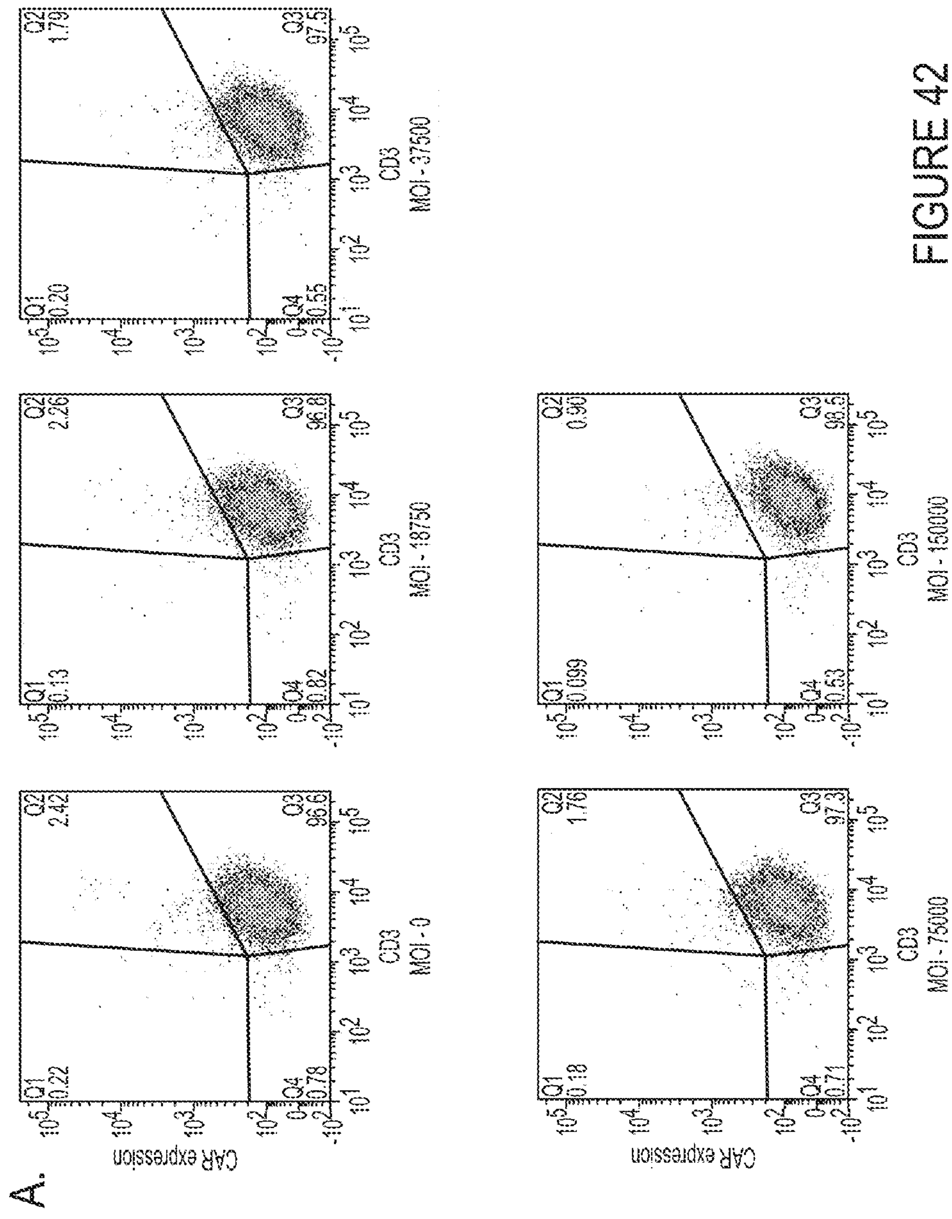
Figure 42:
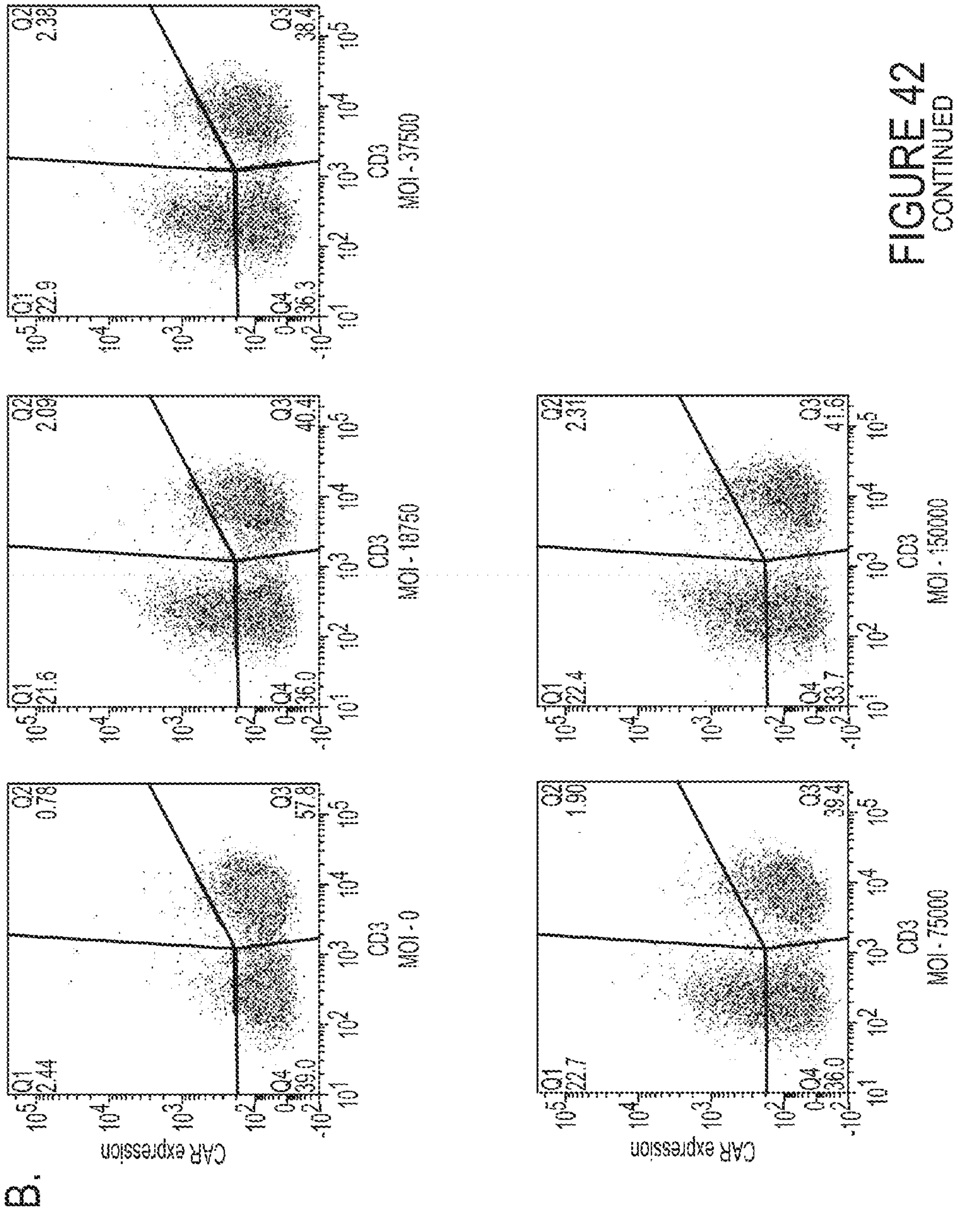

FIG. 42. Cell-surface expression of CD19 chimeric antigen receptor on human T cells. The expression level of the anti-CD19 chimeric antigen receptor was determined in cells that had the CAR gene inserted into the TRC 1-2 recognition sequence using AAV423 as the HDR template. Cell-surface expression was analyzed by flow cytometry. A) Cells that were mock electroporated and mock transduced (MOI—0), and cells that were mock electroporated and transduced with increasing amounts of AAV423. B) Cells that were electroporated with TRC 1-2x.87EE and mock transduced (MOI—0), and cells that were electroporated with TRC 1-2x.87EE and transduced with increasing amounts of AAV423.

Figure 43:
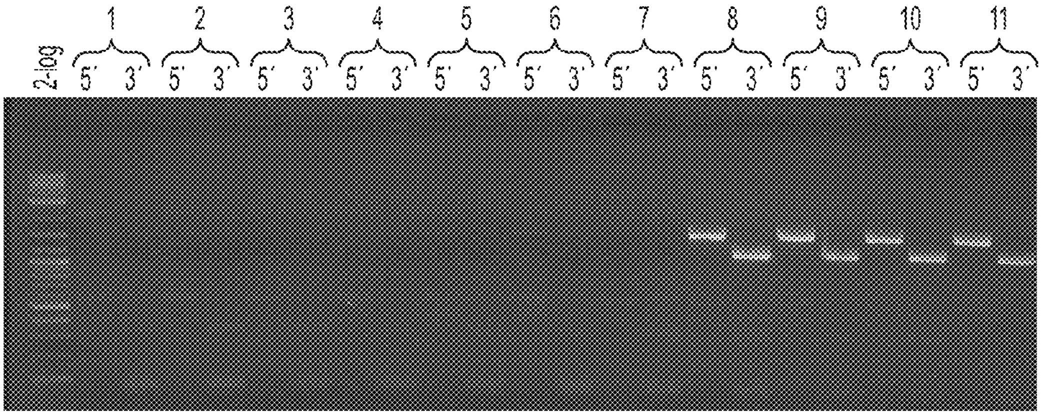

FIG. 43. Insertion of chimeric antigen receptor coding sequence. PCR methods were used to determine if the chimeric antigen receptor coding sequence introduced by AAV423 inserted at the TRC 1-2 recognition site cleaved by the TRC 1-2x.87EE meganuclease.

Figure 44:
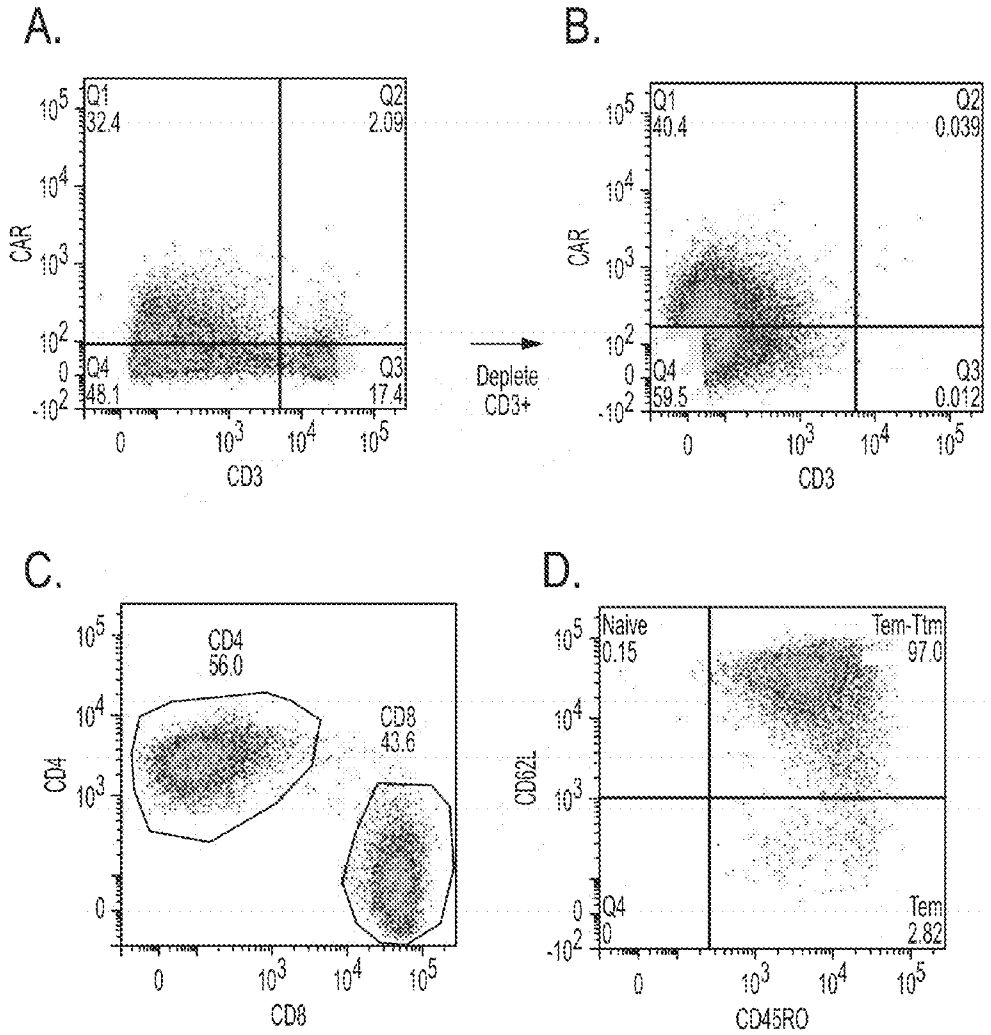

FIG. 44. Phenotype analysis of anti-CD19 CAR T cells. A) Activated T cells were electroporated with TRC 1-2x.87 EE mRNA, then transduced with an AAV6 vector comprising an anti-CD19 CAR expression cassette driven by a JeT promoter and flanked by homology arms. Following 5 days of culture with IL-2 (10 ng/mL), cells were analyzed for cell-surface CD3 and anti-CD19 CAR expression by flow cytometry. B) $CD3^-$ cells were enriched by depleting $CD3^+$ cells using anti-CD3 magnetic beads. Depleted cells were then cultured for 3 days in IL-15 (10 ng/mL) and IL-21 (10 ng/mL) and re-analyzed for cell-surface expression of CD3 and anti-CD19 CAR. C) The purified population of $CD3^-$ CD19-CAR T cells was analyzed by flow cytometry to determine the percentage of cells that were $CD4^+$ and $CD8^+$. D) The purified population of $CD3^-$ CD19-CAR T cells was further analyzed by flow cytometry to determine whether they were central memory T cells, transitional memory T cells, or effector memory T cells by staining for CD62L and CD45RO.

Figure 45:
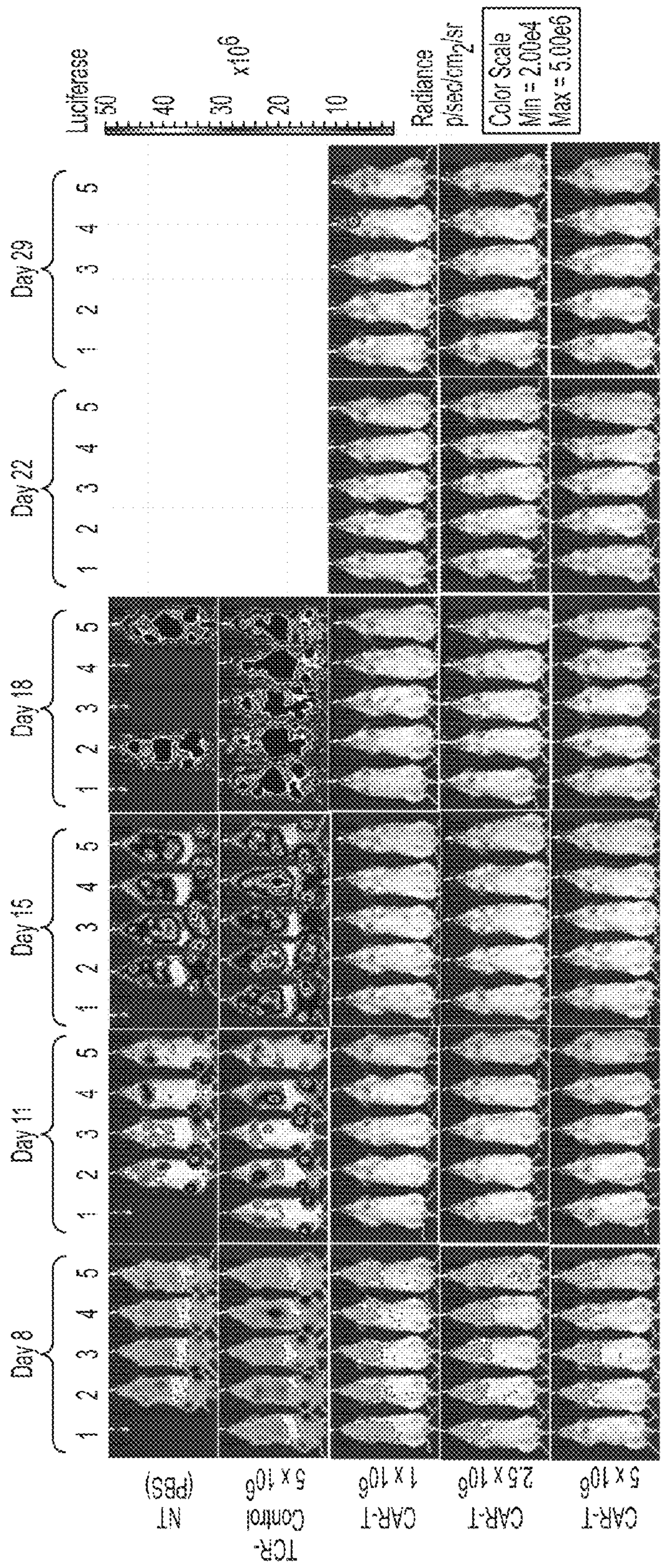

FIG. 45. Raji disseminated lymphoma model. Raji cells stably expressing firefly luciferase (ffLuc)[44] were injected i.v. into 5-6 week old female NSG mice on Day 1, at a dose of $2.0\times10^5$ cells per mouse. On Day 4 mice were injected i.v. with PBS or PBS containing gene edited control TCR KO T cells prepared from the same healthy donor PBMC or PBS containing the indicated doses of CAR T cells prepared from the same donor. On the indicated days, live mice were injected i.p. with Luciferin substrate (150 mg/kg in saline), anesthetized, and Luciferase activity measured after 7 minutes using IVIS SpectrumCT® (Perkin Elmer, Waltham, Mass.). Data was analyzed and exported using Living Image software 4.5.1 (Perkin Elmer, Waltham, Mass.). Luminescence signal intensity is represented by radiance in p/sec/$cm^2$/sr.

BRIEF DESCRIPTION OF THE SEQUENCES

SEQ ID NO: 1 sets forth the nucleotide sequence of the human T cell receptor alpha constant region gene (NCBI Gene ID NO. 28755).

SEQ ID NO: 2 sets forth the amino acid sequence encoded by the human T cell receptor alpha constant region.

SEQ ID NO: 3 sets forth the amino acid sequence of the TRC 1-2 recognition sequence.

SEQ ID NO: 4 sets forth the nucleotide sequence of the TRC 3-4 recognition sequence.

SEQ ID NO: 5 sets forth the nucleotide sequence of the TRC 7-8 recognition sequence.

SEQ ID NO: 6 sets forth the amino acid sequence of I-CreI.

SEQ ID NO: 7 sets forth the amino acid sequence of the LAGLIDADG motif.

SEQ ID NO: 8 sets forth the amino acid sequence of the TRC 1-2x.87 EE meganuclease.

SEQ ID NO: 9 sets forth the amino acid sequence of the TRC 1-2x.87 QE meganuclease.

SEQ ID NO: 10 sets forth the amino acid sequence of the TRC 1-2x.87 EQ meganuclease.

SEQ ID NO: 11 sets forth the amino acid sequence of the TRC 1-2x.87 meganuclease.

SEQ ID NO: 12 sets forth the amino acid sequence of the TRC 1-2x.6 meganuclease.

SEQ ID NO: 13 sets forth the amino acid sequence of the TRC 1-2x.20 meganuclease.

SEQ ID NO: 14 sets forth the amino acid sequence of the TRC 1-2x.55 meganuclease.

SEQ ID NO: 15 sets forth the amino acid sequence of the TRC 1-2x.60 meganuclease.

SEQ ID NO: 16 sets forth the amino acid sequence of the TRC 1-2x.105 meganuclease.

SEQ ID NO: 17 sets forth the amino acid sequence of the TRC 1-2x.163 meganuclease.

SEQ ID NO: 18 sets forth the amino acid sequence of the TRC 1-2x.113_3 meganuclease.

SEQ ID NO: 19 sets forth the amino acid sequence of the TRC 1-2x.5 meganuclease.

SEQ ID NO: 20 sets forth the amino acid sequence of the TRC 1-2x.8 meganuclease.

SEQ ID NO: 21 sets forth the amino acid sequence of the TRC 1-2x.25 meganuclease.

SEQ ID NO: 22 sets forth the amino acid sequence of the TRC 1-2x.72 meganuclease.

SEQ ID NO: 23 sets forth the amino acid sequence of the TRC 1-2x.80 meganuclease.

SEQ ID NO: 24 sets forth the amino acid sequence of the TRC 1-2x.84 meganuclease.

SEQ ID NO: 25 sets forth the amino acid sequence of the TRC 1-2x.120 meganuclease.

SEQ ID NO: 26 sets forth the amino acid sequence of the TRC 1-2x.113_1 meganuclease.

SEQ ID NO: 27 sets forth the amino acid sequence of the TRC 1-2x.113_2 meganuclease.

SEQ ID NO: 28 sets forth the amino acid sequence of the TRC 3-4x.3 meganuclease.

SEQ ID NO: 29 sets forth the amino acid sequence of the TRC 3-4x.19 meganuclease.

SEQ ID NO: 30 sets forth the amino acid sequence of the TRC 7-8x.7 meganuclease.

SEQ ID NO: 31 sets forth the amino acid sequence of the TRC 7-8x.9 meganuclease.

SEQ ID NO: 32 sets forth the amino acid sequence of the TRC 7-8x.14 meganuclease.

SEQ ID NO: 33 sets forth residues 198-344 of the TRC 1-2x.87 EE meganuclease.

SEQ ID NO: 34 sets forth residues 198-344 of the TRC 1-2x.87 QE meganuclease.

SEQ ID NO: 35 sets forth residues 198-344 of the TRC 1-2x.87 EQ meganuclease.

SEQ ID NO: 36 sets forth residues 198-344 of the TRC 1-2x.87 meganuclease.

SEQ ID NO: 37 sets forth residues 198-344 of the TRC 1-2x.6 meganuclease.

SEQ ID NO: 38 sets forth residues 198-344 of the TRC 1-2x.20 meganuclease.

SEQ ID NO: 39 sets forth residues 198-344 of the TRC 1-2x.55 meganuclease.

SEQ ID NO: 40 sets forth residues 198-344 of the TRC 1-2x.60 meganuclease.

SEQ ID NO: 41 sets forth residues 198-344 of the TRC 1-2x.105 meganuclease.

SEQ ID NO: 42 sets forth residues 198-344 of the TRC 1-2x.163 meganuclease.

SEQ ID NO: 43 sets forth residues 198-344 of the TRC 1-2x.113_3 meganuclease.

SEQ ID NO: 44 sets forth residues 7-153 of the TRC 1-2x.5 meganuclease.

SEQ ID NO: 45 sets forth residues 7-153 of the TRC 1-2x.8 meganuclease.

SEQ ID NO: 46 sets forth residues 7-153 of the TRC 1-2x.25 meganuclease.

SEQ ID NO: 47 sets forth residues 7-153 of the TRC 1-2x.72 meganuclease.

SEQ ID NO: 48 sets forth residues 7-153 of the TRC 1-2x.80 meganuclease.

SEQ ID NO: 49 sets forth residues 7-153 of the TRC 1-2x.84 meganuclease.

SEQ ID NO: 50 sets forth residues 7-153 of the TRC 1-2x.120 meganuclease.

SEQ ID NO: 51 sets forth residues 7-153 of the TRC 1-2x.113_1 meganuclease.

SEQ ID NO: 52 sets forth residues 7-153 of the TRC 1-2x.113_2 meganuclease.

SEQ ID NO: 53 sets forth residues 7-153 of the TRC 3-4x.3 meganuclease.

SEQ ID NO: 54 sets forth residues 7-153 of the TRC 3-4x.19 meganuclease.

SEQ ID NO: 55 sets forth residues 7-153 of the TRC 7-8x.7 meganuclease.

SEQ ID NO: 56 sets forth residues 198-344 of the TRC 7-8x.9 meganuclease.

SEQ ID NO: 57 sets forth residues 198-344 of the TRC 7-8x.14 meganuclease.

SEQ ID NO: 58 sets forth residues 7-153 of the TRC 1-2x.87 EE meganuclease.

SEQ ID NO: 59 sets forth residues 7-153 of the TRC 1-2x.87 QE meganuclease.

SEQ ID NO: 60 sets forth residues 7-153 of the TRC 1-2x.87 EQ meganuclease.

SEQ ID NO: 61 sets forth residues 7-153 of the TRC 1-2x.87 meganuclease.

SEQ ID NO: 62 sets forth residues 7-153 of the TRC 1-2x.6 meganuclease.

SEQ ID NO: 63 sets forth residues 7-153 of the TRC 1-2x.20 meganuclease.

SEQ ID NO: 64 sets forth residues 7-153 of the TRC 1-2x.55 meganuclease.

SEQ ID NO: 65 sets forth residues 7-153 of the TRC 1-2x.60 meganuclease.

SEQ ID NO: 66 sets forth residues 7-153 of the TRC 1-2x.105 meganuclease.

SEQ ID NO: 67 sets forth residues 7-153 of the TRC 1-2x.163 meganuclease.

SEQ ID NO: 68 sets forth residues 7-153 of the TRC 1-2x.113_3 meganuclease.

SEQ ID NO: 69 sets forth residues 198-344 of the TRC 1-2x.5 meganuclease.

SEQ ID NO: 70 sets forth residues 198-344 of the TRC 1-2x.8 meganuclease.

SEQ ID NO: 71 sets forth residues 198-344 of the TRC 1-2x.25 meganuclease.

SEQ ID NO: 72 sets forth residues 198-344 of the TRC 1-2x.72 meganuclease.

SEQ ID NO: 73 sets forth residues 198-344 of the TRC 1-2x.80 meganuclease.

SEQ ID NO: 74 sets forth residues 198-344 of the TRC 1-2x.84 meganuclease.

SEQ ID NO: 75 sets forth residues 198-344 of the TRC 1-2x.120 meganuclease.

SEQ ID NO: 76 sets forth residues 198-344 of the TRC 1-2x.113_1 meganuclease.

SEQ ID NO: 77 sets forth residues 198-344 of the TRC 1-2x.113_2 meganuclease.

SEQ ID NO: 78 sets forth residues 198-344 of the TRC 3-4x.3 meganuclease.

SEQ ID NO: 79 sets forth residues 198-344 of the TRC 3-4x.19 meganuclease.

SEQ ID NO: 80 sets forth residues 198-344 of the TRC 7-8x.7 meganuclease.

SEQ ID NO: 81 sets forth residues 7-153 of the TRC 7-8x.9 meganuclease.

SEQ ID NO: 82 sets forth residues 7-153 of the TRC 7-8x.14 meganuclease.

SEQ ID NO: 83 sets forth the nucleotide sequence of the antisense strand of the TRC 1-2 recognition sequence.

SEQ ID NO: 84 sets forth the nucleotide sequence of the antisense strand of the TRC 3-4 recognition sequence.

SEQ ID NO: 85 sets forth the nucleotide sequence of the antisense strand of the TRC 7-8 recognition sequence.

SEQ ID NO: 86 sets forth nucleotides 162-233 of SEQ ID NO:1.

SEQ ID NO: 87 sets forth nucleotides 162-233 of SEQ ID NO:1 comprising a deletion resulting from cleavage and NHEJ.

SEQ ID NO: 88 sets forth nucleotides 162-233 of SEQ ID NO:1 comprising a deletion resulting from cleavage and NHEJ.

SEQ ID NO: 89 sets forth nucleotides 162-233 of SEQ ID NO:1 comprising a deletion resulting from cleavage and NHEJ.

SEQ ID NO: 90 sets forth nucleotides 162-233 of SEQ ID NO:1 comprising a deletion resulting from cleavage and NHEJ.

SEQ ID NO: 91 sets forth nucleotides 162-233 of SEQ ID NO:1 comprising a deletion resulting from cleavage and NHEJ.

SEQ ID NO: 92 sets forth nucleotides 162-233 of SEQ ID NO:1 comprising a deletion resulting from cleavage and NHEJ.

SEQ ID NO: 93 sets forth nucleotides 162-233 of SEQ ID NO:1 comprising a deletion resulting from cleavage and NHEJ.

SEQ ID NO: 94 sets forth nucleotides 162-233 of SEQ ID NO:1 comprising an insertion resulting from cleavage and NHEJ.

SEQ ID NO: 95 sets forth nucleotides 162-233 of SEQ ID NO:1 comprising an insertion resulting from cleavage and NHEJ.

SEQ ID NO: 96 sets forth nucleotides 162-233 of SEQ ID NO:1 comprising a deletion resulting from cleavage and NHEJ.

SEQ ID NO: 97 sets forth nucleotides 162-233 of SEQ ID NO:1 comprising a deletion resulting from cleavage and NHEJ.

SEQ ID NO: 98 sets forth nucleotides 162-233 of SEQ ID NO:1 comprising a deletion resulting from cleavage and NHEJ.

SEQ ID NO: 99 sets forth nucleotides 162-233 of SEQ ID NO:1 comprising a deletion resulting from cleavage and NHEJ.

SEQ ID NO: 100 sets forth nucleotides 162-233 of SEQ ID NO:1 comprising a deletion resulting from cleavage and NHEJ.

SEQ ID NO: 101 sets forth nucleotides 162-233 of SEQ ID NO:1 comprising a deletion resulting from cleavage and NHEJ.

SEQ ID NO: 102 sets forth nucleotides 162-233 of SEQ ID NO:1 comprising a deletion resulting from cleavage and NHEJ.

SEQ ID NO: 103 sets forth nucleotides 162-233 of SEQ ID NO:1 comprising a deletion resulting from cleavage and NHEJ.

SEQ ID NO: 104 sets forth nucleotides 162-233 of SEQ ID NO:1 comprising a deletion resulting from cleavage and NHEJ.

SEQ ID NO: 105 sets forth nucleotides 181-214 of SEQ ID NO:1.

SEQ ID NO: 106 sets forth nucleotides 181-214 of SEQ ID NO:1 comprising an exogenous nucleic acid sequence inserted via homologous recombination.

SEQ ID NO: 107 sets forth the nucleotide sequence of a plasmid used to generate the AAV405 vector.

SEQ ID NO: 108 sets forth the nucleotide sequence of a plasmid used to generate the AAV406 vector.

SEQ ID NO: 109 sets forth the nucleotide sequence of a plasmid used to generate the AAV-CAR100 (AAV408) vector.

SEQ ID NO: 110 sets forth the nucleotide sequence of a plasmid used to generate the AAV-CAR763 (AAV412) vector.

SEQ ID NO: 111 sets forth the amino acid sequence of an anti-CD19 chimeric antigen receptor.

SEQ ID NO: 112 sets forth the amino acid sequence of an anti-CD19 extracellular ligand-binding domain.

SEQ ID NO: 113 sets forth the amino acid sequence of a chimeric antigen receptor intracellular cytoplasmic signaling domain.

SEQ ID NO: 114 sets forth the amino acid sequence of a chimeric antigen receptor intracellular co-stimulatory domain.

SEQ ID NO: 115 sets forth the amino acid sequence of a chimeric antigen receptor signal peptide domain.

SEQ ID NO: 116 sets forth the amino acid sequence of a chimeric antigen receptor hinge region.

SEQ ID NO: 117 sets forth the amino acid sequence of a chimeric antigen receptor transmembrane domain.

SEQ ID NO: 118 sets forth the nucleotide sequence of an EF-1 alpha core promoter.

SEQ ID NO: 119 sets forth the nucleotide sequence of an exogenous polynucleotide insert.

SEQ ID NO: 120 sets forth the nucleotide sequence of the human TCR alpha constant region gene comprising an exogenous nucleic acid sequence inserted within the TRC 1-2 recognition sequence.

SEQ ID NO: 121 sets forth the nucleotide sequence of the human TCR alpha constant region gene comprising an exogenous nucleic acid sequence inserted within the TRC 3-4 recognition sequence.

SEQ ID NO: 122 sets forth the nucleotide sequence of the human TCR alpha constant region gene comprising an exogenous nucleic acid sequence inserted within the TRC 7-8 recognition sequence.

SEQ ID NO: 123 sets forth the nucleic acid sequence of a plasmid used to generate the AAV421 vector.

SEQ ID NO: 124 sets forth the nucleic acid sequence of a plasmid used to generate the AAV422 vector.

SEQ ID NO: 125 sets forth the nucleic acid sequence of a plasmid used to generate the AAV423 vector.

DETAILED DESCRIPTION OF THE INVENTION

1.1 References and Definitions

The patent and scientific literature referred to herein establishes knowledge that is available to those of skill in the art. The issued US patents, allowed applications, published foreign applications, and references, including GenBank database sequences, which are cited herein are hereby incorporated by reference to the same extent as if each was specifically and individually indicated to be incorporated by reference.

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference herein in their entirety.

As used herein, "a," "an," or "the" can mean one or more than one. For example, "a" cell can mean a single cell or a multiplicity of cells.

As used herein, unless specifically indicated otherwise, the word "or" is used in the inclusive sense of "and/or" and not the exclusive sense of "either/or."

As used herein, the term "meganuclease" refers to an endonuclease that binds double-stranded DNA at a recognition sequence that is greater than 12 base pairs. Preferably, the recognition sequence for a meganuclease of the invention is 22 base pairs. A meganuclease can be an endonuclease that is derived from I-CreI, and can refer to an engineered variant of I-CreI that has been modified relative to natural I-CreI with respect to, for example, DNA-binding specificity, DNA cleavage activity, DNA-binding affinity, or dimerization properties. Methods for producing such modified variants of I-CreI are known in the art (e.g., WO 2007/047859). A meganuclease as used herein binds to double-stranded DNA as a heterodimer or as a "single-chain meganuclease" in which a pair of DNA-binding domains are joined into a single polypeptide using a peptide linker. The term "homing endonuclease" is synonymous with the term "meganuclease." Meganucleases of the invention are substantially non-toxic when expressed in cells, particularly in human T cells, such that cells can be transfected and maintained at 37° C. without observing deleterious effects on cell viability or significant reductions in meganuclease cleavage activity when measured using the methods described herein.

As used herein, the term “single-chain meganuclease” refers to a polypeptide comprising a pair of nuclease subunits joined by a linker. A single-chain meganuclease has the organization: N-terminal subunit—Linker—C-terminal subunit. The two meganuclease subunits will generally be non-identical in amino acid sequence and will recognize non-identical DNA sequences. Thus, single-chain meganucleases typically cleave pseudo-palindromic or non-palindromic recognition sequences. A single-chain meganuclease may be referred to as a “single-chain heterodimer” or “single-chain heterodimeric meganuclease” although it is not, in fact, dimeric. For clarity, unless otherwise specified, the term “meganuclease” can refer to a dimeric or single-chain meganuclease.

As used herein, the term “linker” refers to an exogenous peptide sequence used to join two meganuclease subunits into a single polypeptide. A linker may have a sequence that is found in natural proteins, or may be an artificial sequence that is not found in any natural protein. A linker may be flexible and lacking in secondary structure or may have a propensity to form a specific three-dimensional structure under physiological conditions. A linker can include, without limitation, those encompassed by U.S. Pat. No. 8,445,251. In some embodiments, a linker may have an amino acid sequence comprising residues 154-195 of any one of SEQ ID NOs:8-32.

As used herein, the term “TALEN” refers to an endonuclease comprising a DNA-binding domain comprising 16-22 TAL domain repeats fused to any portion of the FokI nuclease domain.

As used herein, the term “Compact TALEN” refers to an endonuclease comprising a DNA-binding domain with 16-22 TAL domain repeats fused in any orientation to any catalytically active portion of nuclease domain of the I-TevI homing endonuclease.

As used herein, the term “CRISPR” refers to a caspase-based endonuclease comprising a caspase, such as Cas9, and a guide RNA that directs DNA cleavage of the caspase by hybridizing to a recognition site in the genomic DNA.

As used herein, the term “megaTAL” refers to a single-chain nuclease comprising a transcription activator-like effector (TALE) DNA binding domain with an engineered, sequence-specific homing endonuclease.

As used herein, with respect to a protein, the term “recombinant” means having an altered amino acid sequence as a result of the application of genetic engineering techniques to nucleic acids that encode the protein, and cells or organisms that express the protein. With respect to a nucleic acid, the term “recombinant” means having an altered nucleic acid sequence as a result of the application of genetic engineering techniques. Genetic engineering techniques include, but are not limited to, PCR and DNA cloning technologies; transfection, transformation and other gene transfer technologies; homologous recombination; site-directed mutagenesis; and gene fusion. In accordance with this definition, a protein having an amino acid sequence identical to a naturally-occurring protein, but produced by cloning and expression in a heterologous host, is not considered recombinant.

As used herein, the term “wild-type” refers to the most common naturally occurring allele (i.e., polynucleotide sequence) in the allele population of the same type of gene, wherein a polypeptide encoded by the wild-type allele has its original functions. The term “wild-type” also refers a polypeptide encoded by a wild-type allele. Wild-type alleles (i.e., polynucleotides) and polypeptides are distinguishable from mutant or variant alleles and polypeptides, which comprise one or more mutations and/or substitutions relative to the wild-type sequence(s). Whereas a wild-type allele or polypeptide can confer a normal phenotype in an organism, a mutant or variant allele or polypeptide can, in some instances, confer an altered phenotype. Wild-type nucleases are distinguishable from recombinant or non-naturally-occurring nucleases.

As used herein with respect to recombinant proteins, the term “modification” means any insertion, deletion or substitution of an amino acid residue in the recombinant sequence relative to a reference sequence (e.g., a wild-type or a native sequence).

As used herein, the term “recognition sequence” refers to a DNA sequence that is bound and cleaved by an endonuclease. In the case of a meganuclease, a recognition sequence comprises a pair of inverted, 9 basepair “half sites” that are separated by four basepairs. In the case of a single-chain meganuclease, the N-terminal domain of the protein contacts a first half-site and the C-terminal domain of the protein contacts a second half-site. Cleavage by a meganuclease produces four basepair 3' “overhangs”. “Overhangs”, or “sticky ends” are short, single-stranded DNA segments that can be produced by endonuclease cleavage of a double-stranded DNA sequence. In the case of meganucleases and single-chain meganucleases derived from I-CreI, the overhang comprises bases 10-13 of the 22 basepair recognition sequence. In the case of a Compact TALEN, the recognition sequence comprises a first CNNNGN sequence that is recognized by the I-TevI domain, followed by a non-specific spacer 4-16 basepairs in length, followed by a second sequence 16-22 bp in length that is recognized by the TAL-effector domain (this sequence typically has a 5' T base). Cleavage by a Compact TALEN produces two basepair 3' overhangs. In the case of a CRISPR, the recognition sequence is the sequence, typically 16-24 basepairs, to which the guide RNA binds to direct Cas9 cleavage. Cleavage by a CRISPR produced blunt ends.

As used herein, the term “target site” or “target sequence” refers to a region of the chromosomal DNA of a cell comprising a recognition sequence for a nuclease.

As used herein, the term “DNA-binding affinity” or “binding affinity” means the tendency of a meganuclease to non-covalently associate with a reference DNA molecule (e.g., a recognition sequence or an arbitrary sequence). Binding affinity is measured by a dissociation constant, $K_d$. As used herein, a nuclease has “altered” binding affinity if the $K_d$ of the nuclease for a reference recognition sequence is increased or decreased by a statistically significant percent change relative to a reference nuclease.

As used herein, the term “homologous recombination” or “HR” refers to the natural, cellular process in which a double-stranded DNA-break is repaired using a homologous DNA sequence as the repair template (see, e.g., Cahill et al. (2006), *Front. Biosci.* 11:1958-1976). The homologous DNA sequence may be an endogenous chromosomal sequence or an exogenous nucleic acid that was delivered to the cell.

As used herein, the term “non-homologous end-joining” or “NHEJ” refers to the natural, cellular process in which a double-stranded DNA-break is repaired by the direct joining of two non-homologous DNA segments (see, e.g., Cahill et al. (2006), *Front. Biosci.* 11:1958-1976). DNA repair by non-homologous end-joining is error-prone and frequently results in the untemplated addition or deletion of DNA sequences at the site of repair. In some instances, cleavage at a target recognition sequence results in NHEJ at a target recognition site. Nuclease-induced cleavage of a target site in the coding sequence of a gene followed by DNA repair by NHEJ can introduce mutations into the coding sequence, such as frameshift mutations, that disrupt gene function. Thus, engineered nucleases can be used to effectively knock-out a gene in a population of cells.

As used herein, a "chimeric antigen receptor" or "CAR" refers to an engineered receptor that confers or grafts specificity for an antigen onto an immune effector cell (e.g., a human T cell). A chimeric antigen receptor typically comprises an extracellular ligand-binding domain or moiety and an intracellular domain that comprises one or more stimulatory domains that transduce the signals necessary for T cell activation. In some embodiments, the extracellular ligand-binding domain or moiety can be in the form of single-chain variable fragments (scFvs) derived from a monoclonal antibody, which provide specificity for a particular epitope or antigen (e.g., an epitope or antigen preferentially present on the surface of a cancer cell or other disease-causing cell or particle). The extracellular ligand-binding domain can be specific for any antigen or epitope of interest. In a particular embodiment, the ligand-binding domain is specific for CD19.

The extracellular domain of a chimeric antigen receptor can also comprise an autoantigen (see, Payne et al. (2016), *Science* 353 (6295): 179-184), that can be recognized by autoantigen-specific B cell receptors on B lymphocytes, thus directing T cells to specifically target and kill autoreactive B lymphocytes in antibody-mediated autoimmune diseases. Such CARs can be referred to as chimeric autoantibody receptors (CAARs), and their use is encompassed by the invention.

The scFvs can be attached via a linker sequence. The intracellular stimulatory domain can include one or more cytoplasmic signaling domains that transmit an activation signal to the immune effector cell following antigen binding. Such cytoplasmic signaling domains can include, without limitation, CD3-zeta. The intracellular stimulatory domain can also include one or more intracellular co-stimulatory domains that transmit a proliferative and/or cell-survival signal after ligand binding. Such intracellular co-stimulatory domains can include, without limitation, a CD28 domain, a 4-1BB domain, an OX40 domain, or a combination thereof. A chimeric antigen receptor can further include additional structural elements, including a transmembrane domain that is attached to the extracellular ligand-binding domain via a hinge or spacer sequence.

As used herein, an "exogenous T cell receptor" or "exogenous TCR" refers to a TCR whose sequence is introduced into the genome of an immune effector cell (e.g., a human T cell) that may or may not endogenously express the TCR. Expression of an exogenous TCR on an immune effector cell can confer specificity for a specific epitope or antigen (e.g., an epitope or antigen preferentially present on the surface of a cancer cell or other disease-causing cell or particle). Such exogenous T cell receptors can comprise alpha and beta chains or, alternatively, may comprise gamma and delta chains. Exogenous TCRs useful in the invention may have specificity to any antigen or epitope of interest.

As used herein, the term "reduced expression" refers to any reduction in the expression of the endogenous T cell receptor at the cell surface of a genetically-modified cell when compared to a control cell. The term reduced can also refer to a reduction in the percentage of cells in a population of cells that express an endogenous polypeptide (i.e., an endogenous T cell receptor) at the cell surface when compared to a population of control cells. Such a reduction may be up to 5%, 10%, 20%, 30%, 40%, 50%, 60%, 70%, 80%, 90%, 95%, or up to 100%. Accordingly, the term "reduced" encompasses both a partial knockdown and a complete knockdown of the endogenous T cell receptor.

As used herein with respect to both amino acid sequences and nucleic acid sequences, the terms "percent identity," "sequence identity," "percentage similarity," "sequence similarity" and the like refer to a measure of the degree of similarity of two sequences based upon an alignment of the sequences that maximizes similarity between aligned amino acid residues or nucleotides, and that is a function of the number of identical or similar residues or nucleotides, the number of total residues or nucleotides, and the presence and length of gaps in the sequence alignment. A variety of algorithms and computer programs are available for determining sequence similarity using standard parameters. As used herein, sequence similarity is measured using the BLASTp program for amino acid sequences and the BLASTn program for nucleic acid sequences, both of which are available through the National Center for Biotechnology Information (www.ncbi.nlm.nih.gov/), and are described in, for example, Altschul et al. (1990), *J. Mol. Biol.* 215:403-410; Gish and States (1993), *Nature Genet.* 3:266-272; Madden et al. (1996), *Meth. Enzymol.* 266:131-141; Altschul et al. (1997), *Nucleic Acids Res.* 25:33 89-3402); Zhang et al. (2000), *J. Comput. Biol.* 7(1-2):203-14. As used herein, percent similarity of two amino acid sequences is the score based upon the following parameters for the BLASTp algorithm: word size=3; gap opening penalty=−11; gap extension penalty=−1; and scoring matrix=BLOSUM62. As used herein, percent similarity of two nucleic acid sequences is the score based upon the following parameters for the BLASTn algorithm: word size=11; gap opening penalty=−5; gap extension penalty=−2; match reward=1; and mismatch penalty=−3.

As used herein with respect to modifications of two proteins or amino acid sequences, the term "corresponding to" is used to indicate that a specified modification in the first protein is a substitution of the same amino acid residue as in the modification in the second protein, and that the amino acid position of the modification in the first proteins corresponds to or aligns with the amino acid position of the modification in the second protein when the two proteins are subjected to standard sequence alignments (e.g., using the BLASTp program). Thus, the modification of residue "X" to amino acid "A" in the first protein will correspond to the modification of residue "Y" to amino acid "A" in the second protein if residues X and Y correspond to each other in a sequence alignment, and despite the fact that X and Y may be different numbers.

As used herein, the term "recognition half-site," "recognition sequence half-site," or simply "half-site" means a nucleic acid sequence in a double-stranded DNA molecule that is recognized by a monomer of a homodimeric or heterodimeric meganuclease, or by one subunit of a single-chain meganuclease.

As used herein, the term "hypervariable region" refers to a localized sequence within a meganuclease monomer or subunit that comprises amino acids with relatively high variability. A hypervariable region can comprise about 50-60 contiguous residues, about 53-57 contiguous residues, or preferably about 56 residues. In some embodiments, the residues of a hypervariable region may correspond to positions 24-79 or positions 215-270 of any one of SEQ ID NOs:8-32. A hypervariable region can comprise one or more residues that contact DNA bases in a recognition sequence and can be modified to alter base preference of the monomer or subunit. A hypervariable region can also comprise one or more residues that bind to the DNA backbone when the meganuclease associates with a double-stranded DNA recognition sequence. Such residues can be modified to alter the binding affinity of the meganuclease for the DNA backbone and the target recognition sequence. In different embodiments of the invention, a hypervariable region may comprise between 1-20 residues that exhibit variability and can be modified to influence base preference and/or DNA-binding affinity. In particular embodiments, a hypervariable region comprises between about 15-18 residues that exhibit variability and can be modified to influence base preference and/or DNA-binding affinity. In some embodiments, variable residues within a hypervariable region correspond to one or more of positions 24, 26, 28, 29, 30, 32, 33, 38, 40, 42, 44, 46, 66, 68, 70, 72, 73, 75, and 77 of any one of SEQ ID NOs:8-32. In other embodiments, variable residues within a hypervariable region correspond to one or more of positions 215, 217, 219, 221, 223, 224, 229, 231, 233, 235, 237, 248, 257, 259, 261, 263, 264, 266, and 268 of any one of SEQ ID NOs:8-32.

As used herein, the terms "T cell receptor alpha constant region gene" and "TCR alpha constant region gene" are used interchangeably and refer to the human gene identified by NCBI Gen ID NO. 28755 (SEQ ID NO:1).

The terms "recombinant DNA construct," "recombinant construct," "expression cassette," "expression construct," "chimeric construct," "construct," and "recombinant DNA fragment" are used interchangeably herein and are single or double-stranded polynucleotides. A recombinant construct comprises an artificial combination of single or double-stranded polynucleotides, including, without limitation, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such a construct may be used by itself or may be used in conjunction with a vector.

As used herein, a "vector" or "recombinant DNA vector" may be a construct that includes a replication system and sequences that are capable of transcription and translation of a polypeptide-encoding sequence in a given host cell. If a vector is used then the choice of vector is dependent upon the method that will be used to transform host cells as is well known to those skilled in the art. Vectors can include, without limitation, plasmid vectors and recombinant AAV vectors, or any other vector known in that art suitable for delivering a gene encoding a meganuclease of the invention to a target cell. The skilled artisan is well aware of the genetic elements that must be present on the vector in order to successfully transform, select and propagate host cells comprising any of the isolated nucleotides or nucleic acid sequences of the invention.

As used herein, a "vector" can also refer to a viral vector. Viral vectors can include, without limitation, retroviral vectors, lentiviral vectors, adenoviral vectors, and adeno-associated viral vectors (AAV).

As used herein, a "polycistronic" mRNA refers to a single messenger RNA that comprises two or more coding sequences (i.e., cistrons) and encodes more than one protein. A polycistronic mRNA can comprise any element known in the art to allow for the translation of two or more genes from the same mRNA molecule including, but not limited to, an IRES element, a T2A element, a P2A element, an E2A element, and an F2A element.

As used herein, a "human T cell" or "T cell" refers to a T cell isolated from a human donor. Human T cells, and cells derived therefrom, include isolated T cells that have not been passaged in culture, T cells that have been passaged and maintained under cell culture conditions without immortalization, and T cells that have been immortalized and can be maintained under cell culture conditions indefinitely.

As used herein, a "control" or "control cell" refers to a cell that provides a reference point for measuring changes in genotype or phenotype of a genetically-modified cell. A control cell may comprise, for example: (a) a wild-type cell, i.e., of the same genotype as the starting material for the genetic alteration that resulted in the genetically-modified cell; (b) a cell of the same genotype as the genetically-modified cell but that has been transformed with a null construct (i.e., with a construct that has no known effect on the trait of interest); or, (c) a cell genetically identical to the genetically-modified cell but that is not exposed to conditions or stimuli or further genetic modifications that would induce expression of altered genotype or phenotype.

As used herein, the recitation of a numerical range for a variable is intended to convey that the invention may be practiced with the variable equal to any of the values within that range. Thus, for a variable that is inherently discrete, the variable can be equal to any integer value within the numerical range, including the end-points of the range. Similarly, for a variable that is inherently continuous, the variable can be equal to any real value within the numerical range, including the end-points of the range. As an example, and without limitation, a variable that is described as having values between 0 and 2 can take the values 0, 1 or 2 if the variable is inherently discrete, and can take the values 0.0, 0.1, 0.01, 0.001, or any other real values ≥0 and ≤2 if the variable is inherently continuous.

2.1 Principle of the Invention

The present invention is based, in part, on the discovery that engineered nucleases can be utilized to recognize and cleave recognition sequences found within the human TCR alpha constant region gene (SEQ ID NO:1), such that NHEJ at the cleavage site disrupts expression of the TCR alpha chain subunit and, ultimately, expression of the T cell receptor at the cell surface. Moreover, according to the invention, an exogenous polynucleotide sequence is inserted into the TCR alpha constant region gene at the nuclease cleavage site, for example by homologous recombination, such that a sequence of interest is concurrently expressed in the cell. Such exogenous sequences can encode, for example, a chimeric antigen receptor, an exogenous TCR receptor, or any other polypeptide of interest.

Thus, the present invention allows for both the knockout of the endogenous T cell receptor and the expression of an exogenous nucleic acid sequence (e.g., a chimeric antigen receptor or exogenous TCR) by targeting a single recognition site with a single engineered nuclease. In particular embodiments where a sequence encoding a chimeric antigen receptor is inserted into the TCR alpha constant region gene, the invention provides a simplified method for producing an allogeneic T cell that expresses an antigen-specific CAR and has reduced expression, or complete knockout, of the endogenous TCR. Such cells can exhibit reduced or no induction of graft-versus-host-disease (GVHD) when administered to an allogeneic subject.

2.2 Nucleases for Recognizing and Cleaving Recognition Sequences within the T Cell Receptor Alpha Constant Region Gene It is known in the art that it is possible to use a site-specific nuclease to make a DNA break in the genome of a living cell, and that such a DNA break can result in permanent modification of the genome via mutagenic NHEJ repair or via homologous recombination with a transgenic DNA sequence. NHEJ can produce mutagenesis at the cleavage site, resulting in inactivation of the allele. NHEJ-associated mutagenesis may inactivate an allele via generation of early stop codons, frameshift mutations producing aberrant non-functional proteins, or could trigger mechanisms such as nonsense-mediated mRNA decay. The use of nucleases to induce mutagenesis via NHEJ can be used to target a specific mutation or a sequence present in a wild-type allele. The use of nucleases to induce a double-strand break in a target locus is known to stimulate homologous recombination, particularly of transgenic DNA sequences flanked by sequences that are homologous to the genomic target. In this manner, exogenous nucleic acid sequences can be inserted into a target locus. Such exogenous nucleic acids can encode, for example, a chimeric antigen receptor, an exogenous TCR, or any sequence or polypeptide of interest.

In different embodiments, a variety of different types of nuclease are useful for practicing the invention. In one embodiment, the invention can be practiced using recombinant meganucleases. In another embodiment, the invention can be practiced using a CRISPR nuclease or CRISPR Nickase. Methods for making CRISPRs and CRISPR Nickases that recognize pre-determined DNA sites are known in the art, for example Ran, et al. (2013) *Nat Protoc.* 8:2281-308. In another embodiment, the invention can be practiced using TALENs or Compact TALENs. Methods for making TALE domains that bind to pre-determined DNA sites are known in the art, for example Reyon et al. (2012) *Nat Biotechnol.* 30:460-5. In a further embodiment, the invention can be practiced using megaTALs.

In preferred embodiments, the nucleases used to practice the invention are single-chain meganucleases. A single-chain meganuclease comprises an N-terminal subunit and a C-terminal subunit joined by a linker peptide. Each of the two domains recognizes half of the recognition sequence (i.e., a recognition half-site) and the site of DNA cleavage is at the middle of the recognition sequence near the interface of the two subunits. DNA strand breaks are offset by four base pairs such that DNA cleavage by a meganuclease generates a pair of four base pair, 3' single-strand overhangs.

In some examples, recombinant meganucleases of the invention have been engineered to recognize and cleave the TRC 1-2 recognition sequence (SEQ ID NO:3). Such recombinant meganucleases are collectively referred to herein as "TRC 1-2 meganucleases." Exemplary TRC 1-2 meganucleases are provided in SEQ ID NOs:8-27.

In additional examples, recombinant meganucleases of the invention have been engineered to recognize and cleave the TRC 3-4 recognition sequence (SEQ ID NO:4). Such recombinant meganucleases are collectively referred to herein as "TRC 3-4 meganucleases." Exemplary TRC 3-4 meganucleases are provided in SEQ ID NOs:28 and 29.

In further examples, recombinant meganucleases of the invention have been engineered to recognize and cleave the TRC 7-8 recognition sequence (SEQ ID NO:5). Such recombinant meganucleases are collectively referred to herein as "TRC 7-8 meganucleases." Exemplary TRC 7-8 meganucleases are provided in SEQ ID NOs:30-32.

Recombinant meganucleases of the invention comprise a first subunit, comprising a first hypervariable (HVR1) region, and a second subunit, comprising a second hypervariable (HVR2) region. Further, the first subunit binds to a first recognition half-site in the recognition sequence (e.g., the TRC1, TRC3, or TRC7 half-site), and the second subunit binds to a second recognition half-site in the recognition sequence (e.g., the TRC2, TRC4, or TRC8 half-site). In embodiments where the recombinant meganuclease is a single-chain meganuclease, the first and second subunits can be oriented such that the first subunit, which comprises the HVR1 region and binds the first half-site, is positioned as the N-terminal subunit, and the second subunit, which comprises the HVR2 region and binds the second half-site, is positioned as the C-terminal subunit. In alternative embodiments, the first and second subunits can be oriented such that the first subunit, which comprises the HVR1 region and binds the first half-site, is positioned as the C-terminal subunit, and the second subunit, which comprises the HVR2 region and binds the second half-site, is positioned as the N-terminal subunit. Exemplary TRC 1-2 meganucleases of the invention are provided in Table 1. Exemplary TRC 3-4 meganucleases of the invention are provided in Table 2. Exemplary TRC 7-8 meganucleases of the invention are provided in Table 3.

TABLE 1

Exemplary recombinant meganucleases engineered to recognize and cleave the TRC 1-2 recognition sequence (SEQ ID NO: 3)

| Meganuclease | AA SEQ ID | TRC1 Subunit Residues | TRC1 Subunit SEQ ID | *TRC1 Subunit % | TRC2 Subunit Residues | TRC2 Subunit SEQ ID | *TRC2 Subunit % |
|---|---|---|---|---|---|---|---|
| TRC 1-2x.87 EE | 8 | 198-344 | 33 | 100 | 7-153 | 58 | 100 |
| TRC 1-2x.87 QE | 9 | 198-344 | 34 | 100 | 7-153 | 59 | 99.3 |
| TRC 1-2x.87 EQ | 10 | 198-344 | 35 | 99.3 | 7-153 | 60 | 100 |
| TRC 1-2x.87 | 11 | 198-344 | 36 | 99.3 | 7-153 | 61 | 99.3 |
| TRC 1-2x.6 | 12 | 198-344 | 37 | 99.3 | 7-153 | 62 | 94.6 |
| TRC 1-2x.20 | 13 | 198-344 | 38 | 99.3 | 7-153 | 63 | 91.2 |
| TRC 1-2x.55 | 14 | 198-344 | 39 | 95.9 | 7-153 | 64 | 91.8 |
| TRC 1-2x.60 | 15 | 198-344 | 40 | 91.8 | 7-153 | 65 | 91.2 |
| TRC 1-2x.105 | 16 | 198-344 | 41 | 95.2 | 7-153 | 66 | 95.2 |
| TRC 1-2x.163 | 17 | 198-344 | 42 | 99.3 | 7-153 | 67 | 99.3 |
| TRC 1-2x.113_3 | 18 | 198-344 | 43 | 99.3 | 7-153 | 68 | 91.2 |
| TRC 1-2x.5 | 19 | 7-153 | 44 | 99.3 | 198-344 | 69 | 93.2 |

TABLE 1-continued

Exemplary recombinant meganucleases engineered to recognize and cleave the TRC 1-2 recognition sequence (SEQ ID NO: 3)

| Meganuclease | AA SEQ ID | TRC1 Subunit Residues | TRC1 Subunit SEQ ID | *TRC1 Subunit % | TRC2 Subunit Residues | TRC2 Subunit SEQ ID | *TRC2 Subunit % |
|---|---|---|---|---|---|---|---|
| TRC 1-2x.8 | 20 | 7-153 | 45 | 92.5 | 198-344 | 70 | 92.5 |
| TRC 1-2x.25 | 21 | 7-153 | 46 | 99.3 | 198-344 | 71 | 98.6 |
| TRC 1-2x.72 | 22 | 7-153 | 47 | 99.3 | 198-344 | 72 | 92.5 |
| TRC 1-2x.80 | 23 | 7-153 | 48 | 99.3 | 198-344 | 73 | 92.5 |
| TRC 1-2x.84 | 24 | 7-153 | 49 | 95.2 | 198-344 | 74 | 98.6 |
| TRC 1-2x.120 | 25 | 7-153 | 50 | 99.3 | 198-344 | 75 | 92.5 |
| TRC 1-2x.113_1 | 26 | 7-153 | 51 | 100 | 198-344 | 76 | 92.5 |
| TRC 1-2x.113_2 | 27 | 7-153 | 52 | 99.3 | 198-344 | 77 | 92.5 |

*"TRC1 Subunit %" and "TRC2 Subunit %" represent the amino acid sequence identity between the TRC1-binding and TRC2-binding subunit regions of each meganuclease and the TRC1-binding and TRC2-binding subunit regions, respectively, of the TRC 1-2x.87 EE meganuclease.

TABLE 2

Exemplary recombinant meganucleases engineered to recognize and cleave the TRC 3-4 recognition sequence (SEQ ID NO: 4)

| Meganuclease | AA SEQ ID | TRC3 Subunit Residues | TRC3 Subunit SEQ ID | *TRC3 Subunit % | TRC4 Subunit Residues | TRC4 Subunit SEQ ID | TRC4 Subunit % |
|---|---|---|---|---|---|---|---|
| TRC 3-4x.3 | 28 | 7-153 | 53 | 100 | 198-344 | 78 | 100 |
| TRC 3-4x.19 | 29 | 7-153 | 54 | 96.6 | 198-344 | 79 | 96.6 |

*"TRC3 Subunit %" and "TRC4 Subunit %" represent the amino acid sequence identity between the TRC3-binding and TRC4-binding subunit regions of each meganuclease and the TRC3-binding and TRC4-binding subunit regions, respectively, of the TRC 3-4x.3 meganuclease.

TABLE 3

Exemplary recombinant meganucleases engineered to recognize and cleave the TRC 7-8 recognition sequence (SEQ ID NO: 5)

| Meganuclease | AA SEQ ID | TRC7 Subunit Residues | TRC7 Subunit SEQ ID | *TRC7 Subunit % | TRC8 Subunit Residues | TRC8 Subunit SEQ ID | TRC8 Subunit % |
|---|---|---|---|---|---|---|---|
| TRC 7-8x.7 | 30 | 7-153 | 55 | 100 | 198-344 | 80 | 100 |
| TRC 7-8x.9 | 31 | 198-344 | 56 | 97.3 | 7-153 | 81 | 91.2 |
| TRC 7-8x.14 | 32 | 198-344 | 57 | 97.9 | 7-153 | 82 | 90.5 |

*"TRC7 Subunit %" and "TRC8 Subunit %" represent the amino acid sequence identity between the TRC7-binding and TRC8-binding subunit regions of each meganuclease and the TRC7-binding and TRC8-binding subunit regions, respectively, of the TRC 7-8x.7 meganuclease.

2.3 Methods for Producing Genetically-Modified Cells

The invention provides methods for producing genetically-modified cells using engineered nucleases that recognize and cleave recognition sequences found within the human TCR alpha constant region gene (SEQ ID NO:1). Cleavage at such recognition sequences can allow for NHEJ at the cleavage site and disrupted expression of the human T cell receptor alpha chain subunit, leading to reduced expression and/or function of the T cell receptor at the cell surface. Additionally, cleavage at such recognition sequences can further allow for homologous recombination of exogenous nucleic acid sequences directly into the TCR alpha constant region gene.

Engineered nucleases of the invention can be delivered into a cell in the form of protein or, preferably, as a nucleic acid encoding the engineered nuclease. Such nucleic acid can be DNA (e.g., circular or linearized plasmid DNA or PCR products) or RNA. For embodiments in which the engineered nuclease coding sequence is delivered in DNA form, it should be operably linked to a promoter to facilitate transcription of the meganuclease gene. Mammalian promoters suitable for the invention include constitutive promoters such as the cytomegalovirus early (CMV) promoter (Thomsen et al. (1984), *Proc Natl Acad Sci USA*. 81(3):659-63) or the SV40 early promoter (Benoist and Chambon (1981), *Nature*. 290(5804):304-10) as well as inducible promoters such as the tetracycline-inducible promoter (Dingermann et al. (1992), *Mol Cell Biol*. 12(9):4038-45).

In some embodiments, mRNA encoding the engineered nuclease is delivered to the cell because this reduces the likelihood that the gene encoding the engineered nuclease will integrate into the genome of the cell. Such mRNA encoding an engineered nuclease can be produced using methods known in the art such as in vitro transcription. In some embodiments, the mRNA is capped using 7-methyl-guanosine. In some embodiments, the mRNA may be polyadenylated.

In particular embodiments, an mRNA encoding an engineered nuclease of the invention can be a polycistronic mRNA encoding two or more nucleases that are simultaneously expressed in the cell. A polycistronic mRNA can encode two or more nucleases of the invention that target different recognition sequences in the same target gene. Alternatively, a polycistronic mRNA can encode at least one nuclease described herein and at least one additional nuclease targeting a separate recognition sequence positioned in the same gene, or targeting a second recognition sequence positioned in a second gene such that cleavage sites are produced in both genes. A polycistronic mRNA can comprise any element known in the art to allow for the translation of two or more genes (i.e., cistrons) from the same mRNA molecule including, but not limited to, an IRES element, a T2A element, a P2A element, an E2A element, and an F2A element.

Purified nuclease proteins can be delivered into cells to cleave genomic DNA, which allows for homologous recombination or non-homologous end-joining at the cleavage site with a sequence of interest, by a variety of different mechanisms known in the art.

In some embodiments, engineered nuclease proteins, or DNA/mRNA encoding engineered nucleases, are coupled to a cell penetrating peptide or targeting ligand to facilitate cellular uptake. Examples of cell penetrating peptides known in the art include poly-arginine (Jearawiriyapaisarn, et al. (2008) *Mol Ther.* 16:1624-9), TAT peptide from the HIV virus (Hudecz et al. (2005), *Med. Res. Rev.* 25: 679-736), MPG (Simeoni, et al. (2003) *Nucleic Acids Res.* 31:2717-2724), Pep-1 (Deshayes et al. (2004) *Biochemistry* 43: 7698-7706, and HSV-1 VP-22 (Deshayes et al. (2005) *Cell Mol Life Sci.* 62:1839-49. In an alternative embodiment, engineered nucleases, or DNA/mRNA encoding engineered nucleases, are coupled covalently or non-covalently to an antibody that recognizes a specific cell-surface receptor expressed on target cells such that the nuclease protein/DNA/mRNA binds to and is internalized by the target cells. Alternatively, engineered nuclease protein/DNA/mRNA can be coupled covalently or non-covalently to the natural ligand (or a portion of the natural ligand) for such a cell-surface receptor. (McCall, et al. (2014) *Tissue Barriers.* 2(4): e944449; Dinda, et al. (2013) *Curr Pharm Biotechnol.* 14:1264-74; Kang, et al. (2014) *Curr Pharm Biotechnol.* 15(3):220-30; Qian et al. (2014) *Expert Opin Drug Metab Toxicol.* 10(11):1491-508).

In some embodiments, engineered nuclease proteins, or DNA/mRNA encoding engineered nucleases, are coupled covalently or, preferably, non-covalently to a nanoparticle or encapsulated within such a nanoparticle using methods known in the art (Sharma, et al. (2014) *Biomed Res* Int. 2014). A nanoparticle is a nanoscale delivery system whose length scale is <1 μm, preferably <100 nm. Such nanoparticles may be designed using a core composed of metal, lipid, polymer, or biological macromolecule, and multiple copies of the recombinant meganuclease proteins, mRNA, or DNA can be attached to or encapsulated with the nanoparticle core. This increases the copy number of the protein/mRNA/DNA that is delivered to each cell and, so, increases the intracellular expression of each engineered nuclease to maximize the likelihood that the target recognition sequences will be cut. The surface of such nanoparticles may be further modified with polymers or lipids (e.g., chitosan, cationic polymers, or cationic lipids) to form a core-shell nanoparticle whose surface confers additional functionalities to enhance cellular delivery and uptake of the payload (Jian et al. (2012) *Biomaterials.* 33(30): 7621-30). Nanoparticles may additionally be advantageously coupled to targeting molecules to direct the nanoparticle to the appropriate cell type and/or increase the likelihood of cellular uptake. Examples of such targeting molecules include antibodies specific for cell-surface receptors and the natural ligands (or portions of the natural ligands) for cell surface receptors.

In some embodiments, the engineered nucleases or DNA/mRNA encoding the engineered nucleases, are encapsulated within liposomes or complexed using cationic lipids (see, e.g., Lipofectamine™, Life Technologies Corp., Carlsbad, Calif.; Zuris et al. (2015) *Nat Biotechnol.* 33: 73-80; Mishra et al. (2011) *J Drug Deliv.* 2011:863734). The liposome and lipoplex formulations can protect the payload from degradation, and facilitate cellular uptake and delivery efficiency through fusion with and/or disruption of the cellular membranes of the cells.

In some embodiments, engineered nuclease proteins, or DNA/mRNA encoding engineered nucleases, are encapsulated within polymeric scaffolds (e.g., PLGA) or complexed using cationic polymers (e.g., PEI, PLL) (Tamboli et al. (2011) *Ther Deliv.* 2(4): 523-536).

In some embodiments, engineered nuclease proteins, or DNA/mRNA encoding engineered nucleases, are combined with amphiphilic molecules that self-assemble into micelles (Tong et al. (2007) *J Gene Med.* 9(11): 956-66). Polymeric micelles may include a micellar shell formed with a hydrophilic polymer (e.g., polyethyleneglycol) that can prevent aggregation, mask charge interactions, and reduce nonspecific interactions outside of the cell.

In some embodiments, engineered nuclease proteins, or DNA/mRNA encoding engineered nucleases, are formulated into an emulsion or a nanoemulsion (i.e., having an average particle diameter of <1 nm) for delivery to the cell. The term "emulsion" refers to, without limitation, any oil-in-water, water-in-oil, water-in-oil-in-water, or oil-in-water-in-oil dispersions or droplets, including lipid structures that can form as a result of hydrophobic forces that drive apolar residues (e.g., long hydrocarbon chains) away from water and polar head groups toward water, when a water immiscible phase is mixed with an aqueous phase. These other lipid structures include, but are not limited to, unilamellar, paucilamellar, and multilamellar lipid vesicles, micelles, and lamellar phases. Emulsions are composed of an aqueous phase and a lipophilic phase (typically containing an oil and an organic solvent). Emulsions also frequently contain one or more surfactants. Nanoemulsion formulations are well known, e.g., as described in US Patent Application Nos. 2002/0045667 and 2004/0043041, and U.S. Pat. Nos. 6,015,832, 6,506,803, 6,635,676, and 6,559,189, each of which is incorporated herein by reference in its entirety.

In some embodiments, engineered nuclease proteins, or DNA/mRNA encoding engineered nucleases, are covalently attached to, or non-covalently associated with, multifunctional polymer conjugates, DNA dendrimers, and polymeric dendrimers (Mastorakos et al. (2015) *Nanoscale.* 7(9): 3845-56; Cheng et al. (2008) *J Pharm Sci.* 97(1): 123-43). The dendrimer generation can control the payload capacity and size, and can provide a high payload capacity. Moreover, display of multiple surface groups can be leveraged to improve stability and reduce nonspecific interactions.

In some embodiments, genes encoding an engineered nuclease are introduced into a cell using a viral vector. Such vectors are known in the art and include lentiviral vectors, adenoviral vectors, and adeno-associated virus (AAV) vectors (reviewed in Vannucci, et al. (2013 *New Microbiol.* 36:1-22). Recombinant AAV vectors useful in the invention can have any serotype that allows for transduction of the virus into the cell and insertion of the nuclease gene into the cell genome. In particular embodiments, recombinant AAV vectors have a serotype of AAV2 or AAV6. Recombinant AAV vectors can also be self-complementary such that they do not require second-strand DNA synthesis in the host cell (McCarty, et al. (2001) *Gene Ther.* 8:1248-54).

If the engineered nuclease genes are delivered in DNA form (e.g. plasmid) and/or via a viral vector (e.g. AAV) they must be operably linked to a promoter. In some embodiments, this can be a viral promoter such as endogenous promoters from the viral vector (e.g. the LTR of a lentiviral vector) or the well-known cytomegalovirus- or SV40 virus-early promoters. In a preferred embodiment, nuclease genes are operably linked to a promoter that drives gene expression preferentially in the target cell (e.g., a human T cell).

The invention further provides for the introduction of an exogenous nucleic acid into the cell, such that the exogenous nucleic acid sequence is inserted into the TRC alpha constant region gene at a nuclease cleavage site. In some embodiments, the exogenous nucleic acid comprises a 5' homology arm and a 3' homology arm to promote recombination of the nucleic acid sequence into the cell genome at the nuclease cleavage site.

Exogenous nucleic acids of the invention may be introduced into the cell by any of the means previously discussed. In a particular embodiment, exogenous nucleic acids are introduced by way of a viral vector, such as a lentivirus, retrovirus, adenovirus, or preferably a recombinant AAV vector. Recombinant AAV vectors useful for introducing an exogenous nucleic acid can have any serotype that allows for transduction of the virus into the cell and insertion of the exogenous nucleic acid sequence into the cell genome. In particular embodiments, the recombinant AAV vectors have a serotype of AAV2 or AAV6. The recombinant AAV vectors can also be self-complementary such that they do not require second-strand DNA synthesis in the host cell.

In another particular embodiment, an exogenous nucleic acid can be introduced into the cell using a single-stranded DNA template. The single-stranded DNA can comprise the exogenous nucleic acid and, in preferred embodiments, can comprise 5' and 3' homology arms to promote insertion of the nucleic acid sequence into the nuclease cleavage site by homologous recombination. The single-stranded DNA can further comprise a 5' AAV inverted terminal repeat (ITR) sequence 5' upstream of the 5' homology arm, and a 3' AAV ITR sequence 3' downstream of the 3' homology arm.

In another particular embodiment, genes encoding an endonuclease of the invention and/or an exogenous nucleic acid sequence of the invention can be introduced into the cell by transfection with a linearized DNA template. In some examples, a plasmid DNA encoding an endonuclease and/or an exogenous nucleic acid sequence can be digested by one or more restriction enzymes such that the circular plasmid DNA is linearized prior to transfection into the cell.

When delivered to a cell, an exogenous nucleic acid of the invention can be operably linked to any promoter suitable for expression of the encoded polypeptide in the cell, including those mammalian promoters and inducible promoters previously discussed. An exogenous nucleic acid of the invention can also be operably linked to a synthetic promoter. Synthetic promoters can include, without limitation, the JeT promoter (WO 2002/012514).

In examples where the genetically-modified cells of the invention are human T cells, or cells derived therefrom, such cells may require activation prior to introduction of a meganuclease and/or an exogenous nucleic acid sequence. For example, T cells can be contacted with anti-CD3 and anti-CD28 antibodies that are soluble or conjugated to a support (i.e., beads) for a period of time sufficient to activate the cells.

Genetically-modified cells of the invention can be further modified to express one or more inducible suicide genes, the induction of which provokes cell death and allows for selective destruction of the cells in vitro or in vivo. In some examples, a suicide gene can encode a cytotoxic polypeptide, a polypeptide that has the ability to convert a non-toxic pro-drug into a cytotoxic drug, and/or a polypeptide that activates a cytotoxic gene pathway within the cell. That is, a suicide gene is a nucleic acid that encodes a product that causes cell death by itself or in the presence of other compounds. A representative example of such a suicide gene is one that encodes thymidine kinase of herpes simplex virus. Additional examples are genes that encode thymidine kinase of varicella zoster virus and the bacterial gene cytosine deaminase that can convert 5-fluorocytosine to the highly toxic compound 5-fluorouracil. Suicide genes also include as non-limiting examples genes that encode caspase-9, caspase-8, or cytosine deaminase. In some examples, caspase-9 can be activated using a specific chemical inducer of dimerization (CID). A suicide gene can also encode a polypeptide that is expressed at the surface of the cell that makes the cells sensitive to therapeutic and/or cytotoxic monoclonal antibodies. In further examples, a suicide gene can encode recombinant antigenic polypeptide comprising an antigenic motif recognized by the anti-CD20 mAb Rituximab and an epitope that allows for selection of cells expressing the suicide gene. See, for example, the RQR8 polypeptide described in WO2013153391, which comprises two Rituximab-binding epitopes and a QBEnd10-binding epitope. For such a gene, Rituximab can be administered to a subject to induce cell depletion when needed.

2.4 Pharmaceutical Compositions

In some embodiments, the invention provides a pharmaceutical composition comprising a genetically-modified cell of the invention, or a population of genetically-modified cells of the invention, and a pharmaceutical carrier. Such pharmaceutical compositions can be prepared in accordance with known techniques. See, e.g., Remington, *The Science And Practice of Pharmacy* ($21^{st}$ ed. 2005). In the manufacture of a pharmaceutical formulation according to the invention, cells are typically admixed with a pharmaceutically acceptable carrier and the resulting composition is administered to a subject. The carrier must, of course, be acceptable in the sense of being compatible with any other ingredients in the formulation and must not be deleterious to the subject. In some embodiments, pharmaceutical compositions of the invention can further comprise one or more additional agents useful in the treatment of a disease in the subject. In additional embodiments, where the genetically-modified cell is a genetically-modified human T cell (or a cell derived therefrom), pharmaceutical compositions of the invention can further include biological molecules, such as cytokines (e.g., IL-2, IL-7, IL-15, and/or IL-21), which promote in vivo cell proliferation and engraftment. Pharmaceutical compositions comprising genetically-modified cells of the invention can be administered in the same composition as an additional agent or biological molecule or, alternatively, can be co-administered in separate compositions.

Pharmaceutical compositions of the invention can be useful for treating any disease state that can be targeted by T cell adoptive immunotherapy. In a particular embodiment, the pharmaceutical compositions of the invention are useful in the treatment of cancer. Such cancers can include, without limitation, carcinoma, lymphoma, sarcoma, blastomas, leukemia, cancers of B-cell origin, breast cancer, gastric cancer, neuroblastoma, osteosarcoma, lung cancer, melanoma, prostate cancer, colon cancer, renal cell carcinoma, ovarian cancer, rhabdomyo sarcoma, leukemia, and Hodgkin's lymphoma. In certain embodiments, cancers of B-cell origin include, without limitation, B-lineage acute lymphoblastic leukemia, B-cell chronic lymphocytic leukemia, and B-cell non-Hodgkin's lymphoma.

2.5 Methods for Producing Recombinant AAV Vectors

In some embodiments, the invention provides recombinant AAV vectors for use in the methods of the invention. Recombinant AAV vectors are typically produced in mammalian cell lines such as HEK-293. Because the viral cap and rep genes are removed from the vector to prevent its self-replication to make room for the therapeutic gene(s) to be delivered (e.g. the endonuclease gene), it is necessary to provide these in trans in the packaging cell line. In addition, it is necessary to provide the "helper" (e.g. adenoviral) components necessary to support replication (Cots D, Bosch A, Chillon M (2013) *Curr. Gene Ther.* 13(5): 370-81). Frequently, recombinant AAV vectors are produced using a triple-transfection in which a cell line is transfected with a first plasmid encoding the "helper" components, a second plasmid comprising the cap and rep genes, and a third plasmid comprising the viral ITRs containing the intervening DNA sequence to be packaged into the virus. Viral particles comprising a genome (ITRs and intervening gene (s) of interest) encased in a capsid are then isolated from cells by freeze-thaw cycles, sonication, detergent, or other means known in the art. Particles are then purified using cesium-chloride density gradient centrifugation or affinity chromatography and subsequently delivered to the gene(s) of interest to cells, tissues, or an organism such as a human patient.

Because recombinant AAV particles are typically produced (manufactured) in cells, precautions must be taken in practicing the current invention to ensure that the site-specific endonuclease is NOT expressed in the packaging cells. Because the viral genomes of the invention comprise a recognition sequence for the endonuclease, any endonuclease expressed in the packaging cell line will be capable of cleaving the viral genome before it can be packaged into viral particles. This will result in reduced packaging efficiency and/or the packaging of fragmented genomes. Several approaches can be used to prevent endonuclease expression in the packaging cells, including:

1. The endonuclease can be placed under the control of a tissue-specific promoter that is not active in the packaging cells. For example, if a viral vector is developed for delivery of (an) endonuclease gene(s) to muscle tissue, a muscle-specific promoter can be used. Examples of muscle-specific promoters include C5-12 (Liu, et al. (2004) *Hum Gene Ther.* 15:783-92), the muscle-specific creatine kinase (MCK) promoter (Yuasa, et al. (2002) *Gene Ther.* 9:1576-88), or the smooth muscle 22 (SM22) promoter (Haase, et al. (2013) *BMC Biotechnol.* 13:49-54). Examples of CNS (neuron)-specific promoters include the NSE, Synapsin, and MeCP2 promoters (Lentz, et al. (2012) *Neurobiol Dis.* 48:179-88). Examples of liver-specific promoters include albumin promoters (such as Palb), human al-antitrypsin (such as PalAT), and hemopexin (such as Phpx) (Kramer, M G et al., (2003) *Mol. Therapy* 7:375-85). Examples of eye-specific promoters include opsin, and corneal epithelium-specific K12 promoters (Martin K R G, Klein R L, and Quigley H A (2002) *Methods* (28): 267-75) (Tong Y, et al., (2007) *J Gene Med,* 9:956-66). These promoters, or other tissue-specific promoters known in the art, are not highly-active in HEK-293 cells and, thus, will not expected to yield significant levels of endonuclease gene expression in packaging cells when incorporated into viral vectors of the present invention. Similarly, the viral vectors of the present invention contemplate the use of other cell lines with the use of incompatible tissue specific promoters (i.e., the well-known HeLa cell line (human epithelial cell) and using the liver-specific hemopexin promoter). Other examples of tissue specific promoters include: synovial sarcomas PDZD4 (cerebellum), C6 (liver), ASB5 (muscle), PPP1R12B (heart), SLC5Al2 (kidney), cholesterol regulation APOM (liver), ADPRHL1 (heart), and monogenic malformation syndromes TP73L (muscle). (Jacox E, et al., (2010) *PLoS One* v.5(8):e12274).
2. Alternatively, the vector can be packaged in cells from a different species in which the endonuclease is not likely to be expressed. For example, viral particles can be produced in microbial, insect, or plant cells using mammalian promoters, such as the well-known cytomegalovirus- or SV40 virus-early promoters, which are not active in the non-mammalian packaging cells. In a preferred embodiment, viral particles are produced in insect cells using the baculovirus system as described by Gao, et al. (Gao, H., et al. (2007) *J. Biotechnol.* 131(2):138-43). An endonuclease under the control of a mammalian promoter is unlikely to be expressed in these cells (Airenne, K J, et al. (2013) *Mol. Ther.* 21(4):739-49). Moreover, insect cells utilize different mRNA splicing motifs than mammalian cells. Thus, it is possible to incorporate a mammalian intron, such as the human growth hormone (HGH) intron or the SV40 large T antigen intron, into the coding sequence of an endonuclease. Because these introns are not spliced efficiently from pre-mRNA transcripts in insect cells, insect cells will not express a functional endonuclease and will package the full-length genome. In contrast, mammalian cells to which the resulting recombinant AAV particles are delivered will properly splice the pre-mRNA and will express functional endonuclease protein. Haifeng Chen has reported the use of the HGH and SV40 large T antigen introns to attenuate expression of the toxic proteins barnase and diphtheria toxin fragment A in insect packaging cells, enabling the production of recombinant AAV vectors carrying these toxin genes (Chen, H (2012) *Mol Ther Nucleic Acids.* 1(11): e57).
3. The endonuclease gene can be operably linked to an inducible promoter such that a small-molecule inducer is required for endonuclease expression. Examples of inducible promoters include the Tet-On system (Clontech; Chen H., et al., (2015) *BMC Biotechnol.* 15(1):4)) and the RheoSwitch system (Intrexon; Sowa G., et al., (2011) *Spine,* 36(10): E623-8). Both systems, as well as similar systems known in the art, rely on ligand-inducible transcription factors (variants of the Tet Repressor and Ecdysone receptor, respectively) that activate transcription in response to a small-molecule activator (Doxycycline or Ecdysone, respectively).

Practicing the current invention using such ligand-inducible transcription activators includes: 1) placing the endonuclease gene under the control of a promoter that responds to the corresponding transcription factor, the endonuclease gene having (a) binding site(s) for the transcription factor; and 2) including the gene encoding the transcription factor in the packaged viral genome The latter step is necessary because the endonuclease will not be expressed in the target cells or tissues following recombinant AAV delivery if the transcription activator is not also provided to the same cells. The transcription activator then induces endonuclease gene expression only in cells or tissues that are treated with the cognate small-molecule activator. This approach is advantageous because it enables endonuclease gene expression to be regulated in a spatio-temporal manner by selecting when and to which tissues the small-molecule inducer is delivered. However, the requirement to include the inducer in the viral genome, which has significantly limited carrying capacity, creates a drawback to this approach.

4. In another preferred embodiment, recombinant AAV particles are produced in a mammalian cell line that expresses a transcription repressor that prevents expression of the endonuclease. Transcription repressors are known in the art and include the Tet-Repressor, the Lac-Repressor, the Cro repressor, and the Lambda-repressor. Many nuclear hormone receptors such as the ecdysone receptor also act as transcription repressors in the absence of their cognate hormone ligand. To practice the current invention, packaging cells are transfected/transduced with a vector encoding a transcription repressor and the endonuclease gene in the viral genome (packaging vector) is operably linked to a promoter that is modified to comprise binding sites for the repressor such that the repressor silences the promoter. The gene encoding the transcription repressor can be placed in a variety of positions. It can be encoded on a separate vector; it can be incorporated into the packaging vector outside of the ITR sequences; it can be incorporated into the cap/rep vector or the adenoviral helper vector; or, most preferably, it can be stably integrated into the genome of the packaging cell such that it is expressed constitutively. Methods to modify common mammalian promoters to incorporate transcription repressor sites are known in the art. For example, Chang and Roninson modified the strong, constitutive CMV and RSV promoters to comprise operators for the Lac repressor and showed that gene expression from the modified promoters was greatly attenuated in cells expressing the repressor (Chang B D, and Roninson I B (1996) *Gene* 183:137-42). The use of a non-human transcription repressor ensures that transcription of the endonuclease gene will be repressed only in the packaging cells expressing the repressor and not in target cells or tissues transduced with the resulting recombinant AAV vector.

2.6 Engineered Nuclease Variants

Embodiments of the invention encompass the engineered nucleases, and particularly the recombinant meganucleases, described herein, and variants thereof. Further embodiments of the invention encompass isolated polynucleotides comprising a nucleic acid sequence encoding the recombinant meganucleases described herein, and variants of such polynucleotides.

As used herein, "variants" is intended to mean substantially similar sequences. A "variant" polypeptide is intended to mean a polypeptide derived from the "native" polypeptide by deletion or addition of one or more amino acids at one or more internal sites in the native protein and/or substitution of one or more amino acids at one or more sites in the native polypeptide. As used herein, a "native" polynucleotide or polypeptide comprises a parental sequence from which variants are derived. Variant polypeptides encompassed by the embodiments are biologically active. That is, they continue to possess the desired biological activity of the native protein; i.e., the ability to recognize and cleave recognition sequences found in the human T cell receptor alpha constant region (SEQ ID NO:1), including, for example, the TRC 1-2 recognition sequence (SEQ ID NO:3), the TRC 3-4 recognition sequence (SEQ ID NO:4), and the TRC 7-8 recognition sequence (SEQ ID NO:5). Such variants may result, for example, from human manipulation. Biologically active variants of a native polypeptide of the embodiments (e.g., SEQ ID NOs:8-32), or biologically active variants of the recognition half-site binding subunits described herein (e.g., SEQ ID NOs:33-82), will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99%, sequence identity to the amino acid sequence of the native polypeptide or native subunit, as determined by sequence alignment programs and parameters described elsewhere herein. A biologically active variant of a polypeptide or subunit of the embodiments may differ from that polypeptide or subunit by as few as about 1-40 amino acid residues, as few as about 1-20, as few as about 1-10, as few as about 5, as few as 4, 3, 2, or even 1 amino acid residue.

The polypeptides of the embodiments may be altered in various ways including amino acid substitutions, deletions, truncations, and insertions. Methods for such manipulations are generally known in the art. For example, amino acid sequence variants can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

A substantial number of amino acid modifications to the DNA recognition domain of the wild-type I-CreI meganuclease have previously been identified (e.g., U.S. Pat. No. 8,021,867) which, singly or in combination, result in recombinant meganucleases with specificities altered at individual bases within the DNA recognition sequence half-site, such that the resulting rationally-designed meganucleases have half-site specificities different from the wild-type enzyme. Table 4 provides potential substitutions that can be made in a recombinant meganuclease monomer or subunit to enhance specificity based on the base present at each half-site position (−1 through −9) of a recognition half-site.

TABLE 4

| | Favored Sense-Strand Base | | | | | | | | | | |
|---|---|---|---|---|---|---|---|---|---|---|---|
| Posn. | A | C | G | T | A/T | A/C | A/G | C/T | G/T | A/G/T | A/C/G/T |
| −1 | Y75<br>L75*<br>C75*<br>Y139*<br>C46*<br>A46* | R70*<br>H75*<br>R75*<br>H46*<br>K46*<br>R46* | K70<br>E70*<br>E75*<br>E46*<br>D46* | Q70*<br>C70<br>L70<br>Y75*<br>Q75*<br>H75*<br>H139<br>Q46*<br>H46* | | | | T46* | | | G70<br>A70<br>S70<br>G46* |
| −2 | Q70<br>T44*<br>A44*<br>V44*<br>I44*<br>L44*<br>N44* | E70<br>D70<br>K44*<br>R44* | H70<br>D44*<br>E44* | Q44* | C44* | | | | | | |
| −3 | Q68<br>C24*<br>I24* | E68<br>F68<br>K24*<br>R24* | R68 | M68<br>C68<br>L68<br>F68 | | H68 | | Y68 | K68 | | |
| −4 | A26*<br>Q77 | E77<br>K26* | R77<br>E26* | | | | | S77<br>Q26* | | | S26* |
| −5 | | E42 | R42 | | | K28* | C28*<br>Q42 | | | | M66<br>K66 |
| −6 | Q40<br>C28* | E40<br>R28* | R40 | C40<br>I40<br>V40<br>C79<br>I79<br>V79<br>Q28* | A40<br>A79<br>A28*<br>H28* | | | | | | S40<br>S28* |
| −7 | N30*<br>Q38 | E38<br>K30*<br>R30* | K38<br>R38<br>E30* | I38<br>L38 | | | C38 | | | | H38<br>N38<br>Q30* |
| −8 | F33<br>Y33 | E33<br>D33 | F33<br>H33 | L33<br>V33<br>I33<br>F33<br>C33 | | R32* | R33 | | | | |
| −9 | | E32 | R32<br>K32 | L32<br>V32<br>A32<br>C32 | | | | D32<br>I32 | | | S32<br>N32<br>H32<br>Q32<br>T32 |

For polynucleotides, a "variant" comprises a deletion and/or addition of one or more nucleotides at one or more sites within the native polynucleotide. One of skill in the art will recognize that variants of the nucleic acids of the embodiments will be constructed such that the open reading frame is maintained. For polynucleotides, conservative variants include those sequences that, because of the degeneracy of the genetic code, encode the amino acid sequence of one of the polypeptides of the embodiments. Variant polynucleotides include synthetically derived polynucleotides, such as those generated, for example, by using site-directed mutagenesis but which still encode a recombinant meganuclease of the embodiments. Generally, variants of a particular polynucleotide of the embodiments will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to that particular polynucleotide as determined by sequence alignment programs and parameters described elsewhere herein. Variants of a particular polynucleotide of the embodiments (i.e., the reference polynucleotide) can also be evaluated by comparison of the percent sequence identity between the polypeptide encoded by a variant polynucleotide and the polypeptide encoded by the reference polynucleotide.

The deletions, insertions, and substitutions of the protein sequences encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by screening the polypeptide for its ability to preferentially recognize and cleave recognition sequences found within the human T cell receptor alpha constant region gene (SEQ ID NO:1).

EXAMPLES

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

Example 1

Characterization of Meganucleases that Recognize and Cleave TRC Recognition Sequences 1. Meganucleases that Recognize and Cleave the TRC 1-2 Recognition Sequence Recombinant meganucleases (SEQ ID NOs:8-27), collectively referred to herein as "TRC 1-2 meganucleases," were engineered to recognize and cleave the TRC 1-2 recognition sequence (SEQ ID NO:3), which is present in the human T cell receptor alpha constant region. Each TRC 1-2 recombinant meganuclease comprises an N-terminal nuclease-localization signal derived from SV40, a first meganuclease subunit, a linker sequence, and a second meganuclease subunit. A first subunit in each TRC 1-2 meganuclease binds to the TRC1 recognition half-site of SEQ ID NO:3, while a second subunit binds to the TRC2 recognition half-site (see, FIG. 1A).

As illustrated in FIGS. 2 and 3, TRC1-binding subunits and TRC2-binding subunits each comprise a 56 base pair hypervariable region, referred to as HVR1 and HVR2, respectively. TRC1-binding subunits are identical outside of the HVR1 region except at position 80 or position 271 (comprising a Q or E residue), and are highly conserved within the HVR1 region. Similarly, TRC2-binding subunits are also identical outside of the HVR2 region except at position 80 or position 271 (comprising a Q or E residue), and at position 139 of meganucleases TRC 1-2x.87 EE, TRC 1-2x.87 QE, TRC 1-2x.87 EQ, TRC 1-2x.87, and TRC 1-2x.163, which comprise an R residue (shaded grey and underlined) Like the HVR1 region, the HVR2 region is also highly conserved.

The TRC1-binding regions of SEQ ID NOs:8-27 are illustrated in FIG. 2 and are provided as SEQ ID NOs:33-52, respectively. Each of SEQ ID NOs:33-52 share at least 90% sequence identity to SEQ ID NO:33, which is the TRC1-binding region of the meganuclease TRC 1-2x.87 EE (SEQ ID NO:8). TRC2-binding regions of SEQ ID NOs:8-27 are illustrated in FIG. 3 and are provided as SEQ ID NOs:58-77, respectively. Each of SEQ ID NOs:58-77 share at least 90% sequence identity to SEQ ID NO:58, which is the TRC2-binding region of the meganuclease TRC 1-2x.87 EE (SEQ ID NO:8).

2. Meganucleases that Recognize and Cleave the TRC 3-4 Recognition Sequence

Recombinant meganucleases (SEQ ID NOs:28 and 29), collectively referred to herein as "TRC 3-4 meganucleases," were engineered to recognize and cleave the TRC 3-4 recognition sequence (SEQ ID NO:4), which is present in the human T cell receptor alpha constant region. Each TRC 3-4 recombinant meganuclease comprises an N-terminal nuclease-localization signal derived from SV40, a first meganuclease subunit, a linker sequence, and a second meganuclease subunit. A first subunit in each TRC 3-4 meganuclease binds to the TRC3 recognition half-site of SEQ ID NO:4, while a second subunit binds to the TRC4 recognition half-site (see, FIG. 1A).

As illustrated in FIGS. 4 and 5, TRC3-binding subunits and TRC4-binding subunits each comprise a 56 base pair hypervariable region, referred to as HVR1 and HVR2, respectively. TRC3-binding subunits are identical outside of the HVR1 region except at position 80 or position 271 (comprising a Q or E residue), and are highly conserved within the HVR1 region. Similarly, TRC4-binding subunits are also identical outside of the HVR2 region except at position 80 or position 271 (comprising a Q or E residue), and are highly conserved within the HVR2 region.

The TRC3-binding regions of SEQ ID NOs:28 and 29 are illustrated in FIG. 4 and are provided as SEQ ID NOs:53 and 54, respectively. SEQ ID NOs:53 and 54 share 96.6% sequence identity. TRC4-binding regions of SEQ ID NOs:28 and 29 are illustrated in FIG. 5 and are provided as SEQ ID NOs:78 and 79, respectively. SEQ ID NOs:78 and 79 also share 96.6% sequence identity.

3. Meganucleases that Recognize and Cleave the TRC 7-8 Recognition Sequence

Recombinant meganucleases (SEQ ID NOs:30-32), collectively referred to herein as "TRC 7-8 meganucleases," were engineered to recognize and cleave the TRC 7-8 recognition sequence (SEQ ID NO:5), which is present in the human T cell receptor alpha constant region. Each TRC 7-8 recombinant meganuclease comprises an N-terminal nuclease-localization signal derived from SV40, a first meganuclease subunit, a linker sequence, and a second meganuclease subunit. A first subunit in each TRC 7-8 meganuclease binds to the TRC7 recognition half-site of SEQ ID NO:5, while a second subunit binds to the TRC8 recognition half-site (see, FIG. 1A).

As illustrated in FIGS. 6 and 7, TRC7-binding subunits and TRC8-binding subunits each comprise a 56 base pair hypervariable region, referred to as HVR1 and HVR2, respectively. TRC7-binding subunits are identical outside of the HVR1 region except at position 80 or position 271 (comprising a Q or E residue), and are highly conserved within the HVR1 region. Similarly, TRC8-binding subunits are also identical outside of the HVR2 region except at position 80 or position 271 (comprising a Q or E residue), and are highly conserved within the HVR2 region.

The TRC7-binding regions of SEQ ID NOs:30-32 are illustrated in FIG. 6 and are provided as SEQ ID NOs:55-57, respectively. Each of SEQ ID NOs:55-57 share at least 90% sequence identity to SEQ ID NO:55, which is the TRC7-binding region of the meganuclease TRC 7-8x.7 (SEQ ID NO:30). TRC8-binding regions of SEQ ID NOs:30-32 are illustrated in FIG. 7 and are provided as SEQ ID NOs:80-82, respectively. Each of SEQ ID NOs:80-82 share at least 90% sequence identity to SEQ ID NO:80, which is the TRC8-binding region of the meganuclease TRC 7-8x.7 (SEQ ID NO:30).

4. Cleavage of Human T Cell Receptor Alpha Constant Region Recognition Sequences in a CHO Cell Reporter Assay To determine whether TRC 1-2, TRC 3-4, and TRC 7-8 meganucleases could recognize and cleave their respective recognition sequences (SEQ ID NOs:3, 4, and 5, respectively), each recombinant meganuclease was evaluated using the CHO cell reporter assay previously described (see, WO/2012/167192 and FIG. 8). To perform the assays, CHO cell reporter lines were produced which carried a non-functional Green Fluorescent Protein (GFP) gene expression cassette integrated into the genome of the cells. The GFP gene in each cell line was interrupted by a pair of recognition sequences such that intracellular cleavage of either recognition sequence by a meganuclease would stimulate a homologous recombination event resulting in a functional GFP gene.

In CHO reporter cell lines developed for this study, one recognition sequence inserted into the GFP gene was the TRC 1-2 recognition sequence (SEQ ID NO:3), the TRC 3-4 recognition sequence (SEQ ID NO:4), or the TRC 7-8 recognition sequence (SEQ ID NO:5). The second recognition sequence inserted into the GFP gene was a CHO-23/24 recognition sequence, which is recognized and cleaved by a control meganuclease called "CHO-23/24". CHO reporter cells comprising the TRC 1-2 recognition sequence and the CHO-23/24 recognition sequence are referred to herein as "TRC 1-2 cells." CHO reporter cells comprising the TRC 3-4 recognition sequence and the CHO-23/24 recognition sequence are referred to herein as "TRC 3-4 cells." CHO reporter cells comprising the TRC 7-8 recognition sequence and the CHO-23/24 recognition sequence are referred to herein as "TRC 7-8 cells."

CHO reporter cells were transfected with plasmid DNA encoding their corresponding recombinant meganucleases (e.g., TRC 1-2 cells were transfected with plasmid DNA encoding TRC 1-2 meganucleases) or encoding the CHO-23/34 meganuclease. In each assay, $4e^5$ CHO reporter cells were transfected with 50 ng of plasmid DNA in a 96-well plate using Lipofectamine 2000 (ThermoFisher) according to the manufacturer's instructions. At 48 hours post-transfection, cells were evaluated by flow cytometry to determine the percentage of GFP-positive cells compared to an untransfected negative control (TRC 1-2bs). As shown in FIG. 9, all TRC 1-2, TRC 3-4, and TRC 7-8 meganucleases were found to produce GFP-positive cells in cell lines comprising their corresponding recognition sequence at frequencies significantly exceeding the negative control.

The efficacy of the TRC 1-2x.87 QE, TRC 1-2x.87 EQ, and TRC 1-2x.87 EE meganucleases was also determined in a time-dependent manner. In this study, TRC 1-2 cells ($1e^6$) were electroporated with $1e^6$ copies of meganuclease mRNA per cell using a BioRad Gene Pulser Xcell according to the manufacturer's instructions. At 1, 4, 6, 8, and 12 days post-transfection, cells were evaluated by flow cytometry to determine the percentage of GFP-positive cells. As shown in FIG. 10, each TRC 1-2 meganuclease exhibited high efficiency at 2 days post-transfection, with greater than 50% GFP-positive cells observed. This effect persisted over the 12 day period, with no evidence of cell toxicity observed.

5. Conclusions

These studies demonstrated that TRC 1-2 meganucleases, TRC 3-4 meganucleases, and TRC 7-8 meganucleases encompassed by the invention can efficiently target and cleave their respective recognition sequences in cells.

Example 2

Cleavage of TRC Recognition Sequences in T Cells and Suppression of Cell-Surface T Cell Receptor Expression 1. Cleavage of the TRC 1-2 Recognition Sequence in Jurkat Cells This study demonstrated that TRC 1-2 meganucleases encompassed by the invention could cleave the TRC 1-2 recognition sequence in Jurkat cells (an immortalized human T lymphocyte cell line). $1e^6$ Jurkat cells were electroporated with $8e^6$ copies of a given TRC 1-2 meganuclease mRNA per cell using a BioRad Gene Pulser Xcell according to the manufacturer's instructions. At 72 hours post-transfection, genomic DNA (gDNA) was harvested from cells and a T7 endonuclease I (T7E) assay was performed to estimate genetic modification at the endogenous TRC 1-2 recognition sequence (FIG. 11). In the T7E assay, the TRC 1-2 locus is amplified by PCR using primers that flank the TRC 1-2 recognition sequence. If there are indels (random insertions or deletions) within the TRC 1-2 locus, the resulting PCR product will consist of a mix of wild-type alleles and mutant alleles. The PCR product is denatured and allowed to slowly reanneal. Slow reannealing allows for the formation of heteroduplexes consisting of wild-type and mutant alleles, resulting in mismatched bases and/or bulges. The T7E1 enzyme cleaves at mismatch sites, resulting in cleavage products that can be visualized by gel electrophoresis. FIG. 11 clearly demonstrates that thirteen different versions of the TRC 1-2 meganucleases generated positive results in the T7E1 assay, indicating effective generation of indels at the endogenous TRC 1-2 recognition sequence.

To further examine the cleavage properties of TRC 1-2 meganucleases, a dose-response experiment was performed in Jurkat cells. $1e^6$ Jurkat cells were electroporated with either 3 μg or 1 μg of a given TRC 1-2 meganuclease mRNA per cell using a BioRad Gene Pulser Xcell according to the manufacturer's instructions. At 96-hours post-transfection, gDNA was harvested and the T7E1 assay was performed as described above. As seen in FIG. 12, fifteen different TRC 1-2 meganucleases showed cleavage at the endogenous TRC 1-2 recognition site, including three different versions of the TRC 1-2x.87 meganuclease. TRC 1-2x.87 EE worked especially well, generating a strong signal in the T7E1 assay with little to no toxicity in Jurkat cells.

2. Cleavage of TRC 1-2 Recognition Sequence in Human T Cells

This study demonstrated that TRC 1-2 meganucleases encompassed by the invention could cleave the TRC 1-2 recognition sequence in human T cells obtained from a donor. CD3+ T cells were stimulated with anti-CD3 and anti-CD28 antibodies for 3 days, then electroporated with mRNA encoding the TRC 1-2x.87 EE meganuclease using the Amaxa 4D-Nucleofector (Lonza) according to the manufacturer's instructions. At 3 days and 7 days post-transfection, gDNA was harvested and the T7E1 assay was performed as described above. FIG. 13A demonstrates that TRC 1-2x.87 EE effectively introduced mutations in the endogenous TRC 1-2 recognition sequence in human T cells, indicating that the meganuclease recognized and cleaved the TRC 1-2 recognition sequence. The intensity of cleavage products does not appear to change between day 3 and day 7 post-transfection, suggesting little or no toxicity due to the TRC 1-2x.87 EE meganuclease. To determine whether the mutations at the endogenous TRC 1-2 recognition sequence were sufficient to eliminate surface expression of the T cell receptor, cells were analyzed by flow cytometry using an anti-CD3 antibody. FIG. 13B shows that approximately 50% of transfected T cells stained negative for CD3, indicating knockout of the T cell receptor. The CD3 negative population did not change significantly between day 3 and day 7 post-transfection, further indicating little or no toxicity associated with the TRC 1-2x.87 EE meganuclease, or the loss of T cell receptor expression.

To verify that loss of CD3 expression was due to mutations in the TRC 1-2 recognition site, gDNA was harvested from transfected T cells and the TRC 1-2 recognition site locus was amplified by PCR. PCR products were cloned into the pCR-blunt vector using the Zero Blunt PCR cloning kit (Thermo Fisher) according to the manufacturer's instructions. Individual colonies were picked and mini-prepped plasmids were sequenced. FIG. 14 shows sequences of several representative deletions that were observed at the TRC 1-2 recognition sequence. The observed sequences are typical of deletions resulting from the non-homologous end joining repair of DNA double-strand breaks generated by endonucleases.

In addition to TRC 1-2x.87 EE, other TRC 1-2 meganucleases were able to knockout the T cell receptor in human T cells, including TRC 1-2x.55, and TRC 1-2x.72, albeit to a lesser extent than knockout previously observed for TRC 1-2x.87 EE (Tables 5 and 6). TRC 1-2x.72 Q47E carries a mutation in the active site of the meganuclease (amino acid 47) and serves as a negative control.

TABLE 5

| | % $CD3^-$ Cells | |
|---|---|---|
| Meganuclease | Day 3 | Day 6 |
| TRC 1-2x.72 Q47E | 0.38 | 1.1 |
| TRC 1-2x.55 | 3.11 | 10.84 |

TABLE 6

| | % $CD3^-$ Cells | |
|---|---|---|
| Meganuclease | Day 3 | Day 5 |
| TRC 1-2x.72 Q47E | 0.29 | 0.4 |
| TRC 1-2x.72 | 2.09 | 4.19 |

3. Conclusions

These studies demonstrated that TRC 1-2 meganucleases encompassed by the invention can recognize and cleave the TRC 1-2 recognition sequence in both Jurkat cells (an immortalized T lymphocyte cell line) and in T cells obtained from a human donor. Further, these studies demonstrated that NHEJ occurs at the meganuclease cleavage site, as evidenced by the appearance of indels. Moreover, TRC 1-2 meganucleases were shown to reduce cell-surface expression of the T cell receptor on human T cells obtained from a donor.

Example 3

Recombinant AAV Vectors for Introducing Exogenous Nucleic Acids into Human T Cells 1. Recombinant AAV Vectors In the present study, two recombinant AAV vectors (referred to as AAV405 and AAV406) were designed to introduce an exogenous nucleic acid sequence, comprising an EagI restriction site, into the genome of human T cells at the TRC 1-2 recognition sequence via homologous recombination. Each recombinant AAV vector was prepared using a triple-transfection protocol, wherein a cell line is transfected with a first plasmid encoding "helper" components (e.g., adenoviral) necessary to support replication, a second plasmid comprising the cap and rep genes, and a third plasmid comprising the viral inverted terminal repeats (ITRs) containing the intervening DNA sequence to be packaged into the virus (e.g., the exogenous nucleic acid sequence) (see, Cots D, Bosch A, Chillon M (2013) *Curr. Gene Ther.* 13(5): 370-81). FIG. 15 illustrates the general approach for using recombinant AAV vectors to introduce an exogenous nucleic acid sequence into the cell genome at the nuclease cleavage site.

AAV405 was prepared using the plasmid illustrated in FIG. 16 (SEQ ID NO:107). As shown, the AAV405 plasmid generally comprises sequences for a 5' ITR, a CMV enhancer and promoter sequence, a 5' homology arm, a nucleic acid sequence comprising the EagI restriction site, an SV40 poly(A) signal sequence, a 3' homology arm, and a 3' ITR. AAV406 was prepared using the plasmid illustrated in FIG. 17 (SEQ ID NO:108). As shown, the AAV406 plasmid comprises similar sequences to those of AAV405, but lacks the CMV enhancer and promoter sequences upstream of the 5' homology arm. The present AAV studies further included the use of an AAV vector encoding GFP (GFP-AAV), which was incorporated as a positive control for AAV transduction efficiency.

2. Introducing Exogenous Nucleic Acid Sequences into the TRC 1-2 Recognition Sequence To test whether AAV templates would be suitable for homology directed repair (HDR) following generation of a double-strand break with TRC 1-2 meganucleases, a series of experiments were performed using human T cells. In the first experiment, the timing of electroporation with TRC 1-2 RNA and transduction with recombinant AAV vectors was determined. Human CD3+ T cells were stimulated with anti-CD3 and anti-CD28 antibodies for 3 days, then electroporated with mRNA encoding the TRC 1-2x.87 EE meganuclease (1 μg) using the Amaxa 4D-Nucleofector (Lonza) according to the manufacturer's instructions. At either 2, 4, or 8 hours post-transfection, cells were transduced with GFP-AAV ($1e^5$ viral genomes per cell). Cells were analyzed by flow cytometry for GFP expression at 72 hours post-transduction. As shown in FIG. 18, the highest transduction efficiency was observed when cells were transduced at 2 hours post-transfection (88% GFP-positive cells). Transduction efficiency decreased significantly as the time between transfection and transduction increased, with 78% GFP-positive cells at 4 hours and 65% GFP-positive cells at 8 hours.

Having determined that efficient viral transduction occurred when cells were transduced 2 hours post-transfection, the AAV405 and AAV406 vectors were used as HDR templates in human T cells. CD3+ T cells were stimulated and transfected with 1 μg TRC 1-2x.87 EE mRNA as described above. At 2 hours post-transfection, cells were either transduced with AAV405 or AAV406 ($1e^5$ viral genomes per cell). As transduction-only controls, cells were mock transfected (with water) and transduced with either AAV405 or AAV406 ($1e^5$ viral genomes per cell). For a meganuclease-only control, cells were transfected with TRC 1-2x.87 EE and then mock transduced (with water) at 2 hours post-transfection.

To determine whether the AAV vectors served as HDR templates, gDNA was harvested from cells and the TRC 1-2 locus was amplified by PCR using primers that recognized sequences beyond the region of homology in the AAV vectors. PCR primers outside of the homology regions only allowed for amplification of the T cell genome, not from the AAV vectors. PCR products were purified and digested with EagI. FIG. 19 shows cleavage of the PCR products amplified from cells that were transfected with TRC 1-2x.87 EE and transduced with either AAV vector (see arrows), indicating insertion of the EagI site into the TRC 1-2 recognition sequence. The PCR products from all of the control cell populations are not cleaved by EagI, demonstrating that the insertion of the EagI site requires creation of a DNA double-strand break by a TRC 1-2 meganuclease.

To further define the insertion of the EagI site into human T cells, individual products from the bulk PCR product were examined. Undigested PCR product generated from the above experiment was cloned into the pCR-blunt vector using the Zero Blunt PCR cloning kit (Thermo Fisher) according to the manufacturer's instructions. Colony PCR was performed using M13 forward and reverse primers (pCR blunt contains M13 forward and reverse priming sites flanking the insert) and a portion of PCR products from cells transfected with TRC 1-2x.87 EE and either AAV405 or AAV406 were analyzed by gel electrophoresis (FIGS. 20A and 21A, respectively). In both cases, there are a mix of full-length PCR products (approximately 1600 bp), smaller inserts, and some empty plasmids (approximately 300 bp). In this assay, bands smaller than full-length but larger than empty plasmids are often times sequences containing large deletions within the TRC 1-2 recognition sequence. In parallel, another portion of PCR products were digested with EagI to determine the percent of clones that contain the EagI recognition site inserted into the TRC 1-2 recognition sequence. FIGS. 20B and 21B show that several PCR products were cleaved with EagI (e.g., FIG. 20B, second row, 6 lanes from the left), generating the expected fragments of approximately 700 and 800 bp. These gels allow for the estimation of EagI insertion to be approximately 25% and 6% for AAV405 and AAV406, respectively (adjusted for empty vectors).

To confirm observations from gel electrophoresis of uncut PCR products and digest with EagI, the remaining portion of each PCR product was sequenced. FIG. 22A shows sequences of several representative deletions and insertions that were observed at the TRC 1-2 recognition sequence. These sequences are typical of sequences resulting from the non-homologous end joining repair of DNA double-strand breaks generated by endonucleases. All PCR products that were cleaved with EagI contained an EagI site inserted into the TRC 1-2 recognition sequence (FIG. 22B).

3. Enhanced AAV Transduction Efficiency

In light of the observation that AAV transduction was more efficient when it was carried out 2 hours post-transfection than when it was carried out later, an experiment was performed to optimize the timing of transfection and transduction. Human CD3+ T cells were stimulated with anti-CD3 and anti-CD28 antibodies for 3 days, then electroporated with the TRC 1-2x.87 EE meganuclease (1 μg) using the Amaxa 4D-Nucleofector (Lonza) according to the manufacturer's instructions. Immediately after transfection or 2 hours post-transfection, cells were transduced with GFP-AAV ($1e^5$ viral genomes per cell). Additionally, non-stimulated cells were transduced with GFP-AAV ($1e^5$ viral genomes per cell). At 72 hours post-transduction, cells were analyzed by flow cytometry for GFP expression. FIG. 23 shows that GFP-AAV transduction performed 2 hours post-transfection resulted in 90% GFP-positive cells, but that transduction immediately after transfection resulted in 98% GFP-positive cells. Resting T cells appeared refractive to AAV transduction, with approximately 0% GFP-positive cells. Non-transduced cells also showed approximately 0% GFP-positive cells.

4. Summary

These studies demonstrate that AAV vectors can be used in conjunction with recombinant meganucleases to incorporate an exogenous nucleic acid sequence into a cleavage site in the TCR alpha constant region via homologous recombination.

Example 4

Recombinant AAV Vectors for Introducing Exogenous Nucleic Acids Encoding a Chimeric Antigen Receptor in Human T Cells 1. Recombinant AAV Vectors In the present study, two recombinant AAV vectors (referred to as AAV-CAR100 and AAV-CAR763) were designed to introduce an exogenous nucleic acid sequence, encoding a chimeric antigen receptor, into the genome of human T cells at the TRC 1-2 recognition sequence via homologous recombination. Each recombinant AAV vector was prepared using the triple-transfection protocol described previously.

AAV-CAR100 (also referred to herein as AAV408) was prepared using the plasmid illustrated in FIG. 24 (SEQ ID NO:109). As shown, the AAV-CAR100 (AAV408) is designed for producing a self-complementary AAV vector, and generally comprises sequences for a 5' ITR, a 5' homology arm, a nucleic acid sequence encoding an anti-CD19 chimeric antigen receptor, an SV40 poly(A) signal sequence, a 3' homology arm, and a 3' ITR. AAV-CAR763 (also referred to herein as AAV412) was prepared using the plasmid illustrated in FIG. 25 (SEQ ID NO:110). As shown, the AAV-CAR763 (AAV412) plasmid generally comprises the same sequences as AAV-CAR100 (AAV408), but is designed for producing a single-stranded AAV vector. Because a single-stranded AAV vector can accommodate a larger payload, the 5' homology arm and the 3' homology arm are longer in AAV-CAR763 (AAV412) than in AAV-CAR100 (AAV408). The present AAV studies will further include the use of an AAV vector encoding GFP (GFP-AAV), which will be incorporated as a positive control for AAV transduction efficiency.

2. Introducing a Chimeric Antigen Receptor Sequence into the TRC 1-2 Recognition Sequence Studies will be conducted to determine the efficiency of using recombinant AAV vectors to insert a chimeric antigen receptor sequence into the TCR alpha constant region gene while, simultaneously, knocking out cell-surface expression of the endogenous TCR receptor.

To confirm transduction efficiency, human CD3+ T cells will be obtained and stimulated with anti-CD3 and anti-CD28 antibodies for 3 days, then electroporated with mRNA encoding the TRC 1-2x.87 EE meganuclease (1 μg) using the Amaxa 4D-Nucleofector (Lonza) according to the manufacturer's instructions. Cells will be transduced with GFP-AAV ($1e^5$ viral genomes per cell) immediately after transfection as described above. Cells will be analyzed by flow cytometry for GFP expression at 72 hours post-transduction to determine transduction efficiency.

AAV-CAR100 (AAV408) and AAV-CAR763 (AAV412) vectors will then be used as HDR templates in human T cells for the insertion of the anti-CD19 chimeric antigen receptor sequence. Human CD3+ T cells will be stimulated and transfected with 1 μg TRC 1-2x.87 EE mRNA as described above. Cells will then be transduced with AAV-CAR100 (AAV408) or AAV-CAR763 (AAV412) ($1e^5$ viral genomes per cell) either immediately after transfection or within 0-8 hours of transfection. As transduction-only controls, cells will be mock transfected (with water) and transduced with either AAV-CAR100 (AAV408) or AAV-CAR763 (AAV412) ($1e^5$ viral genomes per cell). For a meganuclease-only control, cells will be transfected with mRNA encoding TRC 1-2x.87 EE and then mock transduced (with water) immediately post-transfection.

Insertion of the chimeric antigen receptor sequence will be confirmed by sequencing of the cleavage site in the TCR alpha constant region gene. Cell-surface expression of the chimeric antigen receptor will be confirmed by flow cytometry, using an anti-Fab or anti-CD19 antibody. Knockout of the endogenous T cell receptor at the cell surface will be determined by flow cytometry as previously described.

Example 5

Insertion and Expression of Chimeric Antigen Receptor

1. Insertion of Chimeric Antigen Receptor Sequence into the TRC 1-2 Recognition Sequence In the present study, we test whether AAV can provide HDR templates that can be used to insert a chimeric antigen receptor sequence into the TCR alpha constant region gene and, simultaneously, knock out cell-surface expression of the endogenous TCR receptor. In the first experiment, human CD3+ T cells ($1e^6$ cells) were stimulated and electroporated with mRNA encoding the TRC 1-2x.87 EE meganuclease (2 μg) as described above, then immediately transduced with AAV412 ($1e^5$ viral genomes/cell). As controls, cells were mock electroporated, then transduced with AAV412 or electroporated with mRNA encoding TRC 1-2x.87EE, then mock transduced. An additional control of mock electroporated, mock transduced cells was included.

A PCR-based assay was developed to determine whether the AAV HDR template was utilized to repair double-strand breaks at the TRC 1-2 recognition sequence. Three sets of primer pairs were used for PCR analysis. The first set was designed to amplify a region with the homology arms of AAV412. Since this first primer set (referred to as "Inside homolog arms/CAR region" in Table 7) lies within the homology region, it will either amplify the unmodified TRC 1-2 recognition sequence locus of the genome (349 bp), the AAV412 vector input (2603 bp), or the TRC 1-2 recognition sequence into which the CAR gene has been inserted (2603 bp). The second primer set (referred to as "Outside 5' homology arm" in Table 7) includes one primer that anneals within the CAR region of the AAV412 HDR template, one primer that anneals in the human genome, outside of the 5' homology arm of the AAV412 HDR template and will amplify an 1872 bp fragment only if the CAR gene was successfully inserted into the TRC 1-2 recognition sequence. The third primer set (referred to as "Outside 3' homology arm" in Table 7) includes one primer that anneals within the CAR region of the AAV412 HDR template, and one primer that anneals in the human genome, outside of the 3' homology arm of the AAV412 HDR template. Similarly to the second primer set, the third primer set will amplify an 1107 bp fragment only if the CAR gene was successfully inserted into the TRC 1-2 recognition sequence. Taken together, PCR products from all three primer sets will indicate whether the CAR sequence is present in cells (primer set 1), and whether it has been inserted into the TRC 1-2 recognition sequence (primer sets 2 and 3).

On day 4 post-transduction cells were analyzed using the PCR primer pairs described above. Briefly, approximately 3,000 cells were harvested, pelleted, and lysed and PCR was performed to determine whether the CAR gene was inserted into the TRC 1-2 recognition sequence. PCR products were resolved on an agarose gel, shown in FIG. 26 (lane descriptions can be found in Table 7). Lanes 1-3 are PCR products from the sample that was electroporated with mRNA encoding TRC 1-2x.87EE and mock transduced.

As expected, the first primer pair ("Inside homolog arms/ CAR region") amplified the unmodified TRC 1-2 recognition sequence locus, generating a 349 bp band shown in lane 1. Lanes 2 and 3 correspond to primer pairs that only generate a product if the CAR gene has been inserted into the TRC 1-2 recognition sequence, and do not show products. Lanes 7-9 represent samples that were mock electroporated and mock transduced and show the same bands as the TRC 1-2x.87EE mRNA only control described above. Lanes 4-6 show PCR products from the sample that was electroporated with TRC 1-2x.87EE mRNA and transduced with AAV412. Lane 4 shows two bands generated by the first primer pair ("Inside homolog arms/CAR region"), indicating amplification of the unmodified TRC 1-2 recognition sequence locus of the genome (349 bp) and the AAV412 vector input (2603 bp) or the TRC 1-2 recognition sequence into which the CAR gene has been inserted (2603 bp). Lanes 5 and 6 show products generated by the primer pairs that only amplify products if the CAR nucleic acid sequence has been inserted into the TRC 1-2x.87EE recognition site. Both bands are the predicted size (1872 and 1107 bp, respectively). Lanes 10-12 represent the sample that was mock electroporated and transduced with AAV412. Lane 10 shows two bands generated by the first primer pair ("Inside homolog arms/CAR region"), indicating amplification of the unmodified TRC 1-2 recognition sequence locus of the genome (349 bp) and the AAV412 vector input (2603 bp). Lanes 11 and 12 correspond to primer pairs that only generate a product if the CAR gene has been inserted into the TRC 1-2 recognition sequence, and do not show products. The absence of bands in lanes 11 and 12 (which include primers outside of the homology arm) indicates that the 2603 bp band in lane 10 was generated from amplification of the AAV412 input.

Taken together, the PCR analysis clearly demonstrates that CAR genes are introduced into the TRC 1-2x.87EE recognition site when both TRC 1-2x.87EE mRNA and AAV412 are present in cells. Thus, we conclude that AAV412 serves to produce suitable HDR templates that can be used to insert a CAR gene into the TRC 1-2x.87EE recognition sequence.

In a second experiment, human CD3+ T cells were stimulated and electroporated with mRNA encoding the TRC 1-2x.87 EE meganuclease as described above, then immediately transduced with increasing amounts of AAV408 (0 μL, 3.125 μL, 6.25 μL, 12.5 μL, or 25 μL, which corresponds to approximately 0, $3.125e^3$, $6.250e^3$, $1.25e^4$ and $2.5e^4$ viral genomes/cell). As controls, cells were mock electroporated, then transduced with increasing amounts of AAV408. Additional controls included cells that were mock electroporated and mock transduced, as well as cells that were electroporated with TRC 1-2x.87EE mRNA then mock transduced. On day 4 post-transduction, cells were harvested and analyzed as described above, but only using the primer pairs that amplified a product only if the CAR gene has been inserted into the TRC 1-2 recognition sequence. PCR products were resolved on agarose gels, shown in FIG. 27. FIG. 27A shows the PCR products generated using the primer pair described above ("Outside 5' homology arm") which only amplifies a product on the 5' end of the TRC 1-2 recognition sequence locus if the CAR gene has been inserted into that locus. FIG. 27B shows the PCR products generated using the primer pair described above ("Outside 3' homology arm") which only amplifies a product on the 3' end of the TRC 1-2 recognition sequence locus if the CAR gene has been inserted into that locus. Lane descriptions can be found in Table 8. Lanes 1-5 in both FIGS. 27A and 27B represent the samples that were either mock electroporated or mock electroporated then mock transduced. No PCR products are visible in mock electroporated cells, indicating the HDR templates produced by AAV408 are unable to insert the CAR gene into the TRC 1-2 recognition sequence in the absence of TRC 1-2x.87EE mRNA. Lane 6 represents the sample that was electroporated with TRC 1-2x.87EE mRNA and mock transduced. No PCR products are visible, indicating that the CAR gene had not been inserted into the TRC 1-2 recognition sequence. Lanes 7-10 represent samples that were electroporated with TRC 1-2x.87EE mRNA and transduced with increasing amounts of AAV408. The appropriately sized bands for each PCR are evident, indicating that AAV408 can produce HDR donors for repair of the TRC 1-2 recognition sequence, resulting in insertion of the CAR gene.

TABLE 7

| Sample | Nucleofection | Virus (100k MOI) | PCR | Product Size |
|---|---|---|---|---|
| 1 | TRC1-2x87EE | — | Inside homolog arms/ CAR region | Genomic = 349 bp + CD19 = 2603 bp |
| 2 | TRC1-2x87EE | — | Outside 5' homology arm | 1872 bp |
| 3 | TRC1-2x87EE | — | Outside 3' homology arm | 1107 bp |
| 4 | TRC1-2x87EE | AAV412 | Inside homolog arms/ CAR region | Genomic = 349 bp + CD19 = 2603 bp |
| 5 | TRC1-2x87EE | AAV412 | Outside 5' homology arm | 1872 bp |
| 6 | TRC1-2x87EE | AAV412 | Outside 3' homology arm | 1107 bp |
| 7 | Mock (Water) | — | Inside homolog arms/ CAR region | Genomic = 349 bp + CD19 = 2603 bp |
| 8 | Mock (Water) | — | Outside 5' homology arm | 1872 bp |
| 9 | Mock (Water) | — | Outside 3' homology arm | 1107 bp |
| 10 | Mock (Water) | AAV412 | Inside homolog arms/ CAR region | Genomic = 349 bp + CD19 = 2603 bp |
| 11 | Mock (Water) | AAV412 | Outside 5' homology arm | 1872 bp |
| 12 | Mock (Water) | AAV412 | Outside 3' homology arm | 1107 bp |

TABLE 8

| Sample | Nucleofection | Virus (AAV408) μL |
|---|---|---|
| 1 | Mock (Water) | 0 |
| 2 | Mock (Water) | 3.125 |
| 3 | Mock (Water) | 6.25 |
| 4 | Mock (Water) | 12.5 |
| 5 | Mock (Water) | 25 |
| 6 | TRC1-2x87EE | 0 |
| 7 | TRC1-2x87EE | 3.125 |
| 8 | TRC1-2x87EE | 6.25 |
| 9 | TRC1-2x87EE | 12.5 |
| 10 | TRC1-2x87EE | 25 |

The PCR-based assays described above are useful in determining whether the CAR gene had been inserted into the TRC 1-2 recognition sequence, but do not give information on efficiency. To determine the efficiency of CAR insertion, we developed a digital PCR-based assay (schematic shown in FIG. 28A). In this assay, two primer sets are used. The first set amplifies an irrelevant gene sequence and serves a reference sequence to control for template number. The second set consists of one primer that anneals within the CAR gene and one primer that anneals outside of the 3' homology arm, such that a product is only amplified if the CAR gene has been inserted into the TRC 1-2 recognition sequence. A VIC-labeled probe anneals within the amplicon generated from the first primer set and FAM-labeled probe anneals within the amplicon generated by the second set of primers. By dividing the number of amplicons detected by the FAM-labeled probe to the number of reference sequence amplicons detected by the VIC-labeled probe, it is possible to accurately quantitate the percent of TRC 1-2 recognition sequence loci that were modified by insertion of the CAR gene.

FIG. 28B shows the results of the digital PCR assay for samples that were either mock electroporated then transduced, electroporated with TRC 1-2x.87EE mRNA then mock transduced, or electroporated with TRC 1-2x.87EE mRNA then transduced with increasing amounts of AAV408. Digital PCR was performed using genomic DNA isolated from cells approximately 1 week post-transduction. Consistent with the observations from the PCR described in FIG. 27, both control samples (transduction only or electroporation only) were found to have 0% CAR gene inserted into the TRC 1-2x.87EE recognition sequence. Samples that were electroporated with mRNA encoding TRC 1-2x.87EE then transduced with increasing amounts of AAV408 were found to have between approximately 1.5% and 7%. The assay was performed on two different instruments (labeled QX200 and QS3D) and showed remarkable agreement, demonstrating the sensitivity and precision of this digital PCR-based assay.

2. Expression of Anti-CD19 Chimeric Antigen Receptor on T Cells

In addition to determining whether CAR insertion occurred at the molecular level, we sought to determine the expression level of the anti-CD19 chimeric antigen receptor in cells that had the CAR gene inserted into the TRC 1-2 recognition sequence using AAV408 as the HDR template. Additionally, we examined the efficiency in which insertion of the CAR into the TRC 1-2x.87EE recognition sequence resulted in knockout of the T cell receptor. Samples described above and analyzed in FIGS. 27 and 28 were also analyzed for CAR and CD3 expression by flow cytometry. Approximately 4 days post-transduction, cells were labeled with antibodies that recognize the anti-CD19 CAR (anti-Fab-Alexa647) or CD3 ($CD3^-$BB515) and analyzed by flow cytometry. FIG. 29A shows flow cytometry plots, with anti-CAR labeling shown on the Y axis and anti-CD3 labeling shown on the X axis. Cells that were mock electroporated and mock transduced (MOI-0) were overwhelmingly $CD3^+/CAR^-$ (the lower right quadrant, 98.7%). Cells that were mock electroporated then transduced with increasing amounts of AAV408 looked essentially identical to the control cells, with the $CD3^+/CAR^-$ populations at 98.8%, 99, 99%, and 99.1%. Thus we conclude that the AAV408 virus alone is not driving detectable levels of CAR expression, nor is it capable of disrupting expression of the T cell receptor.

FIG. 29B shows flow cytometry plots for samples that were either electroporated with mRNA encoding TRC 1-2x.87EE then mock transduced or cells that were electroporated with TRC 1-2x.87EE then transduced with increasing amounts of AAV408. Cells that were electroporated then mock transduced show 47.1% $CD3^-$ cells, indicating efficient knockout of the T cell receptor complex. Background labeling with the anti-CD19 CAR was very low, with 0.6% in the $CD3^-$ population and 0.78% in the $CD3^+$ population. Samples that were electroporated with mRNA encoding TRC 1-2x.87EE then transduced with increasing amounts of AAV408 showed CAR labeling in the $CD3^-$ population, ranging from 2.09% to 5.9%. There was also a slight increase in CAR labeling in the $CD3^+$ population, ranging from 1.08% to 1.91%. We did not determine the cause of the increase in CARP cells in the $CD3^+$ population, although it is possible that the CAR was inserted into the non-expressed T cell receptor allele (only one allele of the T cell receptor alpha chain is expressed and incorporated into the T cell receptor complex).

These data correlated well with the quantitative digital PCR-based assay described above. For example, at the highest MOI of AAV408 ($2.5e^4$ viral genomes/cell), the digital PCR assay showed approximately 6% CAR insertion, and the flow cytometry assay showed 5.9% $CAR^+/CD3^-$ cells. If one takes into account the $CAR^+/CD3^+$ population, the data are still quite comparable, with the flow cytometry assay showing approximately 7.8% CARP compared to 6% by digital PCR.

Example 6

Characterization of Additional AAV Vectors

1. Insertion of a Chimeric Antigen Receptor Sequence into the TRC 1-2 Recognition Sequence Having shown that AAV vectors could provide suitable HDR templates to insert CAR genes into the TRC 1-2x.87EE recognition sequence, we sought to optimize the configuration of the AAV vector. We generated a vector that could be used to produce self-complementary AAV genomes that included the CAR gene expression cassette driven by a JeT promoter, flanked by short regions of homology to the TRC 1-2 recognition sequence locus and AAV ITRs. This vector is referred to as AAV421 (FIG. 30; SEQ ID NO:123). Short homology arms were necessary due to limited packaging capacity of self-complementary AAV. Additionally, we generated a vector that could be used to produce single-strand AAV genomes that includes the CAR gene expression cassette driven by a CMV promoter, flanked by long homology arms and AAV ITRs. This vector is referred to as AAV422 (FIG. 31; SEQ ID NO:124). Since single-strand AAV genomes have a larger cargo capacity, we were able to utilize longer homology arms than in the self-complementary vector.

To test whether AAV421 and AAV422 were useful to target insertion of the CAR gene into the TRC 1-2 recognition sequence, several experiments similar to those described above were carried out in human $CD3^+$ T cells. In a first experiment, human $CD3^+$ T cells ($1e^6$ cells) were either mock electroporated then transduced with increasing amounts of AAV421 or 422, or electroporated with TRC 1-2x.87EE mRNA (2 μg) then transduced with increasing amounts of AAV421 or AAV422. AAV422 MOIs were significantly higher than AAV421 in this experiment than in the experiments described above (approximate MOIs were $1.25e^4$, $2.5e^4$, $5e^4$ and $1e^5$ viral genomes/cell) because earlier experiments with AAV408 suggested that higher MOIs would result in more efficient CAR insertion. The AAV421 virus stock was not concentrated enough to allow for titers significantly higher than in the experiments described earlier. As controls, cells were electroporated (mock or with TRC 1-2x.87EE mRNA) then mock transduced. As an additional component to this experiment, a "large scale" condition was performed, in which $10e^6$ cells (10 times more than a typical experiment) were electroporated with TRC 1-2x.87EE mRNA then transduced with AAV422 ($2.5e^4$ viral genomes/cell). Lastly, we also tested a second virus stock of AAV421 to compare to the primary virus stock.

Insertion of the CAR was determined by PCR as described above, using primer pairs that only amplify products if the CAR gene has been inserted into the TRC 1-2x.87EE recognition sequence. PCR was resolved by agarose gel, shown in FIGS. 32A and 32B (lane descriptions can be found in Tables 9 and 10). Sample 1 in FIG. 32A was mock electroporated then mock transduced, and samples 2-5 were mock electroporated then transduced with AAV421. The gel shows that none of these samples generated PCR products, indicating that AAV421, in the absence of TRC 1-2x.87EE mRNA, is unable to drive insertion of the CAR gene into the TRC 1-2 recognition sequence. Additionally, the control sample that was electroporated with TRC 1-2x.87EE mRNA then mock transduced (sample 6), did not show any PCR products. Samples 7-10 in FIG. 32A were electroporated with TRC 1-2x.87EE mRNA, then transduced with increasing amounts of AAV421. The gel shows PCR bands for products extending beyond both the 5' and 3' homology arm (the two bands under each sample number), demonstrating integration of the CAR gene into the TRC 1-2 recognition sequence. Lastly in FIG. 32A, lanes 11 and 12 represent samples that were electroporated with TRC 1-2x.87EE mRNA then transduced with AAV422, either starting with $1e^6$ or $10e^6$ cells/sample, respectively. The presence of both PCR bands (larger in the first set, because different primer was used to account for a longer homology arm) indicate successful insertion of the CAR gene into the TRC 1-2 recognition sequence.

Sample 1 in FIG. 32B was mock electroporated then mock transduced, and samples 2-5 were mock electroporated then transduced with increasing amounts of AAV422 (Table 10). The gel shows that none of these samples generated PCR products, indicating that AAV422, in the absence of TRC 1-2x.87EE mRNA, is unable to drive insertion of the CAR gene into the TRC 1-2 recognition sequence. Samples 7-10 in FIG. 32B were electroporated with TRC 1-2x.87EE mRNA, then transduced with increasing amounts of AAV422. The gel shows PCR bands for products extending beyond both the 5' and 3' homology arm, demonstrating integration of the CAR gene into the TRC 1-2 recognition sequence. Lastly, sample 11 represents the sample that was electroporated with TRC 1-2x.87EE mRNA then transduced with a AAV421 from a different virus stock than samples shown in FIG. 32A. The presence of bands indicate insertion of the CAR gene into the TRC 1-2 recognition sequence and confirms reproducibility between different virus stocks. Taken together, FIG. 32 clearly demonstrates that both AAV421 and AAV422 are capable of generating HDR templates suitable for inserting the CAR gene into the TRC 1-2 recognition sequence.

TABLE 9

| Sample | Nucleofection | AAV Virus | μl AAV | MOI (approximate) |
|---|---|---|---|---|
| 1 | Mock (Water) | 421 | 0 | 0 |
| 2 | Mock (Water) | 421 | 3.125 | 3906 |
| 3 | Mock (Water) | 421 | 6.25 | 7813 |
| 4 | Mock (Water) | 421 | 12.5 | 15625 |
| 5 | Mock (Water) | 421 | 25 | 31250 |
| 6 | TRC1-2x87EE | 421 | 0 | 0 |
| 7 | TRC1-2x87EE | 421 | 3.125 | 3906 |
| 8 | TRC1-2x87EE | 421 | 6.25 | 7813 |
| 9 | TRC1-2x87EE | 421 | 12.5 | 15625 |
| 10 | TRC1-2x87EE | 421 | 25 | 31250 |
| 11 | TRC1-2x87EE | 422 | 6.25 | 25000 |
| 12 | TRC1-2x87EE Large Scale | 422 | 62.5 | 25000 |

TABLE 10

| Sample | Nucleofection | AAV Virus | µl AAV | MOI (approximate) |
|---|---|---|---|---|
| 1 | Mock (Water) | 422 | 0 | 0 |
| 2 | Mock (Water) | 422 | 3.125 | 12500 |
| 3 | Mock (Water) | 422 | 6.25 | 25000 |
| 4 | Mock (Water) | 422 | 12.5 | 50000 |
| 5 | Mock (Water) | 422 | 25 | 100000 |
| 6 | TRC1-2x87EE | 422 | 0 | 0 |
| 7 | TRC1-2x87EE | 422 | 3.125 | 12500 |
| 8 | TRC1-2x87EE | 422 | 6.25 | 25000 |
| 9 | TRC1-2x87EE | 422 | 12.5 | 50000 |
| 10 | TRC1-2x87EE | 422 | 25 | 100000 |
| 11 | TRC1-2x87EE | 421B | 25 | 10000 |

2. Expression of Anti-CD19 Chimeric Antigen Receptor on T Cells Using AAV421

Here, we sought to determine the expression level of the anti-CD19 chimeric antigen receptor in cells that had the CAR gene inserted into the TRC 1-2 recognition sequence using AAV421. Samples described above and analyzed in FIG. 32A were also analyzed for CAR and CD3 expression by flow cytometry. Approximately 4 days post-transduction, cells were labeled with antibodies that recognize the anti-CD19 CAR or CD3 and analyzed by flow cytometry. FIG. 33A shows flow cytometry plots for cells that were mock electroporated and transduced with AAV421, along with control cells that were mock electroporated and mock transduced. Cells that were mock electroporated and mock transduced (MOI-0) were overwhelmingly $CD3^+/CAR^-$ (the lower right quadrant, 98.8%). Cells that were mock electroporated then transduced with increasing amounts of AAV421 looked essentially identical to the control cells, with the $CD3^+/CAR^-$ populations at 98.8%, 98.6%, 98.8% and 97.9%. Thus, we conclude that the AAV421 virus alone is not driving detectable levels of CAR expression, nor is it capable of disrupting expression of the T cell receptor.

FIG. 33B shows flow cytometry plots for samples that were either electroporated with TRC 1-2x.87EE mRNA then mock transduced or cells that were electroporated with TRC 1-2x.87EE then transduced with increasing amounts of AAV421. Cells that were electroporated then mock transduced show 56.7% $CD3^-$ cells, indicating efficient knockout of the T cell receptor complex. Background labeling with the anti-CD19 CAR was very low, with 0.48% in the $CD3^-$ population and 0.36% in the $CD3^+$ population. Samples that were electroporated with mRNA encoding TRC 1-2x.87EE then transduced with increasing amounts of AAV412 showed significant amounts of CAR labeling in the $CD3^-$ population, ranging from 4.99% to 13.4%. There was also a slight increase in CAR labeling in the $CD3^+$ population, ranging from 1.27% to 3.95%. As mentioned above, it is possible that the CAR gene was inserted into the non-expressed T cell receptor allele. Also in contrast to experiments with AAV408, the CARP population was much better defined, with a higher mean fluorescence intensity, suggesting that the JeT promoter drives higher expression than the eF1α core promoter.

While evaluating insertion of the CAR gene using AAV421 in conjunction with TRC 1-x.87EE, we sought to determine a method that would allow us to preferentially expand and enrich the $CD3^-/CAR^+$ population. From the experiment described above and shown in FIG. 33, we used cells that were electroporated with TRC 1-2x.87EE mRNA (2 µg) then transduced with AAV421 ($3.13e^4$ viral genomes/cell). Control samples were mock electroporated and mock transduced, mock electroporated and transduced with AAV421, or electroporated with TRC 1-2x.87EE and mock transduced taken from the experiment described above and shown in FIG. 33. As a control enrichment and expansion process, these cells were incubated for 6 days in complete growth medium supplemented with IL-7 and IL-15 (both at 10 ng/mL). Cells were then labeled with antibodies against the anti-CD19 CAR and CD3 and analyzed by flow cytometry (FIG. 34A). Cells that were mock electroporated and mock transduced showed low levels of background staining in the $CD3^-/CAR^+$ quadrant (0.13%). The $CD3^-/CAR^+$ population was essentially the same in samples that were either mock electroporated then transduced with AAV or electroporated with TRC 1-2x.87EE mRNA then mock transduced (0.16% and 0.55%, respectively). Cells that were electroporated with TRC 1-2x.87EE mRNA and mock transduced had a $CD3^-/CAR^-$ population of 53.2%, very close to the amount stained in the first part of this experiment shown in FIG. 33B (56.7%). Cells that were electroporated with TRC 1-2x.87EE and transduced with AAV showed 12.6% $CD3^-/CAR^+$ cells, almost identical to the original labeling of these cells shown in FIG. 33 (13.4%), demonstrating that mixture of IL-7 and IL-15 is insufficient to enrich or expand the specific $CD3^-/CAR^+$ cell population.

We next sought to enrich for the $CD3^-/CAR^+$ population in an antigen-specific manner by incubating the 4 samples described above with IM-9 cells, which present CD19 on the cell surface. IM-9 cells were inactivated by pre-treatment with mitomycin C and incubated with samples at a 1:1 ratio for 6 days in the presence of IL-7 and IL-15 (10 ng/mL). Cells were then labeled with antibodies against CD3 and the anti-CD19 CAR and analyzed by flow cytometry (FIG. 34B). Cells that were mock electroporated and mock transduced showed low levels of background staining in the $CD3^-/CAR^+$ quadrant (0.2%). The $CD3^-/CAR^+$ population was the same in samples that were mock electroporated then transduced with AAV (0.2%) and slightly higher in cells that were electroporated with TRC 1-2x.87EE and mock transduced (1.24%). The increase in $CD3^-/CAR^+$ cells the TRC 1-2x.87EE alone control is considered background since no CAR nucleic acid was ever introduced into the system. Cells that were electroporated with TRC 1-2x.87EE mRNA and mock transduced had a $CD3^-/CAR^-$ population of 42.5%, which is significantly lower than they were prior to expansion (56.7%, FIG. 33) suggesting that CD+ cells may have a growth advantage in this system. However, cells that were electroporated with TRC 1-2x.87EE and transduced with AAV showed 49.9% $CD3^-/CAR^+$ cells, a dramatic increase compared to the original labeling of these cells shown in FIG. 33 (13.4%), demonstrating that incubation of this sample with IM-9 cells in the presence of IL-7 and IL-15 is quite effective in enriching and expanding the $CD3^-/CAR^+$ population. The $CD3^+/CAR^+$ population was also expanded under these conditions, with the mock electroporated/AAV transduced sample and the TRC 1-2x.87EE electroporated/AV transduced sample showing 2.53% and 15.3% $CD3^+/CAR^+$, respectively.

In the cells that were electroporated with TRC 1-2x.87EE then transduced with AAV421, 24.2% of the $CD3^-$ population was $CAR^+$ prior to expansion (FIG. 33B). After incubation in medium supplemented with IL-7 and IL-15, that 25.3% of the $CD3^-$ cells were $CAR^+$ (FIG. 34A) indicating that the ratio of gene knock-in to gene-knockout was unchanged. However, after incubation with IM-9 cells in addition to IL-7 and IL-15, over 80% (80.35%, FIG. 34B) of the $CD3^-$ cells were $CAR^+$, demonstrating that incubation with IM-9 cells resulted in antigen-specific enrichment.

Since mitocmyin C inactives cells very potently and IM-9 cells were not persisting long in the mixed culture, we reasoned that a second infusion of IM-9 cells might further increase enrichment of $CD3^-/CAR^+$ cells. Some of the cells described above and shown in FIG. 34B would mixed with fresh IM-9 cells (pre-treated with mitocmycin C) in medium containing IL-7 and IL-15 and were incubated another 6 days. Cells were then stained for CD3 and anti-CD19 CAR and analyzed by flow cytometry (FIG. 34C). The percentage of $CD3^-/CAR^+$ cells in any of the control samples were essentially unchanged compared to the first round of enrichment on IM-9 cells.

However, the cells that were electroporated with TRC 1-2x.87EE and transduced with AAV421 showed a significant enrichment of the $CD3^-/CAR^+$ population, increasing from 49.9% (after the first round if incubation with IM-9 cells, FIG. 34B) to 65.7% (FIG. 34C). Importantly, 93.75% of the $CD3^-$ population was CARP, indicating further antigen-specific expansion.

3. Expression of Anti-CD19 Chimeric Antigen Receptor on T Cells Using AAV422

We also examined expression of the anti-CD19 CAR from cells in which AAV422 was used to provide the HDR template (described above, PCR results shown in FIG. 32B). Approximately 4 days post-transduction, cells were labeled with antibodies that recognize the anti-CD19 CAR or CD3 and analyzed by flow cytometry. FIG. 35A shows flow cytometry plots for cells that were mock electroporated and transduced with increasing amounts of AAV422, along with control cells that were mock electroporated and mock transduced. Cells that were mock electroporated and mock transduced (MOI-0) were overwhelmingly $CD3^+/CAR^-$ (the lower right quadrant, 98.8%). Cells that were mock electroporated then transduced with increasing amounts of AAV422 looked essentially identical to the control cells, with the $CD3^+/CAR^-$ populations at 98.6%, 98.6%, 98.9% and 98.4%. Thus, the AAV422 vector alone is not driving detectable levels of CAR expression, nor is it capable of disrupting expression of the T cell receptor.

FIG. 35B shows flow cytometry plots for samples that were either electroporated with TRC 1-2x.87EE mRNA then mock transduced or cells that were electroporated with TRC 1-2x.87EE then transduced with increasing amounts of AAV422. Cells that were electroporated then mock transduced show 59.3% $CD3^-$ cells, indicating efficient knockout of the T cell receptor complex. Background labeling with the anti-CD19 CAR was very low, with 1.47% in the $CD3^-$ population and 0.52% in the $CD3^+$ population. Samples that were electroporated with mRNA encoding TRC 1-2x.87EE then transduced with increasing amounts of AAV422 showed significant amounts of CAR labeling in the $CD3^-$ population, ranging from 14.7% to 20.3%. There was also a slight increase in CAR labeling in the $CD3^+$ population, ranging from 2.3% to 2.7%.

Surprisingly, we observed a noticeable increase in T cell receptor knockout efficiency in the presence of AAV422. Overall CD3 knockout efficiency with increasing AAV422 was 71.6%, 74.9%, 77.8% and 74.4% compared to 59.3% in the TRC 1-2x.87EE electroporation alone. In contrast, overall CD3 knockout efficiency with increasing AAV421 was 56.99%, 56.62%, 57.4% and 55.4% compared to 57.18% in the TRC 1-2x.87EE electroporation alone (FIG. 33B). Thus, it appears that electroporation with TRC 1-2x.87EE in the presence of single-stranded AAV genomes, but not self-complimentary AAV genomes, results in an increase in the overall knockout efficiency of the TRC 1-2x.87EE nuclease.

Because of this increase, the percent of $CD3^-$ cells that are $CAR^+$ is not significantly different between cells transduced with AAV421 and AAV422 despite the higher numbers of $CD3^-/CAR^+$ cells. The highest percent of $CD3^-$ cells that were $CAR^+$ using AAV421 was 24.18% (MOI=3.13$e^4$ viral genomes/cell) compared to 26.48% with AAV422 (MOI=1$e^5$ viral genomes/cell). This observation is particularly interesting considering the large difference in MOI between AAV421 and AAV422.

The concept of utilizing IM-9 cells to specifically enrich for $CD3^-/CAR^+$ cells was tested using cells from this experiment. Again, rather than testing the entire panel, we only attempted enrichment of either cells mock electroporated then transduced with AAV422 or electroporated with TRC 1-2x.87EE then transduced with AAV422 (2.5$e^4$ viral genomes/cell) in a new experiment. FIG. 36A shows flow cytometry plots at approximately day 4 post-transduction. Mock electroporated/transduced cells showed background staining of $CD3^-/CAR^+$ cells at 0.13%. In comparison, cells electroporated with TRC 1-2x.87EE the transduced with AAV422 showed 4.44% $CD3^-/CAR^+$ cells. Cells were incubated with IM-9 cells (pre-treated with mitomycin) in the presence of IL-7 and IL-15 for 6 days as described above, then analyzed by flow cytometry. FIG. 36B shows that incubation with IM-9 cells dramatically increased the $CD3^-/CAR^+$ population in AAV422 transduced cells to 35.8%. The $CAR^+$ cells make up 45.2% of the total $CD3^-$ population, compared to 6.69% prior to enrichment (FIG. 36A). As above, we also further enriched by a second addition of IM-9 cells (FIG. 36C). Two rounds of incubation with IM-9 cells resulted in 65.1% $CD3^-/CAR^+$ cells. The $CAR^+$ cells make up 78.25% of the total $CD3^-$ population, indicating significant, antigen-dependent enrichment of $CD3^-/CAR^+$ cells.

These data, in conjunction with the data presented above, clearly demonstrate that cells that have had an anti-CD19 CAR gene inserted into the TRC 1-2 recognition sequence can be successfully enriched by incubation with IM-9 cells in the presence of IL-7 and IL-15, and can result in a $CD3^-$ population that is over 90% CARP in as little as 12 days of culture.

4. Increased Knockout Efficiency Observed when Using Single-Strand AAV Vectors

In the present study, we followed up on the observation that single-stranded AAV vectors increased knockout efficiency of the TRC 1-2x.87EE nuclease. In a first experiment, cells were electroporated with TRC 1-2x.87EE (2 μg) and either mock transduced or transduced with increasing amounts of AAV412 (6.25$e^4$, 1.25$e^4$, 2.5$e^4$ or 5$e^4$ viral genomes/cell). On day 4 post-transduction, cells were labeled with an antibody against CD3 and analyzed by flow cytometry (FIG. 37A). In the mock transduced cells, 20.7% are $CD3^-$ compared to 21.6%, 23.7%, 25.5% and 25% with increasing AAV412, indicating that TRC 1-2x.87EE knockout efficiency is up to 23% higher in the presence of AAV412 (25.5% compared to 20.7%).

To determine whether this increase in knockout efficiency was nuclease specific, in an additional experiment, cells were electroporated with mRNA (2 μg) encoding a nuclease targeting the β2-microglobulin gene and either mock transduced or transduced with increasing amounts of AAV412. Cells were stained for β2-microglobulin on day 4 post-transduction and analyzed by flow cytometry (FIG. 37B). In the mock transduced cells, β2-microglobulin knockout efficiency was 64.5% and increased in the transduced cells to 68.6%, 70.7%, 77.2% and 82.5% with increasing amounts of AAV412, demonstrating an increase in knockout efficiency of up to 27.9% (82.5% compared to 64.5%).

In a parallel experiment, cells were electroporated with TRC 1-2x.87EE mRNA and either mock transduced or transduced with AAV422 (using the same MOIs as AAV412). Cells were labeled with an antibody against CD3 and cells were analyzed by flow cytometry (FIG. 37C). The mock transduced cells showed 62.2% T cell receptor knockout, and with increasing amounts of AAV, the T cell receptor knockout frequency increased to 72.6%, 75.5%, 78.3% and 75.1%. Here, the presence of AAV422 increases the knockout efficiency of TRC 1-2x.87EE by up to 25.8% (78.3% compared to 62.2%). It is striking that the increase in percent knockout efficiency is almost identical between these three experiments, using two different nucleases and two different AAV vectors. Taken together, these data strongly indicate that transduction of cells with single strand AAV vectors increase the knockout efficiency of our nucleases, irrespective of nuclease or AAV cargo.

5. Activity of T Cells Expressing Anti-CD19 Chimeric Antigen Receptor

The above experiments clearly demonstrate the generation of CAR T cells by electroporating cells with TRC 1-2x.87EE mRNA, then immediately transducing cells with AAV421, and that these cells can be enriched for a $CD3^-$/$CAR^+$ population by co-culture with CD19 expressing IM-9 cells. We next examined the activity of these CAR T cells against target cells. In the first experiment, the cells described above and shown in FIG. 34C were used in an IFN-gamma ELISPOT assay, in which either $CD19^+$ Raji cells or $CD19^-$ U937 cells were the target population. As shown in FIG. 38A, when anti-CD19 CAR T cells were incubated with U937 cells, they did not secrete IFN-gamma regardless of the target:effector ratio. Incubating CAR T cells with Raji cells, however, resulted in high levels of IFN-gamma secretion, in a dose-dependent manner, indicating that secretion of IFN-gamma is antigen-specific.

These CAR T cells were also used in a cell killing assay in which luciferase-labeled Raji cells were the target. Briefly, CAR T cells were incubated with luciferase-labeled Raji cells at a ratio of 10:1. At several time points, cells were washed and lysed to measure luciferase activity as a measure of how many cells remained. Control cells showed luciferase activity greater than 5500 arbitrary units (FIG. 38B). Co-incubation for 2, 3, 4 and 5 hours resulted in a decrease in luciferase activity to 4598, 3292, 2750 and 1932 arbitrary units, respectively. Thus, within 5 hours of co-incubation, luciferase activity was reduced approximately 65%, indicating strong cytolytic activity of the CAR T cells.

Taken together, these data demonstrate that anti-CD19 CAR T cells generated according to the methods described herein are effective at killing $CD19^+$ cells.

Example 7

Linearized Plasmid DNA

1. Expression of Chimeric Antigen Receptor from Linearized Plasmid DNA

Since HDR templates produced by AAV are linear DNA molecules, we hypothesized that linear DNA from any source may be a suitable HDR template for inserting a CAR gene into the TRC 1-2 recognition sequence. To test this, we generated several plasmids that contain an anti-CD19 CAR gene flanked by homology arms that are homologous to the TRC 1-2 recognition sequence locus. Different promoters were used in some plasmids, and homology arms were either "short" (200 bp on the 5' homology arm and 180 bp on the 3' homology arm) to mimic the self-complimentary AAV vectors, or "long" (985 bp on the 5' homology arm and 763 bp on the 3' homology arm) to mimic the single strand AAV vectors. Plasmids with short homology arms are labeled "pDS" and those with long homology arms are labeled "pDI." Additionally, some plasmid contained an intron upstream of the CAR gene.

The CAR donor plasmids were linearized at a restriction site in the vector backbone and gel purified. Human $CD3^+$ T cells were either electroporated with the linearized CAR donor plasmid alone (varying amounts between 500 ng and 1000 ng, depending on the concentration of the purified linearized plasmid), or co-electroporated with TRC 1-2.87EE mRNA (2 μg). As controls, cells were either mock electroporated or electroporated with TRC 1-2x.87EE alone. The graphs in FIG. 39 are labelled with descriptions for all electroporations. Approximately 4 days post-electroporation, cells were labelled with antibodies against CD3 and the anti-CD19 CAR and analyzed by flow cytometry (FIG. 39). FIG. 39A shows background $CD3^-$/$CAR^+$ staining of 0.15%. It should be noted that the background $CD3^+$/$CAR^+$ staining was unusually high at 4.31%. FIG. 39B shows cells that were electroporated with TRC 1-2x.87EE mRNA alone, demonstrating 60.8% CD3 knockout. FIGS. 39C and 39D represent samples that were co-electroporated with TRC 1-2x.87EE mRNA and either the long homology arm vector with an EF1α core promoter with an HTLV enhancer or the short homology arm vector with EF1α core promoter (with no enhancer). Interestingly, the linearized CAR donor with the EF1α core promoter alone generated a $CD3^-$/$CAR^+$ population of 2.38%, while the vector harboring the EF1α core promoter with the HTLV enhancer did not generate a significant percentage of $CD3^-$/$CAR^+$ cells. Cells that were electroporated with these two vectors in the absence of TRC 1-2x.87EE mRNA showed no significant increase in the $CD3^-$/$CAR^+$ population (FIGS. 39E and 39F). The increase in the $CD3^-$/$CAR^+$ population with the EF1α core promoter vector in the presence of TRC 1-2x.87EE suggested that a linearized plasmid could serve as an HDR template to repair double strand breaks at the TRC 1-2 recognition sequence.

FIGS. 39G and 39H show two long homology arm constructs that both contain an MND promoter driving expression of the CAR. One of these constructs, shown in FIG. 39G, also contains an intron in the 5' end of the CAR gene. Surprisingly, the long homology arm plasmid with an MND promoter and intron showed significant CAR expression (FIG. 39G, 4.14% $CD3^-$/$CAR^+$) while the intron-less construct (FIG. 39H) did not show detectable CAR expression when co-electroporated with TRC 1-2x.87EE mRNA. A short homology arm plasmid with the MND promoter, but with no intron, was also tested with TRC 1-2x.87EE mRNA and did not demonstrate any CAR expression (FIG. 39I). None of the MND promoter-containing constructs generated any CARP cells in the absence of TRC 1-2x.87EE mRNA (FIGS. 39J, 39K, and 39L).

Lastly in this experiment, we tested a short homology arm construct that contained a JeT promoter driving expression of the CAR and a "long" homology arm construct with a CMV promoter driving expression of the CAR. Alone, neither of these linearized plasmids resulted in significant CARP cells (FIGS. 39O and 39P). When cells were co-electroporated with TRC 1-2x.87EE mRNA, the JeT containing construct showed 2.69% $CD3^-CAR^+$ cells and the CMV containing construct yielded 2.7% $CD3^-$/$CAR^+$ cells.

The flow plots shown in FIG. 39 clearly demonstrate that linearized plasmid DNA that encodes the CAR, flanked by homology arms, can serve as HDR templates to repair DNA breaks caused by TRC 1-2x.87EE, resulting in insertion of the CAR nucleic acid. It is clear that promoter strength plays a significant role in expression of the CAR, and some promoters drive more efficient expression when there is an intron in the gene.

To confirm that insertion of the CAR using linearized DNA constructs was specific to the TRC 1-2 recognition sequence locus, we analyzed cells as described above using primers that sat within the CAR and outside of the homology arms (FIG. 40, Table 11). Samples 1 and 2 are PCR products from cells that were either mock electroporated or electroporated with only mRNA encoding TRC 1-2x.87EE. Consistent with results shown above, no PCR bands are present indicating the lack of CAR gene in the TRC 1-2 recognition site. Samples 3, 4 and 5 are from cells that were co-electroporated with TRC 1-2x.87EE and a linearized CAR homology plasmid (samples names in FIG. 40). Each sample shows two PCR bands of the predicted size indicating insertion of the CAR gene expression cassette into the TRC 1-2 recognition site. Samples 6, 7, and 8 are from cells that were electroporated with the same linearized CAR homology plasmids as samples 3, 4, and 5 but without TRC 1-2x.87EE mRNA. As expected, no PCR bands are present. Samples 9 and 10 are PCR products from cells that were either mock electroporated or electroporated with only mRNA encoding TRC 1-2x.87EE and show no PCR bands. Samples 11, 12, 13 and 14 are from cells that were co-electroporated with TRC 1-2x.87EE and a linearized CAR homology plasmid (samples names in FIG. 40). Each sample shows two PCR bands of the predicted size indicating insertion of the CAR gene into the TRC 1-2 recognition site. Samples 15, 16, 17, and 18 are from cells that were electroporated with the same linearized CAR homology plasmids as samples 11, 12, 13, and 14 but without TRC 1-2x.87EE mRNA. As expected, no PCR bands are present.

FIGS. 39 and 40 clearly demonstrate that co-electroporating human $CD3^+$ T cells with mRNA encoding TRC 1-2x.87EE and a linearized CAR homology plasmid is an effective method to insert the CAR gene into the TRC 1-2 recognition sequence.

TABLE 11

| Sample | Nucleofection | Linearized plasmid |
|---|---|---|
| 1 | Mock (Water) | — |
| 2 | TRC1-2x87EE | — |
| 3 | TRC1-2x87EE | pDS EF1-α Core |
| 4 | TRC1-2x87EE | pDS 200 MND NC |
| 5 | TRC1-2x87EE | pDS 200 JET NC |
| 6 | Mock (Water) | pDS EF1-α Core |
| 7 | Mock (Water) | pDS 200 MND NC |
| 8 | Mock (Water) | pDS 200 JET NC |
| 9 | Mock (Water) | — |
| 10 | TRC1-2x87EE | — |
| 11 | TRC1-2x87EE | pDI EF1-α NC |
| 12 | TRC1-2x87EE | pDI MND intron NC |
| 13 | TRC1-2x87EE | pDI MND NC |
| 14 | TRC1-2x87EE | pDI CMV 985 NC 763 |
| 15 | Mock (Water) | pDI EF1-α NC |
| 16 | Mock (Water) | pDI MND intron NC |
| 17 | Mock (Water) | pDI MND NC |
| 18 | Mock (Water) | pDI CMV 985 NC 763 |
| 19 | Mock (Water) | — |
| 20 | TRC1-2x87EE | — |
| 21 | TRC1-2x87EE | pDS MCS |
| 22 | Mock (Water) | PDS MCS |

Example 8

Characterization of Additional AAV Vectors

1. Use of AAV with JeT Promoter and Long Homology Arms

Collectively, the data shown above indicate that vectors utilizing the JeT promoter drive high, consistent expression of the CAR and that longer homology arms may increase gene insertion efficiency. We designed and generated the vector shown in FIG. 41 (SEQ ID NO:125), which was used to make single-strand AAV with long homology arms, and a JeT promoter driving expression of the anti-CD19 CAR (referred to herein as AAV423). Human $CD3^+$ T cells were electroporated with mRNA encoding TRC 1-2x.87EE and transduced with increasing amounts of AAV423. Since data shown above suggested that higher MOIs may result in increased insertion efficiency, we used titers ranging from $1.875e^4$ to $1.5e^5$. As controls, cells were either electroporated with mRNA encoding TRC 1-2x.87EE then mock transduced or mock electroporated then transduced with increasing amounts of AAV423. On day 6 post-transduction, cells were labeled with antibodies recognizing CD3 or the anti-CD19 CAR and analyzed by flow cytometry. As shown in FIG. 42, cells that were mock electroporated then transduced with increasing amounts of AAV423 are overwhelmingly $CD3^+/CAR^-$ (ranging from 96.6% to 98.5%). Cells that were electroporated with mRNA encoding TRC 1-2x.87EE and mock transduced were 39% $CD3^-$ indicating efficient knockout of the T cell receptor. In these cells, background CAR staining was very low (around 2%). Cells that were electroporated with mRNA encoding TRC 1-2x.87EE then transduced with increasing amounts of AAV423 showed dramatic CAR staining in conjunction with CD3 knockout. $CD3^-/CAR^+$ populations ranged from 21.6% to 22.7%, while $CD3^+/CAR^+$ populations were around 2%. As described above, the presence of single-strand AAV increased the overall gene modification efficiency at the TRC 1-2 recognition site, with total $CD3^-$ populations increasing from 41.44% in the control cells to 57.6%, 59.2%, 58.7%, and 56.1% in cells that were electroporated then transduced with increasing amounts of AV423. The percent of $CD3^-$ cells that were CARP ranged from 37.5% to 39.9% indicating a dramatic increase in insertion efficiency compared to data described above.

To confirm that insertion of the CAR using AAV423 was specific to the TRC 1-2 recognition sequence locus, we analyzed cells as described above using primers that sat within the CAR and outside of the homology arms (FIG. 43, Table 12).

TABLE 12

| Sample | Nucleofection | AAV (μl) | MOI |
|---|---|---|---|
| 1 | Mock (Water) | — | — |
| 2 | Mock (Water) | — | — |
| 3 | Mock (Water) | pDI JET Prep A (3.125) | 18750 |
| 4 | Mock (Water) | pDI JET Prep A (6.25) | 37500 |
| 5 | Mock (Water) | pDI JET Prep A (12.5) | 7500 |
| 6 | Mock (Water) | pDI JET Prep A (25) | 150000 |
| 7 | TRC1-2x87EE | — | — |
| 8 | TRC1-2x87EE | pDI JET Prep A (3.125) | 18750 |
| 9 | TRC1-2x87EE | pDI JET Prep A (6.25) | 37500 |
| 10 | TRC1-2x87EE | pDI JET Prep A (12.5) | 7500 |
| 11 | TRC1-2x87EE | pDI JET Prep A (25) | 150000 |

Samples 1 and 2 are PCR products from cells that were mock electroporated. Consistent with results shown above, no PCR bands are present indicating the lack of CAR gene in the TRC 1-2 recognition site. Samples 3-6 are from cells that were mock electroporated then transduced with increasing amounts of AAV423. Consistent with results above, there are no PCR bands present. Sample 7 is from cells electroporated with mRNA encoding TRC 1-2x.87EE then mock transduced, and shows no PCR bands. Samples 8-11 are from cells electroporated with mRNA encoding TRC 1-2x.87EE then transduced with increasing amounts of AAV423, and show the PCR bands expected if the CAR is inserted into the TRC 1-2 recognition sequence.

Given the ability of AAV423 to insert the CAR sequence into the TRC 1-2 recognition site following cleavage, it is further envisioned that the AAV423 plasmid (FIG. 41) could be linearized by digestion with a and delivered to the cell by digestion with one or more restriction enzymes, such that the T cells could be transfected with a linearized DNA template which could integrate into the TRC 1-2 recognition site and encode an anti-CD19 CAR.

Example 9

In Vivo Efficacy of Anti-CD19 TCR-Negative CAR T Cells

1. Murine Model of Disseminated B Cell Lymphoma

The efficacy of the gene-edited anti-CD19 CAR T cells was evaluated in a murine model of disseminated B cell lymphoma. Activated T cells were electroporated with TRC 1-2x.87 EE mRNA as described above, then transduced with an AAV6 vector comprising an anti-CD19 CAR expression cassette driven by a JeT promoter and flanked by homology arms. Following 5 days of culture with IL-2 (10 ng/mL), cells were analyzed for cell-surface CD3 and anti-CD19 CAR expression by flow cytometry as previously described (FIG. 44A). $CD3^-$ cells were enriched by depleting $CD3^+$ cells using anti-CD3 magnetic beads. Depleted cells were then cultured for 3 days in IL-15 (10 ng/mL) and IL-21 (10 ng/mL) and re-analyzed for cell-surface expression of CD3 and anti-CD19 CAR (FIG. 44B). Isolation of the $CD3^-$ population was quite efficient, yielding 99.9% purity as measured by flow cytometry following depletion of $CD3^+$ cells (FIG. 44B). The purified $CD3^-$ population comprised 56% $CD4^+$ and 44% $CD8^+$ cells (FIG. 44C), and had primarily central memory/transitional memory phenotypes, determined by staining for CD62L and CD45RO (FIG. 44D).

Studies utilizing the Raji disseminated lymphoma model were conducted by Charles River Laboratories International Inc. (Morrisville, N.C., USA). $CD19^+$ Raji cells stably expressing firefly luciferase (ffLuc)[44] were injected i.v. into 5-6 week old female NSG mice on Day 1, at a dose of $2.0\times10^5$ cells per mouse. On Day 4 mice were injected i.v. with PBS or PBS containing gene edited control TCR KO T cells prepared from the same healthy donor PBMC or PBS containing the indicated doses of CAR T cells prepared from the same donor. On the indicated days, live mice were injected i.p. with Luciferin substrate (150 mg/kg in saline), anesthetized, and Luciferase activity measured after 7 minutes using IVIS SpectrumCT (Perkin Elmer, Waltham, Mass.). Data was analyzed and exported using Living Image software 4.5.1 (Perkin Elmer, Waltham, Mass.). Luminescence signal intensity is represented by radiance in p/sec/$cm^2$/sr.

2. Results

As shown in FIG. 45, growth of $CD19^+$ Raji cells was evident in all mice at low levels by day 8, and increased significantly in untreated and $TCR^-$ control groups by day 11. In control groups, significant tumor growth was observed by day 15, and by day 18 or 19 all control groups were euthanized. In contrast, all groups of mice treated with anti-CD19 CAR T cells showed no evidence of tumor growth by day 11 and, with the exception of a single mouse in the low dose group, remained tumor-free through day 29 of the study. Tumor re-growth was observed in three mice in the low dose cohort around day 36. One of the three died at day 42, though imaging revealed only low levels of tumor in this animal, so it is unlikely that death was tumor-related.

3. Conclusions

These results provide clear evidence for in vivo clearance of $CD19^+$ tumor cells by gene-edited $CD3^-$ CAR T cells and support further preclinical development of this platform for allogeneic CAR T cell therapy.

The invention claimed is:

1. A method of immunotherapy for treating cancer in a subject in need thereof, said method comprising administering to said subject a pharmaceutical composition comprising a genetically-modified human T cell and a pharmaceutically acceptable carrier, wherein said genetically-modified human T cell comprises in its genome a modified human T cell receptor (TCR) alpha constant region gene, wherein said modified human TCR alpha constant region gene comprises from 5' to 3':

(a) a 5' region of a human TCR alpha constant region gene which is endogenous to said T cell;

(b) an exogenous nucleic acid sequence encoding a chimeric antigen receptor; and (c) a 3' region of said human TCR alpha constant region gene which is endogenous to said T cell;

wherein said exogenous nucleic acid sequence is inserted in said TCR alpha constant region gene which is endogenous to said T cell at a position within SEQ ID NO: 3, and wherein said chimeric antigen receptor comprises a ligand-binding domain having specificity for an antigen present on a cancer cell, and wherein said genetically-modified human T cell expresses said chimeric antigen receptor and exhibits reduced cell-surface expression of the endogenous T cell receptor when compared to unmodified control cells.

2. The method of claim 1, wherein said exogenous nucleic acid sequence comprises a promoter sequence that drives expression of said chimeric antigen receptor.

3. The method of claim 1, wherein said chimeric antigen receptor comprises an intracellular cytoplasmic signaling domain.

4. The method of claim 1, wherein said chimeric antigen receptor comprises an intracellular co-stimulatory signaling domain.

5. The method of claim 1, wherein said chimeric antigen receptor comprises a signal peptide.

6. The method of claim 1, wherein said chimeric antigen receptor comprises a hinge domain.

7. The method of claim 1, wherein said chimeric antigen receptor comprises a transmembrane domain.

8. The method of claim 1, wherein said ligand-binding domain of said chimeric antigen receptor is specific for CD19.

* * * * *